(12) United States Patent
Dart et al.

(10) Patent No.: US 7,135,484 B2
(45) Date of Patent: Nov. 14, 2006

(54) AZABICYCLIC COMPOUNDS ARE CENTRAL NERVOUS SYSTEM ACTIVE AGENTS

(75) Inventors: Michael J. Dart, Highland Park, IL (US); Xenia B. Searle, Grayslake, IL (US); Karin R. Tietje, Mundelein, IL (US); Richard B. Toupence, South Plainfield, NJ (US)

(73) Assignee: Abbott Laboratories, Abbott Park, IL (US)

( * ) Notice: Subject to any disclaimer, the term of this patent is extended or adjusted under 35 U.S.C. 154(b) by 442 days.

(21) Appl. No.: 10/638,381

(22) Filed: Aug. 12, 2003

(65) Prior Publication Data

US 2004/0152724 A1 Aug. 5, 2004

Related U.S. Application Data

(60) Provisional application No. 60/403,737, filed on Aug. 14, 2002.

(51) Int. Cl.
*A61K 31/44* (2006.01)
*A61K 31/40* (2006.01)
*C07D 401/04* (2006.01)

(52) U.S. Cl. .................. 514/339; 514/422; 546/276.7; 548/517

(58) Field of Classification Search ............... 514/443, 514/339, 422; 548/466, 517; 546/276.7
See application file for complete search history.

(56) References Cited

U.S. PATENT DOCUMENTS

| 2,858,314 | A | 10/1958 | Georgian | |
|---|---|---|---|---|
| 5,929,087 | A | 7/1999 | Efange et al. | 514/314 |
| 6,489,328 | B1 * | 12/2002 | Snow et al. | 514/252.16 |
| 6,844,435 | B1 * | 1/2005 | Snow et al. | 544/250 |
| 2002/0094989 | A1 | 7/2002 | Hale et al. | 514/253.04 |

FOREIGN PATENT DOCUMENTS

| EP | 0 233 793 | 8/1987 |
|---|---|---|
| EP | 0 612 741 | 2/1994 |
| EP | 819690 | 1/1998 |
| EP | 0 899 261 | 3/1999 |
| EP | 1 386 920 | 2/2004 |
| WO | 94/22823 | 10/1994 |
| WO | 95/15312 | 6/1995 |
| WO | 95/17384 | 6/1995 |
| WO | 95/26187 | 10/1995 |
| WO | 97/40012 | 10/1997 |
| WO | 00/44755 | 8/2000 |
| WO | 02/14319 | 2/2002 |
| WO | WO 200214319 A2 * | 2/2002 |
| WO | 02/085890 | 10/2002 |
| WO | 03/004493 | 1/2003 |

OTHER PUBLICATIONS

Arneric et al., "Cholinergic channel modulators as a novel therapeutic strategy for Alzheimer's disease," Exp. Opin. Invest. Drugs 5(1):79-100 (1996).
Arneric et al., "Neuronal nicotinic acetylcholine receptors. Novel targets for central nervous system therapeutics," Psychopharmacology: The Fourth Generation of Progress 95-109 (1995).
Barth et al., "Synthesis of a representative cis/trans pair of 4,5-disubstituted cyclopentenyllithium reagents," J. Org. Chem. 50:2438-2443 (1985).
Becker et al, "Synthesis of N-BOC-3-azabicyclo[3.3.0]octan-7-one via reductive pauson-khand cyclization and subsequent conversion to a novel diazatricyclic ring system," Tetrahedron 49(23):5047-5054 (1993).
Beyerman et al., "The synthesis of thiazole-2-and of theiazole-5-carboxylic acid via a halogen-metal exchange reaction," Trav. Chim. Pays-Bas 73:325 (1954).
Bonjoch et al., "Total synthesis of (±)-deethylibophyllidine: studies of a fischer indolization route and a successful approach via a pummerer rearrangement/thionium ion-mediated indole cyclization," J. Org. Chem. 61(20):7106-7115 (1996).
Butler et al., A study of the proton nuclear magnetic resonance spectra of aryl and mono- and disubstituted-n-methylazoles, Can. J. Chem. 51:2315-2322 (1973).
Caprathe et al., "Dopamine autoreceptor agonists as ptential antipsychotics. 6-propyl-4,5,5a,6,7,8-hexahydrothiazolo[4,5-f]quinolin-2-amine," J. Med. Chem. 34(9):2736-2746 (1991).
Carpes et al., "Steroselective synthesis of conformationally restricted analogues of aspartic and glutamic acids from endocyclic enecarbamates," Tetrahedron Letters 38(11):1869-1872 (1997).
Clayton et al., "A total synthesis of (±) Epibatidine," Tetrahedron Letters 34:7493-7496 (1993).
Corey et al., "(+)-1(S), 5(R), 8(S)-8-phenyl-2-azabicyclo[3.3.0]octan-8-ol N,O-methylboronate (2) and its enantiomer, chiral chemzymes which serve as catalysts for their own enantioselective synthesis," Tetrahedron Letters 30(41):5547-5550 (1989).
DeFaria et al., "[2+2] cycloaddition reaction of cyclic enecarbamates and enamides with ketenes, A short and efficient synthesis of geissman-Waiss lactone," Tetrahedron Letters 34(1):27-30 (1993).

(Continued)

*Primary Examiner*—Kamal A. Saeed
*Assistant Examiner*—Joseph R. Kosack
(74) *Attorney, Agent, or Firm*—B. Gregory Donner

(57) ABSTRACT

Compounds of formula (I)

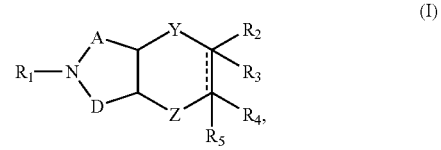

are novel CNS active agents that are useful for treating pain and for treating other disorders associated with the cholinergic system.

5 Claims, No Drawings

OTHER PUBLICATIONS

Efange et al., "Hydroxylated decahydroquinolines as ligands for the vesicular acetylcholine transporter: synthesis and biological evaluation," J. Med. Chem. 42(15):2862-2869 (1999).

Evans et al., "The total synthesis of (±)-naphthyridinomycin. I. Preparation of a key tricyclic lactam intermediate," Tetrahedron Letters 26(16):1907-1910 (1985).

Feldman et al., "Inter- and Intramolecular addition/cyclizations of sulfonamide anions with alkynyliodonium triflates. Synthesis of dihydropyrrole, pyrrole, indole, and tosylenamide heterocycles," J. Org. Chem. 61(16):5440-5452 (1996).

Gais et al., "Enzyme-catalyzed asymmetric synthesis. Enantioselectivity of pig liver esterase catalyzed hydrolyses of 4-substituted meso cyclopentane 1,2-diesters," J. Org. Chem. 54:5115-5122 (1989).

Gobeaux et al., "Intramolecular [2+2] cycloadditions of keteniminium salts derived from α-and β-amino acids. A route to azabicyclic detones." Heterocycles 28(1):29-32 (1989).

Goerdeler et al., "Synthesis and properties of 1,2,4- and 1,3,4-thiodiazole," Chem. Ber. 89(6):1534-1543 (1956).

Guerry, Helv. Chim. Acta 74:163-177 (1991).

Hand et al., "Teleamination of the imidazo[1,2-a]pyridine system," J. Org. Chem. 43(14):2900-2906 (1978).

Heathcock et al., "Total Synthesis of (±)-Fawcettimine," J. Org. Chem. 54:1548-1562 (1989).

Iwamoto et al., "Induction of "petite" mutants of yeast, *Saccharomyces cerevisiae*, by photodynamic action of acriflavine," Chem. Pharm. Bull. 33(7):2762-2766 (1985).

Klemm et al., "Chemistry of thienopyridines. IV. Syntheses of 5-substituted thieno [2,3-b]pyridines(1)," J. Heterocycl. Chem. 5:773-778 (1968).

Klemm et al., "Chemistry of thienopyridines. XXXI. A new synthesis of thieno[3,2-b]pyridine and studies on direct substitution into its thiophene ring [1]," J. Heterocycl. Chem. 21:785-790 (1984).

Larock et al., "Palladium (II)-catalyzed cyclization of olefinic tosylamides," J. Org. Chem. 61(11):3584-3585 (1996).

Lindstrom, "Nicotinic acetylcholine receptors in health and disease," Molecular Neurobiology 15:193-222 (1997).

Littke et al., "Pd/P(t-Bu)$_3$: A mild and general catalyst for stille reactions of aryl chlorides and aryl bromides," J. Am. Chem. Soc. 124:6343-6348 (2002).

Lloyd et al., "The potential of subtype selective neuronal nicotinic acetylcholine receptor agonists as therapeutic agents," Life Sciences 62(17/18):1601-1606 (1998).

Lorvelec et al., "Intramolecular diels-alder reactions involving boryl-3-propenoic acid derivatives," Tetrahedron Letters 39(29):5185-5188 (1998).

Malpass et al., "Reaction of chlorosulphonyl isocyanate with 1,3-dienes. Control of 1,2- and 1,2-addition pathways and the synthesis of Aza-and Oxa-bicyclic systems," J. Chem. Soc. Perkin Trans. I 874-884 (1977).

Mathison et al., "synthesis and Stereochemistry of some 8-substituted 2-methyldecahydroisoquinolines," J. Org. Chem. 39(22):3210-3215 (1974).

McMurry et al., "A method for the regiospecific synthesis of enol triflates by enolate trapping," Tetrahedron Letters 24(10):979-982 (1983).

Miyajima et al., "Synthesis of biologically active 6-azaprostacyclin derivaties," Heterocycles 27(3):643-644 (1988).

Morgan et al., "A novel sulfinylation of alkenes by tosyl cyanide with titanium (IV) chloride," Tetrahedron Letters 40(15):4857-4860 (1999).

Mundy et al., "Reduction of cis-bicyclo[4,3,0]non-3-ene and its 8-substituted heterocyclic analogues," J. Am. Chem. Soc 102(6):2005-2010 (1980).

Neckers et al., "A greatly improved procedure for ruthenium tetraoxide catalyzed oxidation of organic compounds," J. Org. Chem. 46(19):3936-3938 (1981).

Ogata et al., "Synthesis and antibacterial activity of new 7-(aminoazabicycloalkanyl)-quinolonecarboxylic acid," Eur. J. Med. Chem. 26:889-906 (1991).

Ornstein et al., "6-substituted decahydroisoquinoline-3-carboxylic acids as potent and selective conformationally constrained NMDA receptor antagonists," J. Med. Chem. 35(19):3547-3560 (1992).

Overman et al., "Applications of cationic aza-cope rearrangements for alkoloid synthesis. Stereoselective preparation of cis-3a-aryloctahydroindoles and a new short route to amaryllidaceae alkaloids," J. Am. Chem. Soc. 105(22):6629-6637 (1983).

Overman et al., "Stereocontrolled synthesis of substituted *cis*-cyclopenta[b]pyrrolidines," J. Org. Chem. 50:2403-2405 (1985).

Paolini et al., "Aromaticity in heterocyclic systems III. The structure and proton magnetic resonance spectra of certain imidazo[1,2-a]pyridines(1)," J. Heterocycl. Chem. 2:53-62 (1965).

Paolini et al., "Aromaticity in heterocyclic systems. IV. Substitution reactions of imidazo[1,2-α]pyridine and related methyl derivatives," J. Org. Chem. 30:4085-4090 (1965).

Paquette et al., "The azacyclooctatetraene (Azocine) system," J. Am. Chem. Soc. 90(14):3897-3898 (1968).

Pavia et al., "6-alkoxy-N,N-disubstituted-2-pyridinamines as anticonvulsant agents," J. Med. Chem. 30(7):1210-1214 (1987).

Ramon et al., "78. Nonreductive enantioselective ring opening of N-(methylsulfonyl)dicarboximides with diisopropoxytitanium α,α,ά,ά-tetraaryl-1,3-dioxalane-4,5-dimethanolate," Helv. Chim. Acta 79(3):875-894 (1996).

Rice et al., "Salts and derivatives of cis-$\Delta^4$-tetrahydrophthalic acid," J. Org. Chem. 16:501-505 (1951).

Rocca et al., "First metalation of aryl iodides: directed ortho-lithiation of iodopyridines, halogen-dance, and application to synthesis," J. Org. Chem. 58:7832-7838 (1993).

Sakamoto et al., "Condesed heteroaromatic ring systems. XIX Synthesis and reactions of 5-(thibutylstannyl)isoxazoles," Tetrahedron 47:5111 (1991).

Sturla et al., "Catalytic asymmetric cyclocarbonylation of nitrogen-containing enynes," J. Org. Chem. 64:5547-5550 (1999).

Su et al, "Dynamics of anilinium radical α-heterolytic fragmentation processes. Electrofugal group, substituent, and medium effects on desilylation, decarbonoxylation, an retro-aldol cleavage pathways," J. Am. Chem. Soc. 120(41):10676-10686 (1998).

Vidari et al., "Desymmetrization of bicyclo[3.3.0]octane-3,7-dione by the Schmidt reaction: as easy synthesis of tecomanine," Tetrahedron: Asymmetry 8(17):2893-2903 (1997).

Williams et al., "Beyond the Tobaco Debate: dissecting out the therapeutic potential of nicotine," Exp. Opin. Invest. Drugs 5(8):1035-1045 (1996).

Wulff et al. "A regioselective entry to vinyllithiums from unsymmetrical ketones via enol triflates," J. Org. Chem. 51:277-279 (1986).

Xu et al., "Single electron transfer promoted photocyclization reactions of (aminoalkyl)cyclohexenones. Mechanistic and synthetic features of processes involving the generation and reactions of amine cation and α-amino radicals," J. Am. Chem. Soc. 113(23):8863-8878 (1991).

Yasuda et al., "Synthesis of conformationally defined glutamic acid analogues from readily available diels-alder adducts," Chem. Pharm. Bull 43(8):1318-1324 (1995).

Zhang et al., "A short and efficient total synthesis of (±)-epibatidine," J. Org. Chem. 61(20):7189-7191 (1996).

Krow et al., "Synthesis of 5-and 6-(6-chloro-3-pyridyl)-2-azabicyclo [2.2.0]hexanes," Tetrahedron 56(47):9233-9239 (2000).

Martin et al., "Intramolecular [4+2] Cycloadditions as a general strategy for alkaloid synthesis. A novel formal synthesis of lycorine," J. Org. Chem. 47:3634-3643 (1982).

Nakatsuka et al., "Pyrazoles and pharmaceutical compositions containing them for treatment of autoimmune diseases," Jpn. Kokai Tokkyo Koho, p. 31 2002; Database Accession No. 37:88445.

* cited by examiner

AZABICYCLIC COMPOUNDS ARE CENTRAL NERVOUS SYSTEM ACTIVE AGENTS

This application claims priority to U.S. application Ser. No. 60/403,737, filed Aug. 14, 2002.

FIELD OF THE INVENTION

The present invention is directed to a series of azabicyclic compounds and a method for treating pain in mammals.

BACKGROUND OF THE INVENTION

Three major groups of drugs currently used for the treatment of pain include opioids, non-steroidal anti-inflammatory drugs (NSAIDs), and analgesic adjuvants. Opioids such as, but not limited to, morphine act at opioid receptors in the brain and spinal cord to block the transmission of pain signals. However, clinical use of opioids is commonly associated with potential abuse and addiction liabilities, the development of tolerance, and other side effects such as constipation, nausea, and cognitive impairments. NSAIDs typically, but not exclusively, block the production of prostaglandins to prevent sensitization of nerve endings that facilitate the pain signal to the brain. NSAIDs effectively treat mild-to-moderate pain with an inflammatory component, but they have a ceiling effect and are not particularly effective in relieving severe or chronic neuropathic pain. Many commonly prescribed over-the-counter NSAIDs cause gastric distress and bleeding, although the newer COX-2 selective NSAIDs may address these side effects liabilities. Analgesic adjuvants, including certain antidepressants, local anesthetics and anticonvulsants, have been shown to be effective in treating some chromic pain states that have not responded to NSAID or opioid therapy.

A substantial number of medical disorders and conditions produce pain as part of the disorder or condition. Relief of this pain is a major aspect of ameliorating or treating the overall disease or condition. One class of pain reliever may not be effective for a particular patient or group of patients. Therefore, a need exists for novel compounds that treat pain through mechanisms different from the established analgesics.

The compounds of the present invention are novel analgesic compounds that bind to nicotinic acetylcholine receptors. In particular, these compounds are active at one or more of the subtypes of neuronal nicotinic receptors including, but not limited to, alpha4beta2, alpha7, and alpha3beta4. The compounds of the present invention have utility in treating pain and can be administered in combination with an opioid such as, but not limited to, morphine, a non-steroid anti-inflammatory agent such as, but not limited to, aspirin, a tricyclic antidepressant, or an anticonvulsant such as, but not limited to, gabapentin or pregabalin for treating pain. The compounds of the present invention have utility for treating disorders associated with the cholinergic system.

SUMMARY OF THE INVENTION

The present invention discloses novel azabicyclic compounds and a method for treating pain in mammals. More particularly, the present invention is directed to compounds of formula (I):

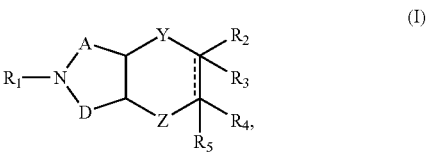

or a pharmaceutically acceptable salt, amide, ester and prodrug thereof, wherein -----represents a single bond or a double bond;

A is selected from a covalent bond or $CH_2$;

D is selected from $CH_2$, $CH_2CH_2$ or $CH_2CH_2CH_2$, provided that when D is $CH_2CH_2CH_2$, then A is a covalent bond;

Y is selected from a covalent bond, $CH_2$, or $CH_2CH_2$;

Z is selected from a covalent bond, $CH_2$, or $CH_2CH_2$, provided that when Z is $CH_2CH_2$, then Y is a covalent bond, and further provided that when Y is $CH_2CH_2$, then Z is a covalent bond;

$R_1$ is selected from hydrogen, alkoxycarbonyl, alkyl, benzyloxycarbonyl, cyanoalkyl, dihydro-3-pyridinylcarbonyl, hydroxy, hydroxyalkyl, phenoxycarbonyl, $-NR_{10}R_{11}$, $(NR_{10}R_{11})$alkyl or $(NR_{10}R_{11})$carbonylalkyl wherein $R_{10}$ and $R_{11}$ are independently selected from hydrogen, alkyl or alkylcarbonyl;

$R_2$ and $R_4$ are independently selected from hydrogen, aryl or heterocycle, provided that one of $R_2$ or $R_4$ is hydrogen; and $R_3$ and $R_5$ are both absent or are independently selected from hydrogen, alkoxy or hydroxy;

provided that when A is a covalent bond, D is $CH_2$ and Y is a covalent bond, then Z is other than a covalent bond; and further provided that when A is a covalent bond, D is $CH_2$ and Z is a covalent bond, then Y is other than a covalent bond.

DETAILED DESCRIPTION OF THE INVENTION

All patents, patent applications, and literature references cited in the specification are herein incorporated by reference in their entirety.

The present invention is directed to compounds of formula (I):

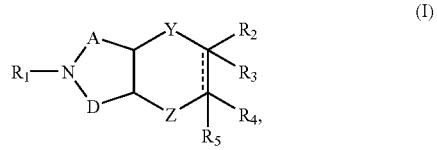

or a pharmaceutically acceptable salt, amide, ester and prodrug thereof, wherein -----represents a single bond or a double bond;

A is selected from a covalent bond or $CH_2$;

D is selected from $CH_2$, $CH_2CH_2$ or $CH_2CH_2CH_2$, provided that when D is $CH_2CH_2CH_2$, then A is a covalent bond;

Y is selected from a covalent bond, $CH_2$, or $CH_2CH_2$;

Z is selected from a covalent bond, $CH_2$, or $CH_2CH_2$, provided that when Z is $CH_2CH_2$, then Y is a covalent bond, and further provided that when Y is $CH_2CH_2$, then Z is a covalent bond;

$R_1$ is selected from hydrogen, alkoxycarbonyl, alkyl, benzyloxycarbonyl, cyanoalkyl, dihydro-3-pyridinylcarbonyl, hydroxy, hydroxyalkyl, phenoxycarbonyl, —$NR_{10}R_{11}$, ($NR_{10}R_{11}$)alkyl or ($NR_{10}R_{11}$)carbonylalkyl wherein $R_{10}$ and $R_{11}$ are independently selected from hydrogen, alkyl or alkylcarbonyl;

$R_2$ and $R_4$ are independently selected from hydrogen, aryl or heterocycle, provided that one of $R_2$ or $R_4$ is hydrogen; and $R_3$ and $R_5$ are both absent or are independently selected from hydrogen, alkoxy or hydroxy;

provided that when A is a covalent bond, D is $CH_2$ and Y is a covalent bond, then Z is other than a covalent bond; and further provided that when A is a covalent bond, D is $CH_2$ and Z is a covalent bond, then Y is other than a covalent bond.

In another embodiment of the present invention, compounds of formula (II) are disclosed

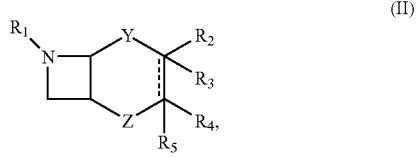

(II)

or a pharmaceutically acceptable salt, amide, ester or prodrug thereof wherein Y, Z, $R_1$, $R_2$, $R_3$, $R_4$ and $R_5$ are as defined in formula (I).

In another embodiment of the present invention, compounds of formula (II) are disclosed wherein Y is a covalent bond; Z is $CH_2$; and $R_1$, $R_2$, $R_3$, $R_4$, and $R_5$ are as defined in formula (I).

In another embodiment of the present invention, compounds of formula (II) are disclosed wherein ----- represents a double bond; Y is a covalent bond; Z is $CH_2$; $R_2$ is hydrogen; $R_3$ and $R_5$ are absent; $R_4$ is heterocycle; and $R_1$ is as defined in formula (I).

In another embodiment of the present invention, compounds of formula (II) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —$C(NH)NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (II) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, and —$C(NH)NR_{10}R_{11}$; and $R_1$, $R_{10}$, and $R_{11}$ are as defined in formula (I).

In another embodiment of the present invention, compounds of formula (II) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, and nitro; and $R_1$ is as defined in formula (I).

In another embodiment of the present invention, compounds of formula (II) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3-pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (II) are disclosed wherein ----- represents a double bond; Y is a covalent bond; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (II) are disclosed wherein ----- represents a double bond; Y is a covalent bond; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (II) are disclosed wherein ----represents a double bond; Y is a covalent bond; Z is $CH_2$; $R_2$ is heterocycle wherein the heterocycle is selected from imidazolyl, isoxazolyl, pyridinyl, tetrazolyl, thiadiazdyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, and —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (II) are disclosed wherein ----represents a double bond; Y is a covalent bond; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, and nitro; $R_3$ and $R_5$ are absent; $R_4$ is hydrogen; and $R_1$ is as defined in formula (I).

In another embodiment of the present invention, compounds of formula (II) are disclosed wherein ----represents a double bond; Y is a covalent bond; Z is $CH_2$; $R_2$ is heterocycle wherein the heterocycle is selected from 3-pyridinyl, 6-bromo-3-pyridinyl, 6-chloro-3-pyridinyl, 6-fluoro-3-pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (II) are disclosed wherein Y is $CH_2$; Z is a covalent bond; and $R_1$, $R_2$, $R_3$, $R_4$, and $R_5$ are as defined in formula (I).

In another embodiment of the present invention, compounds of formula (II) are disclosed wherein ----represents a double bond; Y is $CH_2$; Z is a covalent bond; $R_2$ is heterocycle; $R_3$ and $R_5$ are absent; $R_4$ is hydrogen; and $R_1$ is as defined in formula (I).

In another embodiment of the present invention, compounds of formula (II) are disclosed wherein ----represents a double bond; Y is $CH_2$; Z is a covalent bond; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (II) are disclosed wherein ----represents a double bond; Y is $CH_2$; Z is a covalent bond; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, and —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (II) are disclosed wherein ----represents a double bond; Y is $CH_2$; Z is a covalent bond; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, and nitro; $R_3$ and $R_5$ are absent; $R_4$ is hydrogen; and $R_1$ is as defined in formula (I).

In another embodiment of the present invention, compounds of formula (II) are disclosed wherein ----represents a double bond; Y is $CH_2$; Z is a covalent bond; $R_2$ is heterocycle wherein the heterocycle is selected from 3-pyridinyl, 6-bromo-3-pyridinyl, 6-chloro-3-pyridinyl, 6-fluoro-3-pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (II) are disclosed wherein Y is a covalent bond; Z is $CH_2CH_2$; and $R_1$, $R_2$, $R_3$, $R_4$, and $R_5$ are as defined in formula (I).

In another embodiment of the present invention, compounds of formula (II) are disclosed wherein ----represents a double bond; Y is a covalent bond; Z is CH₂CH₂; R₂ is hydrogen; R₃ and R₅ are absent; R₄ is heterocycle; and R₁ is as defined in formula (I).

In another embodiment of the present invention, compounds of formula (II) are disclosed wherein ----- represents a double bond; Y is a covalent bond; Z is CH₂CH₂; R₂ is hydrogen; R₃ and R₅ are absent; R₄ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR₁₀R₁₁, —NR₁₀R₁₁, (NR₁₀R₁₁)alkyl, (NR₁₀R₁₁)carbonyl, (NR₁₀R₁₁)carbonylalkyl, (NR₁₀R₁₁)sulfonyl, —NR₁₂S(O)₂R₁₃, —C(NR₁₂)NR₁₃R₁₄, —CH₂C(NR₁₂)NR₁₃R₁₄, —C(NOR₁₂)R₁₃, —C(NCN)R₁₂, —C(NNR₁₂R₁₃)R₁₄, —S(O)₂OR₁₂, or —S(O)₂R₁₂; R₁₂, R₁₃, and R₁₄ are independently selected from hydrogen, alkyl, aryl, or arylalkyl; and R₁, R₁₀, and R₁₁ are as defined in formula (I).

In another embodiment of the present invention, compounds of formula (II) are disclosed wherein ----- represents a double bond; Y is a covalent bond; Z is CH₂CH₂; R₂ is hydrogen; R₃ and R₅ are absent; R₄ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR₁₀R₁₁)sulfonyl, and —C(NH)NR₁₀R₁₁; and R₁, R₁₀, and R₁₁ are as defined in formula (I).

In another embodiment of the present invention, compounds of formula (II) are disclosed wherein ----- represents a double bond; Y is a covalent bond; Z is CH₂CH₂; R₂ is hydrogen; R₃ and R₅ are absent; R₄ is heterocycle wherein the heterocycle is pyridinyl substituted with 0, 1, or 2 substituents independently selected from alkenyl, alkenyloxy, alkoxy, alkyl, alkynyl, cyano, halogen, and nitro; and R₁ is as defined in formula (I).

In another embodiment of the present invention, compounds of formula (II) are disclosed wherein ----- represents a double bond; Y is a covalent bond; Z is CH₂CH₂; R₂ is hydrogen; R₃ and R₅ are absent; R₄ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and R₁ is as defined in formula (I).

In another embodiment of the present invention, compounds of formula (II) are disclosed wherein ----- represents a double bond; Y is a covalent bond; Z is CH₂CH₂; R₂ is heterocycle; R₃ and R₅ are absent; R₄ is hydrogen; and R₁ is as defined in formula (I).

In another embodiment of the present invention, compounds of formula (II) are disclosed wherein ----- represents a double bond; Y is a covalent bond; Z is CH₂CH₂; R₂ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR₁₀R₁₁, —NR₁₀R₁₁, (NR₁₀R₁₁)alkyl, (NR₁₀R₁₁)carbonyl, (NR₁₀R₁₁)carbonylalkyl, (NR₁₀R₁₁)sulfonyl, —NR₁₂S(O)₂R₁₃, —C(NR₁₂)NR₁₃R₁₄, —CH₂C(NR₁₂)NR₁₃R₁₄, —C(NOR₁₂)R₁₃, —C(NCN)R₁₂, —C(NNR₁₂R₁₃)R₁₄, —S(O)₂OR₁₂, or —S(O)₂R₁₂; R₃ and R₅ are absent; R₄ is hydrogen; R₁₂, R₁₃, and R₁₄ are independently selected from hydrogen, alkyl, aryl, or arylalkyl; and R₁, R₁₀, and R₁₁ are as defined in formula (I).

In another embodiment of the present invention, compounds of formula (II) are disclosed wherein ----- represents a double bond; Y is a covalent bond; Z is CH₂CH₂; R₂ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR₁₀R₁₁)sulfonyl, and —C(NH)NR₁₀R₁₁; R₃ and R₅ are absent; R₄ is hydrogen; and R₁, R₁₀, and R₁₁ are as defined in formula (I).

In another embodiment of the present invention, compounds of formula (II) are disclosed wherein ----- represents a double bond; Y is a covalent bond; Z is CH₂CH₂; R₂ is heterocycle wherein the heterocycle is pyridinyl substituted with 0, 1, or 2 substituents independently selected from alkenyl, alkenyloxy, alkoxy, alkyl, alkynyl, cyano, halogen, and nitro; R₃ and R₅ are absent; R₄ is hydrogen; and R₁ is as defined in formula (I).

In another embodiment of the present invention, compounds of formula (II) are disclosed wherein ----- represents a double bond; Y is a covalent bond; Z is CH₂CH₂; R₂ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (II) are disclosed wherein Y is $CH_2$; Z is $CH_2$; and $R_1$, $R_2$, $R_3$, $R_4$, and $R_5$ are as defined in formula (I).

In another embodiment of the present invention, compounds of formula (II) are disclosed wherein ͞ ͞ ͞ represents a double bond; Y is $CH_2$; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (II) are disclosed wherein ͞ ͞ ͞ represents a double bond; Y is $CH_2$; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2C(NR_{12})NR_{13}R_{14}$, —C($NOR_{12}$)$R_{13}$, —C(NCN)$R_{12}$, —C($NNR_{12}R_{13}$)$R_{14}$, —S(O)$_2$)OR$_{12}$, or —S(O)$_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (II) are disclosed wherein ͞ ͞ ͞ represents a double bond; Y is $CH_2$; Z is $CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, and —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (II) are disclosed wherein ͞ ͞ ͞ represents a double bond; Y is $CH_2$; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, and nitro; $R_3$ and $R_5$ are absent; $R_4$ is hydrogen; and $R_1$ is as defined in formula (I).

In another embodiment of the present invention, compounds of formula (II) are disclosed wherein ͞ ͞ ͞ represents a double bond; Y is $CH_2$; Z is $CH_2$; $R_2$ is heterocycle wherein the heterocycle is selected from 3-pyridinyl, 6-bromo-3-pyridinyl, 6-chloro-3-pyridinyl, 6-fluoro-3-pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (II) are disclosed wherein Y is $CH_2CH_2$; Z is a covalent bond; and $R_1$, $R_2$, $R_3$, $R_4$, and $R_5$ are as defined in formula (I).

Representative compounds of formula (II) include, but are not limited to:

(cis)-4-(3-pyridinyl)-7-azabicyclo[4.2.0]oct-4-ene;
(cis)-4-(6-chloro-3-pyridinyl)-7-azabicyclo[4.2.0]oct-4-ene;
(cis)-4-(6-bromo-3-pyridinyl)-7-azabicyclo[4.2.0]oct-4-ene;
(cis)-4-(6-fluoro-3-pyridinyl)-7-azabicyclo[4.2.0]oct-4-ene;
(cis)-4-(6-methyl-3-pyridinyl)-7-azabicyclo[4.2.0]oct-4-ene;
(cis)-5-(7-azabicyclo[4.2.0]oct-4-en-4-yl)nicotinonitrile;
(cis)-4-(5-methyl-3-pyridinyl)-7-azabicyclo[4.2.0]oct-4-ene;
(cis)-4-(5-chloro-3-pyridinyl)-7-azabicyclo[4.2.0]oct-4-ene;
(cis)-4-(5-fluoro-3-pyridinyl)-7-azabicyclo[4.2.0]oct-4-ene;
(cis)-4-(5-bromo-3-pyridinyl)-7-azabicyclo[4.2.0]oct-4-ene;
(cis)-4-(5-vinyl-3-pyridinyl)-7-azabicyclo[4.2.0]oct-4-ene;
(cis)-4-(5-methoxy-3-pyridinyl)-7-azabicyclo[4.2.0]oct-4-ene;
(cis)-4-[5-(vinyloxy)-3-pyridinyl]-7-azabicyclo[4.2.0]oct-4-ene;
(cis)-4-(5-ethynyl-3-pyridinyl)-7-azabicyclo[4.2.0]oct-4-ene;
(cis)-4-(5,6-dichloro-3-pyridinyl)-7-azabicyclo[4.2.0]oct-4-ene;
(cis)-4-(6-bromo-5-chloro-3-pyridinyl)-7-azabicyclo[4.2.0]oct-4-ene;
(cis)-5-(7-azabicyclo[4.2.0]oct-4-en-4-yl)-2-methylnicotinonitrile;
(cis)-5-(7-azabicyclo[4.2.0]oct-4-en-4-yl)-2-chloronicotinonitrile;
(cis)-5-(7-azabicyclo[4.2.0]oct-4-en-4-yl)-2-bromonicotinonitrile;
(cis)-4-(6-chloro-5-methyl-3-pyridinyl)-7-azabicyclo[4.2.0]oct-4-ene;
(cis)-4-(6-bromo-5-methyl-3-pyridinyl)-7-azabicyclo[4.2.0]oct-4-ene;
(cis)-4-(5-methoxy-6-methyl-3-pyridinyl)-7-azabicyclo[4.2.0]oct-4-ene;
(cis)-4-(6-chloro-5-methoxy-3-pyridinyl)-7-azabicyclo[4.2.0]oct-4-ene;
(cis)-4-(6-bromo-5-methoxy-3-pyridinyl)-7-azabicyclo[4.2.0]oct-4-ene;

(cis)-4-(3-methyl-5-isoxazolyl)-7-azabicyclo[4.2.0]oct-4-ene;
(cis)-2-(7-azabicyclo[4.2.0]oct-4-en-4-yl)furo[3,2-b]pyridine;
(cis)-3-(6-chloro-3-pyridinyl)-6-azabicyclo[3.2.0]hept-3-ene;
(cis)-3-(6-bromo-3-pyridinyl)-6-azabicyclo[3.2.0]hept-3-ene;
(cis)-3-(6-fluoro-3-pyridinyl)-6-azabicyclo[3.2.0]hept-3-ene;
(cis)-3-(6-methyl-3-pyridinyl)-6-azabicyclo[3.2.0]hept-3-ene;
(cis)-5-(6-azabicyclo[3.2.0]hept-3-en-3-yl)nicotinonitrile;
(cis)-3-(5-methyl-3-pyridinyl)-6-azabicyclo[3.2.0]hept-3-ene;
(cis)-3-(5-chloro-3-pyridinyl)-6-azabicyclo[3.2.0]hept-3-ene;
(cis)-3-(5-fluoro-3-pyridinyl)-6-azabicyclo[3.2.0]hept-3-ene;
(cis)-3-(5-bromo-3-pyridinyl)-6-azabicyclo[3.2.0]hept-3-ene;
(cis)-3-(5-vinyl-3-pyridinyl)-6-azabicyclo[3.2.0]hept-3-ene;
(cis)-3-(5-methoxy-3-pyridinyl)-6-azabicyclo[3.2.0]hept-3-ene;
(cis)-3-(5-vinyloxy-3-pyridinyl)-6-azabicyclo[3.2.0]hept-3-ene;
(cis)-3-(5-ethynyl-3-pyridinyl)-6-azabicyclo[3.2.0]hept-3-ene;
(cis)-3-(5,6-dichloro-3-pyridinyl)-6-azabicyclo[3.2.0]hept-3-ene;
(cis)-3-(6-bromo-5-chloro-3-pyridinyl)-6-azabicyclo[3.2.0]hept-3-ene;
(cis)-5-(6-azabicyclo[3.2.0]hept-3-en-3-yl)-2-methylnicotinonitrile;
(cis)-5-(6-azabicyclo[3.2.0]hept-3-en-3-yl)-2-chloronicotinonitrile;
(cis)-5-(6-azabicyclo[3.2.0]hept-3-en-3-yl)-2-bromonicotinonitrile;
(cis)-3-(6-chloro-5-methyl-3-pyridinyl)-6-azabicyclo[3.2.0]hept-3-ene;
(cis)-3-(6-bromo-5-methyl-3-pyridinyl)-6-azabicyclo[3.2.0]hept-3-ene;
(cis)-3-(5-methoxy-6-methyl-3-pyridinyl)-6-azabicyclo[3.2.0]hept-3-ene;
(cis)-3-(6-chloro-5-methoxy-3-pyridinyl)-6-azabicyclo[3.2.0]hept-3-ene;
(cis)-3-(6-bromo-5-methoxy-3-pyridinyl)-6-azabicyclo[3.2.0]hept-3-ene;
(cis)-3-(3-methyl-5-isoxazolyl)-6-azabicyclo[3.2.0]hept-3-ene
(cis)-2-(6-azabicyclo[3.2.0]hept-3-en-3-yl)furo[3,2-b]pyridine;
(cis)-4-(6-chloro-3-pyridinyl)-7-azabicyclo[4.2.0]oct-3-ene;
(cis)-4-(6-bromo-3-pyridinyl)-7-azabicyclo[4.2.0]oct-3-ene;
(cis)-4-(6-fluoro-3-pyridinyl)-7-azabicyclo[4.2.0]oct-3-ene;
(cis)-4-(6-methyl-3-pyridinyl)-7-azabicyclo[4.2.0]oct-3-ene;
(cis)-5-(7-azabicyclo[4.2.0]oct-3-en-4-yl)nicotinonitrile;
(cis)-4-(5-methyl-3-pyridinyl)-7-azabicyclo[4.2.0]oct-3-ene;
(cis)-4-(5-chloro-3-pyridinyl)-7-azabicyclo[4.2.0]oct-3-ene;
(cis)-4-(5-fluoro-3-pyridinyl)-7-azabicyclo[4.2.0]oct-3-ene;
(cis)-4-(5-bromo-3-pyridinyl)-7-azabicyclo[4.2.0]oct-3-ene;
(cis)-4-(5-vinyl-3-pyridinyl)-7-azabicyclo[4.2.0]oct-3-ene;
(cis)-4-(5-methoxy-3-pyridinyl)-7-azabicyclo[4.2.0]oct-3-ene;
(cis)-4-(5-vinyloxy-3-pyridinyl)-7-azabicyclo[4.2.0]oct-3-ene;
(cis)-4-(5-ethynyl-3-pyridinyl)-7-azabicyclo[4.2.0]oct-3-ene;
(cis)-4-(5,6-dichloro-3-pyridinyl)-7-azabicyclo[4.2.0]oct-3-ene;
(cis)-4-(6-bromo-5-chloro-3-pyridinyl)-7-azabicyclo[4.2.0]oct-3-ene;
(cis)-5-(7-azabicyclo[4.2.0]oct-3-en-4-yl)-2-methylnicotinonitrile;
(cis)-5-(7-azabicyclo[4.2.0]oct-3-en-4-yl)-2-chloronicotinonitrile;
(cis)-5-(7-azabicyclo[4.2.0]oct-3-en-4-yl)-2-bromonicotinonitrile;
(cis)-4-(6-chloro-5-methyl-3-pyridinyl)-7-azabicyclo[4.2.0]oct-3-ene;
(cis)-4-(6-bromo-5-methyl-3-pyridinyl)-7-azabicyclo[4.2.0]oct-3-ene;
(cis)-4-(5-methoxy-6-methyl-3-pyridinyl)-7-azabicyclo[4.2.0]oct-3-ene;
(cis)-4-(6-chloro-5-methoxy-3-pyridinyl)-7-azabicyclo[4.2.0]oct-3-ene;
(cis)-4-(6-bromo-5-methoxy-3-pyridinyl)-7-azabicyclo[4.2.0]oct-3-ene;
(cis)-4-(3-methyl-5-isoxazolyl)-7-azabicyclo[4.2.0]oct-3-ene;
(cis)-2-(7-azabicyclo[4.2.0]oct-3-en-4-yl)furo[3,2-b]pyridine;
(cis)-3-(3-pyridinyl)-6-azabicyclo[3.2.0]hept-2-ene;
(cis)-3-(6-chloro-3-pyridinyl)-6-azabicyclo[3.2.0]hept-2-ene;
(cis)-3-(6-bromo-3-pyridinyl)-6-azabicyclo[3.2.0]hept-2-ene;
(cis)-3-(6-fluoro-3-pyridinyl)-6-azabicyclo[3.2.0]hept-2-ene;
(cis)-3-(6-methyl-3-pyridinyl)-6-azabicyclo[3.2.0]hept-2-ene;
(cis)-5-(6-azabicyclo[3.2.0]hept-2-en-3-yl)nicotinonitrile;
(cis)-3-(5-methyl-3-pyridinyl)-6-azabicyclo[3.2.0]hept-2-ene;
(cis)-3-(5-chloro-3-pyridinyl)-6-azabicyclo[3.2.0]hept-2-ene;
(cis)-3-(5-fluoro-3-pyridinyl)-6-azabicyclo[3.2.0]hept-2-ene;
(cis)-3-(5-bromo-3-pyridinyl)-6-azabicyclo[3.2.0]hept-2-ene;
(cis)-3-(5-vinyl-3-pyridinyl)-6-azabicyclo[3.2.0]hept-2-ene;
(cis)-3-(5-methoxy-3-pyridinyl)-6-azabicyclo[3.2.0]hept-2-ene;
(cis)-3-(5-vinyloxy-3-pyridinyl)-6-azabicyclo[3.2.0]hept-2-ene;
(cis)-3-(5-ethynyl-3-pyridinyl)-6-azabicyclo[3.2.0]hept-2-ene;
(cis)-3-(5,6-dichloro-3-pyridinyl)-6-azabicyclo[3.2.0]hept-2-ene;
(cis)-3-(6-bromo-5-chloro-3-pyridinyl)-6-azabicyclo[3.2.0]hept-2-ene;
(cis)-5-(6-azabicyclo[3.2.0]hept-2-en-3-yl)-2-methylnicotinonitrile;
(cis)-5-(6-azabicyclo[3.2.0]hept-2-en-3-yl)-2-chloronicotinonitrile;
(cis)-5-(6-azabicyclo[3.2.0]hept-2-en-3-yl)-2-bromonicotinonitrile;
(cis)-3-(6-chloro-5-methyl-3-pyridinyl)-6-azabicyclo[3.2.0]hept-2-ene;

(cis)-3-(6-bromo-5-methyl-3-pyridinyl)-6-azabicyclo[3.2.0]hept-2-ene;
(cis)-3-(5-methoxy-6-methyl-3-pyridinyl)-6-azabicyclo[3.2.0]hept-2-ene;
(cis)-3-(6-chloro-5-methoxy-3-pyridinyl)-6-azabicyclo[3.2.0]hept-2-ene;
(cis)-3-(6-bromo-5-methoxy-3-pyridinyl)-6-azabicyclo[3.2.0]hept-2-ene;
(cis)-3-(3-methyl-5-isoxazolyl)-6-azabicyclo[3.2.0]hept-2-ene;
(cis)-2-(6-azabicyclo[3.2.0]hept-2-en-3-yl)furo[3,2-b]pyridine;
(cis)-5-(3-pyridinyl)-7-azabicyclo[4.2.0]oct-4-ene;
(cis)-5-(6-chloro-3-pyridinyl)-7-azabicyclo[4.2.0]oct-4-ene;
(cis)-5-(6-bromo-3-pyridinyl)-7-azabicyclo[4.2.0]oct-4-ene;
(cis)-5-(6-fluoro-3-pyridinyl)-7-azabicyclo[4.2.0]oct-4-ene;
(cis)-5-(6-methyl-3-pyridinyl)-7-azabicyclo[4.2.0]oct-4-ene;
(cis)-5-(7-azabicyclo[4.2.0]oct-4-en-5-yl)nicotinonitrile;
(cis)-5-(5-methyl-3-pyridinyl)-7-azabicyclo[4.2.0]oct-4-ene;
(cis)-5-(5-chloro-3-pyridinyl)-7-azabicyclo[4.2.0]oct-4-ene;
(cis)-5-(5-fluoro-3-pyridinyl)-7-azabicyclo[4.2.0]oct-4-ene;
(cis)-5-(5-bromo-3-pyridinyl)-7-azabicyclo[4.2.0]oct-4-ene;
(cis)-5-(5-vinyl-3-pyridinyl)-7-azabicyclo[4.2.0]oct-4-ene;
(cis)-5-(5-methoxy-3-pyridinyl)-7-azabicyclo[4.2.0]oct-4-ene;
(cis)-5-(5-vinyloxy-3-pyridinyl)-7-azabicyclo[4.2.0]oct-4-ene;
(cis)-5-(5-ethynyl-3-pyridinyl)-7-azabicyclo[4.2.0]oct-4-ene;
(cis)-5-(5,6-dichloro-3-pyridinyl)-7-azabicyclo[4.2.0]oct-4-ene;
(cis)-5-(6-bromo-5-chloro-3-pyridinyl)-7-azabicyclo[4.2.0]oct-4-ene;
(cis)-5-(7-azabicyclo[4.2.0]oct-4-en-5-yl)-2-methylnicotinonitrile;
(cis)-5-(7-azabicyclo[4.2.0]oct-4-en-5-yl)-2-bromonicotinonitrile;
(cis)-5-(7-azabicyclo[4.2.0]oct-4-en-5-yl)-2-chloronicotinonitrile;
(cis)-5-(6-chloro-5-methyl-3-pyridinyl)-7-azabicyclo[4.2.0]oct-4-ene;
(cis)-5-(6-bromo-5-methyl-3-pyridinyl)-7-azabicyclo[4.2.0]oct-4-ene;
(cis)-5-(5-methoxy-6-methyl-3-pyridinyl)-7-azabicyclo[4.2.0]oct-4-ene;
(cis)-5-(6-chloro-5-methoxy-3-pyridinyl)-7-azabicyclo[4.2.0]oct-4-ene;
(cis)-5-(6-bromo-5-methoxy-3-pyridinyl)-7-azabicyclo[4.2.0]oct-4-ene;
(cis)-2-(7-azabicyclo[4.2.0]oct-4-en-5-yl)furo[3,2-b]pyridine;
(cis)-5-(3-methyl-5-isoxazolyl)-7-azabicyclo[4.2.0]oct-4-ene;
(cis)-4-(3-pyridinyl)-6-azabicyclo[3.2.0]hept-3-ene;
(cis)-4-(6-chloro-3-pyridinyl)-6-azabicyclo[3.2.0]hept-3-ene;
(cis)-4-(6-bromo-3-pyridinyl)-6-azabicyclo[3.2.0]hept-3-ene;
(cis)-4-(6-fluoro-3-pyridinyl)-6-azabicyclo[3.2.0]hept-3-ene;
(cis)-4-(6-methyl-3-pyridinyl)-6-azabicyclo[3.2.0]hept-3-ene;
(cis)-5-(6-azabicyclo[3.2.0]hept-3-en-4-yl)nicotinonitrile;
(cis)-4-(5-methyl-3-pyridinyl)-6-azabicyclo[3.2.0]hept-3-ene;
(cis)-4-(5-chloro-3-pyridinyl)-6-azabicyclo[3.2.0]hept-3-ene;
(cis)-4-(5-fluoro-3-pyridinyl)-6-azabicyclo[3.2.0]hept-3-ene;
(cis)-4-(5-bromo-3-pyridinyl)-6-azabicyclo[3.2.0]hept-3-ene;
(cis)-4-(5-vinyl-3-pyridinyl)-6-azabicyclo[3.2.0]hept-3-ene;
(cis)-4-(5-methoxy-3-pyridinyl)-6-azabicyclo[3.2.0]hept-3-ene;
(cis)-4-(5-vinyloxy-3-pyridinyl)-6-azabicyclo[3.2.0]hept-3-ene;
(cis)-4-(5-ethynyl-3-pyridinyl)-6-azabicyclo[3.2.0]hept-3-ene;
(cis)-4-(5,6-dichloro-3-pyridinyl)-6-azabicyclo[3.2.0]hept-3-ene;
(cis)-4-(6-bromo-5-chloro-3-pyridinyl)-6-azabicyclo[3.2.0]hept-3-ene;
(cis)-5-(6-azabicyclo[3.2.0]hept-3-en-4-yl)-2-methylnicotinonitrile;
(cis)-5-(6-azabicyclo[3.2.0]hept-3-en-4-yl)-2-chloronicotinonitrile;
(cis)-5-(6-azabicyclo[3.2.0]hept-3-en-4-yl)-2-bromonicotinonitrile;
(cis)-4-(6-chloro-5-methyl-3-pyridinyl)-6-azabicyclo[3.2.0]hept-3-ene;
(cis)-4-(6-bromo-5-methyl-3-pyridinyl)-6-azabicyclo[3.2.0]hept-3-ene;
(cis)-4-(5-methoxy-6-methyl-3-pyridinyl)-6-azabicyclo[3.2.0]hept-3-ene;
(cis)-4-(6-chloro-5-methoxy-3-pyridinyl)-6-azabicyclo[3.2.0]hept-3-ene;
(cis)-4-(6-bromo-5-methoxy-3-pyridinyl)-6-azabicyclo[3.2.0]hept-3-ene;
(cis)-4-(3-methyl-5-isoxazolyl)-6-azabicyclo[3.2.0]hept-3-ene;
(cis)-2-(6-azabicyclo[3.2.0]hept-3-en-4-yl)furo[3,2-b]pyridine; or a pharmaceutically acceptable salt, amide, ester or prodrug thereof.

In another embodiment of the present invention, compounds of formula (III) are disclosed

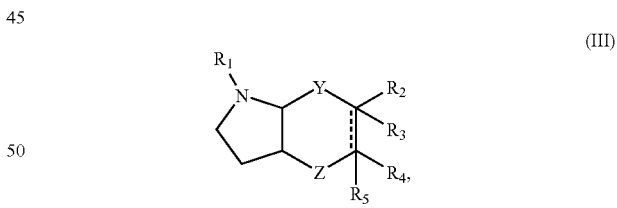

or a pharmaceutically acceptable salt, amide, ester or prodrug thereof wherein Y, Z, $R_1$, $R_2$, $R_3$, $R_4$, and $R_5$ are as defined in formula (I).

In another embodiment of the present invention, compounds of formula (III) are disclosed wherein Y is a covalent bond; Z is a covalent bond; and $R_1$, $R_2$, $R_3$, $R_4$, and $R_5$ are as defined in formula (I).

In another embodiment of the present invention, compounds of formula (III) are disclosed wherein Y is a covalent bond; Z is $CH_2$; and $R_1$, $R_2$, $R_3$, $R_4$, and $R_5$ are as defined in formula (I).

In another embodiment of the present invention, compounds of formula (III) are disclosed wherein ----- represents a double bond; Y is a covalent bond; Z is CH 2; $R_2$ is hydrogen; $R_3$ and $R_5$ are absent; $R_4$ is heterocycle; and $R_1$ is as defined in formula (I).

In another embodiment of the present invention, compounds of formula (III) are disclosed wherein -----represents a double bond; Y is a covalent bond; Z is $CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2C(NR_{12})NR_{13}R_{14}$, —C($NOR_{12}$)$R_{13}$, —C (NCN)$R_{12}$, —C($NNR_{12}R_{13}$)$R_{14}$, —S(O)$_2OR_{12}$, or —S(O)$_2R_{12}$; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (III) are disclosed wherein -----represents a double bond; Y is a covalent bond; Z is $CH_2$; $R_2$ is hydrogen; $R_3$ and $R_5$ are absent; $R_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; and $R_1$, $R_{10}$, and $R_{11}$ are as defined in formula (I).

In another embodiment of the present invention, compounds of formula (III) are disclosed wherein -----represents a double bond; Y is a covalent bond; Z is $CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (III) are disclosed wherein -----represents a double bond; Y is a covalent bond; Z is $CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (III) are disclosed wherein -----represents a double bond; Y is a covalent bond; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (III) are disclosed wherein -----represents a double bond; Y is a covalent bond; Z is $CR_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2C(NR_{12})NR_{13}R_{14}$, —C($NOR_{12}$)$R_{13}$, —C(NCN)$R_{12}$, —C($NNR_{12}R_{13}$)$R_{14}$, —S(O)$_2OR_{12}$, or —S(O)$_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (III) are disclosed -----wherein represents a double bond; Y is a covalent bond; Z is $CR_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (III) are disclosed wherein -----represents a double bond; Y is a covalent bond; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (III) are disclosed wherein -----represents a double bond; Y is a covalent bond; Z is $CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (III) are disclosed wherein Y is $CH_2$; Z is a covalent bond; and $R_1$, $R_2$, $R_3$, $R_4$, and $R_5$ are as defined in formula (I).

In another embodiment of the present invention, compounds of formula (III) are disclosed wherein ----- represents a double bond; Y is $CH_2$; Z is a covalent bond; $R_2$ is heterocycle; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is $CH_2$; Z is a covalent bond; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (III) are disclosed wherein ----- represents a double bond; Y is $CH_2$; Z is a covalent bond; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (III) are disclosed wherein ----- represents a double bond; Y is $CH_2$; Z is a covalent bond; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is $CH_2$; Z is a covalent bond; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (III) are disclosed wherein Y is a covalent bond; Z is $CH_2CH_2$; and $R_1$, $R_2$, $R_3$, $R_4$ and $R_5$ are as defined in formula (I).

In another embodiment of the present invention, compounds of formula (III) are disclosed wherein ----- represents a double bond; Y is a covalent bond; Z is $CH_2CH_2$; $R_2$ is hydrogen; $R_3$ and $R_5$ are absent; $R_4$ is heterocycle; and $R_1$ is as defined in formula (I).

In another embodiment of the present invention, compounds of formula (III) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_{2OR_{12}}$, or —$S(O)_2R_{12}$; $R_{12}$, $R_{13}$, and $R_{14}$ are independently selected from hydrogen, alkyl, aryl, or arylalkyl; and $R_1$, $R_{10}$, and $R_{11}$, are as defined in formula (I).

In another embodiment of the present invention, compounds of formula (III) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, $(NR_{10}R_{11})$sulfonyl, or —$C(NH)NR_{10}R_{11}$; and $R_1$, $R_{10}$, and $R_{11}$ are as defined in formula (I).

In another embodiment of the present invention, compounds of formula (III) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (III) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (III) are disclosed wherein ----- represents a double bond; Y is a covalent bond; Z is $CH_2CH_2$; $R_2$ is heterocycle; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is a covalent bond; Z is $CH_2CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, $(NR_{10}R_{11})$alkyl, $(NR_{10}R_{11})$carbonyl, $(NR_{10}R_{11})$carbonylalkyl, $(NR_{10}R_{11})$sulfonyl, —$NR_{12}S(O)_2R_{13}$, —$C(NR_{12})NR_{13}R_{14}$, —$CH_2C(NR_2)NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (III) are disclosed wherein ----- represents a double bond; Y is a covalent bond; Z is $CH_2CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, $(NR_{10}R_{11})$sulfonyl, or —$C(NH)NR_{10}R_{11}$; $R_3$ and $R_5$ are absent; $R_4$ is hydrogen; and $R_1$, $R_{10}$, and $R_{11}$, are as defined in formula (I).

In another embodiment of the present invention, compounds of formula (III) are disclosed wherein ----- represents a double bond; Y is a covalent bond; Z is $CH_2CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is a covalent bond; Z is $CH_2CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (III) are disclosed wherein Y is $CH_2$; Z is $CH_2$; and $R_1$, $R_2$, $R_3$, $R_4$, and $R_5$ are as defined in formula (I).

In another embodiment of the present invention, compounds of formula (III) are disclosed wherein ----- represents a double bond; Y is $CH_2$; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is $CH_2$; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, $(NR_{10}R_{11})$ alkyl, $(NR_{10}R_{11})$carbonyl, $(NR_{10}R_{11})$carbonylalkyl, $(NR_{10}R_{11})$sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (III) we disclosed wherein ----- represents a double bond; Y is $CH_2$; Z is $CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, $(NR_{10}R_{11})$sulfonyl, or —$C(NH)NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (III) are disclosed wherein ----- represents a double bond; Y is $CH_2$; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is $CH_2$; Z is $CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6bromo-5-methoxy-3-pyridinyl; $R_3$ and $R_5$ are absent; $R_4$ is hydrogen; and $R_1$ is as defined in formula (I).

In another embodiment of the present invention, compounds of formula (III) are disclosed wherein Y is $CH_2CH_2$; Z is a covalent bond; and $R_1$, $R_2$, $R_3$, $R_4$, and $R_5$ are as defined in formula (I).

Representative compounds of formula (III) include, but are not limited to:
(cis)-5-(3-pyridinyl)-1,2,3,3a,4,6a-hexahydrocyclopenta[b]pyrrole;
(cis)-5-(3-pyridinyl)-1,2,3,3a,6,6a-hexahydrocyclopenta[b]pyrrole;
(cis)-6-(3-pyridinyl)-2,3,3a,4,5,7a-hexahydro-1H-indole;
(cis)-6-(6-chloro-3-pyridinyl)-2,3,3a,4,5,7a-hexahydro-1H-indole;
(cis)-6-(6-bromo-3-pyridinyl)-2,3,3a,4,5,7a-hexahydro-1H-indole;
(cis)-6-(6-fluoro-3-pyridinyl)-2,3,3a,4,5,7a-hexahydro-1H-indole;
(cis)-6-(6-methyl-3-pyridinyl)-2,3,3a,4,5,7a-hexahydro-1H-indole;
(cis)-5-(2,3,3a,4,5,7a-hexahydro-1H-indol-6-yl)nicotinonitrile;
(cis)-6-(5-methyl-3-pyridinyl)-2,3,3a,4,5,7a-hexahydro-1H-indole;
(cis)-6-(5-chloro-3-pyridinyl)-2,3,3a,4,5,7a-hexahydro-1H-indole;
(cis)-6-(5-fluoro-3-pyridinyl)-2,3,3a,4,5,7a-hexahydro-1H-indole;
(cis)-6-(5-bromo-3-pyridinyl)-2,3,3a,4,5,7a-hexahydro-1H-indole;
(cis)-6-(5-vinyl-3-pyridinyl)-2,3,3a,4,5,7a-hexahydro-1H-indole;
(cis)-6-(5-methoxy-3-pyridinyl)-2,3,3a,4,5,7a-hexahydro-1H-indole;
(cis)-6-(5-vinyloxy-3-pyridinyl)-2,3,3a,4,5,7a-hexahydro-1H-indole;
(cis)-6-(5-ethynyl-3-pyridinyl)-2,3,3a,4,5,7a-hexahydro-1H-indole;
(cis)-6-(5,6-dichloro-3-pyridinyl)-2,3,3a,4,5,7a-hexahydro-1H-indole;
(cis)-6-(6-bromo-5-chloro-3-pyridinyl)-2,3,3a,4,5,7a-hexahydro-1H-indole;
(cis)-5-(2,3,3a,4,5,7a-hexahydro-1H-indol-6-yl)-2-methylnicotinonitrile;
(cis)-2-chloro-5-(2,3,3a,4,5,7a-hexahydro-1H-indol-6-yl)nicotinonitrile;
(cis)-2-bromo-5-(2,3,3a,4,5,7a-hexahydro-1H-indol-6-yl)nicotinonitrile;
(cis)-6-(6-chloro-5-methyl-3-pyridinyl)-2,3,3a,4,5,7a-hexahydro-1H-indole;
(cis)-6-(6-bromo-5-methyl-3-pyridinyl)-2,3,3a,4,5,7a-hexahydro-1H-indole;
(cis)-6-(5-methoxy-6-methyl-3-pyridinyl)-2,3,3a,4,5,7a-hexahydro-1H-indole;
(cis)-6-(6-chloro-5-methoxy-3-pyridinyl)-2,3,3a,4,5,7a-hexahydro-1H-indole;
(cis)-6-(6-bromo-5-methoxy-3-pyridinyl)-2,3,3a,4,5,7a-hexahydro-1H-indole;
(cis)-6-(3-methyl-5-isoxazolyl)-2,3,3a,4,5,7a-hexahydro-1H-indole;
(cis)-2-(2,3,3a,4,5,7a-hexahydro-1H-indol-6-yl)furo[3,2-b]pyridine;
(cis)-5-(6-chloro-3-pyridinyl)-1,2,3,3a,4,6a-hexahydrocyclopenta[b]pyrrole;
(cis)-5-(6-bromo-3-pyridinyl)-1,2,3,3a,4,6a-hexahydrocyclopenta[b]pyrrole;
(cis)-5-(6-fluoro-3-pyridinyl)-1,2,3,3a,4,6a-hexahydrocyclopenta[b]pyrrole;
(cis)-5-(6-methyl-3-pyridinyl)-1,2,3,3a,4,6a-hexahydrocyclopenta[b]pyrrole;
(cis)-5-(1,2,3,3a,4,6a-hexahydrocyclopenta[b]pyrrol-5-yl)nicotinonitrile
(cis)-5-(5-methyl-3-pyridinyl)-1,2,3,3a,4,6a-hexahydrocyclopenta[b]pyrrole;
(cis)-5-(5-chloro-3-pyridinyl)-1,2,3,3a,4,6a-hexahydrocyclopenta[b]pyrrole;
(cis)-5-(5-fluoro-3-pyridinyl)-1,2,3,3a,4,6a-hexahydrocyclopenta[b]pyrrole;
(cis)-5-(5-bromo-3-pyridinyl)-1,2,3,3a,4,6a-hexahydrocyclopenta[b]pyrrole;
(cis)-5-(5-vinyl-3-pyridinyl)-1,2,3,3a,4,6a-hexahydrocyclopenta[b]pyrrole;
(cis)-5-(5-methoxy-3-pyridinyl)-1,2,3,3a,4,6a-hexahydrocyclopenta[b]pyrrole;
(cis)-5-(5-vinyloxy-3-pyridinyl)-1,2,3,3a,4,6a-hexahydrocyclopenta[b]pyrrole;
(cis)-5-(5-ethynyl-3-pyridinyl)-1,2,3,3a,4,6a-hexahydrocyclopenta[b]pyrrole;
(cis)-5-(5,6-dichloro-3-pyridinyl)-1,2,3,3a,4,6a-hexahydrocyclopenta[b]pyrrole;

(cis)-5-(6-bromo-5-chloro-3-pyridinyl)-1,2,3,3a,4,6a-hexahydrocyclopenta[b]pyrrole;
(cis)-5-(1,2,3,3a,4,6a-hexahydrocyclopenta[b]pyrrol-5-yl)-2-methylnicotinonitrile
(cis)-2-chloro-5-(1,2,3,3a,4,6a-hexahydrocyclopenta[b]pyrrol-5-yl)nicotinonitrile
(cis)-2-bromo-5-(1,2,3,3a,4,6a-hexahydrocyclopenta[b]pyrrol-5-yl)nicotinonitrile
(cis)-5-(6-chloro-5-methyl-3-pyridinyl)-1,2,3,3a,4,6a-hexahydrocyclopenta[b]pyrrole;
(cis)-5-(6-bromo-5-methyl-3-pyridinyl)-1,2,3,3a,4,6a-hexahydrocyclopenta[b]pyrrole;
(cis)-5-(5-methoxy-6-methyl-3-pyridinyl)-1,2,3,3a,4,6a-hexahydrocyclopenta[b]pyrrole;
(cis)-5-(6-chloro-5-methoxy-3-pyridinyl)-1,2,3,3a,4,6a-hexahydrocyclopenta[b]pyrrole;
(cis)-5-(6-bromo-5-methoxy-3-pyridinyl)-1,2,3,3a,4,6a-hexahydrocyclopenta[b]pyrrole;
(cis)-5-(3-methyl-5-isoxazolyl)-1,2,3,3a,4,6a-hexahydrocyclopenta[b]pyrrole;
(cis)-2-(1,2,3,3a,4,6a-hexahydrocyclopenta[b]pyrrol-5-yl)furo[3,2-b]pyridine;
(cis)-6-(3-pyridinyl)-2,3,3a,4,7,7a-hexahydro-1H-indole;
(cis)-6-(6-chloro-3-pyridinyl)-2,3,3a,4,7,7a-hexahydro-1H-indole;
(cis)-6-(6-bromo-3-pyridinyl)-2,3,3a,4,7,7a-hexahydro-1H-indole;
(cis)-6-(6-fluoro-3-pyridinyl)-2,3,3a,4,7,7a-hexahydro-1H-indole;
(cis)-6-(6-methyl-3-pyridinyl)-2,3,3a,4,7,7a-hexahydro-1H-indole;
(cis)-5-(2,3,3,a,4,7,7a-hexahydro-1H-indol-6-yl)nicotinonitrile;
(cis)-6-(5-methyl-3-pyridinyl)-2,3,3a,4,7,7a-hexahydro 1H-indole;
(cis)-6-(5-chloro-3-pyridinyl)-2,3,3a,4,7,7a-hexahydro-1H-indole;
(cis)-6-(5-fluoro-3-pyridinyl)-2,3,3a,4,7,7a-hexahydro-1H-indole;
(cis)-6-(5-bromo-3-pyridinyl)-2,3,3a,4,7,7a-hexahydro-1H-indole;
(cis)-6-(5-vinyl-3-pyridinyl)-2,3,3a,4,7,7a-hexahydro-1H-indole;
(cis)-6-(5-methoxy-3-pyridinyl)-2,3,3a,4,7,7a-hexahydro-1H-indole;
(cis)-6-(5-vinyloxy-3-pyridinyl)-2,3,3a,4,7,7a-hexahydro-1H-indole;
(cis)-6-(5-ethynyl-3-pyridinyl)-2,3,3a,4,7,7a-hexahydro-1H-indole;
(cis)-6-(5,6-dichloro-3-pyridinyl)-2,3,3a,4,7,7a-hexahydro-1H-indole;
(cis)-6-(6-bromo-5-chloro-3-pyridinyl)-2,3,3a,4,7,7a-hexahydro-1H-indole;
(cis)-5-(2,3,3a,4,7,7a-hexahydro-1H-indol-6-yl)-2-methylnicotinonitrile;
(cis)-2-chloro-5-(2,3,3a,4,7,7a-hexahydro-1H-indol-6-yl)nicotinonitrile;
(cis)-2-bromo-5-(2,3,3a,4,7,7a-hexahydro-1H-indol-6-yl)nicotinonitrile;
(cis)-6-(6-chloro-5-methyl-3-pyrdinyl)-2,3,3a,4,7,7a-hexahydro-1H-indole;
(cis)-6-(6-bromo-5-methyl-3-pyridinyl)-2,3,3a,4,7,7a-hexahydro-1H-indole;
(cis)-6-(5-methoxy-6-methyl-3-pyridinyl)-2,3,3a,4,7,7a-hexahydro-1H-indole;
(cis)-6-(6-chloro-5-methoxy-3-pyridinyl)-2,3,3a,4,7,7a-hexahydro-1H-indole;
(cis)-6-(6-bromo-5-methoxy-3-pyridinyl)-2,3,3a,4,7,7a-hexahydro-1H-indole;
(cis)-6-(3-methyl-5-isoxazolyl)-2,3,3a,4,7,7a-hexahydro-1H-indole;
(cis)-2-(2,3,3a,4,7,7a-hexahydro-1H-indol-6-yl)furo[3,2-b]pyridine;
(cis)-5-(3-pyridinyl)-1,2,3,3a,6,6a-hexahydrocyclopenta[b]pyrrole;
(cis)-5-(6-chloro-3-pyridinyl)-1,2,3,3a,6,6a-hexahydrocyclopenta[b]pyrrole;
(cis)-5-(6-bromo-3-pyridinyl)-1,2,3,3a,6,6a-hexahydrocyclopenta[b]pyrrole;
(cis)-5-(6-fluoro-3-pyridinyl)-1,2,3,3a,6,6a-hexahydrocyclopenta[b]pyrrole;
(cis)-5-(6-methyl-3-pyridinyl)-1,2,3,3a,6,6a-hexahydrocyclopenta[b]pyrrole;
(cis)-5-(1,2,3,3a,6,6a-hexahydrocyclopenta[b]pyrrol-5-yl)nicotinonitrile;
(cis)-5-(5-methyl-3-pyridinyl)-1,2,3,3a,6,6a-hexahydrocyclopenta[b]pyrrole;
(cis)-5-(5-chloro-3-pyridinyl)-1,2,3,3a,6,6a-hexahydrocyclopenta[b]pyrrole;
(cis)-5-(5-fluoro-3-pyridinyl)-1,2,3,3a,6,6a-hexahydrocyclopenta[b]pyrrole;
(cis)-5-(5-bromo-3-pyridinyl)-1,2,3,3a,6,6a-hexahydrocyclopenta[b]pyrrole;
(cis)-5-(5-vinyl-3-pyridinyl)-1,2,3,3a,6,6a-hexahydrocyclopenta[b]pyrrole;
(cis)-5-(5-methoxy-3-pyridinyl)-1,2,3,3a,6,6a-hexahydrocyclopenta[b]pyrrole;
(cis)-5-(5-vinyloxy-3-pyridinyl)-1,2,3,3a,6,6a-hexahydrocyclopenta[b]pyrrole;
(cis)-5-(5-ethynyl-3-pyridinyl)-1,2,3,3a,6,6a-hexahydrocyclopenta[b]pyrrole;
(cis)-5-(5,6-dichloro-3-pyridinyl)-1,2,3,3a,6,6a-hexahydrocyclopenta[b]pyrrole;
(cis)-5-(6-bromo-5-chloro-3-pyridinyl)-1,2,3,3a,6,6a-hexahydrocyclopenta[b]pyrrole;
(cis)-5-(1,2,3,3a,6,6a-hexahydrocyclopenta[b]pyrrol-5-yl)-2-methylnicotinonitrile;
(cis)-2-chloro-5-(1,2,3,3a,6,6a-hexahydrocyclopenta[b]pyrrol-5-yl)nicotinonitrile;
(cis)-2-bromo-5-(1,2,3,3a,6,6a-hexahydrocyclopenta[b]pyrrol-5-yl)nicotinonitrile;
(cis)-5-(6-chloro-5-methyl-3-pyridinyl)-1,2,3,3a,6,6a-hexahydrocyclopenta[b]pyrrole;
(cis)-5-(6-bromo-5-methyl-3-pyridinyl)-1,2,3,3a,6,6a-hexahydrocyclopenta[b]pyrrole;
(cis)-5-(5-methoxy-6-methyl-3-pyridinyl)-1,2,3,3a,6,6a-hexahydrocyclopenta[b]pyrrole;
(cis)-5-(6-chloro-5-methoxy-3-pyridinyl)-1,2,3,3a,6,6a-hexahydrocyclopenta[b]pyrrole;
(cis)-5-(6-bromo-5-methoxy-3-pyridinyl)-1,2,3,3a,6,6a-hexahydrocyclopenta[b]pyrrole;
(cis)-5-(3-methyl-5-isoxazolyl)-1,2,3,3a,6,6a-hexahydrocyclopenta[b]pyrrole;
(cis)-2-(1,2,3,3a,6,6a-hexahydrocyclopenta[b]pyrrol-5-yl)furo[3,2-b]pyridine;
(cis)-7-(3-pyridinyl)-2,3,3a,4,5,7a-hexahydro-1H-indole;
(cis)-7-(6-chloro-3-pyridinyl)-2,3,3a,4,5,7a-hexahydro-1H-indole;
(cis)-7-(6-bromo-3-pyridinyl)-2,3,3a,4,5,7a-hexahydro-1H-indole;
(cis)-7-(6-fluoro-3-pyridinyl)-2,3,3a,4,5,7a-hexahydro-1H-indole;
(cis)-7-(6-methyl-3-pyridinyl)-2,3,3a,4,5,7a-hexahydro-1H-indole;

(cis)-5-(2,3,3a,4,5,7a-hexahydro-1H-indol-7-yl)nicotinonitrile;
(cis)-7-(5-methyl-3-pyridinyl)-2,3,3a,4,5,7a-hexahydro-1H-indole;
(cis)-7-(5-chloro-3-pyridinyl)-2,3,3a,4,5,7a-hexahydro-1H-indole;
(cis)-7-(5-fluoro-3-pyridinyl)-2,3,3a,4,5,7a-hexahydro-1H-indole;
(cis)-7-(5-bromo-3-pyridinyl)-2,3,3a,4,5,7a-hexahydro-1H-indole;
(cis)-7-(5-vinyl-3-pyridinyl)-2,3,3a,4,5,7a-hexahydro-1H-indole;
(cis)-7-(5-methoxy-3-pyridinyl)-2,3,3a,4,5,7a-hexahydro-1H-indole;
(cis)-7-(5-vinyloxy-3-pyridinyl)-2,3,3a,4,5,7a-hexahydro-1H-indole;
(cis)-7-(5-ethynyl-3-pyridinyl)-2,3,3a,4,5,7a-hexahydro-1H-indole;
(cis)-7-(5,6-dichloro-3-pyridinyl)-2,3,3a,4,5,7a-hexahydro-1H-indole;
(cis)-7-(6-bromo-5-chloro-3-pyridinyl)-2,3,3a,4,5,7a-hexahydro-1H-indole;
(cis)-5-(2,3,3a,4,5,7a-hexahydro-1H-indol-7-yl)-2-methylnicotinonitrile;
(cis)-2-chloro-5-(2,3,3a,4,5,7a-hexahydro-1H-indol-7-yl)nicotinonitrile;
(cis)-2-bromo-5-(2,3,3a,4,5,7a-hexahydro-1H-indol-7-yl)nicotinonitrile;
(cis)-7-(6-chloro-5-methyl-3-pyridinyl)-2,3,3a,4,5,7a-hexahydro-1H-indole;
(cis)-7-(6-bromo-5-methyl-3-pyridinyl)-2,3,3a,4,5,7a-hexahydro-1H-indole;
(cis)-7-(5-methoxy-6-methyl-3-pyridinyl)-2,3,3a,4,5,7a-hexahydro-1H-indole;
(cis)-7-(6-chloro-5-methoxy-3-pyridinyl)-2,3,3a,4,5,7a-hexahydro-1H-indole;
(cis)-7-(6-bromo-5-methoxy-3-pyridinyl)-2,3,3a,4,5,7a-hexahydro-1H-indole;
(cis)-2-(2,3,3a,4,5,7a-hexahydro-1H-indol-7-yl)furo[3,2-b]pyridine;
(cis)-7-(3-methyl-5-isoxazolyl)-2,3,3a,4,5,7a-hexahydro-1H-indole;
(cis)-6-(3-pyridinyl)-1,2,3,3a,4,6a-hexahydrocyclopenta[b]pyrrole;
(cis)-6-(6-chloro-3-pyridinyl)-1,2,3,3a,4,6a-hexahydrocyclopenta[b]pyrrole;
(cis)-6-(6-bromo-3-pyridinyl)-1,2,3,3a,4,6a-hexahydrocyclopenta[b]pyrrole;
(cis)-6-(6-fluoro-3-pyridinyl)-1,2,3,3a,4,6a-hexahydrocyclopenta[b]pyrrole;
(cis)-6-(6-methyl-3-pyridinyl)-1,2,3,3a,4,6a-hexahydrocyclopenta[b]pyrrole;
(cis)-5-(1,2,3,3a,4,6a-hexahydrocyclopenta[b]pyrrol-6-yl)nicotinonitrile;
(cis)-6-(5-methyl-3-pyridinyl)-1,2,3,3a,4,6a-hexahydrocyclopenta[b]pyrrole;
(cis)-6-(5-chloro-3-pyridinyl)-1,2,3,3a,4,6a-hexahydrocyclopenta[b]pyrrole;
(cis)-6-(5-fluoro-3-pyridinyl)-1,2,3,3a,4,6a-hexahydrocyclopenta[b]pyrrole;
(cis)-6-(5-bromo-3-pyridinyl)-1,2,3,3a,4,6a-hexahydrocyclopenta[b]pyrrole;
(cis)-6-(5-vinyl-3-pyridinyl)-1,2,3,3a,4,6a-hexahydrocyclopenta[b]pyrrole;
(cis)-6-(5-vinyloxy-3-pyridinyl)-1,2,3,3a,4,6a-hexahydrocyclopenta[b]pyrrole;
(cis)-6-(5-ethynyl-3-pyridinyl)-1,2,3,3a,4,6a-hexahydrocyclopenta[b]pyrrole;
(cis)-6-(5,6-dichloro-3-pyridinyl)-1,2,3,3a,4,6a-hexahydrocyclopenta[b]pyrrole;
(cis)-6-(6-bromo-5-chloro-3-pyridinyl)-1,2,3,3a,4,6a-hexahydrocyclopenta[b]pyrrole;
(cis)-5-(1,2,3,3a,4,6a-hexahydrocyclopenta[b]pyrrol-6-yl)-2-methylnicotinonitrile;
(cis)-2-chloro-5-(1,2,3,3a,4,6a-hexahydrocyclopenta[b]pyrrol-6-yl)nicotinonitrile;
(cis)-2-bromo-5-(1,2,3,3a,4,6a-hexahydrocyclopenta[b]pyrrol-6-yl)nicotinonitrile;
(cis)-6-(6-chloro-5-methyl-3-pyridinyl)-1,2,3,3a,4,6a-hexahydrocyclopenta[b]pyrrole;
(cis)-6-(6-bromo-5-methyl-3-pyridinyl)-1,2,3,3a,4,6a-hexahydrocyclopenta[b]pyrrole;
(cis)-6-(5-methoxy-6-methyl-3-pyridinyl)-1,2,3,3a,4,6a-hexahydrocyclopenta[b]pyrrole;
(cis)-6-(6-chloro-5-methoxy-3-pyridinyl)-1,2,3,3a,4,6a-hexahydrocyclopenta[b]pyrrole;
(cis)-6-(6-bromo-5-methoxy-3-pyridinyl)-1,2,3,3a,4,6a-hexahydrocyclopenta[b]pyrrole;
(cis)-6-(3-methyl-5-isoxazolyl)-1,2,3,3a,4,6a-hexahydrocyclopenta[b]pyrrole;
(cis)-2-(1,2,3,3a,4,6a-hexahydrocyclopenta[b]pyrrol-6-yl)furo[3,2-b]pyridine; or a pharmaceutically acceptable salt, amide, ester and prodrugs thereof.

In another embodiment of the present invention, compounds of formula (IV) are disclosed

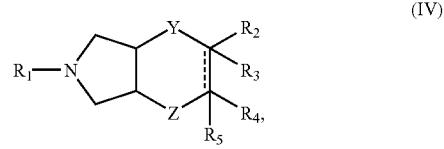

(IV)

or a pharmaceutically acceptable salt, amide, ester or prodrugs thereof wherein Y, Z, $R_1$, $R_2$, $R_3$, $R_4$ and $R_5$ are as defined in formula (I).

In another embodiment of the present invention, compounds of formula (IV) are disclosed wherein Y is a covalent bond; Z is a covalent bond; and $R_1$, $R_2$, $R_3$, $R_4$, and $R_5$ are as defined in formula (I).

In another embodiment of the present invention, compounds of formula (IV) are disclosed wherein ----- represents a double bond; Y is a covalent bond; Z is a covalent bond; $R_2$ is hydrogen; $R_3$ and $R_5$ are absent; $R_4$ is heterocycle; and $R_1$ is as defined in formula (I).

In another embodiment of the present invention, compounds of formula (IV) are disclosed wherein ----- represents a double bond; Y is a covalent bond; Z is a covalent bond; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (IV) are disclosed wherein ----- represents a double bond; Y is a covalent bond; Z is a covalent bond; R$_2$ is hydrogen; R$_3$ and R$_5$ are absent; R$_4$ is heterocycle wherein the heterocycle is selected from imidazolyl, isoxazolyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; and R$_1$, R$_{10}$, and R$_{11}$ are as defined in formula (I).

In another embodiment of the present invention, compounds of formula (IV) are disclosed wherein ----- represents a double bond; Y is a covalent bond; Z is a covalent bond; R$_2$ is hydrogen; R$_3$ and R$_5$ are absent; R$_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and R$_1$ is as defined in formula (I).

In another embodiment of the present invention, compounds of formula (IV) are disclosed wherein ----- represents a double bond; Y is a covalent bond; Z is a covalent bond; R$_2$ is hydrogen; R$_3$ and R$_5$ are absent; R$_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and R$_1$ is as defined in formula (I).

In another embodiment of the present invention, compounds of formula (IV) are disclosed wherein ----- represents a single bond; Y is a covalent bond; Z is a covalent bond; R$_2$, R$_3$ and R$_5$ are hydrogen; R$_4$ is heterocycle; and R$_1$ is as defined in formula (I).

In another embodiment of the present invention, compounds of formula (IV) are disclosed wherein ----- represents a single bond; Y is a covalent bond; Z is a covalent bond; R$_2$, R$_3$ and R$_5$ are hydrogen; R$_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazolyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (IV) are disclosed wherein ----- represents a single bond; Y is a covalent bond; Z is a covalent bond; R$_2$, R$_3$ and R$_5$ are hydrogen; R$_4$ is heterocycle wherein the heterocycle is selected from imidazolyl, isoxazolyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; and R$_1$, R$_{10}$, and R$_{11}$ are as defined in formula (I).

In another embodiment of the present invention, compounds of formula (IV) are disclosed wherein ----- represents a single bond; Y is a covalent bond; Z is a covalent bond; R$_2$, R$_3$, and R$_5$ are hydrogen; R$_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and R$_1$ is as defined in formula (I).

In another embodiment of the present invention, compounds of formula (IV) are disclosed wherein ----- represents a single bond; Y is a covalent bond; Z is a covalent; R$_2$, R$_3$, and R$_5$ are hydrogen; R$_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and R$_1$ is as defined in formula (I).

In another embodiment of the present invention, compounds of formula (IV) are disclosed wherein Y is a covalent bond; Z is CH$_2$; and R$_1$, R$_2$, R$_3$, R$_4$ and R$_5$ are as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle; and $R_1$ is as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, phenyl, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_{12}$, $R_{13}$, and $R_{14}$ are independently selected from hydrogen, alkyl, aryl, or arylalkyl; and $R_1$, $R_{10}$ and $R_{11}$ are as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from imidazolyl, isoxazolyl, pyridazinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, phenyl, ($NR_{10}R_{11}$)sulfonyl, or —C(NH)$NR_{10}R_{11}$; and $R_1$, $R_{10}$, and $R_{11}$ are as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridi-nyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is pyridazinyl substituted with phenyl; and $R_1$ is as defined in formula (I).

In another embodiment of the present invention, compounds of formula (IV) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is 4-phenylpyridazinyl; and $R_1$ is hydrogen or methyl.

In another embodiment of the present invention, compounds of formula (IV) are disclosed wherein ----- represents a single bond; Y is a covalent bond; Z is $CH_2$; $R_2$ and $R_3$ are hydrogen; $R_5$ is selected from hydrogen or hydroxy; $R_4$ is heterocycle; and $R_1$ is as defined in formula (I).

In another embodiment of the present invention, compounds of formula (IV) are disclosed wherein ----- represents a single bond; Y is a covalent bond; Z is $CH_2$; $R_2$ and $R_3$ are hydrogen; $R_5$ is selected from hydrogen or hydroxy; $R_4$ is selected from heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (IV) are disclosed wherein ----- represents a single bond; Y is a covalent bond; Z is $CH_2$; $R_2$ and $R_3$ are hydrogen; $R_5$ is selected from hydrogen or hydroxy; $R_4$ is selected from heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; and $R_1$, $R_{10}$, and $R_{11}$ are as defined in formula (I).

In another embodiment of the present invention, compounds of formula (IV) are disclosed wherein ----- represents a single bond; Y is a covalent bond; Z is $CH_2$; $R_2$ and $R_3$ are hydrogen; $R_5$ is selected from hydrogen or hydroxy; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (IV) are disclosed wherein ----- represents a single bond; Y is a covalent bond; Z is $CH_2$; $R_2$ and $R_3$ are hydrogen; $R_5$ is selected from hydrogen or hydroxy; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (IV) are disclosed wherein ----- represents a double bond; Y is a covalent bond; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (IV) are disclosed wherein ----- represents a double bond; Y is a covalent bond; Z is $CH_2$; $R_2$ is selected from heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2C(NR_{12})NR_{13}R_{14}$, —C($NOR_{12}$)$R_{13}$, —C(NCN)$R_{12}$, —C($NNR_{12}R_{13}$)$R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (IV) are disclosed wherein ----- represents a double bond; Y is a covalent bond; Z is $CH_2$; $R_2$ is selected from heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (IV) are disclosed wherein ----- represents a double bond; Y is a covalent bond; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (III) are disclosed wherein ----- represents a double bond; Y is a covalent bond; Z is $CH_2$; $R_2$ is heterocycle wherein the heterocycle is selected from 3-pyridinyl, 6-bromo-3-pyridinyl, 6-chloro-3-pyridinyl, 6fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (IV) are disclosed wherein ----- represents a single bond; Y is a covalent bond; Z is $CH_2$; $R_2$ is heterocycle; $R_3$ is selected from hydrogen or hydroxy; $R_4$ and $R_5$ are hydrogen; and $R_1$ is as defined in formula (I).

In another embodiment of the present invention, compounds of formula (IV) are disclosed wherein ----- represents a single bond; Y is a covalent bond; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2C(NR_{12})NR_{13}R_{14}$, —C($NOR_{12}$)$R_{13}$, —C(NCN)$R_{12}$, —C($NNR_{12}R_{13}$)$R_{14}$, —$S(O)_2OR_{12}$, or —$S(O)_2R_{12}$; $R_3$ is selected from hydrogen or hydroxy; $R_4$ and $R_5$ are hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (IV) are disclosed wherein ----- represents a single bond; Y is a covalent bond; Z is $CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, $(NR_{10}R_{11})$sulfonyl, or —C(NH)$NR_{10}R_{11}$; $R_3$ is selected from hydrogen or hydroxy; $R_4$ and $R_5$ are hydrogen; and $R_1$, $R_{10}$, and $R_{11}$ are as defined in formula (I).

In another embodiment of the present invention, compounds of formula (IV) are disclosed wherein ----- represents a single bond; Y is a covalent bond; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ is selected from hydrogen or hydroxy; $R_4$ and $R_5$ are hydrogen; and $R_1$ is as defined in formula (I).

In another embodiment of the present invention, compounds of formula (III) are disclosed wherein ----- represents a single bond; Y is a covalent bond; Z is $CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ is selected from hydrogen or hydroxy; $R_4$ and $R_5$ are hydrogen; and $R_1$ is as defined in formula (I).

In another embodiment of the present invention, compounds of formula (IV) are disclosed wherein Y is a covalent bond; Z is $CH_2CH_2$; and $R_1$, $R_2$, $R_3$, $R_4$, and $R_5$ are as defined in formula (I).

In another embodiment of the present invention, compounds of formula (IV) are disclosed wherein ----- represents a double bond; Y is a covalent bond; Z is $CH_2CH_2$; $R_2$ is hydrogen; $R_3$ and $R_5$ are absent; $R_4$ is heterocycle; and $R_1$ is as defined in formula (I).

In another embodiment of the present invention, compounds of formula (IV) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, $(NR_{10}R_{11})$alkyl, $(NR_{10}R_{11})$carbonyl, $(NR_{10}R_{11})$carbonylalkyl, $(NR_{10}R_{11})$sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —C(NCN)$R_{12}$, —$C(NNR_{12}R_{13})R_{14}$, —$S(O)_2OR_{12}$, or —$S(O)_2R_{12}$; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (IV) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, $(NR_{10}R_{11})$sulfonyl, or —C(NH)$NR_{10}R_{11}$; and $R_1$, $R_{10}$, and $R_{11}$ are as defined in formula (I).

In another embodiment of the present invention, compounds of formula (IV) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (IV) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-S-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (IV) are disclosed wherein ----- represents a double bond; Y is a covalent bond; Z is $CH_2CH_2$; $R_2$ is heterocycle; $R_3$ and $R_5$ are absent; $R_4$ is hydrogen; and $R_1$ is as defined in formula (I).

In another embodiment of the present invention, compounds of formula (IV) are disclosed wherein ----- represents a double bond; Y is a covalent bond; Z is $CH_2CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_3$ and R$_5$ are absent; R$_4$ is hydrogen; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (IV) are disclosed wherein ----- represents a double bond; Y is a covalent bond; Z is CH$_2$CH$_2$; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (IV) are disclosed wherein ----- represents a double bond; Y is a covalent bond; Z is CH$_2$CH$_2$; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (IV) are disclosed wherein ----- represents a double bond; Y is a covalent bond; Z is CH$_2$CH$_2$; R$_2$ is heterocycle wherein the heterocycle is selected from 3-pyridinyl, 6-bromo-3-pyridinyl, 6-chloro-3-pyridinyl, 6fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; R$_3$ and R$_5$ are absent; R$_4$ is hydrogen; and R$_1$ is as defined in formula (I).

In another embodiment of the present invention, compounds of formula (IV) are disclosed wherein Y is CH$_2$; Z is CH$_2$; and R$_1$, R$_2$, R$_3$, R$_4$, and R$_5$ are as defined in formula (I).

In another embodiment of the present invention, compounds of formula (IV) are disclosed wherein ----- represents a double bond; Y is CH$_2$; Z is CH$_2$; R$_2$ is heterocycle; R$_3$ and R$_5$ are absent; R$_4$ is hydrogen; and R$_1$ is as defined in formula (I).

In another embodiment of the present invention, compounds of formula (IV) are disclosed wherein ----- represents a double bond; Y is CH$_2$; Z is CH$_2$; R$_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_3$ and R$_5$ are absent; R$_4$ is hydrogen; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (IV) are disclosed wherein ----- represents a double bond; Y is CH$_2$; Z is CH$_2$; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (IV) are disclosed wherein ----- represents a double bond; Y is CH$_2$; Z is CH$_2$; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (IV) are disclosed wherein ----- represents a double bond; Y is CH$_2$; Z is CH$_2$; R$_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6bromo-5-methoxy-3-pyridinyl; R$_3$ and R$_5$ are absent; R$_4$ is hydrogen; and R$_1$ is as defined in formula (I).

Representative compounds of formula (IV) include, but are not limited to:

(cis)-5-(6-chloro-3-pyridinyl)-1,2,3,3a,4,6a-hexahydrocyclopenta[c]pyrrole;

(cis)-5-(5-methoxy-3-pyridinyl)-1,2,3,3a,4,6a-hexahydrocyclopenta[c]pyrrole;

(cis)-5-(6-chloro-5-methyl-3-pyridinyl)-1,2,3,3a,4,6a-hexahydrocyclopenta[c]pyrrole;

(cis)-5-(3-pyridinyl)-1,2,3,3a,4,6a-hexahydrocyclopenta[c]pyrrole;
(cis)-5-(3-methyl-5-isoxazolyl)-1,2,3,3a,4,6a-hexahydrocyclopenta[c]pyrrole;
(cis)-5-(5,6-dichloro-3-pyridinyl)-1,2,3,3a,4,6a-hexahydrocyclopenta[c]pyrrole;
(cis)-2-methyl-5-(3-methyl-5-isoxazolyl)-1,2,3,3a,4,6a-hexahydrocyclopenta[c]pyrrole;
(cis)-5-(5-chloro-3-pyridinyl)-1,2,3,3a,4,6a-hexahydrocyclopenta[c]pyrrole;
(cis)-5-(3-bromo-1,2,4-thiadiazol-5-yl)-1,2,3,3a,4,6a-hexahydrocyclopenta[c]pyrrole;
(cis)-5-(1,3-thiazol-2-yl)-1,2,3,3a,4,6a-hexahydrocyclopenta[c]pyrrole;
(cis)-5-(3,5-dimethyl-4-isoxazolyl)-1,2,3,3a,4,6a-hexahydrocyclopenta[c]pyrrole;
(cis)-5-(1H-imidazol-4-yl)-1,2,3,3a,4,6a-hexahydrocyclopenta[c]pyrrole;
(cis)-5-(1,3-thiazol-5-yl)-1,2,3,3a,4,6a-hexahydrocyclopenta[c]pyrrole;
(cis)-5-(imidazo[1,2-a]pyridin-3-yl)-1,2,3,3a,4,6a-hexahydrocyclopenta[c]pyrrole;
(cis)-5-(imidazo[1,2-a]pyridin-6-yl)-1,2,3,3a,4,6a-hexahydrocyclopenta[c]pyrrole;
(cis)-5-(thieno[3,2-b]pyridin-2-yl)-1,2,3,3a,4,6a-hexahydrocyclopenta[c]pyrrole;
(cis)-5-(1,2,3,3a,4,6a-hexahydrocyclopenta[c]pyrrol-5-yl)-2-thiophenesulfonamide;
(cis)-5-(6-methyl-3-pyridinyl)-1,2,3,3a,4,6a-hexahydrocyclopenta[c]pyrrole;
(cis)-5-(2-methyl-3-pyridinyl)-1,2,3,3a,4,6a-hexahydrocyclopenta[c]pyrrole;
(cis)-5-(6-chloro-5-fluoro-3-pyridinyl)-1,2,3,3a,4,6a-hexahydrocyclopenta[c]pyrrole;
(cis)-5-(6-fluoro-3-pyridinyl)-1,2,3,3a,4,6a-hexahydrocyclopenta[c]pyrrole;
(cis)-5-(1,2,3,3a,4,6a-hexahydrocyclopenta[c]pyrrol-5-yl)-2-thiophenecarboximidamide;
(cis)-5-(2-methyl-2H-tetrazol-5-yl)-1,2,3,3a,4,6a-hexahydrocyclopenta[c]pyrrole;
(cis)-5-(thieno[2,3-b]pyridin-5-yl)-1,2,3,3a,4,6a-hexahydrocyclopenta[c]pyrrole;
(cis)-5-(imidazo[1,2-a]pyridin-7-yl)-1,2,3,3a,4,6a-hexahydrocyclopenta[c]pyrrole;
(cis)-5-(2-pyridinyl)-1,2,3,3a,4,6a-hexahydrocyclopenta[c]pyrrole;
(cis)-5-(4-pyridinyl)-1,2,3,3a,4,6a-hexahydrocyclopenta[c]pyrrole;
(cis)-5-(5-nitro-1,3-thiazol-2-yl)-1,2,3,3a,4,6a-hexahydrocyclopenta[c]pyrrole;
(cis)-5-(6-methyl-2-pyridinyl)-1,2,3,3a,4,6a-hexahydrocyclopenta[c]pyrrole;
(cis)-5-(1,3,4-thiadiazol-2-yl)-1,2,3,3a,4,6a-hexahydrocyclopenta[c]pyrrole;
(endo)-5-(3-pyridinyl)octahydrocyclopenta[c]pyrrole;
(cis)-5-(6-chloro-3-pyridinyl)octahydrocyclopenta[c]pyrrol-5-ol;
(endo)-5-(6-chloro-3-pyridinyl)octahydrocyclopenta[c]pyrrole;
(exo)-5-(6-chloro-3-pyridinyl)octahydrocyclopenta[c]pyrrole;
(cis)-5-(5-bromo-3-pyridinyl)-1,2,3,3a,4,6a-hexahydrocyclopenta[c]pyrrole;
(cis)-5-(5-vinyl-3-pyridinyl)-1,2,3,3a,4,6a-hexahydrocyclopenta[c]pyrrole;
(cis)-5-(1,2,3,3a,4,6a-hexahydrocyclopenta[c]pyrrol-5-yl)nicotinonitrile;
(cis)-5-(6-chloro-3-pyridinyl)-1,2,3,3a,4,6a-hexahydrocyclopenta[c]pyrrole;
(cis)-5-(6-chloro-3-pyridinyl)-1,2,3,3a,4,6a-hexahydrocyclopenta[c]pyrrole;
(cis)-6-(6-chloro-3-pyridinyl)-1,2,3,3a,4,6a-hexahydrocyclopenta[c]pyrrole;
(cis)-4-(3-pyridinyl)octahydrocyclopenta[c]pyrrol-4-ol;
(endo)-4-(6-chloro-3-pyridinyl)octahydrocyclopenta[c]pyrrole;
(cis)-6-(6-methyl-3-pyridinyl)-3-azabicyclo[3.2.0]hept-6-ene;
(endo)-6-(6-chloro-3-pyridinyl)-3-azabicyclo[3.2.0]heptane;
(exo)-6-(6-chloro-3-pyridinyl)-3-azabicyclo[3.2.0]heptane;
(cis)-6-(5,6-dichloro-3-pyridinyl)-3-azabicyclo[3.2.0]hept-6-ene;
(endo)-6-(5,6-dichloro-3-pyridinyl)-3-azabicyclo[3.2.0]heptane;
(cis)-5-(6-phenylpyridazin-3-yl)-1,2,3,3a,4,6a-hexahydrocyclopenta[c]pyrrole;
(cis)-2-methyl-5-(6-phenylpyridazin-3-yl)-1,2,3,3a,4,6a-hexahydrocyclopenta[c]pyrrole;
(cis)-5-(6-bromo-3-pyridinyl)-1,2,3,3a,4,6a-hexahydrocyclopenta[c]pyrrole;
(cis)-5-(5-methyl-3-pyridinyl)-1,2,3,3a,4,6a-hexahydrocyclopenta[c]pyrrole;
(cis)-5-(6-chloro-5-methoxy-3-pyridinyl)-1,2,3,3a,4,6a-hexahydrocyclopenta[c]pyrrole;
(cis)-5-(6-bromo-5-methoxy-3-pyridinyl)-1,2,3,3a,4,6a-hexahydrocyclopenta[c]pyrrole;
(cis)-5-(5-methoxy-6-methyl-3-pyridinyl)-1,2,3,3a,4,6a-hexahydrocyclopenta[c]pyrrole;
(cis)-2-chloro-5-(1,2,3,3a,4,6a-hexahydrocyclopenta[c]pyrrol-5-yl)nicotinonitrile;
(cis)-2-bromo-5-(1,2,3,3a,4,6a-hexahydrocyclopenta[c]pyrrol-5-yl)nicotinonitrile;
(cis)-5-(1,2,3,3a,4,6a-hexahydrocyclopenta[c]pyrrol-5-yl)-2-methylnicotinonitrile;
(cis)-5-(5-bromo-6-chloro-3-pyridinyl)-1,2,3,3a,4,6a-hexahydrocyclopenta[c]pyrrole;
(cis)-5-(5,6-dibromo-3-pyridinyl)-1,2,3,3a,4,6a-hexahydrocyclopenta[c]pyrrole;
(cis)-5-(6-bromo-5-chloro-3-pyridinyl)-1,2,3,3a,4,6a-hexahydrocyclopenta[c]pyrrole;
(cis)-5-(5-chloro-6-methyl-3-pyridinyl)-1,2,3,3a,4,6a-hexahydrocyclopenta[c]pyrrole;
(cis)-5-(5-bromo-6-methyl-3-pyridinyl)-1,2,3,3a,4,6a-hexahydrocyclopenta[c]pyrrole;
(cis)-5-(6-bromo-5-methyl-3-pyridinyl)-1,2,3,3a,4,6a-hexahydrocyclopenta[c]pyrrole;
(cis)-2-(1,2,3,3a,4,6a-hexahydrocyclopenta[c]pyrrol-5-yl)furo[3,2-b]pyridine;
(cis)-7-(3-pyridinyl)-2,3,3a,4,5,7a-hexahydro-1H-isoindole;
(cis)-7-(6-chloro-3-pyridinyl)-2,3,3a,4,5,7a-hexahydro-1H-isoindole;
(cis)-7-(6-bromo-3-pyridinyl)-2,3,3a,4,5,7a-hexahydro-1H-isoindole;
(cis)-7-(6-fluoro-3-pyridinyl)-2,3,3a,4,5,7a-hexahydro-1H-isoindole;
(cis)-7-(6-methyl-3-pyridinyl)-2,3,3a,4,5,7a-hexahydro-1H-isoindole;
(cis)-5-(2,3,3a,6,7,7a-hexahydro-1H-isoindol-4-yl)nicotinonitrile;
(cis)-7-(5-methyl-3-pyridinyl)-2,3,3a,4,5,7a-hexahydro-1H-isoindole;
(cis)-7-(5-chloro-3-pyridinyl)-2,3,3a,4,5,7a-hexahydro-1H-isoindole;

(cis)-7-(5-bromo-3-pyridinyl)-2,3,3a,4,5,7a-hexahydro-1H-isoindole;
(cis)-7-(5-fluoro-3-pyridinyl)-2,3,3a,4,5,7a-hexahydro-1H-isoindole;
(cis)-7-(5-vinyl-3-pyridinyl)-2,3,3a,4,5,7a-hexahydro-1H-isoindole;
(cis)-7-(5-methoxy-3-pyridinyl)-2,3,3a,4,5,7a-hexahydro-1H-isoindole;
(cis)-7-(5-vinyloxy-3-pyridinyl)-2,3,3a,4,5,7a-hexahydro-1H-isoindole;
(cis)-7-(5-ethynyl-3-pyridinyl)-2,3,3a,4,5,7a-hexahydro-1H-isoindole;
(cis)-7-(5,6-dichloro-3-pyridinyl)-2,3,3a,4,5,7a-hexahydro-1H-isoindole;
(cis)-7-(6-bromo-5-chloro-3-pyridinyl)-2,3,3a,4,5,7a-hexahydro-1H-isoindole;
(cis)-5-(2,3,3a,6,7,7a-hexahydro-1H-isoindol-4-yl)-2-methylnicotinonitrile;
(cis)-2-chloro-5-(2,3,3a,6,7,7a-hexahydro-1H-isoindol-4-yl)nicotinonitrile;
(cis)-2-bromo-5-(2,3,3a,6,7,7a-hexahydro-1H-isoindol-4-yl)nicotinonitrile;
(cis)-7-(6-chloro-5-methyl-3-pyridinyl)-2,3,3a,4,5,7a-hexahydro-1H-isoindole;
(cis)-7-(6-bromo-5-methyl-3-pyridinyl)-2,3,3a,4,5,7a-hexahydro-1H-isoindole;
(cis)-7-(5-methoxy-6-methyl-3-pyridinyl)-2,3,3a,4,5,7a-hexahydro-1H-isoindole;
(cis)-7-(6-chloro-5-methoxy-3-pyridinyl)-2,3,3a,4,5,7a-hexahydro-1H-isoindole;
(cis)-7-(6-bromo-5-methoxy-3-pyridinyl)-2,3,3a,4,5,7a-hexahydro-1H-isoindole;
(cis)-7-(3-methyl-5-isoxazolyl)-2,3,3a,4,5,7a-hexahydro-1H-isoindole;
(cis)-2-(2,3,3a,6,7,7a-hexahydro-1H-isoindol-4-yl)furo[3,2-b]pyridine;
(cis)-6-(3-pyridinyl)-1,2,3,3a,4,6a-hexahydrocyclopenta[c]pyrrole;
(cis)-6-(6-chloro-3-pyridinyl)-1,2,3,3a,4,6a-hexahydrocyclopenta[c]pyrrole;
(cis)-6-(6-bromo-3-pyridinyl)-1,2,3,3a,4,6a-hexahydrocyclopenta[c]pyrrole;
(cis)-6-(6-methyl-3-pyridinyl)-1,2,3,3a,4,6a-hexahydrocyclopenta[c]pyrrole;
(cis)-6-(6-fluoro-3-pyridinyl)-1,2,3,3a,4,6a-hexahydrocyclopenta[c]pyrrole;
(cis)-5-(1,2,3,3a,6,6a-hexahydrocyclopenta[c]pyrrol-4-yl)nicotinonitrile;
(cis)-6-(5-methyl-3-pyridinyl)-1,2,3,3a,4,6a-hexahydrocyclopenta[c]pyrrole;
(cis)-6-(5-chloro-3-pyridinyl)-1,2,3,3a,4,6a-hexahydrocyclopenta[c]pyrrole;
(cis)-6-(5-fluoro-3-pyridinyl)-1,2,3,3a,4,6a-hexahydrocyclopenta[c]pyrrole;
(cis)-6-(5-bromo-3-pyridinyl)-1,2,3,3a,4,6a-hexahydrocyclopenta[c]pyrrole;
(cis)-6-(5-vinyl-3-pyridinyl)-1,2,3,3a,4,6a-hexahydrocyclopenta[c]pyrrole;
(cis)-6-(5-methoxy-3-pyridinyl)-1,2,3,3a,4,6a-hexahydrocyclopenta[c]pyrrole;
(cis)-6-(5-vinyloxy-3-pyridinyl)-1,2,3,3a,4,6a-hexahydrocyclopenta[c]pyrrole;
(cis)-6-(5-ethynyl-3-pyridinyl)-1,2,3,3a,4,6a-hexahydrocyclopenta[c]pyrrole;
(cis)-6-(5,6-dichloro-3-pyridinyl)-1,2,3,3a,4,6a-hexahydrocyclopenta[c]pyrrole;
(cis)-6-(6-bromo-5-chloro-3-pyridinyl)-1,2,3,3a,4,6a-hexahydrocyclopenta[c]pyrrole;
(cis)-5-(1,2,3,3a,6,6a-hexahydrocyclopenta[c]pyrrol-4-yl)-2-methylnicotinonitrile;
(cis)-2-chloro-5-(1,2,3,3a,6,6a-hexahydrocyclopenta[c]pyrrol-4-yl)nicotinonitrile;
(cis)-2-bromo-5-(1,2,3,3a,6,6a-hexahydrocyclopenta[c]pyrrol-4-yl)nicotinonitrile;
(cis)-6-(6-chloro-5-methyl-3-pyridinyl)-1,2,3,3a,4,6a-hexahydrocyclopenta[c]pyrrole;
(cis)-6-(6-bromo-5-methyl-3-pyridinyl)-1,2,3,3a,4,6a-hexahydrocyclopenta[c]pyrrole;
(cis)-6-(5-methoxy-6-methyl-3-pyridinyl)-1,2,3,3a,4,6a-hexahydrocyclopenta[c]pyrrole;
(cis)-6-(6-chloro-5-methoxy-3-pyridinyl)-1,2,3,3a,4,6a-hexahydrocyclopenta[c]pyrrole;
(cis)-6-(6-bromo-5-methoxy-3-pyridinyl)-1,2,3,3a,4,6a-hexahydrocyclopenta[c]pyrrole;
(cis)-6-(3-methyl-5-isoxazolyl)-1,2,3,3a,4,6a-hexahydrocyclopenta[c]pyrrole;
(cis)-2-(1,2,3,3a,6,6a-hexahydrocyclopenta[c]pyrrol-4-yl)furo[3,2-b]pyridine;
(cis)-6-(3-pyridinyl)-2,3,3a,4,5,7a-hexahydro-1H-isoindole;
(cis)-6-(6-methyl-3-pyridinyl)-2,3,3a,4,5,7a-hexahydro-1H-isoindole;
(cis)-6-(6-bromo-3-pyridinyl)-2,3,3a,4,5,7a-hexahydro-1H-isoindole;
(cis)-6-(6-chloro-3-pyridinyl)-2,3,3a,4,5,7a-hexahydro-1H-isoindole;
(cis)-6-(6-fluoro-3-pyridinyl)-2,3,3a,4,5,7a-hexahydro-1H-isoindole;
(cis)-5-(2,3,3a,6,7,7a-hexahydro-1H-isoindol-5-yl)nicotinonitrile;
(cis)-6-(5-methyl-3-pyridinyl)-2,3,3a,4,5,7a-hexahydro-1H-isoindole;
(cis)-6-(5-chloro-3-pyridinyl)-2,3,3a,4,5,7a-hexahydro-1H-isoindole;
(cis)-6-(5-fluoro-3-pyridinyl)-2,3,3a,4,5,7a-hexahydro-1H-isoindole;
(cis)-6-(5-bromo-3-pyridinyl)-2,3,3a,4,5,7a-hexahydro-1H-isoindole;
(cis)-6-(5-vinyl-3-pyridinyl)-2,3,3a,4,5,7a-hexahydro-1H-isoindole;
(cis)-6-(5-methoxy-3-pyridinyl)-2,3,3a,4,5,7a-hexahydro-1H-isoindole;
(cis)-6-(5-vinyloxy-3-pyridinyl)-2,3,3a,4,5,7a-hexahydro-1H-isoindole;
(cis)-6-(5-ethynyl-3-pyridinyl)-2,3,3a,4,5,7a-hexahydro-1H-isoindole;
(cis)-6-(5,6-dichloro-3-pyridinyl)-2,3,3a,4,5,7a-hexahydro-1H-isoindole;
(cis)-6-(6-bromo-5-chloro-3-pyridinyl)-2,3,3a,4,5,7a-hexahydro-1H-isoindole;
(cis)-5-(2,3,3a,6,7,7a-hexahydro-1H-isoindol-5-yl)-2-methylnicotinonitrile;
(cis)-2-chloro-5-(2,3,3a,6,7,7a-hexahydro-1H-isoindol-5-yl)nicotinonitrile;
(cis)-2-bromo-5-(2,3,3a,6,7,7a-hexahydro-1H-isoindol-5-yl)nicotinonitrile;
(cis)-6-(6-chloro-5-methyl-3-pyridinyl)-2,3,3a,4,5,7a-hexahydro-1H-isoindole;
(cis)-6-(6-bromo-5-methyl-3-pyridinyl)-2,3,3a,4,5,7a-hexahydro-1H-isoindole;
(cis)-6-(5-methoxy-6-methyl-3-pyridinyl)-2,3,3a,4,5,7a-hexahydro-1H-isoindole;
(cis)-6-(6-chloro-5-methoxy-3-pyridinyl)-2,3,3a,4,5,7a-hexahydro-1H-isoindole;

(cis)-6-(6-bromo-5-methoxy-3-pyridinyl)-2,3,3a,4,5,7a-hexahydro-1H-isoindole;
(cis)-6-(3-methyl-5-isoxazolyl)-2,3,3a,4,5,7a-hexahydro-1H-isoindole;
(cis)-2-(2,3,3a,6,7,7a-hexahydro-1H-isoindol-5-yl)furo[3,2-b]pyridine;
(cis)-5-(3-pyridinyl)-2,3,3a,4,7,7a-hexahydro-1H-isoindole;
(cis)-5-(6-methyl-3-pyridinyl)-2,3,3a,4,7,7a-hexahydro-1H-isoindole;
(cis)-5-(6-chloro-3-pyridinyl)-2,3,3a,4,7,7a-hexahydro-1H-isoindole;
(cis)-5-(6-bromo-3-pyridinyl)-2,3,3a,4,7,7a-hexahydro-1H-isoindole;
(cis)-5-(6-fluoro-3-pyridinyl)-2,3,3a,4,7,7a-hexahydro-1H-isoindole;
(cis)-5-(2,3,3a,4,7,7a-hexahydro-1H-isoindol-5-yl)nicotinonitrile;
(cis)-5-(5-methyl-3-pyridinyl)-2,3,3a,4,7,7a-hexahydro-1H-isoindole;
(cis)-5-(5-chloro-3-pyridinyl)-2,3,3a,4,7,7a-hexahydro-1H-isoindole;
(cis)-5-(5-fluoro-3-pyridinyl)-2,3,3a,4,7,7a-hexahydro-1H-isoindole;
(cis)-5-(5-bromo-3-pyridinyl)-2,3,3a,4,7,7a-hexahydro-1H-isoindole;
(cis)-5-(5-vinyl-3-pyridinyl)-2,3,3a,4,7,7a-hexahydro-1H-isoindole;
(cis)-5-(5-methoxy-3-pyridinyl)-2,3,3a,4,7,7a-hexahydro-1H-isoindole;
(cis)-5-(5-vinyloxy-3-pyridinyl)-2,3,3a,4,7,7a-hexahydro-1H-isoindole;
(cis)-5-(5-ethynyl-3-pyridinyl)-2,3,3a,4,7,7a-hexahydro-1H-isoindole;
(cis)-5-(5,6-dichloro-3-pyridinyl)-2,3,3a,4,7,7a-hexahydro-1H-isoindole;
(cis)-5-(6-bromo-5-chloro-3-pyridinyl)-2,3,3a,4,7,7a-hexahydro-1H-isoindole;
(cis)-5-(2,3,3a,4,7,7a-hexahydro-1H-isoindol-5-yl)-2-methylnicotinonitrile;
(cis)-2-chloro-5-(2,3,3a,4,7,7a-hexahydro-1H-isoindol-5-yl)nicotinonitrile;
(cis)-2-bromo-5-(2,3,3a,4,7,7a-hexahydro-1H-isoindol-5-yl)nicotinonitrile;
(cis)-5-(6-chloro-5-methyl-3-pyridinyl)-2,3,3a,4,7,7a-hexahydro-1H-isoindole;
(cis)-5-(6-bromo-5-methyl-3-pyridinyl)-2,3,3a,4,7,7a-hexahydro-1H-isoindole;
(cis)-5-(5-methoxy-6-methyl-3-pyridinyl)-2,3,3a,4,7,7a-hexahydro-1H-isoindole;
(cis)-5-(6-chloro-5-methoxy-3-pyridinyl)-2,3,3a,4,7,7a-hexahydro-1H-isoindole;
(cis)-5-(6-bromo-5-methoxy-3-pyridinyl)-2,3,3a,4,7,7a-hexahydro-1H-isoindole;
(cis)-2-(2,3,3a,4,7,7a-hexahydro-1H-isoindol-5-yl)furo[3,2-b]pyridine;
(cis)-5-(3-methyl-5-isoxazolyl)-2,3,3a,4,7,7a-hexahydro-1H-isoindole;
(cis)-6-(3-pyridinyl)-3-azabicyclo[3.2.0]hept-6-ene;
(cis)-6-(6-bromo-3-pyridinyl)-3-azabicyclo[3.2.0]hept-6-ene;
(cis)-6-(6-fluoro-3-pyridinyl)-3-azabicyclo[3.2.0]hept-6-ene;
(cis)-6-(6-methyl-3-pyridinyl)-3-azabicyclo[3.2.0]hept-6-ene;
(cis)-5-(3-azabicyclo[3.2.0]hept-6-en-6-yl)nicotinonitrile;
(cis)-6-(5-chloro-3-pyridinyl)-3-azabicyclo[3.2.0]hept-6-ene;
(cis)-6-(5-bromo-3-pyridinyl)-3-azabicyclo[3.2.0]hept-6-ene;
(cis)-6-(5-fluoro-3-pyridinyl)-3-azabicyclo[3.2.0]hept-6-ene;
(cis)-6-(5-methyl-3-pyridinyl)-3-azabicyclo[3.2.0]hept-6-ene;
(cis)-6-(5-vinyl-3-pyridinyl)-3-azabicyclo[3.2.0]hept-6-ene;
(cis)-6-(5-methoxy-3-pyridinyl)-3-azabicyclo[3.2.0]hept-6-ene;
(cis)-6-(5-vinyloxy-3-pyridinyl)-3-azabicyclo[3.2.0]hept-6-ene;
(cis)-6-(5-ethynyl-3-pyridinyl)-3-azabicyclo[3.2.0]hept-6-ene;
(cis)-6-(6-bromo-5-chloro-3-pyridinyl)-3-azabicyclo[3.2.0]hept-6-ene;
(cis)-5-(3-azabicyclo[3.2.0]hept-6-en-6-yl)-2-methylnicotinonitrile;
(cis)-5-(3-azabicyclo[3.2.0]hept-6-en-6-yl)-2-bromonicotinonitrile;
(cis)-5-(3-azabicyclo[3.2.0]hept-6-en-6-yl)-2-chloronicotinonitrile;
(cis)-6-(6-chloro-5-methyl-3-pyridinyl)-3-azabicyclo[3.2.0]hept-6-ene;
(cis)-6-(6-bromo-5-methyl-3-pyridinyl)-3-azabicyclo[3.2.0]hept-6-ene;
(cis)-6-(5-methoxy-6-methyl-3-pyridinyl)-3-azabicyclo[3.2.0]hept-6-ene;
(cis)-6-(6-bromo-5-methoxy-3-pyridinyl)-3-azabicyclo[3.2.0]hept-6-ene;
(cis)-6-(6-chloro-5-methoxy-3-pyridinyl)-3-azabicyclo[3.2.0]hept-6-ene; or a pharmaceutically acceptable salt, amide, ester or prodrugs thereof.

In another embodiment of the present invention, compounds of formula (V) are disclosed

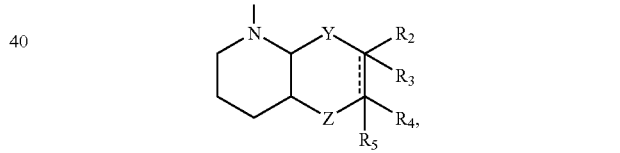

or a pharmaceutically acceptable salt, amide, ester or prodrug thereof wherein Y, Z, $R_1$, $R_2$, $R_3$, $R_4$, and $R_5$ are as defined in formula (I).

In another embodiment of the present invention, compounds of formula (V) are disclosed wherein Y is a covalent bond; Z is a covalent bond; and $R_1$, $R_2$, $R_3$, $R_4$, and $R_5$ are as defined in formula (I).

In another embodiment of the present invention, compounds of formula (V) are disclosed wherein Y is a covalent bond; Z is $CH_2$; and $R_1$, $R_2$, $R_3$, $R_4$, and $R_5$ are as defined in formula (I).

In another embodiment of the present invention, compounds of formula (V) are disclosed wherein ----- represents a double bond; Y is a covalent bond; Z is $CH_2$; $R_2$ is hydrogen; $R_3$ and $R_5$ are absent; $R_4$ is heterocycle; and $R_1$ is as defined in formula (I).

In another embodiment of the present invention, compounds of formula (V) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (V) are disclosed wherein ----represents a double bond; Y is a covalent bond; Z is CH$_2$; R$_2$ is hydrogen; R$_3$ and R$_5$ are absent; R$_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; and R$_1$, R$_{10}$, and R$_{11}$ are as defined in formula (I).

In another embodiment of the present invention, compounds of formula (V) are disclosed wherein ----represents a double bond; Y is a covalent bond; Z is CH$_2$; R$_2$ is hydrogen; R$_3$ and R$_5$ are absent; R$_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and R$_1$ is as defined in formula (I).

In another embodiment of the present invention, compounds of formula (V) are disclosed wherein ----represents a double bond; Y is a covalent bond; Z is CH$_2$; R$_2$ is hydrogen; R$_3$ and R$_5$ are absent; R$_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and R$_1$ is as defined in formula (I).

In another embodiment of the present invention, compounds of formula (V) are disclosed wherein ----represents a double bond; Y is a covalent bond; Z is CH$_2$; R$_2$ is heterocycle; R$_3$ and R$_5$ are absent; R$_4$ is hydrogen; and R$_1$ is as defined in formula (I).

In another embodiment of the present invention, compounds of formula (V) are disclosed wherein ----represents a double bond; Y is a covalent bond; Z is CH$_2$; R$_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo [2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno [2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_3$ and R$_5$ are absent; R$_4$ is hydrogen; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (V) are disclosed wherein ----represents a double bond; Y is a covalent bond; Z is CH$_2$; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH) NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (V) are disclosed wherein ----represents a double bond; Y is a covalent bond; Z is CH$_2$; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (V) are disclosed wherein ----represents a double bond; Y is a covalent bond; Z is CH$_2$; R$_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy- 3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (V) are disclosed wherein Y is $CH_2$; Z is a covalent bond; and $R_1$, $R_2$, $R_3$, $R_4$, and $R_5$ are as defined in formula (I).

In another embodiment of the present invention, compounds of formula (V) are disclosed wherein ---- represents a double bond; Y is $CH_2$; Z is a covalent bond; $R_2$ is heterocycle; $R_3$ and $R_5$ are absent; $R_4$ is hydrogen; and $R_1$ is as defined in formula (I).

In another embodiment of the present invention, compounds of formula (V) are disclosed wherein ---- represents a double bond; Y is $CH_2$; Z is a covalent bond; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (V) are disclosed wherein ---- represents a double bond; Y is $CH_2$; Z is a covalent bond; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (V) are disclosed wherein ---- represents a double bond; Y is $CH_2$; Z is a covalent bond; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (V) are disclosed wherein ---- represents a double bond; Y is $CH_2$; Z is a covalent bond; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (V) are disclosed wherein Y is a covalent bond; Z is $CH_2CH_2$; and $R_1$, $R_2$, $R_3$, $R_4$, and $R_5$ are as defined in formula (I).

In another embodiment of the present invention, compounds of formula (V) are disclosed wherein ---- represents a double bond; Y is a covalent bond; Z is $CH_2CH_2$; $R_2$ is hydrogen; $R_3$ and $R_5$ are absent; $R_4$ is heterocycle; and $R_1$ is as defined in formula (I).

In another embodiment of the present invention, compounds of formula (V) are disclosed wherein ---- represents a double bond; Y is a covalent bond; Z is $CH_2CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (V) are disclosed wherein ---- represents a double bond; Y is a covalent bond; Z is $CH_2CH_2$; $R_2$ is hydrogen; $R_3$ and $R_5$ are absent; $R_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; and $R_1$, $R_{10}$, and $R_{11}$ are as defined in formula (I).

In another embodiment of the present invention, compounds of formula (V) are disclosed wherein ---- represents a double bond; Y is a covalent bond; Z is $CH_2CH_2$; $R_2$ is hydrogen; $R_3$ and $R_5$ are absent; $R_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and $R_1$ is as defined in formula (I).

In another embodiment of the present invention, compounds of formula (V) are disclosed wherein ----- represents a double bond; Y is a covalent bond; Z is $CH_2CH_2$; $R_2$ is hydrogen; $R_3$ and $R_5$ are absent; $R_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (V) are disclosed wherein ----- represents a double bond; Y is a covalent bond; Z is $CH_2CH_2$; $R_2$ is heterocycle; $R_3$ and $R_5$ are absent; $R_4$ is hydrogen; and $R_1$ is as defined in formula (I).

In another embodiment of the present invention, compounds of formula (V) are disclosed wherein ----- represents a double bond; Y is a covalent bond; Z is $CH_2CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (V) are disclosed wherein ----- represents a double bond; Y is a covalent bond; Z is $CH_2CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (V) are disclosed wherein ----- represents a double bond; Y is a covalent bond; Z is $CH_2CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (V) are disclosed wherein ----- represents a double bond; Y is a covalent bond; Z is $CH_2CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (V) are disclosed wherein Y is $CH_2$; Z is $CH_2$; and $R_1$, $R_2$, $R_3$, $R_4$, and $R_5$ are as defined in formula (I).

In another embodiment of the present invention, compounds of formula (V) are disclosed wherein ----- represents a double bond; Y is $CH_2$; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (V) are disclosed wherein ----- represents a double bond; Y is $CH_2$; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —$C(NR_{12})NR_{13}R_{14}$, —$CH_2C(NR_{12})NR_{13}R_{14}$, —$C(NOR_{12})R_{13}$, —$C(NCN)R_{12}$, —$C(NNR_{12}R_{13})R_{14}$, —$S(O)_2OR_{12}$, or —$S(O)_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (V) are disclosed wherein ----- represents a double bond; Y is CH$_2$; Z is CH$_2$; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (V) are disclosed wherein ----- represents a double bond; Y is CH$_2$; Z is CH$_2$; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (V) are disclosed wherein ----- represents a double bond; Y is CH$_2$; Z is CH$_2$; R$_2$ is heterocycle wherein the heterocycle is selected from 3-pyridinyl, 6-bromo-3-pyridinyl, 6-chloro-3-pyridinyl, 6-fluoro-3-pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; R$_3$ and R$_5$ are absent; R$_4$ is hydrogen; and R$_1$ is as defined in formula (I).

In another embodiment of the present invention, compounds of formula (V) are disclosed wherein Y is CH$_2$CH$_2$; Z is a covalent bond; and R$_1$, R$_2$, R$_3$, R$_4$, and R$_5$ are as defined in formula (I).

Representative compounds of formula (V) include, but are not limited to:
(cis)-8-(3-pyridinyl)-1,2,3,4,4a,5,6,8a-octahydroquinoline;
(cis)-8-(6-chloro-3-pyridinyl)-1,2,3,4,4a,5,6,8a-octahydroquinoline;
(cis)-8-(6-bromo-3-pyridinyl)-1,2,3,4,4a,5,6,8a-octahydroquinoline;
(cis)-8-(6-fluoro-3-pyridinyl)-1,2,3,4,4a,5,6,8a-octahydroquinoline;
(cis)-8-(6-methyl-3-pyridinyl)-1,2,3,4,4a,5,6,8a-octahydroquinoline;
(cis)-5-(1,2,3,4,4a,5,6,8a-octahydro-8-quinolinyl)nicotinonitrile;
(cis)-8-(5-methyl-3-pyridinyl)-1,2,3,4,4a,5,6,8a-octahydroquinoline;
(cis)-8-(5-chloro-3-pyridinyl)-1,2,3,4,4a,5,6,8a-octahydroquinoline;
(cis)-8-(5-fluoro-3-pyridinyl)-1,2,3,4,4a,5,6,8a-octahydroquinoline;
(cis)-8-(5-bromo-3-pyridinyl)-1,2,3,4,4a,5,6,8a-octahydroquinoline;
(cis)-8-(5-vinyl-3-pyridinyl)-1,2,3,4,4a,5,6,8a-octahydroquinoline;
(cis)-8-(5-methoxy-3-pyridinyl)-1,2,3,4,4a,5,6,8a-octahydroquinoline;
(cis)-8-(5-vinyloxy-3-pyridinyl)-1,2,3,4,4a,5,6,8a-octahydroquinoline;
(cis)-8-(5-ethynyl-3-pyridinyl)-1,2,3,4,4a,5,6,8a-octahydroquinoline;
(cis)-8-(5,6-dichloro-3-pyridinyl)-1,2,3,4,4a,5,6,8a-octahydroquinoline;
(cis)-8-(6-bromo-5-chloro-3-pyridinyl)-1,2,3,4,4a,5,6,8a-octahydroquinoline;
(cis)-2-methyl-5-(1,2,3,4,4a,5,6,8a-octahydro-8-quinolinyl)nicotinonitrile;
(cis)-2-bromo-5-(1,2,3,4,4a,5,6,8a-octahydro-8-quinolinyl)nicotinonitrile;
(cis)-2-chloro-5-(1,2,3,4,4a,5,6,8a-octahydro-8-quinolinyl)nicotinonitrile;
(cis)-8-(6-chloro-5-methyl-3-pyridinyl)-1,2,3,4,4a,5,6,8a-octahydroquinoline;
(cis)-8-(5-methoxy-6-methyl-3-pyridinyl)-1,2,3,4,4a,5,6,8a-octahydroquinoline;
(cis)-8-(6-chloro-5-methoxy-3-pyridinyl)-1,2,3,4,4a,5,6,8a-octahydroquinoline;
(cis)-8-(6-bromo-5-methoxy-3-pyridinyl)-1,2,3,4,4a,5,6,8a-octahydroquinoline;
(cis)-8-(3-methyl-5-isoxazolyl)-1,2,3,4,4a,5,6,8a-octahydroquinoline;
(cis)-8-furo[3,2-b]pyridin-2-yl-1,2,3,4,4a,5,6,8a-octahydroquinoline;
(cis)-7-(3-pyridinyl)-2,3,4,4a,5,7a-hexahydro-1H-cyclopenta[b]pyridine;
(cis)-7-(6-chloro-3-pyridinyl)-2,3,4,4a,5,7a-hexahydro-1H-cyclopenta[b]pyridine;
(cis)-7-(6-bromo-3-pyridinyl)-2,3,4,4a,5,7a-hexahydro-1H-cyclopenta[b]pyridine;
(cis)-7-(6-fluoro-3-pyridinyl)-2,3,4,4a,5,7a-hexahydro-1H-cyclopenta[b]pyridine;
(cis)-7-(6-methyl-3-pyridinyl)-2,3,4,4a,5,7a-hexahydro-1H-cyclopenta[b]pyridine;
(cis)-5-(2,3,4,4a,5,7a-hexahydro-1H-cyclopenta[b]pyridin-7-yl)nicotinonitrile;
(cis)-7-(5-methyl-3-pyridinyl)-2,3,4,4a,5,7a-hexahydro-1H-cyclopenta[b]pyridine;
(cis)-7-(5-chloro-3-pyridinyl)-2,3,4,4a,5,7a-hexahydro-1H-cyclopenta[b]pyridine;
(cis)-7-(5-bromo-3-pyridinyl)-2,3,4,4a,5,7a-hexahydro-1H-cyclopenta[b]pyridine;
(cis)-7-(5-fluoro-3-pyridinyl)-2,3,4,4a,5,7a-hexahydro-1H-cyclopenta[b]pyridine;
(cis)-7-(5-vinyl-3-pyridinyl)-2,3,4,4a,5,7a-hexahydro-1H-cyclopenta[b]pyridine;
(cis)-7-(5-methoxy-3-pyridinyl)-2,3,4,4a,5,7a-hexahydro-1H-cyclopenta[b]pyridine;
(cis)-7-(5-vinyloxy-3-pyridinyl)-2,3,4,4a,5,7a-hexahydro-1H-cyclopenta[b]pyridine;
(cis)-7-(5-ethynyl-3-pyridinyl)-2,3,4,4a,5,7a-hexahydro-1H-cyclopenta[b]pyridine;
(cis)-7-(5,6-dichloro-3-pyridinyl)-2,3,4,4a,5,7a-hexahydro-1H-cyclopenta[b]pyridine;
(cis)-7-(6-bromo-5-chloro-3-pyridinyl)-2,3,4,4a,5,7a-hexahydro-1H-cyclopenta[b]pyridine;
(cis)-5-(2,3,4,4a,5,7a-hexahydro-1H-cyclopenta[b]pyridin-7-yl)-2-methylnicotinonitrile;
(cis)-2-bromo-5-(2,3,4,4a,5,7a-hexahydro-1H-cyclopenta[b]pyridin-7-yl)nicotinonitrile;
(cis)-2-chloro-5-(2,3,4,4a,5,7a-hexahydro-1H-cyclopenta[b]pyridin-7-yl)nicotinonitrile;
(cis)-7-(6-chloro-5-methyl-3-pyridinyl)-2,3,4,4a,5,7a-hexahydro-1H-cyclopenta[b]pyridine;
(cis)-7-(6-bromo-5-methyl-3-pyridinyl)-2,3,4,4a,5,7a-hexahydro-1H-cyclopenta[b]pyridine;

(cis)-7-(5-methoxy-6-methyl-3-pyridinyl)-2,3,4,4a,5,7a-hexahydro-1H-cyclopenta[b]pyridine;
(cis)-7-(6-chloro-5-methoxy-3-pyridinyl)-2,3,4,4a,5,7a-hexahydro-1H-cyclopenta[b]pyridine;
(cis)-7-(6-bromo-5-methoxy-3-pyridinyl)-2,3,4,4a,5,7a-hexahydro-1H-cyclopenta[b]pyridine;
(cis)-7-(3-methyl-5-isoxazolyl)-2,3,4,4a,5,7a-hexahydro-1H-cyclopenta[b]pyridine;
(cis)-2-(2,3,4,4a,5,7a-hexahydro-1H-cyclopenta[b]pyridin-7-yl)furo[3,2-b]pyridine;
(cis)-7-(3-pyridinyl)-1,2,3,4,4a,5,6,8a-octahydroquinoline;
(cis)-7-(6-chloro-3-pyridinyl)-1,2,3,4,4a,5,6,8a-octahydroquinoline;
(cis)-7-(6-bromo-3-pyridinyl)-1,2,3,4,4a,5,6,8a-octahydroquinoline;
(cis)-7-(6-fluoro-3-pyridinyl)-1,2,3,4,4a,5,6,8a-octahydroquinoline;
(cis)-7-(6-methyl-3-pyridinyl)-1,2,3,4,4a,5,6,8a-octahydroquinoline;
(cis)-5-(1,2,3,4,4a,5,6,8a-octahydro-7-quinolinyl)nicotinonitrile;
(cis)-7-(5-methyl-3-pyridinyl)-1,2,3,4,4a,5,6,8a-octahydroquinoline;
(cis)-7-(5-chloro-3-pyridinyl)-1,2,3,4,4a,5,6,8a-octahydroquinoline;
(cis)-7-(5-fluoro-3-pyridinyl)-1,2,3,4,4a,5,6,8a-octahydroquinoline;
(cis)-7-(5-bromo-3-pyridinyl)-1,2,3,4,4a,5,6,8a-octahydroquinoline;
(cis)-7-(5-vinyl-3-pyridinyl)-1,2,3,4,4a,5,6,8a-octahydroquinoline;
(cis)-7-(5-methoxy-3-pyridinyl)-1,2,3,4,4a,5,6,8a-octahydroquinoline;
(cis)-7-(5-vinyloxy-3-pyridinyl)-1,2,3,4,4a,5,6,8a-octahydroquinoline;
(cis)-7-(5-ethynyl-3-pyridinyl)-1,2,3,4,4a,5,6,8a-octahydroquinoline;
(cis)-2-methyl-5-(1,2,3,4,4a,5,6,8a-octahydro-7-quinolinyl)nicotinonitrile;
(cis)-2-bromo-5-(1,2,3,4,4a,5,6,8a-octahydro-7-quinolinyl)nicotinonitrile;
(cis)-2-chloro-5-(1,2,3,4,4a,5,6,8a-octahydro-7-quinolinyl)nicotinonitrile;
(cis)-7-(5,6-dichloro-3-pyridinyl)-1,2,3,4,4a,5,6,8a-octahydroquinoline;
(cis)-7-(6-bromo-5-chloro-3-pyridinyl)-1,2,3,4,4a,5,6,8a-octahydroquinoline;
(cis)-7-(6-chloro-5-methyl-3-pyridinyl)-1,2,3,4,4a,5,6,8a-octahydroquinoline;
(cis)-7-(6-bromo-5-methyl-3-pyridinyl)-1,2,3,4,4a,5,6,8a-octahydroquinoline;
(cis)-7-(5-methoxy-6-methyl-3-pyridinyl)-1,2,3,4,4a,5,6,8a-octahydroquinoline;
(cis)-7-(6-chloro-5-methoxy-3-pyridinyl)-1,2,3,4,4a,5,6,8a-octahydroquinoline;
(cis)-7-(6-bromo-5-methoxy-3-pyridinyl)-1,2,3,4,4a,5,6,8a-octahydroquinoline;
(cis)-7-furo[3,2-b]pyridin-2-yl-1,2,3,4,4a,5,6,8a-octahydroquinoline;
(cis)-7-(3-methyl-5-isoxazolyl)-1,2,3,4,4a,5,6,8a-octahydroquinoline;
(cis)-6-(3-pyridinyl)-2,3,4,4a,5,7a-hexahydro-1H-cyclopenta[b]pyridine;
(cis)-6-(5-chloro-3-pyridinyl)-2,3,4,4a,5,7a-hexahydro-1H-cyclopenta[b]pyridine;
(cis)-6-(5-bromo-3-pyridinyl)-2,3,4,4a,5,7a-hexahydro-1H-cyclopenta[b]pyridine;
(cis)-6-(5-fluoro-3-pyridinyl)-2,3,4,4a,5,7a-hexahydro-1H-cyclopenta[b]pyridine;
(cis)-6-(5-methyl-3-pyridinyl)-2,3,4,4a,5,7a-hexahydro-1H-cyclopenta[b]pyridine;
(cis)-5-(2,3,4,4a,5,7a-hexahydro-1H-cyclopenta[b]pyridin-6-yl)nicotinonitrile;
(cis)-6-(5-methyl-3-pyridinyl)-2,3,4,4a,5,7a-hexahydro-1H-cyclopenta[b]pyridine;
(cis)-6-(5-chloro-3-pyridinyl)-2,3,4,4a,5,7a-hexahydro-1H-cyclopenta[b]pyridine;
(cis)-6-(5-fluoro-3-pyridinyl)-2,3,4,4a,5,7a-hexahydro-1H-cyclopenta[b]pyridine;
(cis)-6-(5-bromo-3-pyridinyl)-2,3,4,4a,5,7a-hexahydro-1H-cyclopenta[b]pyridine;
(cis)-6-(5-vinyl-3-pyridinyl)-2,3,4,4a,5,7a-hexahydro-1H-cyclopenta[b]pyridine;
(cis)-6-(5-methoxy-3-pyridinyl)-2,3,4,4a,5,7a-hexahydro-1H-cyclopenta[b]pyridine;
(cis)-6-(5-vinyloxy-3-pyridinyl)-2,3,4,4a,5,7a-hexahydro-1H-cyclopenta[b]pyridine;
(cis)-6-(5-ethynyl-3-pyridinyl)-2,3,4,4a,5,7a-hexahydro-1H-cyclopenta[b]pyridine;
(cis)-6-(5,6-dichloro-3-pyridinyl)-2,3,4,4a,5,7a-hexahydro-1H-cyclopenta[b]pyridine;
(cis)-6-(6-bromo-5-chloro-3-pyridinyl)-2,3,4,4a,5,7a-hexahydro-1H-cyclopenta[b]pyridine;
(cis)-5-(2,3,4,4a,5,7a-hexahydro-1H-cyclopenta[b]pyridin-6-yl)-2-methylnicotinonitrile;
(cis)-2-bromo-5-(2,3,4,4a,5,7a-hexahydro-1H-cyclopenta[b]pyridin-6-yl)nicotinonitrile;
(cis)-2-chloro-5-(2,3,4,4a,5,7a-hexahydro-1H-cyclopenta[b]pyridin-6-yl)nicotinonitrile;
(cis)-6-(6-chloro-5-methyl-3-pyridinyl)-2,3,4,4a,5,7a-hexahydro-1H-cyclopenta[b]pyridine;
(cis)-6-(6-bromo-5-methyl-3-pyridinyl)-2,3,4,4a,5,7a-hexahydro-1H-cyclopenta[b]pyridine;
(cis)-6-(5-methoxy-6-methyl-3-pyridinyl)-2,3,4,4a,5,7a-hexahydro-1H-cyclopenta[b]pyridine;
(cis)-6-(6-chloro-5-methoxy-3-pyridinyl)-2,3,4,4a,5,7a-hexahydro-1H-cyclopenta[b]pyridine;
(cis)-6-(6-bromo-5-methoxy-3-pyridinyl)-2,3,4,4a,5,7a-hexahydro-1H-cyclopenta[b]pyridine;
(cis)-6-(3-methyl-5-isoxazolyl)-2,3,4,4a,5,7a-hexahydro-1H-cyclopenta[b]pyridine;
(cis)-2-(2,3,4,4a,5,7a-hexahydro-1H-cyclopenta[b]pyridin-6-yl)furo[3,2-b]pyridine;
(cis)-7-(3-pyridinyl)-1,2,3,4,4a,5,8,8a-octahydroquinoline;
(cis)-7-(6-bromo-3-pyridinyl)-1,2,3,4,4a,5,8,8a-octahydroquinoline;
(cis)-7-(6-chloro-3-pyridinyl)-1,2,3,4,4a,5,8,8a-octahydroquinoline;
(cis)-7-(6-fluoro-3-pyridinyl)-1,2,3,4,4a,5,8,8a-octahydroquinoline;
(cis)-7-(6-methyl-3-pyridinyl)-1,2,3,4,4a,5,8,8a-octahydroquinoline;
(cis)-5-(1,2,3,4,4a,5,8,8a-octahydro-7-quinolinyl)nicotinonitrile;
(cis)-7-(5-methyl-3-pyridinyl)-1,2,3,4,4a,5,8,8a-octahydroquinoline;
(cis)-7-(5-chloro-3-pyridinyl)-1,2,3,4,4a,5,8,8a-octahydroquinoline;
(cis)-7-(5-fluoro-3-pyridinyl)-1,2,3,4,4a,5,8,8a-octahydroquinoline;
(cis)-7-(5-bromo-3-pyridinyl)-1,2,3,4,4a,5,8,8a-octahydroquinoline;
(cis)-7-(5-vinyl-3-pyridinyl)-1,2,3,4,4a,5,8,8a-octahydroquinoline;

(cis)-7-(5-methoxy-3-pyridinyl)-1,2,3,4,4a,5,8,8a-octahydroquinoline;
(cis)-7-(5-vinyloxy-3-pyridinyl)-1,2,3,4,4a,5,8,8a-octahydroquinoline;
(cis)-7-(5-ethynyl-3-pyridinyl)-1,2,3,4,4a,5,8,8a-octahydroquinoline;
(cis)-7-(5,6-dichloro-3-pyridinyl)-1,2,3,4,4a,5,8,8a-octahydroquinoline;
(cis)-7-(6-bromo-5-chloro-3-pyridinyl)-1,2,3,4,4a,5,8,8a-octahydroquinoline;
(cis)-2-methyl-5-(1,2,3,4,4a,5,8,8a-octahydro-7-quinolinyl)nicotinonitrile;
(cis)-2-bromo-5-(1,2,3,4,4a,5,8,8a-octahydro-7-quinolinyl)nicotinonitrile;
(cis)-2-chloro-5-(1,2,3,4,4a,5,8,8a-octahydro-7-quinolinyl)nicotinonitrile;
(cis)-7-(6-chloro-5-methyl-3-pyridinyl)-1,2,3,4,4a,5,8,8a-octahydroquinoline;
(cis)-7-(6-bromo-5-methyl-3-pyridinyl)-1,2,3,4,4a,5,8,8a-octahydroquinoline;
(cis)-7-(5-methoxy-6-methyl-3-pyridinyl)-1,2,3,4,4a,5,8,8a-octahydroquinoline;
(cis)-7-(6-chloro-5-methoxy-3-pyridinyl)-1,2,3,4,4a,5,8,8a-octahydroquinoline;
(cis)-7-(6-bromo-5-methoxy-3-pyridinyl)-1,2,3,4,4a,5,8,8a-octahydroquinoline;
(cis)-7-(3-methyl-5-isoxazolyl)-1,2,3,4,4a,5,8,8a-octahydroquinoline;
(cis)-7-furo[3,2-b]pyridin-2-yl-1,2,3,4,4a,5,8,8a-octahydroquinoline;
(cis)-6-(3-pyridinyl)-2,3,4,4a,7,7a-hexahydro-1H-cyclopenta[b]pyridine;
(cis)-6-(6-chloro-3-pyridinyl)-2,3,4,4a,7,7a-hexahydro-1H-cyclopenta[b]pyridine;
(cis)-6-(6-fluoro-3-pyridinyl)-2,3,4,4a,7,7a-hexahydro-1H-cyclopenta[b]pyridine;
(cis)-6-(6-bromo-3-pyridinyl)-2,3,4,4a,7,7a-hexahydro-1H-cyclopenta[b]pyridine;
(cis)-6-(6-methyl-3-pyridinyl)-2,3,4,4a,7,7a-hexahydro-1H-cyclopenta[b]pyridine;
(cis)-5-(2,3,4,4a,7,7a-hexahydro-1H-cyclopenta[b]pyridin-6-yl)nicotinonitrile;
(cis)-6-(5-chloro-3-pyridinyl)-2,3,4,4a,7,7a-hexahydro-1H-cyclopenta[b]pyridine;
(cis)-6-(5-methyl-3-pyridinyl)-2,3,4,4a,7,7a-hexahydro-1H-cyclopenta[b]pyridine;
(cis)-6-(5-bromo-3-pyridinyl)-2,3,4,4a,7,7a-hexahydro-1H-cyclopenta[b]pyridine;
(cis)-6-(5-fluoro-3-pyridinyl)-2,3,4,4a,7,7a-hexahydro-1H-cyclopenta[b]pyridine;
(cis)-6-(5-vinyl-3-pyridinyl)-2,3,4,4a,7,7a-hexahydro-1H-cyclopenta[b]pyridine;
(cis)-6-(5-methoxy-3-pyridinyl)-2,3,4,4a,7,7a-hexahydro-1H-cyclopenta[b]pyridine;
(cis)-6-(5-vinyloxy-3-pyridinyl)-2,3,4,4a,7,7a-hexahydro-1H-cyclopenta[b]pyridine;
(cis)-6-(5-ethynyl-3-pyridinyl)-2,3,4,4a,7,7a-hexahydro-1H-cyclopenta[b]pyridine;
(cis)-6-(5,6-dichloro-3-pyridinyl)-2,3,4,4a,7,7a-hexahydro-1H-cyclopenta[b]pyridine;
(cis)-6-(6-bromo-5-chloro-3-pyridinyl)-2,3,4,4a,7,7a-hexahydro-1H-cyclopenta[b]pyridine;
(cis)-5-(2,3,4,4a,7,7a-hexahydro-1H-cyclopenta[b]pyridin-6-yl)-2-methylnicotinonitrile;
(cis)-2-bromo-5-(2,3,4,4a,7,7a-hexahydro-1H-cyclopenta[b]pyridin-6-yl)nicotinonitrile;
(cis)-2-chloro-5-(2,3,4,4a,7,7a-hexahydro-1H-cyclopenta[b]pyridin-6-yl)nicotinonitrile;
(cis)-6-(6-chloro-5-methyl-3-pyridinyl)-2,3,4,4a,7,7a-hexahydro-1H-cyclopenta[b]pyridine;
(cis)-6-(6-bromo-5-methyl-3-pyridinyl)-2,3,4,4a,7,7a-hexahydro-1H-cyclopenta[b]pyridine;
(cis)-6-(5-methoxy-6-methyl-3-pyridinyl)-2,3,4,4a,7,7a-hexahydro-1H-cyclopenta[b]pyridine;
(cis)-6-(6-chloro-5-methoxy-3-pyridinyl)-2,3,4,4a,7,7a-hexahydro-1H-cyclopenta[b]pyridine;
(cis)-6-(6-bromo-5-methoxy-3-pyridinyl)-2,3,4,4a,7,7a-hexahydro-1H-cyclopenta[b]pyridine;
(cis)-6-(3-methyl-5-isoxazolyl)-2,3,4,4a,7,7a-hexahydro-1H-cyclopenta[b]pyridine;
(cis)-2-(2,3,4,4a,7,7a-hexahydro-1H-cyclopenta[b]pyridin-6-yl)furo[3,2-b]pyridine; or a pharmaceutically acceptable salt, amide, ester and prodrug thereof.

In another embodiment of the present invention, compounds of formula (VI) are disclosed

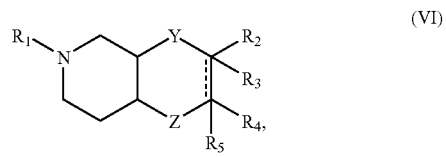

(VI)

or a pharmaceutically acceptable salt, amide, ester and prodrug thereof wherein Y, Z, $R_1$, $R_2$, $R_3$, $R_4$ and $R_5$ are as defined in formula (I).

In another embodiment of the present invention, compounds of formula (VI) are disclosed wherein Y is a covalent bond; Z is a covalent bond; and $R_1$, $R_2$, $R_3$, $R_4$, and $R_5$ are as defined in formula (I).

In another embodiment of the present invention, compounds of formula (VI) are disclosed wherein Y is a covalent bond; Z is $CH_2$; and $R_1$, $R_2$, $R_3$, $R_4$, and $R_5$ are as defined in formula (I).

In another embodiment of the present invention, compounds of formula (VI) are disclosed wherein ----- represents a double bond; Y is a covalent bond; Z is $CH_2$; $R_2$ is hydrogen; $R_3$ and $R_5$ are absent; $R_4$ is heterocycle; and $R_1$ is as defined in formula (I).

In another embodiment of the present invention, compounds of formula (VI) are disclosed wherein ----- represents a double bond; Y is a covalent bond; Z is $CH_2$; $R_2$ is hydrogen; $R_3$ and $R_5$ are absent; $R_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (VI) are disclosed wherein ---- represents a double bond; Y is a covalent bond; Z is CH$_2$; R$_2$ is hydrogen; R$_3$ and R$_5$ are absent; R$_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; and R$_1$, R$_{10}$, and R$_{11}$ are as defined in formula (I).

In another embodiment of the present invention, compounds of formula (VI) are disclosed wherein ---- represents a double bond; Y is a covalent bond; Z is CH$_2$; R$_2$ is hydrogen; R$_3$ and R$_5$ are absent; R$_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and R$_1$ is as defined in formula (I).

In another embodiment of the present invention, compounds of formula (VI) are disclosed wherein ---- represents a double bond; Y is a covalent bond; Z is CH$_2$; R$_2$ is hydrogen; R$_3$ and R$_5$ are absent; R$_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and R$_1$ is as defined in formula (I).

In another embodiment of the present invention, compounds of formula (VI) are disclosed wherein ---- represents a double bond; Y is a covalent bond; Z is CH$_2$; R$_2$ is heterocycle; R$_3$ and R$_5$ are absent; R$_4$ is hydrogen; and R$_1$ is as defined in formula (I).

In another embodiment of the present invention, compounds of formula (VI) are disclosed wherein ---- represents a double bond; Y is a covalent bond; Z is CH$_2$; R$_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_3$ and R$_5$ are absent; R$_4$ is hydrogen; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (VI) are disclosed wherein ---- represents a double bond; Y is a covalent bond; Z is CH$_2$; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (VI) are disclosed wherein ---- represents a double bond; Y is a covalent bond; Z is CH$_2$; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (VI) are disclosed wherein ---- represents a double bond; Y is a covalent bond; Z is CH$_2$; R$_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; R$_3$ and R$_5$ are absent; R$_4$ is hydrogen; and R$_1$ is as defined in formula (I).

In another embodiment of the present invention, compounds of formula (VI) are disclosed wherein Y is CH$_2$; Z is a covalent bond; and R$_1$, R$_2$, R$_3$, R$_4$, and R$_5$ are as defined in formula (I).

In another embodiment of the present invention, compounds of formula (VI) are disclosed wherein ---- represents a double bond; Y is CH$_2$; Z is a covalent bond; R$_2$ is heterocycle; R$_3$ and R$_5$ are absent; R$_4$ is hydrogen; and R$_1$ is as defined in formula (I).

In another embodiment of the present invention, compounds of formula (VI) are disclosed wherein ---- represents a double bond; Y is CH$_2$; Z is a covalent bond; R$_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrroyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_3$ and R$_5$ are absent; R$_4$ is hydrogen; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (VI) are disclosed wherein ----- represents a double bond; Y is CH$_2$; Z is a covalent bond; R$_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; R$_3$ and R$_5$ are absent; R$_4$ is hydrogen; and R$_1$, R$_{10}$, and R$_{11}$ are as defined in formula (I).

In another embodiment of the present invention, compounds of formula (VI) are disclosed wherein ----- represents a double bond; Y is CH$_2$; Z is a covalent bond; R$_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; R$_3$ and R$_5$ are absent; R$_4$ is hydrogen; and R$_1$ is as defined in formula (I).

In another embodiment of the present invention, compounds of formula (VI) are disclosed wherein ----- represents a double bond; Y is CH$_2$; Z is a covalent bond; R$_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; R$_3$ and R$_5$ are absent; R$_4$ is hydrogen; and R$_1$ is as defined in formula (I).

In another embodiment of the present invention, compounds of formula (VI) are disclosed wherein Y is a covalent bond; Z is CH$_2$CH$_2$; and R$_1$, R$_2$, R$_3$, R$_4$, and R$_5$ are as defined in formula (I).

In another embodiment of the present invention, compounds of formula (VI) are disclosed wherein ----- represents a double bond; Y is a covalent bond; Z is CH$_2$CH$_2$; R$_2$ is hydrogen; R$_3$ and R$_5$ are absent; R$_4$ is heterocycle; and R$_1$ is as defined in formula (I).

In another embodiment of the present invention, compounds of formula (VI) are disclosed wherein ----- represents a double bond; Y is a covalent bond; Z is CH$_2$CH$_2$; R$_2$ is hydrogen; R$_3$ and R$_5$ are absent; R$_4$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, or —S(O)$_2$R$_{12}$; R$_{12}$, R$_{13}$, and R$_{14}$ are independently selected from hydrogen, alkyl, aryl, or arylalkyl; and R$_1$, R$_{10}$, and R$_{11}$ are as defined in formula (I).

In another embodiment of the present invention, compounds of formula (VI) are disclosed wherein ----- represents a double bond; Y is a covalent bond; Z is CH$_2$CH$_2$; R$_2$ is hydrogen; R$_3$ and R$_5$ are absent; R$_4$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, (NR$_{10}$R$_{11}$)sulfonyl, or —C(NH)NR$_{10}$R$_{11}$; and R$_1$, R$_{10}$, and R$_{11}$ are as defined in formula (I).

In another embodiment of the present invention, compounds of formula (VI) are disclosed wherein ----- represents a double bond; Y is a covalent bond; Z is CH$_2$CH$_2$; R$_2$ is hydrogen; R$_3$ and R$_5$ are absent; R$_4$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; and R$_1$ is as defined in formula (I).

In another embodiment of the present invention, compounds of formula (VI) are disclosed wherein ----- represents a double bond; Y is a covalent bond; Z is CH$_2$CH$_2$; R$_2$ is hydrogen; R$_3$ and R$_5$ are absent; R$_4$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; and $R_1$ is as defined in formula (I).

In another embodiment of the present invention, compounds of formula (VI) are disclosed wherein ----- represents a double bond; Y is a covalent bond; Z is $CH_2CH_2$; $R_2$ is heterocycle; $R_3$ and $R_5$ are absent; $R_4$ is hydrogen; and $R_1$ is as defined in formula (I).

In another embodiment of the present invention, compounds of formula (VI) are disclosed wherein ----- represents a double bond; Y is a covalent bond; Z is $CH_2CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_{12}$)$NR_{13}R_{14}$, —$CH_2$C($NR_{12}$)$NR_{13}R_{14}$, —C($NOR_{12}$)$R_{13}$, —C(NCN)$R_{12}$, —C($NNR_{12}R_{13}$)$R_{14}$, —S(O)$_2OR_{12}$, or —S(O)$_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (VI) are disclosed wherein ----- represents a double bond; Y is a covalent bond; Z is $CH_2CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (VI) are disclosed wherein ----- represents a double bond; Y is a covalent bond; Z is $CH_2CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (VI) are disclosed wherein ----- represents a double bond; Y is a covalent bond; Z is $CH_2CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (VI) are disclosed wherein Y is $CH_2$; Z is $CH_2$; and $R_1$, $R_2$, $R_3$, $R_4$, and $R_5$ are as defined in formula (I).

In another embodiment of the present invention, compounds of formula (VI) are disclosed wherein ----- represents a double bond; Y is $CH_2$; Z is $CH_2$; $R_2$ is heterocycle; $R_3$ and $R_5$ are absent; $R_4$ is hydrogen; and $R_1$ is as defined in formula (I).

In another embodiment of the present invention, compounds of formula (VI) are disclosed wherein ----- represents a double bond; Y is $CH_2$; Z is $CH_2$; $R_2$ is heterocycle wherein the heterocycle is selected from furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl or thieno[2,3-b]pyridinyl wherein the heterocycle is substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)$NR_{10}R_{11}$, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)sulfonyl, —$NR_{12}S(O)_2R_{13}$, —C($NR_2$)$NR_{13}R_{14}$, —$CH_2$C($NR_{12}$)$NR_{13}R_{14}$, —C($NOR_{12}$)$R_{13}$, —C(NCN)$R_{12}$, —C($NNR_{12}R_{13}$)$R_{14}$, —S(O)$_2OR_{12}$, or —S(O)$_2R_{12}$; $R_3$ and $R_5$ are absent; $R_4$ is hydrogen; $R_{12}$, $R_{13}$, and $R_{14}$ are independently selected from hydrogen, alkyl, aryl, or arylalkyl; and $R_1$, $R_{10}$, and $R_{11}$ are as defined in formula (I).

In another embodiment of the present invention, compounds of formula (VI) are disclosed wherein ----- represents a double bond; Y is $CH_2$; Z is $CH_2$; $R_2$ is heterocycle wherein the heterocycle is selected from imidazolyl, isoxazolyl, pyridinyl, tetrazolyl, thiadiazolyl, thiazolyl, thienyl, imidazo[1,2-a]pyridinyl, thieno[3,2-b]pyridinyl or thieno[2,3-b]pyridinyl wherein the heterocycle is substituted with 0, 1, or 2 substituents independently selected from alkenyl, alkenyloxy, alkoxy, alkyl, alkynyl, cyano, halogen, nitro, ($NR_{10}R_{11}$)sulfonyl, or —C(NH)$NR_{10}R_{11}$; $R_3$ and $R_5$ are absent; $R_4$ is hydrogen; and $R_1$, $R_{10}$, and $R_{11}$ are as defined in formula (I).

In another embodiment of the present invention, compounds of formula (VI) are disclosed wherein ----- represents a double bond; Y is $CH_2$; Z is $CH_2$; $R_2$ is heterocycle wherein the heterocycle is pyridinyl substituted with 0, 1, or 2 substituents independently selected from alkenyl, alkenyloxy, alkoxy, alkyl, alkynyl, cyano, halogen, or nitro; $R_3$ and $R_5$ are absent; $R_4$ is hydrogen; and $R_1$ is as defined in formula (I).

In another embodiment of the present invention, compounds of formula (VI) are disclosed wherein ----- represents a double bond; Y is $CH_2$; Z is $CH_2$; $R_2$ is heterocycle wherein the heterocycle is selected from 3-pyridinyl, 6-bromo-3-pyridinyl, 6-chloro-3-pyridinyl, 6-fluoro-3 pyridinyl, 6-methyl-3-pyridinyl, 5-cyano-3-pyridinyl, 5-methyl-3-pyridinyl, 5-chloro-3-pyridinyl, 5-fluoro-3-pyridinyl, 5-bromo-3-pyridinyl, 5-vinyl-3-pyridinyl, 5-methoxy-3-pyridinyl, 5-vinyloxy-3-pyridinyl, 5-ethynyl-3-pyridinyl, 5,6-dichloro-3-pyridinyl, 6-bromo-5-chloro-3-pyridinyl, 5-cyano-6-methyl-3-pyridinyl, 6-chloro-5-cyano-3-pyridinyl, 6-bromo-5-cyano-3-pyridinyl, 6-chloro-5-methyl-3-pyridinyl, 6-bromo-5-methyl-3-pyridinyl, 5-methoxy-6-methyl-3-pyridinyl, 6-chloro-5-methoxy-3-pyridinyl, or 6-bromo-5-methoxy-3-pyridinyl; $R_3$ and $R_5$ are absent; $R_4$ is hydrogen; and $R_1$ is as defined in formula (I).

In another embodiment of the present invention, compounds of formula (VI) are disclosed wherein Y is $CH_2CH_2$; Z is a covalent bond; and $R_1$, $R_2$, $R_3$, $R_4$, and $R_5$ are as defined in formula (I).

Representative compounds of formula (VI) include, but are not limited to:
(cis)-8-(3-pyridinyl)-1,2,3,4,4a,5,6,8a-octahydroisoquinoline;
(cis)-8-(6-chloro-3-pyridinyl)-1,2,3,4,4a,5,6,8a-octahydroisoquinoline;
(cis)-8-(6-bromo-3-pyridinyl)-1,2,3,4,4a,5,6,8a-octahydroisoquinoline;
(cis)-8-(6-fluoro-3-pyridinyl)-1,2,3,4,4a,5,6,8a-octahydroisoquinoline;
(cis)-8-(6-methyl-3-pyridinyl)-1,2,3,4,4a,5,6,8a-octahydroisoquinoline;
(cis)-5-(1,2,3,4,4a,5,6,8a-octahydro-8-isoquinolinyl)nicotinonitrile;
(cis)-8-(5-chloro-3-pyridinyl)-1,2,3,4,4a,5,6,8a-octahydroisoquinoline;
(cis)-8-(5-bromo-3-pyridinyl)-1,2,3,4,4a,5,6,8a-octahydroisoquinoline;
(cis)-8-(5-fluoro-3-pyridinyl)-1,2,3,4,4a,5,6,8a-octahydroisoquinoline;
(cis)-8-(5-methyl-3-pyridinyl)-1,2,3,4,4a,5,6,8a-octahydroisoquinoline;
(cis)-8-(5-vinyl-3-pyridinyl)-1,2,3,4,4a,5,6,8a-octahydroisoquinoline;
(cis)-8-(5-methoxy-3-pyridinyl)-1,2,3,4,4a,5,6,8a-octahydroisoquinoline;
(cis)-8-(5-vinyloxy-3-pyridinyl)-1,2,3,4,4a,5,6,8a-octahydroisoquinoline;
(cis)-8-(5-ethynyl-3-pyridinyl)-1,2,3,4,4a,5,6,a-octahydroisoquinoline;
(cis)-8-(5,6-dichloro-3-pyridinyl)-1,2,3,4,4a,5,6,8a-octahydroisoquinoline;
(cis)-8-(6-bromo-5-chloro-3-pyridinyl)-1,2,3,4,4a,5,6,8a-octahydroisoquinoline;
(cis)-2-methyl-5-(c1,2,3,4,4a,5,6,8a-octahydro-8-isoquinolinyl)nicotinonitrile;
(cis)-2-bromo-5-(1,2,3,4,4a,5,6,8a-octahydro-8-isoquinolinyl)nicotinonitrile;
(cis)-2-chloro-5-(1,2,3,4,4a,5,6,8a-octahydro-8-isoquinolinyl)nicotinonitrile;
(cis)-8-(6-chloro-5-methyl-3-pyridinyl)-1,2,3,4,4a,5,6,8a-octahydroisoquinoline;
(cis)-8-(6-bromo-5-methyl-3-pyridinyl)-1,2,3,4,4a,5,6,8a-octahydroisoquinoline;
(cis)-8-(5-methoxy-6-methyl-3-pyridinyl)-1,2,3,4,4a,5,6,8a-octahydroisoquinoline;
(cis)-8-(6-bromo-5-methoxy-3-pyridinyl)-1,2,3,4,4a,5,6,8a-octahydroisoquinoline;
(cis)-8-(6-chloro-5-methoxy-3-pyridinyl)-1,2,3,4,4a,5,6,8a-octahydroisoquinoline;
(cis)-8-(3-methyl-5-isoxazolyl)-1,2,3,4,4a,5,6,8a-octahydroisoquinoline;
(cis)-8-furo[3,2-b]pyridin-2-yl-1,2,3,4,4a,5,6,8a-octahydroisoquinoline;
(cis)-7-(3-pyridinyl)-2,3,4,4a,5,7a-hexahydro-1H-cyclopenta[c]pyridine;
(cis)-7-(6-chloro-3-pyridinyl)-2,3,4,4a,5,7a-hexahydro-1H-cyclopenta[c]pyridine;
(cis)-7-(6-bromo-3-pyridinyl)-2,3,4,4a,5,7a-hexahydro-1H-cyclopenta[c]pyridine;
(cis)-7-(6-fluoro-3-pyridinyl)-2,3,4,4a,5,7a-hexahydro-1H-cyclopenta[c]pyridine;
(cis)-7-(6-methyl-3-pyridinyl)-2,3,4,4a,5,7a-hexahydro-1H-cyclopenta[c]pyridine;
(cis)-5-(2,3,4,4a,5,7a-hexahydro-1H-cyclopenta[c]pyridin-7-yl)nicotinonitrile;
(cis)-7-(5-methyl-3-pyridinyl)-2,3,4,4a,5,7a-hexahydro-1H-cyclopenta[c]pyridine;
(cis)-7-(5-chloro-3-pyridinyl)-2,3,4,4a,5,7a-hexahydro-1H-cyclopenta[c]pyridine;
(cis)-7-(5-bromo-3-pyridinyl)-2,3,4,4a,5,7a-hexahydro-1H-cyclopenta[c]pyridine;
(cis)-7-(5-fluoro-3-pyridinyl)-2,3,4,4a,5,7a-hexahydro-1H-cyclopenta[c]pyridine;
(cis)-7-(5-vinyl-3-pyridinyl)-2,3,4,4a,5,7a-hexahydro-1H-cyclopenta[c]pyridine;
(cis)-7-(5-methoxy-3-pyridinyl)-2,3,4,4a,5,7a-hexahydro-1H-cyclopenta[c]pyridine;
(cis)-7-(5-vinyloxy-3-pyridinyl)-2,3,4,4a,5,7a-hexahydro-1H-cyclopenta[c]pyridine;
(cis)-7-(5-ethynyl-3-pyridinyl)-2,3,4,4a,5,7a-hexahydro-1H-cyclopenta[c]pyridine;
(cis)-5-(2,3,4,4a,5,7a-hexahydro-1H-cyclopenta[c]pyridin-7-yl)-2-methylnicotinonitrile;
(cis)-2-bromo-5-(2,3,4,4a,5,7a-hexahydro-1H-cyclopenta[c]pyridin-7-yl)nicotinonitrile;
(cis)-2-chloro-5-(2,3,4,4a,5,7a-hexahydro-1H-cyclopenta[c]pyridin-7-yl)nicotinonitrile;
(cis)-7-(5,6-dichloro-3-pyridinyl)-2,3,4,4a,5,7a-hexahydro-1H-cyclopenta[c]pyridine;
(cis)-7-(6-bromo-5-chloro-3-pyridinyl)-2,3,4,4a,5,7a-hexahydro-1H-cyclopenta[c]pyridine;
(cis)-7-(6-chloro-5-methyl-3-pyridinyl)-2,3,4,4a,5,7a-hexahydro-1H-cyclopenta[c]pyridine;
(cis)-7-(6-bromo-5-methyl-3-pyridinyl)-2,3,4,4a,5,7a-hexahydro-1H-cyclopenta[c]pyridine;
(cis)-7-(5-methoxy-6-methyl-3-pyridinyl)-2,3,4,4a,5,7a-hexahydro-1H-cyclopenta[c]pyridine;
(cis)-7-(6-chloro-5-methoxy-3-pyridinyl)-2,3,4,4a,5,7a-hexahydro-1H-cyclopenta[c]pyridine;
(cis)-7-(6-bromo-5-methoxy-3-pyridinyl)-2,3,4,4a,5,7a-hexahydro-1H-cyclopenta[c]pyridine;
(cis)-2-(2,3,4,4a,5,7a-hexahydro-1H-cyclopenta[c]pyridin-7-yl)furo[3,2-b]pyridine;
(cis)-7-(3-methyl-5-isoxazolyl)-2,3,4,4a,5,7a-hexahydro-1H-cyclopenta[c]pyridine;
(cis)-7-(3-pyridinyl)-1,2,3,4,4a,5,6,8a-octahydroisoquinoline;
(cis)-7-(6-chloro-3-pyridinyl)-1,2,3,4,4a,5,6,8a-octahydroisoquinoline;

(cis)-7-(6-bromo-3-pyridinyl)-1,2,3,4,4a,5,6,8a-octahydroisoquinoline;
(cis)-7-(6-fluoro-3-pyridinyl)-1,2,3,4,4a,5,6,8a-octahydroisoquinoline;
(cis)-7-(6-methyl-3-pyridinyl)-1,2,3,4,4a,5,6,8a-octahydroisoquinoline;
(cis)-5-(1,2,3,4,4a,5,6,8a-octahydro-7-isoquinolinyl)nicotinonitrile;
(cis)-7-(5-methyl-3-pyridinyl)-1,2,3,4,4a,5,6,8a-octahydroisoquinoline;
(cis)-7-(5-chloro-3-pyridinyl)-1,2,3,4,4a,5,6,8a-octahydroisoquinoline;
(cis)-7-(5-bromo-3-pyridinyl)-1,2,3,4,4a,5,6,8a-octahydroisoquinoline;
(cis)-7-(5-fluoro-3-pyridinyl)-1,2,3,4,4a,5,6,8a-octahydroisoquinoline;
(cis)-7-(5-vinyl-3-pyridinyl)-1,2,3,4,4a,5,6,8a-octahydroisoquinoline;
(cis)-7-(5-methoxy-3-pyridinyl)-1,2,3,4,4a,5,6,8a-octahydroisoquinoline;
(cis)-7-(5-vinyloxy-3-pyridinyl)-1,2,3,4,4a,5,6,8a-octahydroisoquinoline;
(cis)-7-(5-ethynyl-3-pyridinyl)-1,2,3,4,4a,5,6,8a-octahydroisoquinoline;
(cis)-7-(5,6-dichloro-3-pyridinyl)-1,2,3,4,4a,5,6,8a-octahydroisoquinoline;
(cis)-7-(6-bromo-5-chloro-3-pyridinyl)-1,2,3,4,4a,5,6,8a-octahydroisoquinoline;
(cis)-2-methyl-5-(1,2,3,4,4a,5,6,8a-octahydro-7-isoquinolinyl)nicotinonitrile;
(cis)-2-bromo-5-(1,2,3,4,4a,5,6,8a-octahydro-7-isoquinolinyl)nicotinonitrile;
(cis)-2-chloro-5-(1,2,3,4,4a,5,6,8a-octahydro-7-isoquinolinyl)nicotinonitrile;
(cis)-7-(6-chloro-5-methyl-3-pyridinyl)-1,2,3,4,4a,5,6,8a-octahydroisoquinoline;
(cis)-7-(6-bromo-5-methyl-3-pyridinyl)-1,2,3,4,4a,5,6,8a-octahydroisoquinoline;
(cis)-7-(5-methoxy-6-methyl-3-pyridinyl)-1,2,3,4,4a,5,6,8a-octahydroisoquinoline;
(cis)-7-(6-chloro-5-methoxy-3-pyridinyl)-1,2,3,4,4a,5,6,8a-octahydroisoquinoline;
(cis)-7-(6-bromo-5-methoxy-3-pyridinyl)-1,2,3,4,4a,5,6,8a-octahydroisoquinoline;
(cis)-8-(3-methyl-5-isoxazolyl)-1,2,3,4,4a,5,6,8a-octahydroisoquinoline;
(cis)-8-furo[3,2-b]pyridin-2-yl-1,2,3,4,4a,5,6,8a-octahydroisoquinoline;
(cis)-6-(3-pyridinyl)-2,3,4,4a,5,7a-hexahydro-1H-cyclopenta[c]pyridine;
(cis)-6-(6-chloro-3-pyridinyl)-2,3,4,4a,5,7a-hexahydro-1H-cyclopenta[c]pyridine;
(cis)-6-(6-bromo-3-pyridinyl)-2,3,4,4a,5,7a-hexahydro-1H-cyclopenta[c]pyridine;
(cis)-6-(6-fluoro-3-pyridinyl)-2,3,4,4a,5,7a-hexahydro-1H-cyclopenta[c]pyridine;
(cis)-6-(6-methyl-3-pyridinyl)-2,3,4,4a,5,7a-hexahydro-1H-cyclopenta[c]pyridine;
(cis)-5-(2,3,4,4a,5,7a-hexahydro-1H-cyclopenta[c]pyridin-6-yl)nicotinonitrile;
(cis)-6-(5-chloro-3-pyridinyl)-2,3,4,4a,5,7a-hexahydro-1H-cyclopenta[c]pyridine;
(cis)-6-(5-bromo-3-pyridinyl)-2,3,4,4a,5,7a-hexahydro-1H-cyclopenta[c]pyridine;
(cis)-6-(5-fluoro-3-pyridinyl)-2,3,4,4a,5,7a-hexahydro-1H-cyclopenta[c]pyridine;
(cis)-6-(5-methyl-3-pyridinyl)-2,3,4,4a,5,7a-hexahydro-1H-cyclopenta[c]pyridine;
(cis)-6-(5-vinyl-3-pyridinyl)-2,3,4,4a,5,7a-hexahydro-1H-cyclopenta[c]pyridine;
(cis)-6-(5-methoxy-3-pyridinyl)-2,3,4,4a,5,7a-hexahydro-1H-cyclopenta[c]pyridine;
(cis)-6-(5-vinyloxy-3-pyridinyl)-2,3,4,4a,5,7a-hexahydro-1H-cyclopenta[c]pyridine;
(cis)-6-(5-ethynyl-3-pyridinyl)-2,3,4,4a,5,7a-hexahydro-1H-cyclopenta[c]pyridine;
(cis)-6-(5,6-dichloro-3-pyridinyl)-2,3,4,4a,5,7a-hexahydro-1H-cyclopenta[c]pyridine;
(cis)-6-(6-bromo-5-chloro-3-pyridinyl)-2,3,4,4a,5,7a-hexahydro-1H-cyclopenta[c]pyridine;
(cis)-5-(2,3,4,4a,5,7a-hexahydro-1H-cyclopenta[c]pyridin-6-yl)-2-methylnicotinonitrile;
(cis)-2-chloro-5-(2,3,4,4a,5,7a-hexahydro-1H-cyclopenta[c]pyridin-6-yl)nicotinonitrile;
(cis)-2-bromo-5-(2,3,4,4a,5,7a-hexahydro-1H-cyclopenta[c]pyridin-6-yl)nicotinonitrile;
(cis)-6-(6-chloro-5-methyl-3-pyridinyl)-2,3,4,4a,5,7a-hexahydro-1H-cyclopenta[c]pyridine;
(cis)-6-(6-bromo-5-methyl-3-pyridinyl)-2,3,4,4a,5,7a-hexahydro-1H-cyclopenta[c]pyridine;
(cis)-6-(5-methoxy-6-methyl-3-pyridinyl)-2,3,4,4a,5,7a-hexahydro-1H-cyclopenta[c]pyridine;
(cis)-6-(6-bromo-5-methoxy-3-pyridinyl)-2,3,4,4a,5,7a-hexahydro-1H-cyclopenta[c]pyridine;
(cis)-6-(6-chloro-5-methoxy-3-pyridinyl)-2,3,4,4a,5,7a-hexahydro-1H-cyclopenta[c]pyridine;
(cis)-6-(3-methyl-5-isoxazolyl)-2,3,4,4a,5,7a-hexahydro-1H-cyclopenta[c]pyridine;
(cis)-2-(2,3,4,4a,5,7a-hexahydro-1H-cyclopenta[c]pyridin-6-yl)furo[3,2-b]pyridine;
(cis)-7-(3-pyridinyl)-1,2,3,4,4a,5,8,8a-octahydroisoquinoline;
(cis)-7-(6-methyl-3-pyridinyl)-1,2,3,4,4a,5,8,8a-octahydroisoquinoline;
(cis)-7-(6-chloro-3-pyridinyl)-1,2,3,4,4a,5,8,8a-octahydroisoquinoline;
(cis)-7-(6-bromo-3-pyridinyl)-1,2,3,4,4a,5,8,8a-octahydroisoquinoline;
(cis)-7-(6-fluoro-3-pyridinyl)-1,2,3,4,4a,5,8,8a-octahydroisoquinoline;
(cis)-5-(1,2,3,4,4a,5,8,8a-octahydro-7-isoquinolinyl)nicotinonitrile;
(cis)-7-(5-methyl-3-pyridinyl)-1,2,3,4,4a,5,8,8a-octahydroisoquinoline;
(cis)-7-(5-chloro-3-pyridinyl)-1,2,3,4,4a,5,8,8a-octahydroisoquinoline;
(cis)-7-(5-bromo-3-pyridinyl)-1,2,3,4,4a,5,8,8a-octahydroisoquinoline;
(cis)-7-(5-fluoro-3-pyridinyl)-1,2,3,4,4a,5,8,8a-octahydroisoquinoline;
(cis)-7-(5,6-dichloro-3-pyridinyl)-1,2,3,4,4a,5,8,8a-octahydroisoquinoline;
(cis)-7-(6-bromo-5-chloro-3-pyridinyl)-1,2,3,4,4a,5,8,8a-octahydroisoquinoline;
(cis)-2-methyl-5-(1,2,3,4,4a,5,8,8a-octahydro-7-isoquinolinyl)nicotinonitrile;
(cis)-2-chloro-5-(1,2,3,4,4a,5,8,8a-octahydro-7-isoquinolinyl)nicotinonitrile;
(cis)-2-bromo-5-(1,2,3,4,4a,5,8,8a-octahydro-7-isoquinolinyl)nicotinonitrile;
(cis)-7-(6-chloro-5-methyl-3-pyridinyl)-1,2,3,4,4a,5,8,8a-octahydroisoquinoline;

(cis)-7-(6-bromo-5-methyl-3-pyridinyl)-1,2,3,4,4a,5,8,8a-octahydroisoquinoline;
(cis)-7-(5-methoxy-6-methyl-3-pyridinyl)-1,2,3,4,4a,5,8,8a-octahydroisoquinoline;
(cis)-7-(6-chloro-5-methoxy-3-pyridinyl)-1,2,3,4,4a,5,8,8a-octahydroisoquinoline;
(cis)-7-(6-bromo-5-methoxy-3-pyridinyl)-1,2,3,4,4a,5,8,8a-octahydroisoquinoline;
(cis)-7-(3-methyl-5-isoxazolyl)-1,2,3,4,4a,5,8,8a-octahydroisoquinoline;
(cis)-7-furo[3,2-b]pyridin-2-yl-1,2,3,4,4a,5,8,8a-octahydroisoquinoline;
(cis)-6-(3-pyridinyl)-2,3,4,4a,7,7a-hexahydro-1H-cyclopenta[c]pyridine;
(cis)-6-(6-chloro-3-pyridinyl)-2,3,4,4a,7,7a-hexahydro-1H-cyclopenta[c]pyridine;
(cis)-6-(6-bromo-3-pyridinyl)-2,3,4,4a,7,7a-hexahydro-1H-cyclopenta[c]pyridine;
(cis)-6-(6-fluoro-3-pyridinyl)-2,3,4,4a,7,7a-hexahydro-1H-cyclopenta[c]pyridine;
(cis)-6-(6-methyl-3-pyridinyl)-2,3,4,4a,7,7a-hexahydro-1H-cyclopenta[c]pyridine;
(cis)-5-(2,3,4,4a,7,7a-hexahydro-1H-cyclopenta[c]pyridin-6-yl)nicotinonitrile;
(cis)-6-(5-chloro-3-pyridinyl)-2,3,4,4a,7,7a-hexahydro-1H-cyclopenta[c]pyridine;
(cis)-6-(5-bromo-3-pyridinyl)-2,3,4,4a,7,7a-hexahydro-1H-cyclopenta[c]pyridine;
(cis)-6-(5-fluoro-3-pyridinyl)-2,3,4,4a,7,7a-hexahydro-1H-cyclopenta[c]pyridine;
(cis)-6-(5-methyl-3-pyridinyl)-2,3,4,4a,7,7a-hexahydro-1H-cyclopenta[c]pyridine;
(cis)-6-(5-vinyl-3-pyridinyl)-2,3,4,4a,7,7a-hexahydro-1H-cyclopenta[c]pyridine;
(cis)-6-(5-methoxy-3-pyridinyl)-2,3,4,4a,7,7a-hexahydro-1H-cyclopenta[c]pyridine;
(cis)-6-(5-vinyloxy-3-pyridinyl)-2,3,4,4a,7,7a-hexahydro-1H-cyclopenta[c]pyridine;
(cis)-6-(5-ethynyl-3-pyridinyl)-2,3,4,4a,7,7a-hexahydro-1H-cyclopenta[c]pyridine;
(cis)-6-(5,6-dichloro-3-pyridinyl)-2,3,4,4a,7,7a-hexahydro-1H-cyclopenta[c]pyridine;
(cis)-6-(6-bromo-5-chloro-3-pyridinyl)-2,3,4,4a,7,7a-hexahydro-1H-cyclopenta[c]pyridine;
(cis)-5-(2,3,4,4a,7,7a-hexahydro-1H-cyclopenta[c]pyridin-6-yl)-2-methylnicotinonitrile;
(cis)-2-chloro-5-(2,3,4,4a,7,7a-hexahydro-1H-cyclopenta[c]pyridin-6-yl)nicotinonitrile;
(cis)-2-bromo-5-(2,3,4,4a,7,7a-hexahydro-1H-cyclopenta[c]pyridin-6-yl)nicotinonitrile;
(cis)-6-(6-bromo-5-methyl-3-pyridinyl)-2,3,4,4a,7,7a-hexahydro-1H-cyclopenta[c]pyridine;
(cis)-6-(6-chloro-5-methyl-3-pyridinyl)-2,3,4,4a,7,7a-hexahydro-1H-cyclopenta[c]pyridine;
(cis)-6-(5-methoxy-6-methyl-3-pyridinyl)-2,3,4,4a,7,7a-hexahydro-1H-cyclopenta[c]pyridine;
(cis)-6-(6-chloro-5-methoxy-3-pyridinyl)-2,3,4,4a,7,7a-hexahydro-1H-cyclopenta[c]pyridine;
(cis)-6-(6-bromo-5-methoxy-3-pyridinyl)-2,3,4,4a,7,7a-hexahydro-1H-cyclopenta[c]pyridine;
(cis)-6-(3-methyl-5-isoxazolyl)-2,3,4,4a,7,7a-hexahydro-1H-cyclopenta[c]pyridine;
(cis)-2-(2,3,4,4a,7,7a-hexahydro-1H-cyclopenta[c]pyridin-6-yl)furo[3,2-b]pyridine; or a pharmaceutically acceptable salt, amide, ester and prodrug thereof.

Another embodiment of the present invention relates to pharmaceutical compositions comprising a therapeutically effective amount of a compound of formula (I-VI) or a pharmaceutically acceptable salt thereof. The compostion may be in combination with a pharmaceutically acceptable carrier.

Another embodiment of the present invention relates to a method of treating a disorder, such as Alzheimer's disease, Parkinson's disease, memory dysfunction, Tourette's syndrome, sleep disorders, attention deficit hyperactivity disorder, neurodegeneration, inflammation, neuroprotection, amyotrophic lateral sclerosis, anxiety, depression, mania, schizophrenia, nicotinic withdrawal syndrome, anorexia and other eating disorders, AIDS-induced dementia, epilepsy, urinary incontinence, substance abuse, smoking cessation and inflammatory bowel syndrome, in a mammal in need of such treatment comprising administering to the mammal a therapeutically effective amount of a compound of formula (I-VI) or a pharmaceutically acceptable salt, amide, ester or prodrug thereof.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof in combination with a pharmaceutically acceptable carrier.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof in combination with an opioid.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof in combination with a non-steroid anti-inflammatory agent.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof in combination with a tricyclic antidepressant.

Another embodiment of the present invention relates to a method for treating pain in a mammal in need of such treatment comprising administering to the mammal a therapeutically effective amount of a compound of formula (I-VI) or a pharmaceutically acceptable salt, amide, ester or prodrug thereof in combination with an anticonvulsant such as gabapentin or pregabalin.

Definition of Terms

As used throughout this specification and the appended claims, the following terms have the following meanings.

The term "alkenyl" as used herein, means a straight or branched chain hydrocarbon containing from 2 to 10 carbons, preferably 2 to 6 carbon atoms, preferably in a straight chain, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, 2-(sec-butylcarbonyl)ethyl, 2-(isopropoxycarbonyl)ethyl, and 2-(tert-butoxycarbonyl)ethyl.

The term "alkyl" as used herein, means a straight or branched chain hydrocarbon containing from 1 to 10 carbon atoms, preferably 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and tert-butylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms, preferably 2 to 6 carbon atoms, preferably in a straight chain, and containing at least one carbon-carbon triple bond. Representative examples of alkynyl include, but are not limited, to acetylenyl, 1-propynyl, 2-propynyl, 3-butynyl, 2-pentynyl, 3-methyl-1-pentynyl, 3,4-dimethyl-1-pentynyl, and 1-butynyl.

The term "aryl" as used herein, means a monocyclic-ring system, or a fused bicyclic-ring system wherein one or more of the fused rings are aromatic. Representative examples of aryl include, but are not limited to, azulenyl, indanyl, indenyl, naphthyl, phenyl, and tetrahydronaphthyl.

The aryl groups of this invention are substituted with 0, 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$ sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$O R$_{12}$ and —S(O)$_2$R$_{12}$ wherein R$_{12}$, R$_{13}$ and R$_{14}$ are independently selected from hydrogen, alkyl, alkylcarbonyl, aryl, and arylalkyl, as defined herein. The aryl groups of this invention can be further substituted with an additional aryl group, as defined herein, or an additional heterocycle, as defined herein, wherein the additional aryl group and the additional heterocycle are substituted with 0, 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$) carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$) NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$ and —S(O)$_2$R$_{12}$ wherein R$_{12}$, R$_{13}$ and R$_{14}$ are independently selected from hydrogen, alkyl, alkylcarbonyl, aryl, and arylalkyl, as defined herein.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 1,2-difluoroethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above heterocyclic ring systems fused to an aryl group as defined herein, a cycloalkyl group as defined herein, or another heterocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, cinnolinyl, furopyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, pyranopyridyl, quinolinyl, quinolizinyl, quinoxalinyl, quinazolinyl, tetrahydroisoquinolinyl, tetrahydroquinolinyl, thienopyridinyl, thieno[3,2-b]pyridinyl, thieno [2,3-b]pyridinyl and thiopyranopyridyl. Tricyclic rings systems are exemplified by any of the above bicyclic ring systems fused to an aryl group as defined herein, a cycloalkyl group as defined herein, or a heterocyclic ring system. Representative examples of tricyclic ring systems include, but are not limited to, acridinyl, carbazolyl, carbolinyl, dibenzo[b,d]furanyl, dibenzo[b,d]thienyl, naphtho [2,3-b]furan, naphtho[2,3-b]thienyl, phenazinyl, phenothiazinyl, phenoxazinyl, thianthrenyl, thioxanthenyl and xanthenyl.

The heterocycles of this invention are substituted with 0, 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, and —S(O)$_2$R$_{12}$ wherein R$_{12}$, R$_{13}$ and R$_{14}$ are independently selected from hydrogen, alkyl, alkylcarbonyl, aryl, and arylalkyl as defined herein. The heterocycles of this invention can be further substituted with an additional aryl group, as defined herein, or an additional heterocycle, as defined herein, wherein the additional aryl group and the additional heterocycle can be substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, triphenylmethyl (trityl), —C(NH)NR$_{10}$R$_{11}$, —NR$_{10}$R$_{11}$, (N$_{10}$R$_{11}$R )alkyl, (NR$_{10}$R$_{11}$) carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$) NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, and —S(O)$_2$R$_{12}$ wherein R$_{12}$, R$_{13}$, and R$_{14}$ are independently selected from hydrogen, alkyl, aryl, and arylalkyl, as defined herein Representative examples include, but are not limited to, 5-[amino(imino)methyl]thien-2-yl, 5-(aminosulfonyl)thien-2-yl, 5-bromo-3-pyridinyl, 3-bromo-1,2,4-thiadiazol-5-yl, 6-chloro-3-pyridinyl, 5-chloro-3-pyridinyl, 6-chloro-5-fluoro-3-pyridinyl, 6-chloro-5-methyl-3-pyridinyl, 5-cyano-3-pyridinyl, 5,6-dichloro-3-pyridinyl, 3,5-dimethyl-4-isoxazolyl, 6-fluoro-3-pyridinyl, 5-methoxy-3-pyridinyl, 3-methyl-5-isoxazolyl, 2-methyl-3-pyridinyl, 6-methyl-3-pyridinyl, 6-methyl-2-pyridinyl, 2-methyl-2H-tetrazol-5-yl, 5-nitro-1,3-thiazol-2-yl, 6-phenyl-3-pyridazinyl, and 5-vinyl-3-pyridinyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl, and 2-ethyl-4-hydroxyheptyl.

The term "mercapto" as used herein, means a —SH group.

The term "mercaptoalkyl" as used herein, means at least one mercapto group, as defined herein, appended to the parent molecular moiety through an alkyl group, as defined herein. Representative examples of mercaptoalkyl include, but are not limited to, thiomethyl, 2-thioethyl and 3-thiopropyl.

The term "—NR$_{10}$R$_{11}$" as used herein, means two groups, R$_{10}$ and R$_{11}$, which are appended to the parent molecular moiety through a nitrogen atom. R$_{10}$ and R$_{11}$ are independently selected from hydrogen, alkyl, alkylcarbonyl, aryl, and arylalkyl as defined herein. Representative examples of —NR$_{10}$R$_{11}$ include, but are not limited to, acetylamino, amino, benzylamino, methylamino, dimethylamino, ethylamino, phenylamino, and methylcarbonylamino.

The term "(NR$_{10}$R$_{11}$)alkyl" as used herein, means a —NR$_{10}$R$_{11}$, as defined herein, appended to the parent molecular moiety through an alkyl group, as defined herein. Representative examples of (NR$_{10}$R$_{11}$)alkyl include, but are not limited, aminomethyl, (methylamino)methyl, 2-aminoethyl, and (dimethylamino)methyl.

The term "(NR$_{10}$R$_{11}$)carbonyl" as used herein, means a —NR$_{10}$R$_{11}$ group, as defined herein, appended to the parent molecular moiety through a carbonyl group, as defined herein. Representative examples of (NR$_{10}$R$_{11}$)carbonyl include, but are not limited to, aminocarbonyl, dimethylaminocarbonyl, methylaminocarbonyl, and ethylaminocarbonyl.

The term "$(NR_{10}R_{11})$carbonylalkyl" as used herein, means a $(NR_{10}R_{11})$carbonyl group, as defined herein, appended to the parent molecular moiety through an alkyl group, as defined herein. Representative examples of $(NR_{10}R_{11})$carbonylalkyl include, but are not limited to, 2-amino-2-oxoethyl, 2-(methylamino)-2-oxoethyl, 4-amino-4-oxobutyl, and 4-(dimethylamino)-4-oxobutyl.

The term "$(NR_{10}R_{11})$sulfonyl" as used herein, means a —$NR_{10}R_{11}$ group, as defined herein, appended to the parent molecular moiety through a sulfonyl group, as defined herein. Representative examples of $(NR_{10}R_{11})$sulfonyl include, but are not limited to, aminosulfonyl, dimethylaminosulfonyl, methylaminosulfonyl, ethylaminosulfonyl, phenylaminosulfonyl and benzylaminosulfonyl.

The term "nitrogen protecting group" or "N-protecting group" as used herein, means those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), trifluoroacetyl, and triphenylmethyl (trityl).

The term "nitro" as used herein, means a —$NO_2$ group.
The term "oxo" as used herein, means a =O moiety.
The term "oxy" as used herein, means a —O— moiety.
The term "sulfonyl" as used herein, means a —$SO_2$— group.

Compounds of the present invention were named by ACD/ChemSketch version 5.0 (developed by Advanced Chemistry Development, Inc., Toronto, ON, Canada) or were given names which appeared to be consistent with ACD nomenclature.

It is to be understood that compounds of the present invention can be either cis or trans and that the cis and trans arrangements are included within the scope of the present invention.

The present invention contemplates stereoisomers and mixtures thereof which are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Determination of Biological Activity

In Vitro Data

Determination of Nicotinic Acetylcholine Receptor Binding Potencies

Compounds of the present invention were subjected to an in vitro assay against the nicotinic acetylcholine receptor as described below and were found to be effective binders to the receptor. The In Vitro protocols for determination of nicotinic acetylcholine channel receptor binding potencies of ligands were determined as follows.

Binding of [$^3$H]-cytisine ([$^3$H]-CYT) to neuronal nicotinic acetylcholine receptors was accomplished using crude synaptic membrane preparations from whole rat brain (Pabreza et al., Molecular Pharmacol., 1990, 39:9). Washed membranes were stored at −80° C. prior to use. Frozen aliquots were slowly thawed and resuspended in 20 volumes of buffer (containing: 120 mM NaCl, 5 mM KCl, 2 mM $MgCl_2$, 2 mM $CaCl_2$ and 50 mM Tris-Cl, pH 7.4 @4° C.). After centrifuging at 20,000× g for 15 minutes, the pellets were resuspended in 30 volumes of buffer.

The test compounds were dissolved in water to make 10 mM stock solutions. This solution was then diluted (1:100) with buffer (as above) and further taken through seven serial log dilutions to produce test solutions from $10^{-5}$ to $10^{-11}$ M.

Homogenate (containing 125–150 µg protein) was added to triplicate tubes containing the range of concentrations of test compound described above and [$^3$H]-CYT (1.25 nM) in a final volume of 500 µL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 µM (−)-nicotine and values were expressed as a percentage of total binding. $IC_{50}$ values were determined with the RS-1 (BBN) nonlinear least squares curve-fitting program and $IC_{50}$ values were converted to Ki values using the Cheng and Prusoff correction ($K_i=IC_{50}/(1+$[ligand]/Kd of ligand).

Representative compounds of the present invention bound to nicotinic acetylcholine receptors with binding affinities from 2300 nM to 0.029 nM. Preferred compounds of the present invention bound to nicotinic acetylcholine receptors with binding affinities less than or equal to 100 nM.

In Vivo Data

Determination of Effectiveness of Nicotinic Acetylcholine Receptor Ligands as Analgesic Agents in the Mouse Hot Plate Paradigm An in vivo protocol was utilized to determine the effectiveness of nicotinic acetylcholine receptor ligands as analgesic agents in the mouse hot plate paradigm.

Separate groups of mice, (n=8/group) were utilized for dose group. All drugs were administered by the intraperitoneal route of administration. Test drugs were dissolved in water to make a 6.2 mM stock solution. Animals were dosed with this solution (10 mL/kg body weight) for a 62 micromol/kg dose. Lower doses were administered similarly, following serial dilution of the stock solution in half-log increments. Animals were dosed 30 minutes prior to testing in the hot plate. The hot-plate utilized was an automated analgesia monitor (Model #AHP16AN, Omnitech Electronics, Inc. of Columbus, Ohio). The temperature of the hot plate was maintained at 55° C. and a cut-off time of 180 seconds was utilized. Latency until the tenth jump was recorded as the dependent measure. An increase in the tenth jump latency relative to the control was considered an effect.

Representative compounds of the present invention showed an antinociceptive effect in the mouse hot plate paradigm at doses ranging from 62 µmol/kg to 6.2 µmol/kg. Preferred compounds of the present invention showed an antinociceptive effect in the mouse hot plate paradigm at doses less than or equal to 62 µmol/kg.

Determination of Effectiveness of Nicotinic Acetylcholine Receptor Ligands as Analgesic Agents in the Rat Formalin Test Another in vivo protocol utilized to determine the effectiveness of nicotinic acetylcholine receptor ligands as analgesic agents was the rat formalin test.

Male Sprague-Dawley rats (Charles River, Portage, Mich.) weighing 200 to 400 grams were used for all experiments. After a 20 minute period of acclimation to individual cages, 50 μL of a 5% formalin solution was injected subcutaneous into the dorsal aspect of one of the rear paws and the rats were then returned to the clear observation cages suspended above mirror panels. Rats were observed during phase 2 of the formalin test which was defined as the 20 minute period from 30 to 50 minutes after formalin injection. The investigator recorded nocifensive behaviors in the injected paw of four animals during the session by observing the animals for one 15 second observation period during each 1 minute interval. Nocifensive behaviors recorded included flinching, licking or biting the injected paw. In dose-response studies, the test compound (or saline) was administered intraperitoneally 5 minutes before injection of formalin.

Representative compounds of the present invention showed an antinociceptive effect in the rat formalin test at doses ranging from 62 μmol/kg to 1.9 μmol/kg. Preferred compounds of the present invention showed an antinociceptive effect in the rat formalin test at doses less than or equal to 62 μmol/kg.

The in vitro and in vivo data demonstrates that compounds of the present invention bind to the nicotinic acetylcholine receptor and are useful for treating pain.

The ability of the compounds of the present invention, including but not limited to those specified in the examples, to treat pain via the nicotinic acetylcholine receptors and the cholinergic system can be further demonstrated by Williams, M.; Arneric, S. P.: Beyond the Tobacco Debate: dissecting out the therapeutic potential of nicotine. Exp. Opin. Invest. Drugs (1996)5(8): 1035–1045; and Arneric, S. P.; Sullivan, J. P.; Williams, W.: Neuronal nicotinic acetylcholine receptors. Novel targets for central nervous system therapeutics. in: Psychopharmacology: The Fourth Generation of Progress. Bloom F E, Kupfer D J (Eds.), Raven Press, New York (1995): 95–109.

Additionally, compounds of the present invention are useful for ameliorating or preventing disorders affected by nicotinic acetylcholine receptors and the cholinergic system, such as Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, substance abuse, smoking cessation and inflammatory bowel syndrome.

The ability of the compounds of the present invention, including but not limited to those specified in the examples, to treat Alzheimer's disease can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100; Lindstrom, J.: Nicotinic Acetylchloline Receptors in Health and Disease. Molecular Neurobiology (1997) 15: 193–222; and Lloyd, G K; Menzaghi, F; Bontempi B; Suto, C; Siegel, R; Akong, M; Stauderman, K; Velicelebi, G; Johnson, E; Harpold, M M; Rao, T S; Sacaan, A I; Chavez-Noriega, L E; Washburn, M S; Vernier, J M; Cosford, N D P; McDonald, L A: The potential of subtype selective neuronal nicotinic acetylcholine receptor agonists as therapeutic agents. Life Sciences (1998)62(17/18): 1601–1606.

The ability of the compounds of the present invention, including but not limited to those specified in the examples, to treat Parkinson's disease can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Lindstrom, J.: Nicotinic Acetylchloline Receptors in Health and Disease. Molecular Neurobiology (1997) 15: 193–222; and Lloyd, G K; Menzaghi, F; Bontempi B; Suto, C; Siegel, R; Akong, M; Stauderman, K; Velicelebi, G; Johnson, E; Harpold, M M; Rao, T S; Sacaan, A I; Chavez-Noriega, L E; Washburn, M S; Vernier, J M; Cosford, N D P; McDonald, L A: The potential of subtype selective neuronal nicotinic acetylcholine receptor agonists as therapeutic agents. Life Sciences (1998)62(17/18): 1601–1606.

The ability of the compounds of the present invention, including but not limited to those specified in the examples, to treat memory dysfunction can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat Tourette's syndrome can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat sleeping disorders can be demonstrated by Williams, M.; Arneric, S. P.: Beyond the Tobacco Debate: dissecting out the therapeutic potential of nicotine. Exp. Opin. Invest. Drugs (1996)5(8): 1035–1045.

The ability of the compounds of the present invention, including but not limited to those specified in the examples, to treat attention deficit hyperactivity disorder can be demonstrated by Williams, M.; Arneric, S. P.: Beyond the Tobacco Debate: dissecting out the therapeutic potential of nicotine. Exp. Opin. Invest. Drugs (1996)5(8): 1035–1045; and Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100.

The ability of the compounds of the present invention, including but not limited to those specified in the examples, to treat neurodegeneration and to provide neuroprotection can be demonstrated by Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100.

The ability of the compounds of the present invention, including but not limited to those specified in the examples, to treat inflammation can be demonstrated by Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100.

The ability of the compounds of the present invention, including but not limited to those specified in the examples, to treat amyotrophic lateral sclerosis can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100.

The ability of the compounds of the present invention, including but not limited to those specified in the examples, to treat anxiety can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Arneric, S. P.; Holladay, M. W.; Sullivan, J. P.: Cholinergic channel modulators as a novel therapeutic strategy for Alzheimer's disease. Exp. Opin. Invest. Drugs (1996) 5(1): 79–100.

The ability of the compounds of the present invention, including but not limited to those specified in the examples, to treat depression can be demonstrated by Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109.

The ability of the compounds of the present invention, including but not limited to those specified in the examples, to treat mania and schizophrenia can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat anorexia and other eating disorders can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat AIDS-induced dementia can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat epilepsy can be demonstrated by Williams, M.; Arneric, S. P.: Beyond the Tobacco Debate: dissecting out the therapeutic potential of nicotine. Exp. Opin. Invest. Drugs (1996)5(8): 1035–1045; Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109; and Lindstrom, J.: Nicotinic Acetylchloline Receptors in Health and Disease. Molecular Neurobiology (1997) 15: 193–222.

The ability of the compounds of the present invention, including but not limited to those specified in the examples, to treat urinary incontinence can be demonstrated by Williams, M.; Arneric, S. P.: Beyond the Tobacco Debate: dissecting out the therapeutic potential of nicotine. Exp. Opin. Invest. Drugs (1996)5(8): 1035–1045.

The ability of the compounds of the present invention, including but not limited to those specified in the examples, to treat premenstrual syndrome can be demonstrated by Williams, M.; Arneric, S. P.: Beyond the Tobacco Debate: dissecting out the therapeutic potential of nicotine. Exp. Opin. Invest. Drugs (1996)5(8): 1035–1045; and Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109.

The ability of the compounds of the present invention, including but not limited to those specified in the examples, to treat substance abuse can be demonstrated by Williams, M.; Arneric, S. P.: Beyond the Tobacco Debate: dissecting out the therapeutic potential of nicotine. Exp. Opin. Invest. Drugs (1996)5(8): 1035–1045; and Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109.

The ability of the compounds of the present invention, including but not limited to those specified in the examples, to treat smoking cessation can be demonstrated by Williams, M.; Arneric, S. P.: Beyond the Tobacco Debate: dissecting out the therapeutic potential of nicotine. Exp. Opin. Invest. Drugs (1996)5(8): 1035–1045; and Arneric, S. P.; Sullivan, J. P.; Williams, W.: Neuronal nicotinic acetylcholine receptors. Novel targets for central nervous system theraputics. in: Psychopharmacology: The Fourth Generation of Progress. Bloom F E, Kupfer D J (Eds.), Raven Press, New York (1995): 95–109.

The ability of the compounds of the present invention, including but not limited to those specified in the examples, to treat inflammatory bowel syndrome can be demonstrated by Williams, M.; Arneric, S. P.: Beyond the Tobacco Debate: dissecting out the therapeutic potential of nicotine. Exp. Opin. Invest. Drugs (1996)5(8): 1035–1045; and Lindstrom, J.: Nicotinic Acetylchloline Receptors in Health and Disease. Molecular Neurobiology (1997) 15: 193–222.

The term "pharmaceutically acceptable carrier," as used herein, means a nontoxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Dosage forms for topical administration of a compound of the present invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions, and mode of administration.

When used in the above or other treatments, a therapeutically effective amount of one of the compounds of the present invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the present invention means a sufficient amount of the compound to treat disorders, at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of the present invention administered to a mammal, and particularly a human, may range from about 0.01 to about 50 mg/kg/day. More preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more nontoxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The present invention contemplates pharmaceutically active compounds either chemically synthesized or formed by in vivo biotransformation to compounds of formula (I-VI).

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The term "pharmaceutically acceptable salt, ester, amide, and prodrug," as used herein, refers to carboxylate salts, amino acid addition salts, zwitterions, esters, amides, and prodrugs of compounds of formula (I-VI) which are within the scope of sound medical judgement, suitable for use in contact with the tissues of humans and lower animals without undue toxicity, irritation, allergic response, and the like, are commensurate with a reasonable benefit/risk ratio, and are effective for their intended use. Representative examples include, but are not limited to, 5-(1,2,3,3a,4,6a- hexahydrocyclopenta[c]pyrrol-5-yl)-3-pyridinyl acetate, 5-(1,2,3,3a,4,6a-hexahydrocyclopenta[c]pyrrol-5-yl)-3-pyridinyl benzoate, 2-chloro-5-(1,2,3,3a,4,6a-hexahydrocyclopenta[c]pyrrol-5-yl)-3-pyridinyl benzoate, 2-chloro-5-(1,2,3,3a,4,6a-hexahydrocyclopenta[c]pyrrol-5-yl)-3-pyridinyl acetate, [2-chloro-5-(1,2,3,3a,4,6a-hexahydrocyclopenta[c]pyrrol-5-yl)-3-pyridinyl]methyl benzoate, [2-chloro-5-(1,2,3,3a,4,6a-hexahydrocyclopenta[c]pyrrol-5-yl)-3-pyridinyl]methyl acetate, [5-(1,2,3,3a,4,6a-hexahydrocyclopenta[c]pyrrol-5-yl)-3-pyridinyl]methyl acetate, [5-(1,2,3,3a,4,6a-hexahydrocyclopenta[c]pyrrol-5-yl)-3-pyridinyl]methyl benzoate, 2-acetyl-5-(3-pyridinyl)-1,2,3,3a,4,6a-hexahydrocyclopenta[c]pyrrole, 2-acetyl-5-(6-chloro-3-pyridinyl)-1,2,3,3a,4,6a-hexahydrocyclopenta[c]pyrrole, 5-(6-chloro-3-pyridinyl)-2-(trifluoroacetyl)-1,2,3,3a,4,6a-hexahydrocyclopenta[c]pyrrole, 5-(3-pyridinyl)-2-(trifluoroacetyl)-1,2,3,3a,4,6a-hexahydrocyclopenta[c]pyrrole, 2-benzoyl-5-(3-pyridinyl)-1,2,3,3a,4,6a-hexahydrocyclopenta[c]pyrrole, 2-benzoyl-5-(6-chloro-3-pyridinyl)-1,2,3,3a,4,6a-hexahydrocyclopenta[c]pyrrole, phenyl 5-(6-chloro-3-pyridinyl)-3,3a,4,6a-tetrahydrocyclopenta[c]pyrrole-2(1H)-carboxylate, and phenyl 5-(3-pyridinyl)-3,3a,4,6a-tetrahydrocyclopenta[c]pyrrole-2(1H)-carboxylate.

The compounds of the present invention can be used in the form of pharmaceutically acceptable salts derived from inorganic or organic acids. The term "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as maleic acid, fumaric acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the present invention include phosphate, tris and acetate.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I-VI), for example, by hydrolysis in blood.

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I-VI) may be prepared according to conventional methods.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I-VI) may be prepared according to conventional methods.

Abbreviations

Abbreviations which have been used in the descriptions of the Schemes and the Examples that follow are: Ac for acetyl; acyl for alkylcarbonyl; AIBN for 2,2'-azobis(2-methylpropionitrile) N,N-dimethylformamide; Bn for benzyl; dppf for 1,1'-bis(diphenylphosphino)ferrocene; DMAP for dimethylaminopyridine; DME for 1,2-dimethoxyethane; DMSO for dimethylsulfoxide; EtOAc for ethyl acetate; EtOH for ethanol; formalin for a solution of formaldehyde (37% by weight) in water; HPLC for high pressure liquid chromatography; LAH for lithium aluminum hydride; LDA for lithium diisopropylamine; MeOH for methanol; Ms for mesylate —$SO_2CH_3$; Tf for (trifluoromethyl)sulfonyl (—$SO_2CF_3$); TFA for trifluoroacetic acid; THF for tetrahydrofuran; TMS for trimethylsilyl; Ts or tosyl for p-$CH_3$($C_6H_4$)$SO_2$—; and TsOH for para-toluenesulfonic acid.

Preparation of Compounds of the Present Invention

The compounds and processes of the present invention will be better understood in connection with the following synthetic schemes and methods which illustrate a means by which the compounds of the invention can be prepared.

The compounds of this invention can be prepared by a variety of procedures and synthetic routes. Representative procedures and synthetic routes are shown in, but are not limited to, Schemes 1–49.

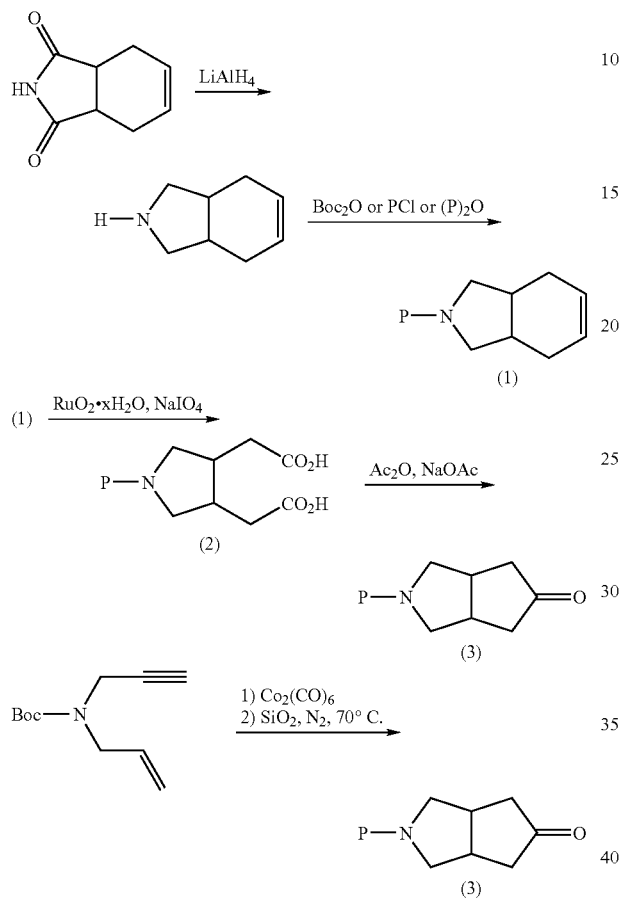

Scheme 1

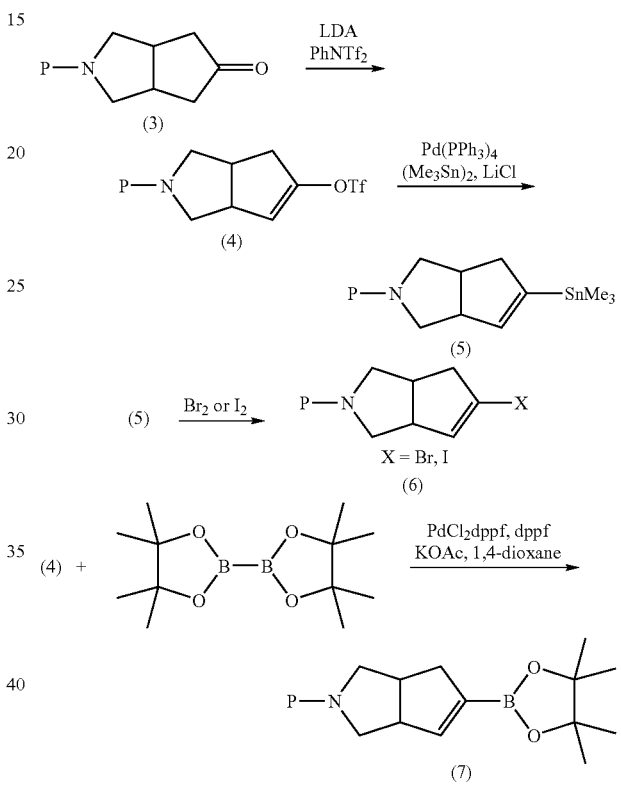

Scheme 2

Nitrogen-protected (cis)-hexahydrocyclopenta[c]pyrrol-5 (1H)-ones of general formula (3), wherein P is a suitable nitrogen protecting group such as, but not limited to, alkyl, benzyl, triphenylmethyl (trityl), acyl, p-toluenesulfonyl (Ts), benzyloxy carbonyl (Cbz) or tert-butoxycarbonyl (Boc), may be prepared as described in Scheme 1. (cis)-3a,4,7,7a-Tetrahydro-1H-isoindole-1,3(2H)-dione, purchased commercially or prepared as described in Helv. Chim. Acta (1996) 79(3), 875–894 and J. Org. Chem. (1951) 16, 501–505, may be treated with lithium aluminum hydride to provide (cis)2,3,3a,4,7,7a-hexahydro-1H-isoindole as described in J. Am. Chem. Soc. (1980) 102(6), 2005–2010. (cis)-2,3,3a,4,7,7a-Hexahydro-1H-isoindole may be treated with a nitrogen protecting group precursor such as, but not limited to, di-tert-butyl dicarbonate or benzyl chloroformate to provide nitrogen protected isoindoles of general formula (1). Nitrogen protected isoindoles of general formula (1) may be oxidatively cleaved in the presence of ruthenium(IV) oxide hydrate and sodium periodate as described in J. Org. Chem. (1981) 46(19), 3936–3938 and Chem. Pharm. Bull. (1995) 43(8), 1318–1324) to provide diacids of general formula (2). Diacids of general formula (2) may be treated with acetic anhydride and sodium acetate as described in J. Org. Chem. (1989) 54, 5115–5122 to provide nitrogen-protected (cis)-hexahydrocyclopenta[c]pyrrol-5(1H)-ones of general formula (3).

Alternatively, tert-butyl (cis)-5-oxohexahydrocyclopenta [c]pyrrole-2(1H)-carboxylate may be prepared by treating tert-butyl allyl(2-propynyl)carbamate to a reductive Pauson-Khand cyclocarbonylation as described in Tetrahedron (1993) 49(23), 5047–5054. An asymmetric cyclocarbonylation has also been reported in J. Org. Chem. (1999) 64, 5547–5550 that can allow access to analogs in high enantiomeric excess.

Vinyl triflates of general formula (4), vinyl stannanes of general formula (5), vinyl halides of general formula (6) and vinyl boronates of general formula (7), wherein P is a suitable nitrogen protecting group such as, but not limited to, alkyl, benzyl, trityl, acyl, p-toluenesulfonyl (Ts), benzyloxy carbonyl (Cbz) or tert-butoxycarbonyl (Boc), may be prepared as described in Scheme 2. Nitrogen-protected (cis)-hexahydrocyclopenta[c]pyrrol-5(1H)-ones of general formula (3) may be treated with a base such as, but not limited to, lithium diisopropylamide or sodium bis(trimethylsilyl) amide or potassium bis(trimethylsilyl)amide and N-phenyltrifluormethanesulfonimide to provide vinyl triflates of general formula (4) as described in Tetrahedron Lett. (1983) 24(10), 979–282. Vinyl triflates of general formula (4) may be further elaborated into vinyl stannanes of general formula (5) as described in J. Org. Chem. (1986) 51, 277–279. Vinyl stannanes of general formula (5) may be treated with bromine or iodine to provide vinyl halides of general formula (6) as described in J. Org. Chem. (1985) 50, 2438–2443. Vinyl triflates of general formula (4) may also be converted into vinyl boronates of general formula (7) as described in Tetrahedron Lett. (2000) 41(19), 3705–3708.

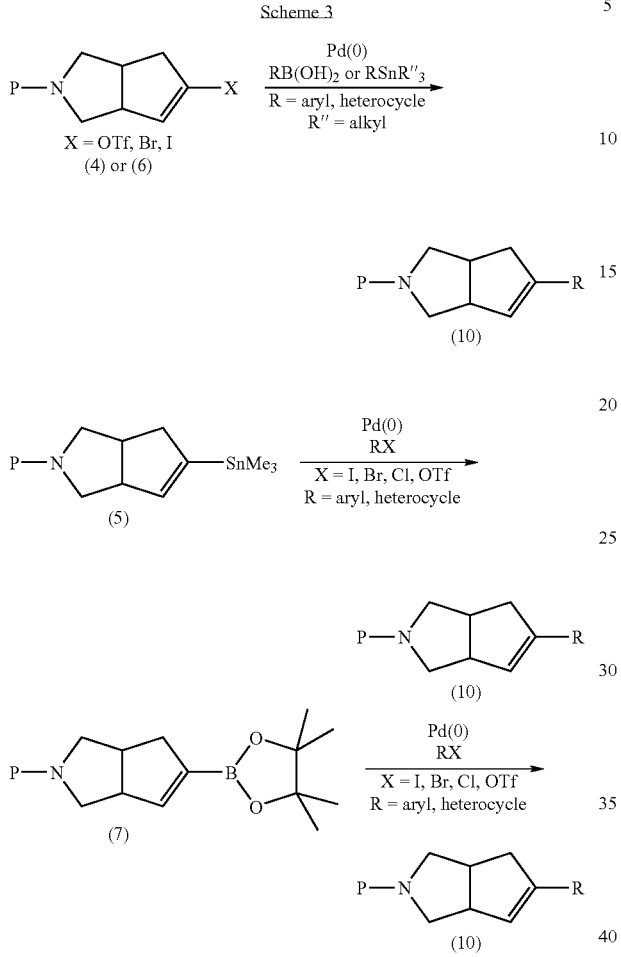

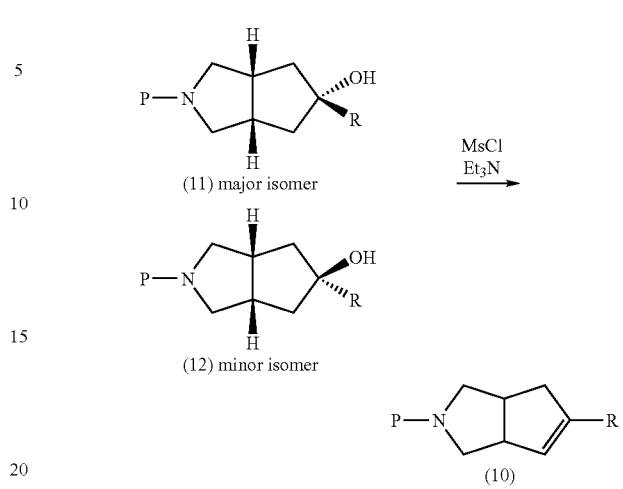

Azabicyclic compounds of general formula (10), wherein P is a suitable nitrogen protecting group such as, but not limited to, alkyl, benzyl, trityl, acyl, p-toluenesulfonyl (Ts) and R is aryl or heterocycle, may be prepared as described in Scheme 3. Vinyl triflates of general formula (4) or vinyl halides of general formula (6) may be treated with a palladium catalyst and an aryl or heterocyclic boronic acid (or an analogous aryl or heterocyclic stannane) to provide azabicyclic compounds of general formula (10). Vinyl stannanes of general formula (5) may be treated with a palladium catalyst and an aryl halide or a heterocyclic halide (or triflate) to provide azabicyclic compounds of general formula (10). Vinyl boronates of general formula (7) may be treated with a palladium catalyst and an aryl halide or a heterocyclic halide (or triflate) to provide azabicyclic compounds of general formula (10).

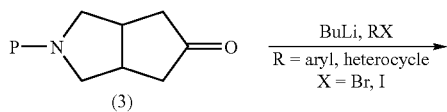

An alternative method of preparing azabicyclic compounds of general formula (10), wherein P is a suitable nitrogen protecting group such as, but not limited to, alkyl, benzyl, trityl, acyl, p-toluenesulfonyl (Ts) and R is aryl or heterocycle, may be used as described in Scheme 4. Nitrogen-protected (cis)-hexahydrocyclopenta[c]pyrrol-5(1H)-ones of general formula (3) may be treated with n-butyllithium or tert-butyllithium and an aryl halide or a heterocyclic halide to provide alcohols of general formula (11) and general formula (12). In general, the major diasteroemer produced in additions of aryl or heterocyclic anions to fused azabicyclic ketones such as, but not limited to, (3) and other related fused bicyclic aminoketones described herein is expected to result from nucleophilic addition to the exo (or convex) face of the azabicyclic ketone as illustrated in Scheme 4. The diastereomers (11) and (12) can be separated with standard chromatographic techniques used by those skilled in the art of organic chemistry. Alcohols of general formula (11) and general formula (12) may be treated with methanesulfonyl chloride and triethylamine to provide azabicyclic compounds of general formula (10).

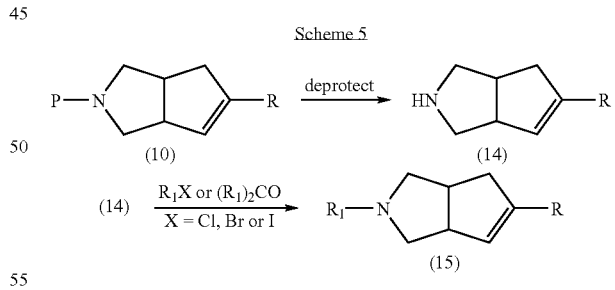

Azabicycles of general formula (14) and azabicycles of general formula (15), wherein R is aryl or heterocycle and $R_1$ is as defined in formula (I), may be prepared as described in Scheme 5. The nitrogen protecting group in azabicycles of general formula (10) may be removed under conditions known to those of skill in the art of organic chemistry to provide azabicycles of general formula (14). Azabicycles of general formula (14) may be treated with alkylating or acylating reagents and a base such as, but not limited to, triethylamine to provide azabicycles of general formula (15).

Scheme 6

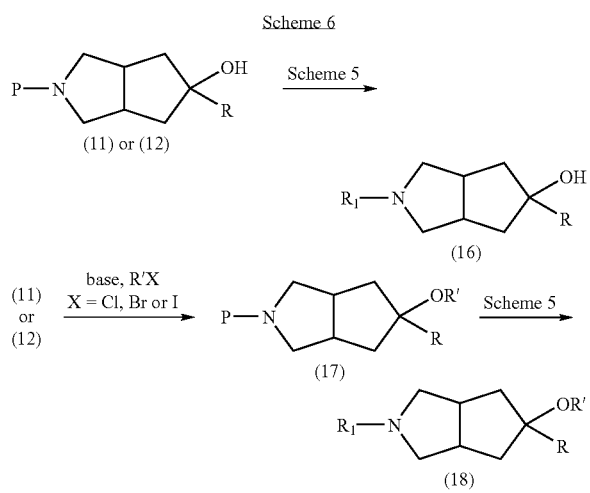

Azabicycles of general formula (16) and azabicycles of general formula (18), wherein R is aryl or heterocycle, R' is alkyl and $R_1$ is as defined in formula (I), may be prepared as described in Scheme 6. Alcohols of general formula (11) or (12) may be processed as described in Scheme 5 to provide azabicycles of general formula (16). Alcohols of general formula (11) or (12) may also be treated with a base such as, but not limited to, sodium hydride and an alkylating reagent to provide alkoxy compounds of general formula (17). Alkoxy compounds of general formula (17) may be processed as described in Scheme 5 to provide azabicycles of general formula (18).

Scheme 7

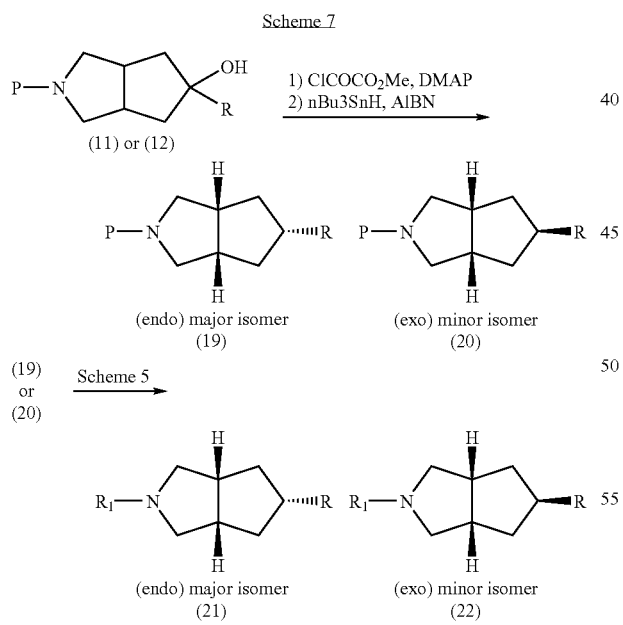

Azabicycles of general formula (21) and (22), wherein R is aryl or heterocycle and $R_1$ is as defined in formula (I), may be prepared as described in Scheme 7. Alcohols of general formula (11) or (12) may be deoxygenated by treatment with methyl chlorooxoacetate followed by tributyltin hydride as described in J. Org. Chem. (1996) 61(20), 7189–7191 to provide azabicyclics of general formula (19) and (20). In general, the major diastereomer produced in deoxygenation reactions performed on compounds (11) or (12) and related fused azabicyclic systems described herein is expected to be the endo-substituted isomer. Azabicyclics of general formula (19) and (20) may be processed as described in Scheme 5 to provide azabicyclics of general formula (21) and (22). The diastereomers (21) and (22) can be separated with standard chromatographic techniques used by those skilled in the art of organic chemistry.

Scheme 8

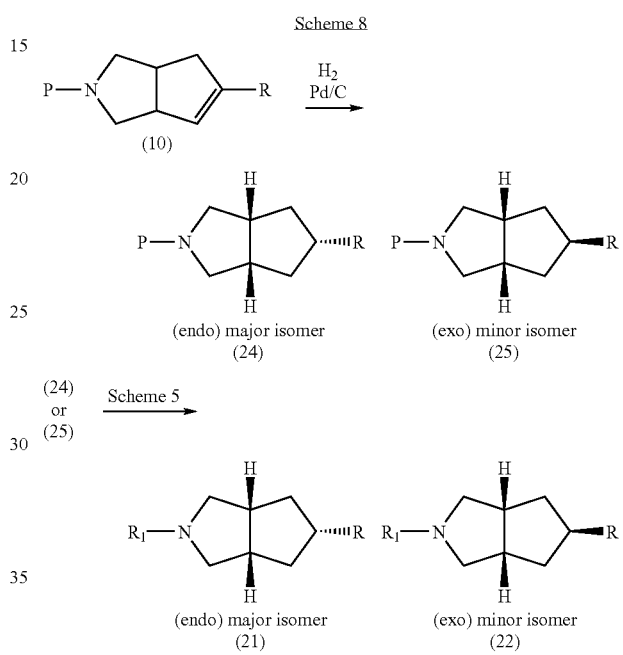

Alternatively, azabicyclics of general formula (21) and (22), wherein R is aryl or heterocycle and $R_1$ is as defined in formula (I), may be prepared as described in Scheme 8. Azabicycles of general formula (10) may be treated with a catalyst such as, but not limited to, palladium on carbon under an atmosphere of hydrogen to provide azabicycles of general formula (24) and (25). In general, the major diastereomer produced in hydrogenation reactions performed on compounds of general formula (10) and related azabicyclic olefins described herein is expected to be the endo-substituted isomer. Azabicycles of general formula (24) and (25) may be processed as described in Scheme 5 to provide azabicycles of general formula (21) and (22).

Scheme 9

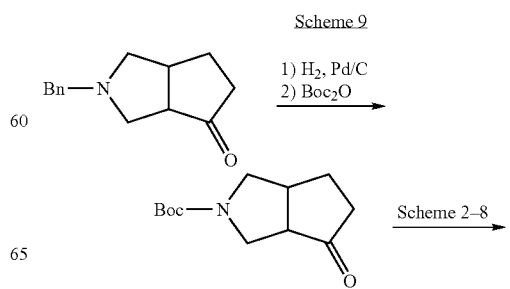

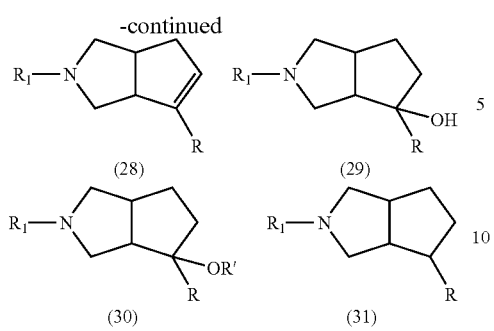

Azabicycles of general formula (28), (29), (30) and (31), wherein R is aryl or heterocycle, R' is alkyl and $R_1$ is as defined in formula (I), may be prepared as described in Scheme 9. (cis)-2-Benzylhexahydrocyclopenta[c]pyrrol-4 (1H)-one, prepared as described in Chem. Pharm. Bull. (1985) 33(7), 2762–2766, may be treated with a transition metal catalyst such as, but not limited to, palladium on carbon under an atmosphere of hydrogen in the presence of di-tert-butyl dicarbonate to provide tert-butyl (cis)-4-oxohexahydrocyclopenta[c]pyrrole-2(1H)-carboxylate. tert-Butyl (cis)-4-oxohexahydrocyclopenta[c]pyrrole-2(1H)-carboxylate may be processed as described in Schemes 2–8 to provide azabicycles of general formula (28), (29), (30) and (31).

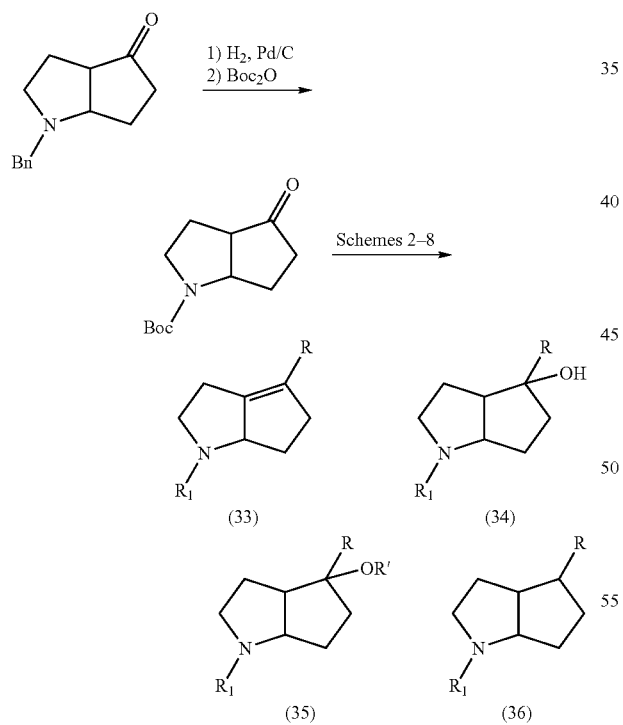

Azabicycles of general formula (33), (34), (35) and (36), wherein R is aryl or heterocycle, R' is alkyl and $R_1$ is as defined in formula (I), may be prepared as described in Scheme 10. (cis)-1-Benzylhexahydrocyclopenta[b]pyrrol-4 (1H)-one, prepared as described in J. Org. Chem.(1985) 50, 2403–2405, may be treated with a transition metal catalyst such as, but not limited to, palladium on carbon under an atmosphere of hydrogen in the presence of di-tert-butyl dicarbonate to provide tert-butyl (cis)-4-oxohexahydrocyclopenta[b]pyrrole-1(2H)-carboxylate. tert-Butyl (cis)-4-oxohexahydrocyclopenta[b]pyrrole-1(2H)-carboxylate may be processed as described in Schemes 2–8 to provide azabicycles of general formula (33), (34), (35) and (36).

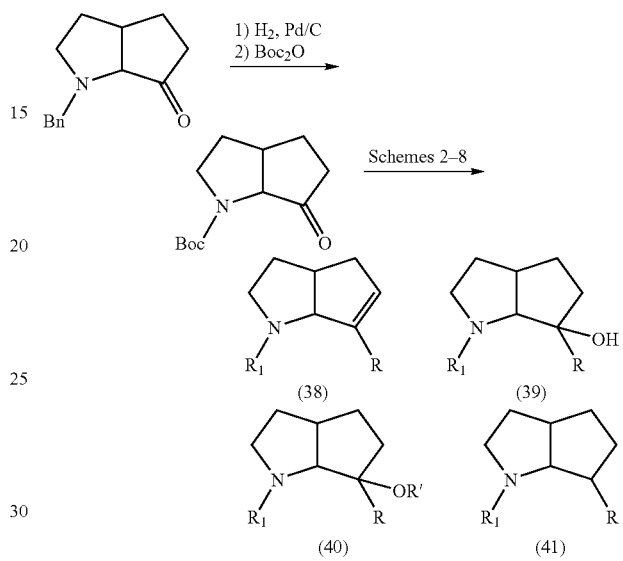

Azabicycles of general formula (38), (39), (40) and (41), wherein R is aryl or heterocycle, R' is alkyl and $R_1$ is as defined in formula (I), may be prepared as described in Scheme 11. (cis)-1-Benzylhexahydrocyclopenta[b]pyrrol-6 (1H)-one, prepared as described in Tetrahedron Lett. (1989) 30(41), 5547–5550, may be treated with a transition metal catalyst such as, but not limited to, palladium on carbon under an atmosphere of hydrogen in the presence of di-tert-butyl dicarbonate to provide tert-butyl (cis)-6-oxohexahydrocyclopenta[b]pyrrole-1(2H)-carboxylate. tert-Butyl (cis)-6-oxohexahydrocyclopenta[b]pyrrole-1(2H)-carboxylate may be processed as described in Schemes 2–8 to provide azabicycles of general formula (38), (39), (40) and (41).

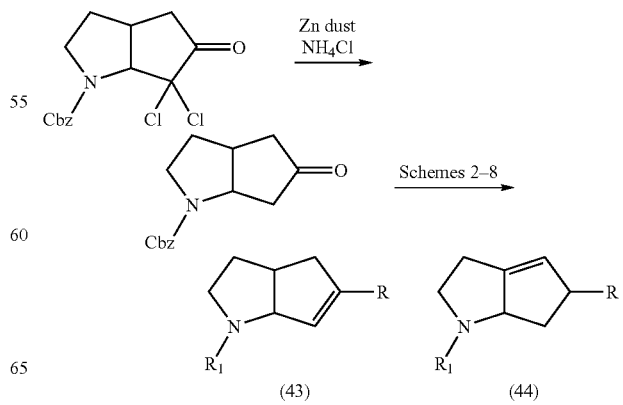

-continued

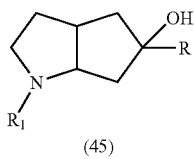 (45)   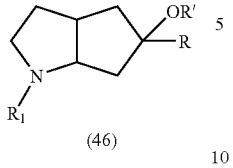 (46)

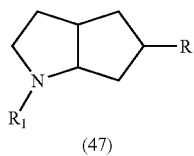 (47)

Azabicycles of general formula (43), (44), (45), (46) and (47), wherein R is aryl or heterocycle, R' is alkyl and R¹ is as defined in formula (I), may be prepared as described in Scheme 12. Benzyl (cis)-6,6-dichloro-5-oxohexahydrocyclopenta[b]pyrrole-1(2H)-carboxylate, prepared as described in Tetrahedron Lett. (1997) 38(11), 1869–1872, may be treated with zinc dust and ammonium chloride to provide benzyl (cis)-5-oxohexahydrocyclopenta[b]pyrrole-1(2H)-carboxylate. Benzyl (cis)-5-oxohexahydrocyclopenta[b]pyrrole-1(2H)-carboxylate may be processed as described in Schemes 2–8 to provide azabicycles of general formula (43), (44), (45), (46) and (47).

Scheme 13

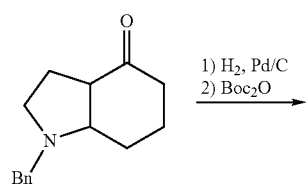

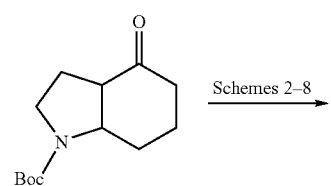

-continued

(51)   (52)

Azabicycles of general formula (49), (50), (51) and (52), wherein R is aryl or heterocycle, R' is alkyl and $R_1$ is as defined in formula (I), may be prepared as described in Scheme 13. (cis)-1-Benzyloctahydro-4H-indol-4-one, prepared as described in J. Am. Chem. Soc. (1983) 105(22), 6629–6637, may be treated with a transition metal catalyst such as, but not limited to, palladium on carbon under an atmosphere of hydrogen in the presence of di-tert-butyl dicarbonate to provide tert-butyl (cis)-4-oxooctahydro-1H-indole-1-carboxylate. tert-Butyl (cis)-4-oxooctahydro-1H-indole-1-carboxylate may be processed as described in Schemes 2–8 to provide azabicycles of general formula (49), (50), (51) and (52).

Scheme 14

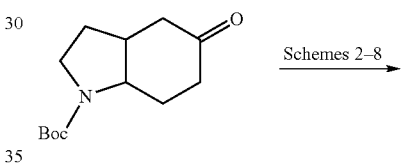

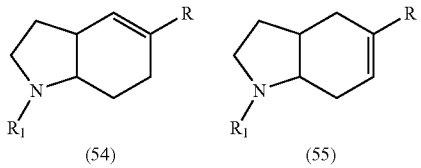
(54)   (55)

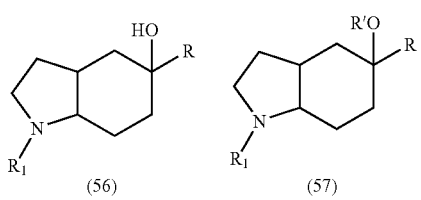
(56)   (57)

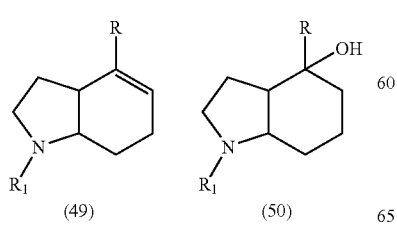
(58)

Azabicycles of general formula (54), (55), (56), (57) and (58), wherein R is aryl or heterocycle, R' is alkyl and $R_1$ is as defined in formula (I), may be prepared as described in Scheme 14. tert-Butyl (cis)-5-oxooctahydro-1H-indole-1-carboxylate, prepared as described in J. Med. Chem. (1992) 35(19), 3547–3560, may be processed as described in Schemes 2–8 to provide azabicycles of general formula (54), (55), (56), (57) and (58).

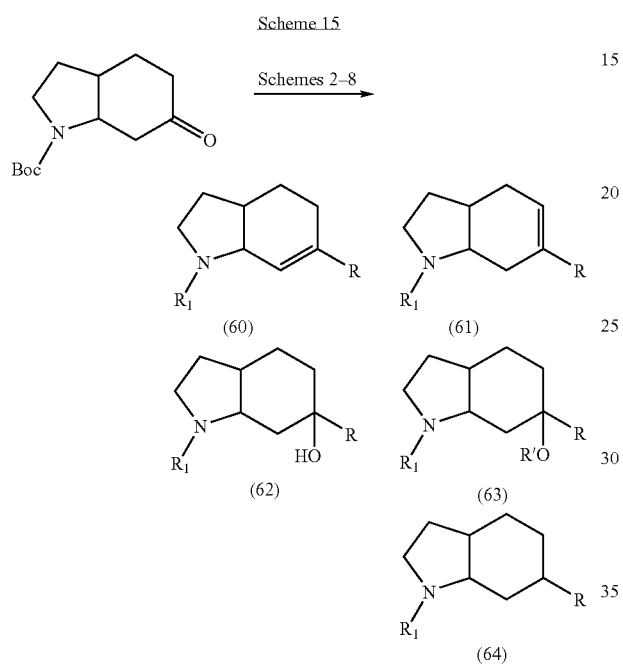

Azabicycles of general formula (60), (61), (62), (63) and (64), wherein R is aryl or heterocycle, R' is alkyl and $R_1$ is as defined in formula (I), may be prepared as described in Scheme 15. tert-Butyl (cis)-6-oxooctahydro-1H-indole-1-carboxylate, prepared as described in J. Org. Chem. (1996) 61(20), 7106–7115, may be processed as described in Schemes 2–8 to provide azabicycles of general formula (60), (61), (62), (63) and (64).

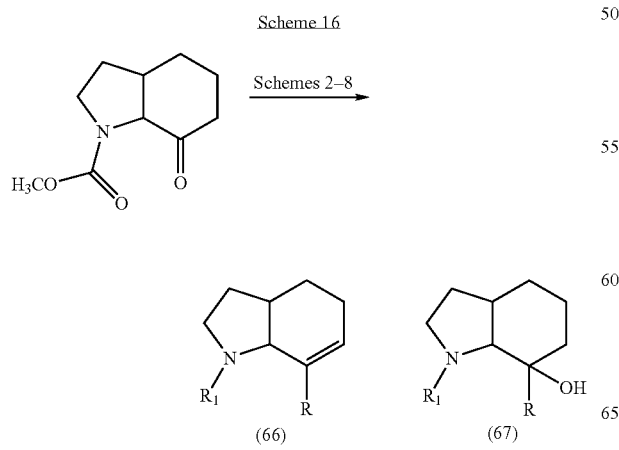

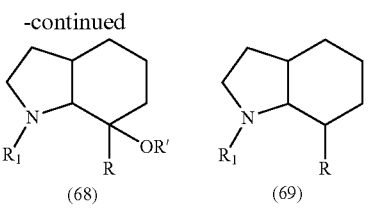

Azabicycles of general formula (66), (67), (68) and (69), wherein R is aryl or heterocycle, R' is alkyl and $R_1$ is as defined in formula (I), may be prepared as described in Scheme 16. Methyl (cis)-7-oxooctahydro-1H-indole-1-carboxylate, prepared as described in J. Chem. Soc. Perkin Trans. I (1995) 2671–2672, may be processed as described in Schemes 2–8 to provide azabicycles of general formula (66), (67), (68) and (69).

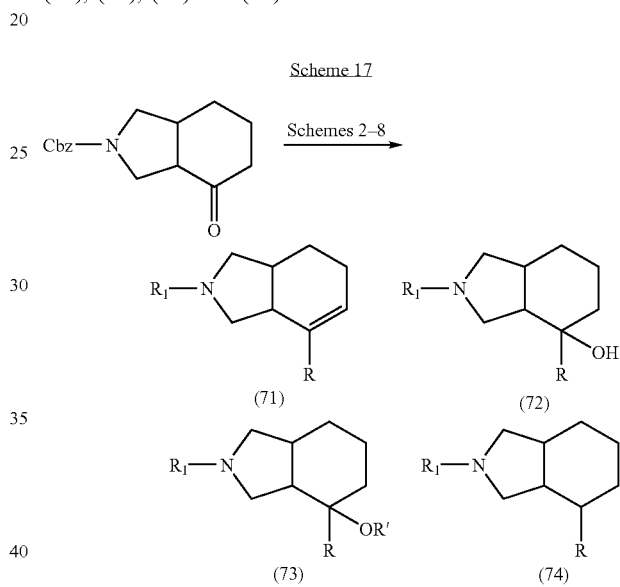

Azabicycles of general formula (71), (72), (73) and (74), wherein R is aryl or heterocycle, R' is alkyl and $R_1$ is as defined in formula (I), may be prepared as described in Scheme 17. Benzyl (cis)-4-oxooctahydro-2H-isoindole-2-carboxylate, prepared as described in Eur. J. Med. Chem. (1991) 26, 889–906, may be processed as described in Schemes 2–8 to provide azabicycles of general formula (71), (72), (73) and (74).

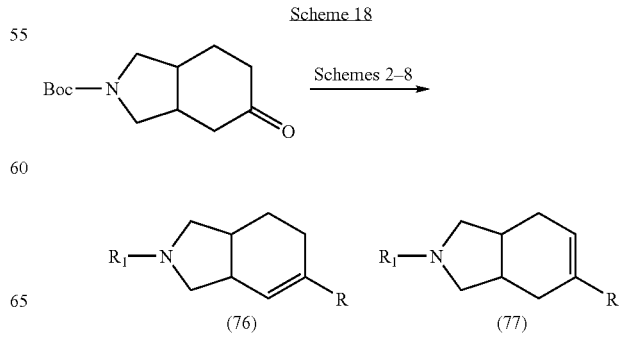

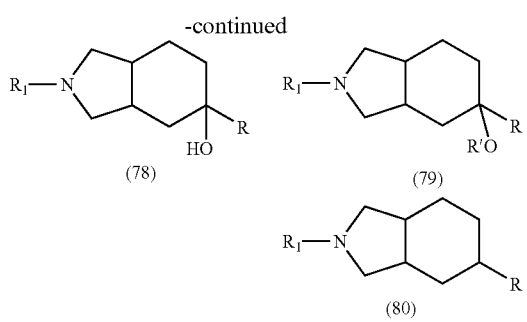

(78) (79) (80)

Azabicycles of general formula (76), (77), (78), (79) and (80), wherein R is aryl or heterocycle, R' is alkyl and $R_1$ is as defined in formula (I), may be prepared as described in Scheme 18. tert-Butyl (cis)-5-oxooctahydro-2H-isoindole-2-carboxylate, prepared as described in WO 9806720, may be processed as described in Schemes 2–8 to provide azabicycles of general formula (76), (77), (78), (79) and (80).

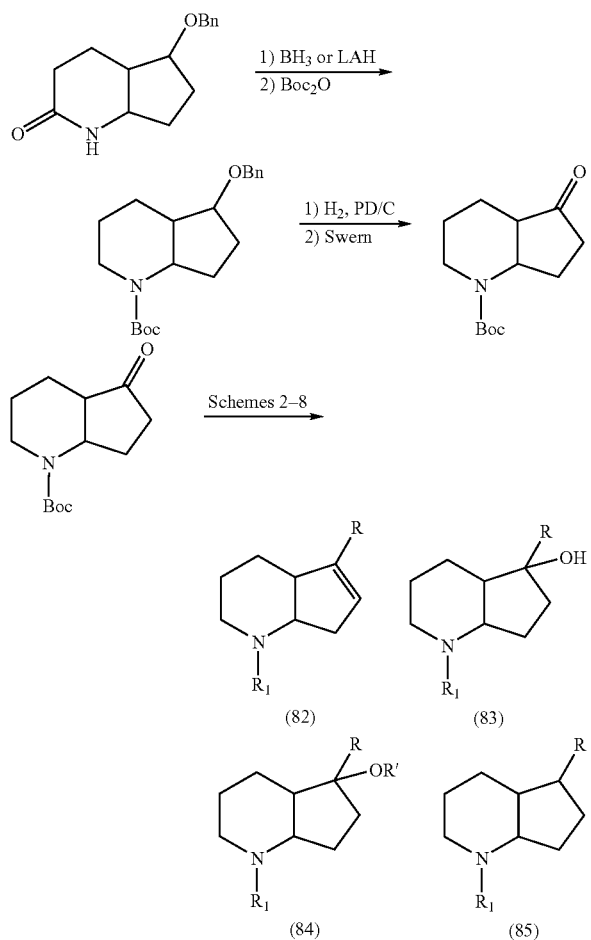

(82) (83) (84) (85)

Azabicycles of general formula (82), (83), (84) and (85), wherein R is aryl or heterocycle, R' is alkyl and $R_1$ is as defined in formula (I), may be prepared as described in Scheme 19. (cis)-5-(Benzyloxy)octahydro-2H-cyclopenta[b]pyridin-2-one, prepared as described in WO 9526187, may be treated with a reducing agent such as, but not limited to, borane-tetrahydrofuran complex or lithium aluminum hydride and then treated with di-tert-butyl dicarbonate (another suitable nitrogen protecting reagent may also be used such as, but not limited to, benzyl chloroformate) to provide tert-butyl (cis)-5-(benzyloxy)octahydro-1H-cyclopenta[b] pyridine-1-carboxylate. tert-Butyl (cis)-5-(benzyloxy)octahydro-1H-cyclopenta[b]pyridine-1-carboxylate may be treated with a transition metal catalyst such as, but not limited to, palladium on carbon under a hydrogen atmosphere and then treated with an oxidizing agent to provide tert-butyl (cis)-5-oxooctahydro-1H-cyclopenta[b]pyridine-1-carboxylate. tert-Butyl (cis)-5-oxooctahydro-1H-cyclopenta[b]pyridine-1-carboxylate may be processed as described in Schemes 2–8 to provide azabicycles of general formula (82), (83), (84) and (85).

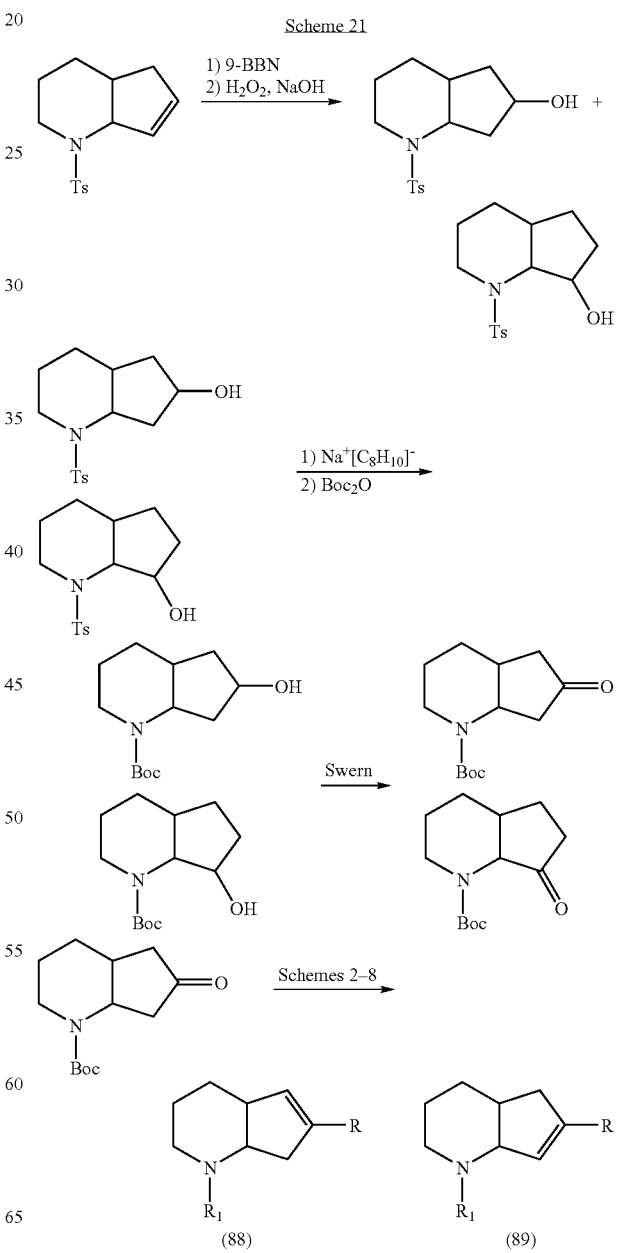

(88) (89)

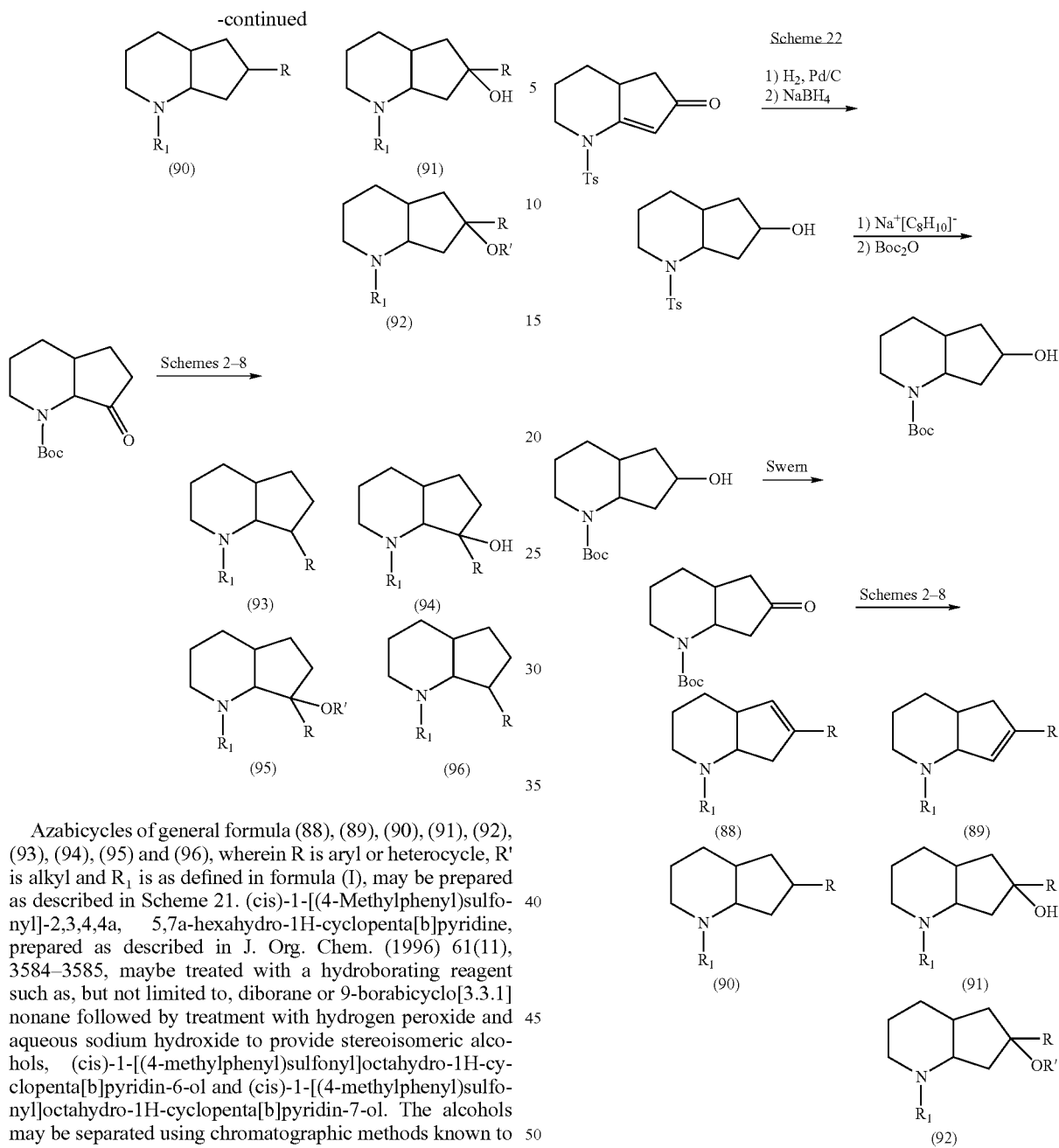

Azabicycles of general formula (88), (89), (90), (91), (92), (93), (94), (95) and (96), wherein R is aryl or heterocycle, R' is alkyl and R₁ is as defined in formula (I), may be prepared as described in Scheme 21. (cis)-1-[(4-Methylphenyl)sulfonyl]-2,3,4,4a, 5,7a-hexahydro-1H-cyclopenta[b]pyridine, prepared as described in J. Org. Chem. (1996) 61(11), 3584–3585, maybe treated with a hydroborating reagent such as, but not limited to, diborane or 9-borabicyclo[3.3.1] nonane followed by treatment with hydrogen peroxide and aqueous sodium hydroxide to provide stereoisomeric alcohols, (cis)-1-[(4-methylphenyl)sulfonyl]octahydro-1H-cyclopenta[b]pyridin-6-ol and (cis)-1-[(4-methylphenyl)sulfonyl]octahydro-1H-cyclopenta[b]pyridin-7-ol. The alcohols may be separated using chromatographic methods known to those of skill in the art of organic chemistry. The alcohols may be treated with sodium naphthalenide and then treated with di-tert-butyl dicarbonate to provide tert-butyl (cis)-6-hydroxyoctahydro-1H-cyclopenta[b]pyridine-1-carboxylate or tert-butyl (cis)-7-hydroxyoctahydro-1H-cyclopenta[b]pyridine-1-carboxylate. The alcohols may be oxidized under Swern conditions (DMSO/oxalyl chloride/triethylamine) to provide the corresponding ketones, tert-butyl (cis)-6-oxooctahydro-1H-cyclopenta[b]pyridine-1-carboxylate or tert-butyl (cis)-7-oxooctahydro-1H-cyclopenta[b]pyridine-1-carboxylate. tert-Butyl (cis)-6-oxooctahydro-1H-cyclopenta[b]pyridine-1-carboxylate may be processed as described in Schemes 2–8 to provide azabicycles of general formula (88), (89), (90), (91) and (92). tert-Butyl (cis)-7-oxooctahydro-1H-cyclopenta[b]pyridine-1-carboxylate may be processed as described in Schemes 2–8 to provide azabicycles of general formula (93), (94), (95) and (96).

An alternative method of preparing azabicycles of general formula (88), (89), (90), (91) and (92), wherein R is aryl or heterocycle, R' is alkyl and R₁ is as defined in formula (I), may be used as described in Scheme 22. 1-[(4-Methylphenyl)sulfonyl]-1,2,3,4,4a,5-hexahydro-6H-cyclopenta[b]pyridin-6-one, prepared as described in J. Org. Chem. (1996) 61(16), 5540–5552, may be treated with a transition metal catalyst such as, but not limited to, palladium on carbon under a hydrogen atmosphere and then treated with a reducing agent such as, but not limited to, sodium borohydride to provide stereoisomeric alcohols. The stereoisomeric alcohols may be treated with sodium naphthalenide and then treated with di-tert-butyl dicarbonate to provide the N-boc protected stereoisomeric alcohols. The N-boc protected stereoisomeric alcohols may be oxidized under Swern conditions (DMSO/oxalyl chloride/triethylamine) to provide tert-butyl (cis)-6-oxooctahydro-1H-cyclopenta[b]pyridine-1-carboxylate. tert-Butyl (cis)-6-oxooctahydro-1H-cyclopenta[b]pyridine-1-carboxylate may be processed as described in Schemes 2–8 to provide azabicycles of general formula (88), (89), (90), (91) and (92).

Scheme 23

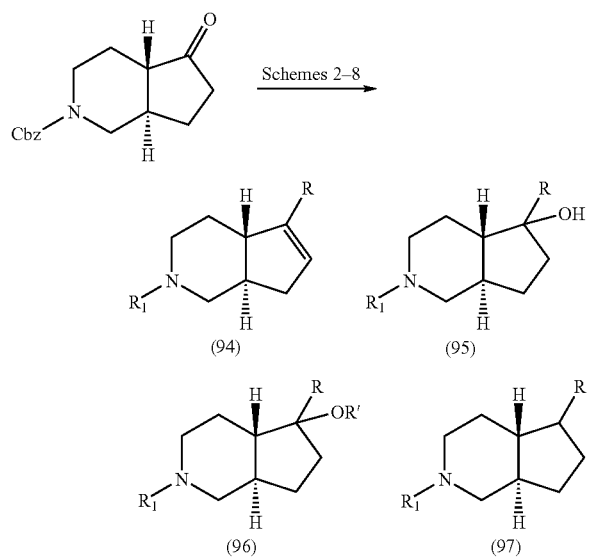

(94)    (95)

(96)    (97)

Azabicycles of general formula (94), (95), (96) and (97), wherein R is aryl or heterocycle, R' is alkyl and $R_1$ is as defined in formula (I), may be prepared as described in Scheme 23. Benzyl (trans)-5-oxooctahydro-2H-cyclopenta[c]pyridine-2-carboxylate, prepared as described in Eur. J. Med. Chem. (1991) 26, 889–906, maybe processed as described in Schemes 2–8 to provide azabicycles of general formula (94), (95), (96) and (97).

Scheme 24

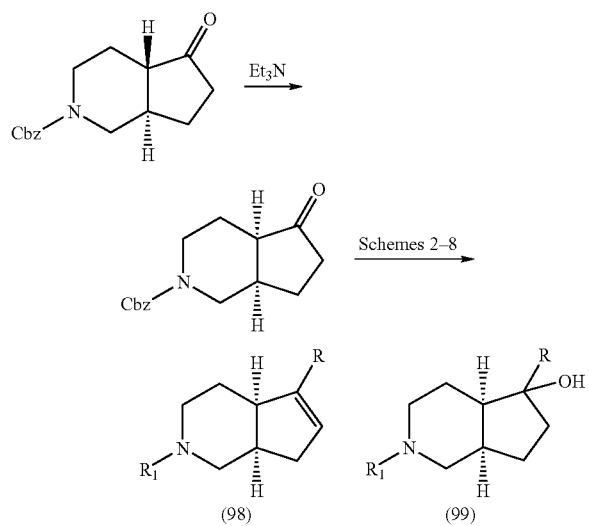

(98)    (99)

-continued

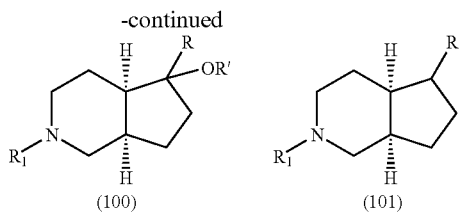

(100)    (101)

Azabicycles of general formula (98), (99), (100) and (101), wherein R is aryl or heterocycle, R' is alkyl and $R_1$ is as defined in formula (I), may be prepared as described in Scheme 24. Benzyl (trans)-5-oxooctahydro-2H-cyclopenta[c]pyridine-2-carboxylate, prepared as described in Eur. J. Med. Chem. (1991) 26, 889–906, may be epimerized with a base such as, but not limited to, triethylamine to provide benzyl (cis)-5-oxooctahydro-2H-cyclopenta[c]pyridine-2-carboxylate. Benzyl (cis)-5-oxooctahydro-2H-cyclopenta[c]pyridine-2-carboxylate may be processed as described in Schemes 2–8 to provide azabicycles of general formula (98), (99), (100) and (101).

Scheme 25

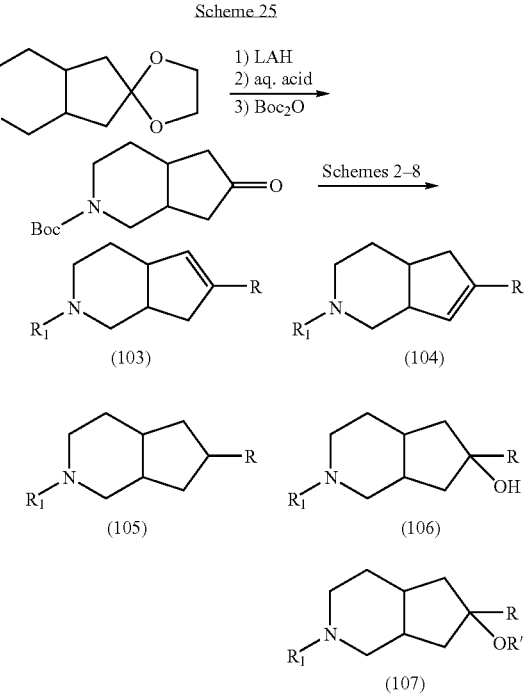

(103)    (104)

(105)    (106)

(107)

Azabicycles of general formula (103), (104), (105), (106) and (107), wherein R is aryl or heterocycle, R' is alkyl and $R_1$ is as defined in formula (I), may be prepared as described in Scheme 25. (cis)-Hexahydro-spiro[6H-cyclopenta[c]pyridine-6,2'-[1,3]dioxolan]-3(2H)-one, prepared as described in Tetrahedron: Asymmetry (1997) 8(17), 2893–2903 may be treated with a reducing agent such as, but not limited to, borane tetrahydrofuran complex or lithium aluminum hydride, treated with aqueous acid and then treated with di-tert-butyl dicarbonate to provide tert-butyl (cis)-6-oxooctahydro-2H-cyclopenta[c]pyridine-2-carboxylate. tert-Butyl (cis)-6-oxooctahydro-2H-cyclopenta[c]pyridine-2-carboxylate may be processed as described in Schemes 2–8 to provide azabicycles of general formula (103), (104), (105), (106) and (107).

Scheme 26

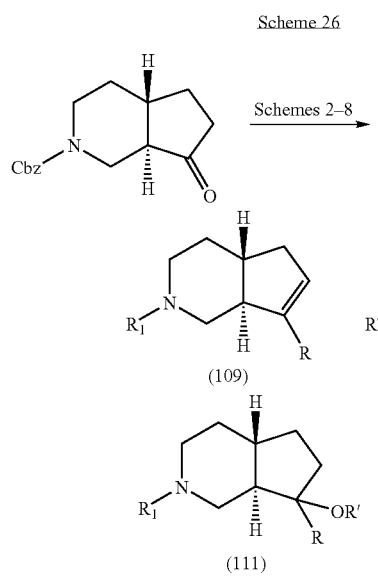

Azabicycles of general formula (109), (110), (111) and (112), wherein R is aryl or heterocycle, R' is alkyl and R₁ is as defined in formula (I), may be prepared as described in Scheme 26. Benzyl (trans)-7-oxooctahydro-2H-cyclopenta[c]pyridine-2-carboxylate, prepared as described in Eur. J. Med. Chem. (1991) 26, 889–906, may be processed as described in Schemes 2–8 to provide azabicycles of general formula (109), (110), (111) and (112).

Scheme 27

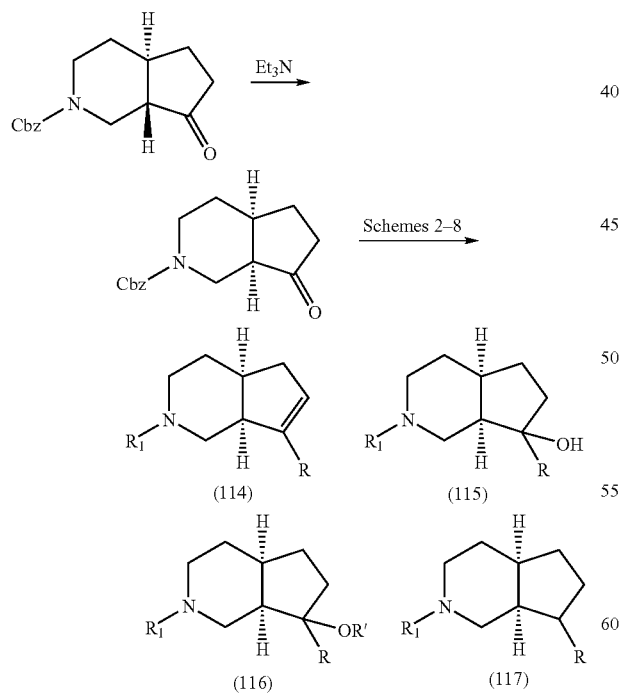

Azabicycles of general formula (114), (115), (116) and (117), wherein R is aryl or heterocycle, R' is alkyl and R₁ is as defined in formula (I), may be prepared as described in Scheme 27. Benzyl (trans)-7-oxooctahydro-2H-cyclopenta[c]pyridine-2-carboxylate, prepared as described in Eur. J. Med. Chem. (1991) 26, 889–906, may be epimerized with a base such as, but not limited to, triethylamine to provide benzyl (cis)-7-oxooctahydro-2H-cyclopenta[c]pyridine-2-carboxylate. Benzyl (cis)-7-oxooctahydro-2H-cyclopenta[c]pyridine-2-carboxylate may be processed as described in Schemes 2–8 to provide azabicycles of general formula (114), (115), (116) and (117).

Scheme 28

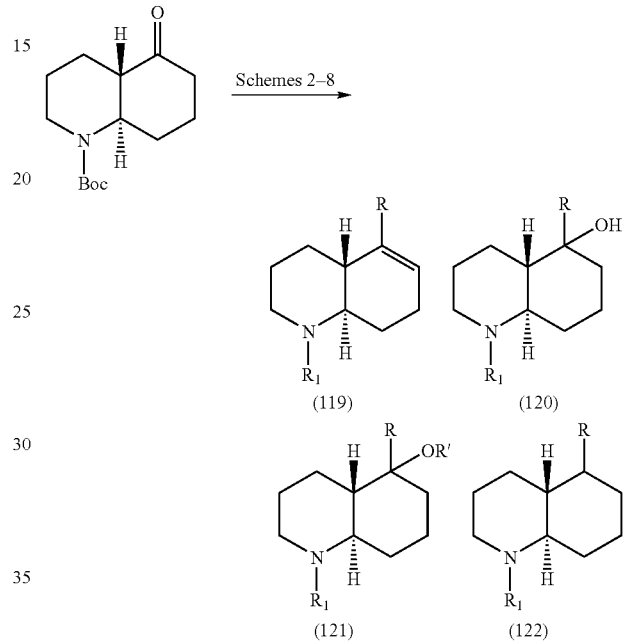

Azabicycles of general formula (119), (120), (121) and (122), wherein R is aryl or heterocycle, R' is alkyl and R₁ is as defined in formula (I), may be prepared as described in Scheme 28. tert-Butyl (trans)-5-oxooctahydro-1(2H)-quinolinecarboxylate, prepared as described in J. Med. Chem. (1991) 34(9), 2736–2746, may be processed as described in Schemes 2–8 to provide azabicycles of general formula (119), (120), (121) and (122).

Scheme 29

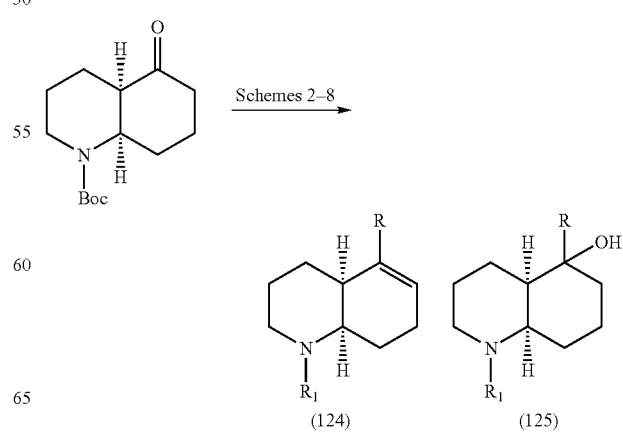

-continued

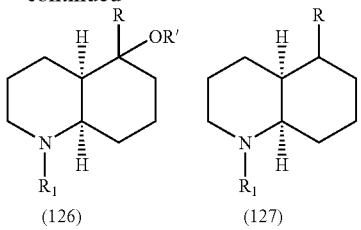

(126)   (127)

Azabicycles of general formula (124), (125), (126) and (127), wherein R is aryl or heterocycle, R' is alkyl and $R_1$ is as defined in formula (I), may be prepared as described in Scheme 29. tert-Butyl (cis)-5-oxooctahydro-1(2H)-quinolinecarboxylate, prepared as described in J. Med. Chem. (1991) 34(9), 2736–2746, may be processed as described in Schemes 2–8 to provide azabicycles of general formula (124), (125), (126) and (127).

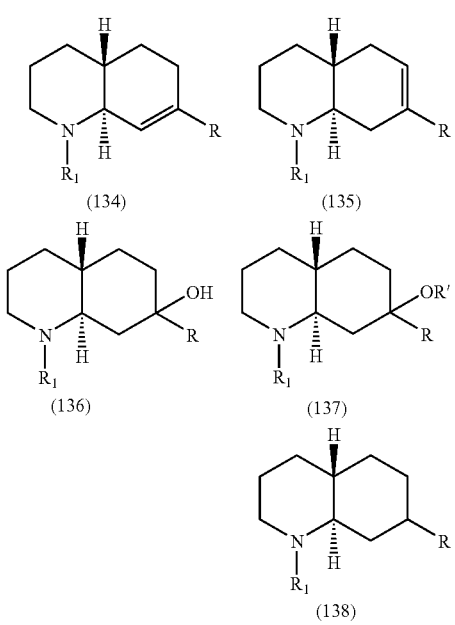

(134)   (135)

(136)   (137)

(138)

Azabicycles of general formula (129), (130), (131), (132), (133), (134), (135), (136), (137) and (138), wherein R is aryl or heterocycle, R' is alkyl and $R_1$ is as defined in formula (I), may be prepared as described in Scheme 30. (trans)-1,2,3,4,4a,5,8,8a-Octahydroquinoline, prepared as described in J. Med. Chem. (1999) 42(15), 2862–2869, may be treated with di-tert-butyl dicarbonate in a solvent such as, but not limited to, THF or 1,4-dioxane to provide tert-butyl (trans)-3,4,4a,5,8,8a-hexahydro-1(2H)-quinolinecarboxylate. tert-Butyl (trans)-3,4,4a,5,8,8a-hexahydro-1(2H)-quinolinecarboxylate may be processed as described in Scheme 21 to provide ketones tert-butyl (trans)-6-oxooctahydro-1(2H)-quinolinecarboxylate and tert-butyl (trans)-7-oxooctahydro-1(2H)-quinolinecarboxylate. The ketones may be separated using methods known to those of skill in the art of organic chemistry such as, but not limited to, chromatography. tert-Butyl (trans)-6-oxooctahydro-1(2H)-quinolinecarboxylate may be processed as described in Schemes 2–8 to provide azabicycles of general formula (129), (130), (131), (132) and (133). tert-Butyl (trans)-7-oxooctahydro-1(2H)-quinolinecarboxylate may be processed as described in Schemes 2–8 to provide azabicycles of general formula (134), (135), (136), (137) and (138).

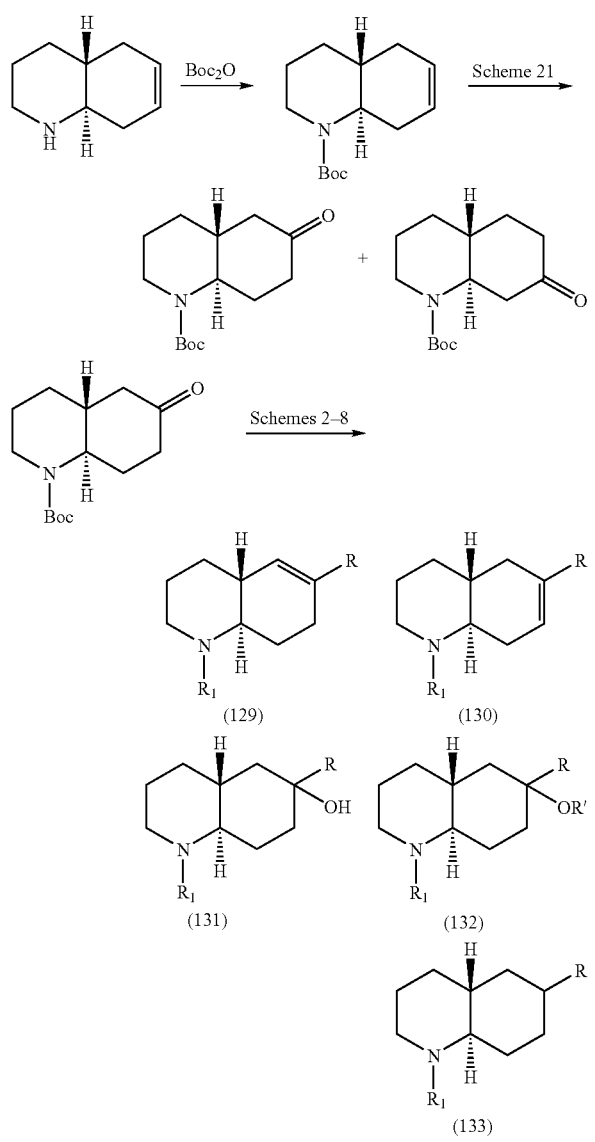

Scheme 30

(129)   (130)

(131)   (132)

(133)

Scheme 31

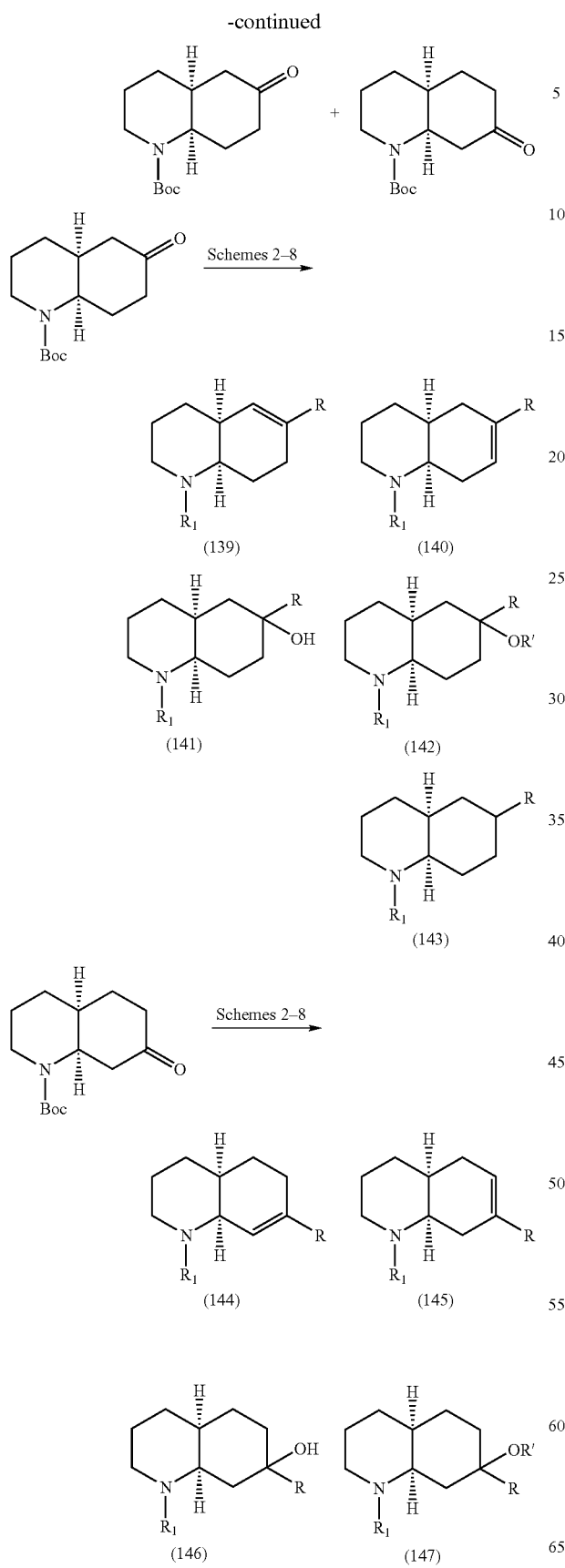
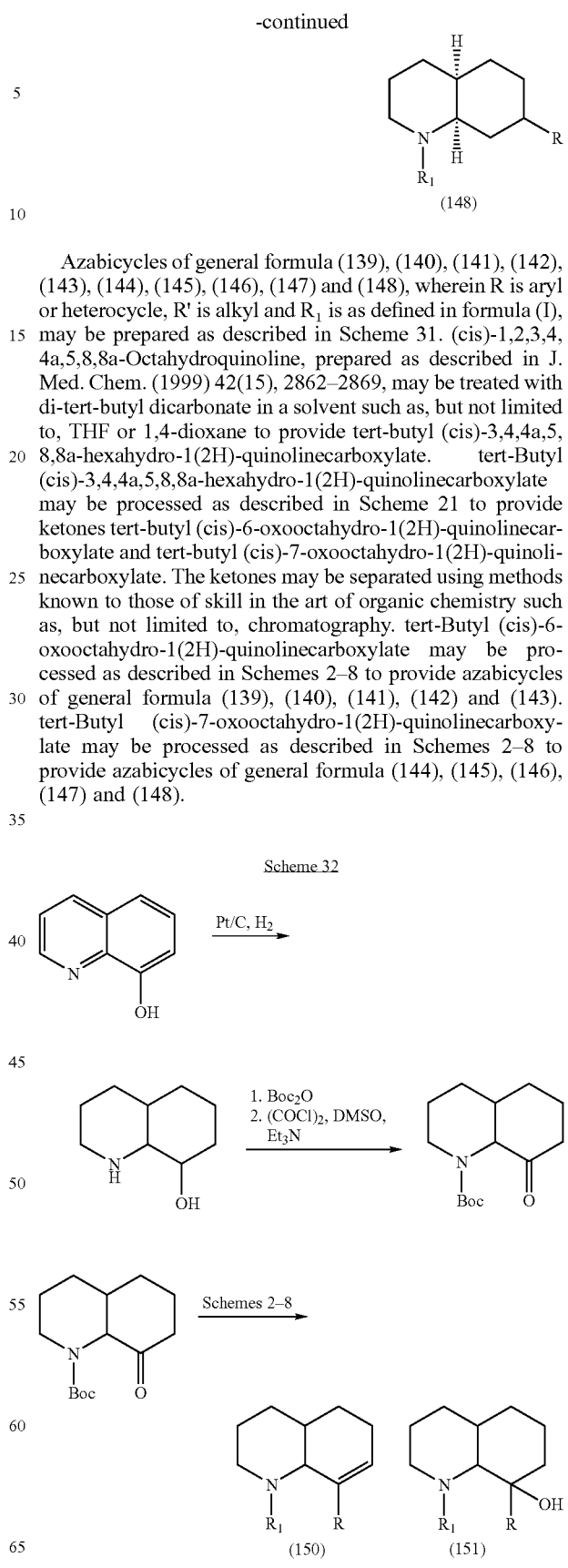

Azabicycles of general formula (139), (140), (141), (142), (143), (144), (145), (146), (147) and (148), wherein R is aryl or heterocycle, R' is alkyl and R₁ is as defined in formula (I), may be prepared as described in Scheme 31. (cis)-1,2,3,4, 4a,5,8,8a-Octahydroquinoline, prepared as described in J. Med. Chem. (1999) 42(15), 2862–2869, may be treated with di-tert-butyl dicarbonate in a solvent such as, but not limited to, THF or 1,4-dioxane to provide tert-butyl (cis)-3,4,4a,5, 8,8a-hexahydro-1(2H)-quinolinecarboxylate. tert-Butyl (cis)-3,4,4a,5,8,8a-hexahydro-1(2H)-quinolinecarboxylate may be processed as described in Scheme 21 to provide ketones tert-butyl (cis)-6-oxooctahydro-1(2H)-quinolinecarboxylate and tert-butyl (cis)-7-oxooctahydro-1(2H)-quinolinecarboxylate. The ketones may be separated using methods known to those of skill in the art of organic chemistry such as, but not limited to, chromatography. tert-Butyl (cis)-6-oxooctahydro-1(2H)-quinolinecarboxylate may be processed as described in Schemes 2–8 to provide azabicycles of general formula (139), (140), (141), (142) and (143). tert-Butyl (cis)-7-oxooctahydro-1(2H)-quinolinecarboxylate may be processed as described in Schemes 2–8 to provide azabicycles of general formula (144), (145), (146), (147) and (148).

-continued

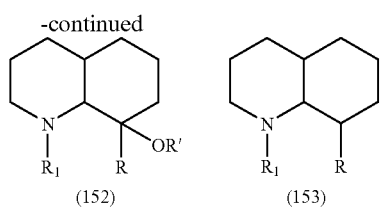

(152)　　(153)

Azabicycles of general formula (150), (151), (152) and (153), wherein R is aryl or heterocycle, R' is alkyl and R₁ is as defined in formula (I), may be prepared as described in Scheme 32. 8-Quinolinol, purchased from Aldrich, may be treated with a platinum catalyst such as, but not limited to, platinum on carbon under a hydrogen atmosphere to provide (cis)-decahydro-8-quinolinol. (cis)-Decahydro-8-quinolinol may be treated with a nitrogen protecting group reagent such as, but not limited to, di-tert-butyl dicarbonate and then oxidized under Swern conditions to provided tert-butyl (cis)-8-oxooctahydro-1(2H)-quinolinecarboxylate. tert-Butyl (cis)-8-oxooctahydro-1(2H)-quinolinecarboxylate may be processed as described in Schemes 2–8 to provide azabicycles of general formula (150), (151), (152) and (153).

Scheme 33

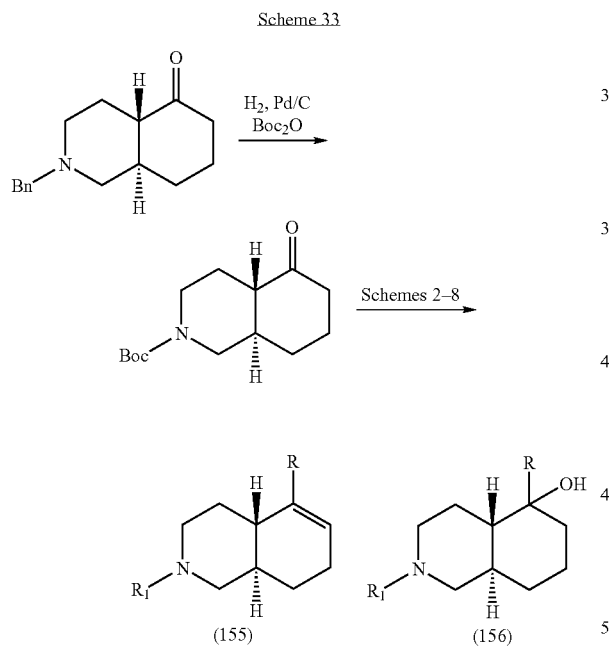

Azabicycles of general formula (155), (156), (157) and (158), wherein R is aryl or heterocycle, R' is alkyl and R₁ is as defined in formula (I), may be prepared as described in Scheme 33. (trans)-2-Benzyloctahydro-5(1H)-isoquinolinone, prepared as described in J. Am. Chem. Soc. (1991) 113(23), 8863–8878, may be treated with a metal catalyst such as, but not limited to, palladium on carbon under a hydrogen atmosphere in the presence of di-tert-butyl dicarbonate to provide tert-butyl (trans)-5-oxooctahydro-2(1H)-isoquinolinecarboxylate. tert-Butyl (trans)-5-oxooctahydro-2(1H)-isoquinolinecarboxylate may be processed as described in Schemes 2–8 to provide azabicycles of general formula (155), (156), (157) and (158).

Scheme 34

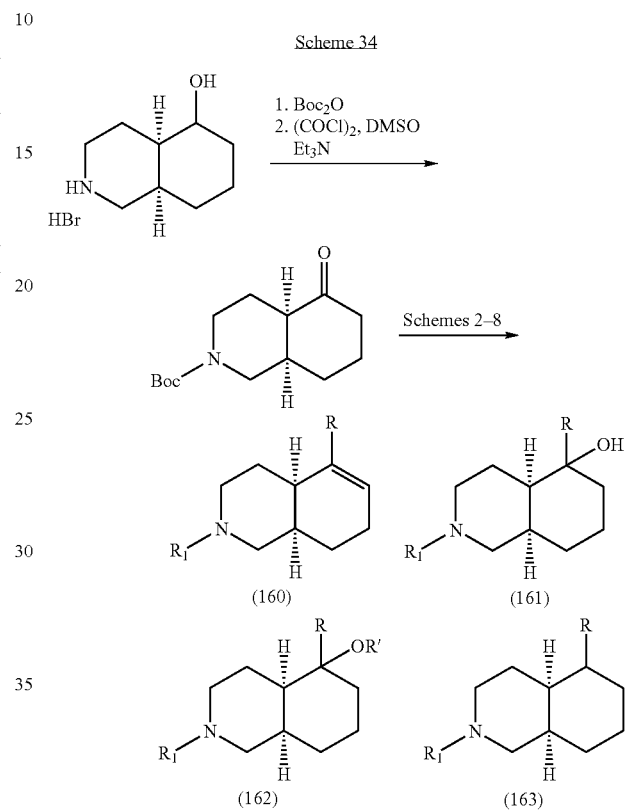

Azabicycles of general formula (160), (161), (162) and (163), wherein R is aryl or heterocycle, R' is alkyl and R₁ is as defined in formula (I), may be prepared as described in Scheme 34. (cis)-Decahydro-5-isoquinolinol hydrobromide, prepared as described in J. Med. Chem. (1968) 11(5), 997–100, may be treated with di-tert-butyl dicarbonate and then oxidized under Swern conditions to provide tert-butyl (cis)-5-oxooctahydro-2(1H)-isoquinolinecarboxylate. tert-Butyl (cis)-5-oxooctahydro-2(1H)-isoquinolinecarboxylate may be processed as described in Schemes 2–8 to provide azabicycles of general formula (160), (161), (162) and (163).

Scheme 35

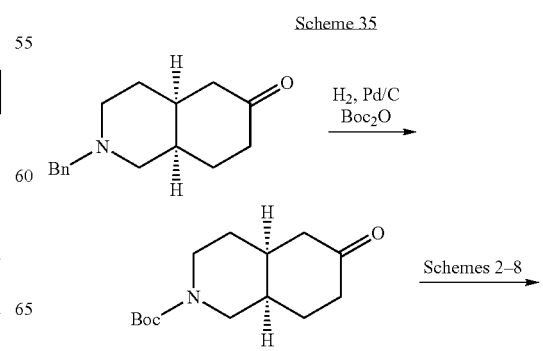

-continued

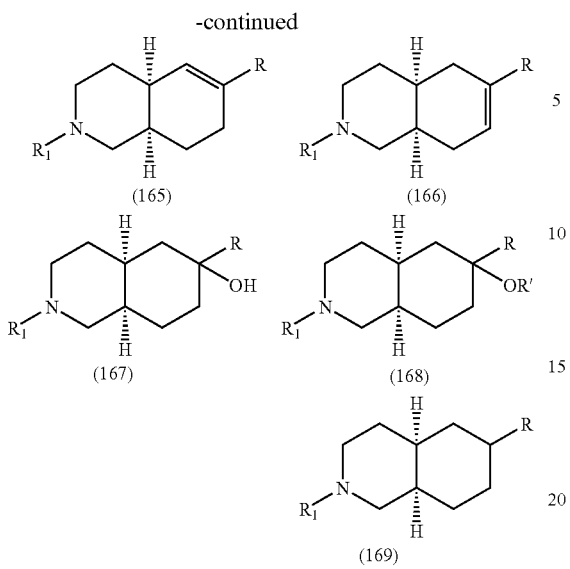

Azabicycles of general formula (165), (166), (167), (168) and (169), wherein R is aryl or heterocycle, R' is alkyl and R₁ is as defined in formula (I), may be prepared as described in Scheme 35. (cis)-2-Benzyloctahydro-6(2H)-isoquinolinone, prepared as described in J. Med. Chem. (1987) 30(7), 1210–1214, may be treated with a transition metal catalyst such as, but not limited to, palladium on carbon under an atmosphere of hydrogen in the presence of di-tert-butyl dicarbonate to provide tert-butyl (cis)-6-oxooctahydro-2 (1H)-isoquinolinecarboxylate. tert-Butyl (cis)-6-oxooctahydro-2(1H)-isoquinolinecarboxylate may be processed as described in Schemes 2–8 to provide azabicycles of general formula (165), (166), (167), (168) and (169).

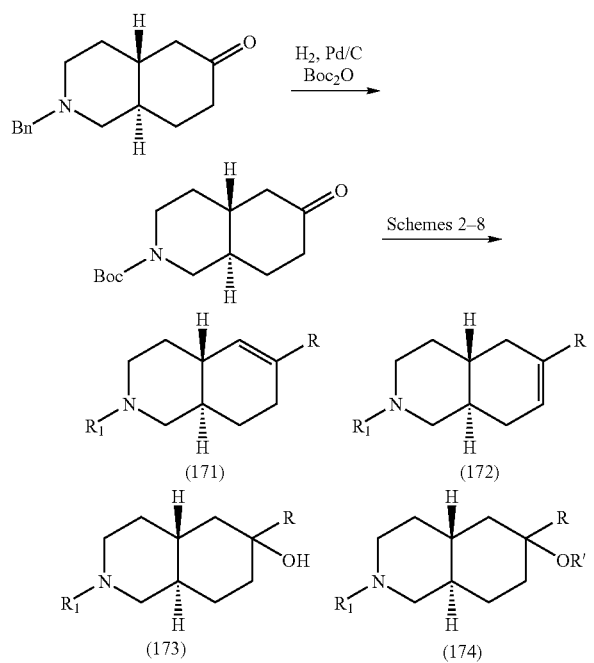

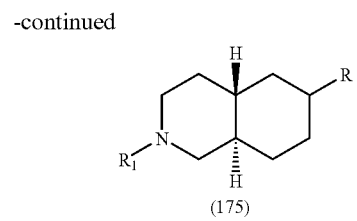

Azabicycles of general formula (171), (172), (173), (174) and (175), wherein R is aryl or heterocycle, R' is alkyl and R₁ is as defined in formula (I), may be prepared as described in Scheme 36. (trans)-2-Benzyloctahydro-6(2H)-isoquinolinone, prepared as described in J. Med. Chem. (1987) 30(7), 1210–1214, may be treated with a transition metal catalyst such as, but not limited to, palladium on carbon under an atmosphere of hydrogen in the presence of di-tert-butyl dicarbonate to provide tert-butyl (trans)-6-oxooctahydro-2 (1H)-isoquinolinecarboxylate. tert-Butyl (trans)-6-oxooctahydro-2(1H)-isoquinolinecarboxylate may be processed as described in Schemes 2–8 to provide azabicycles of general formula (171), (172), (173), (174) and (175).

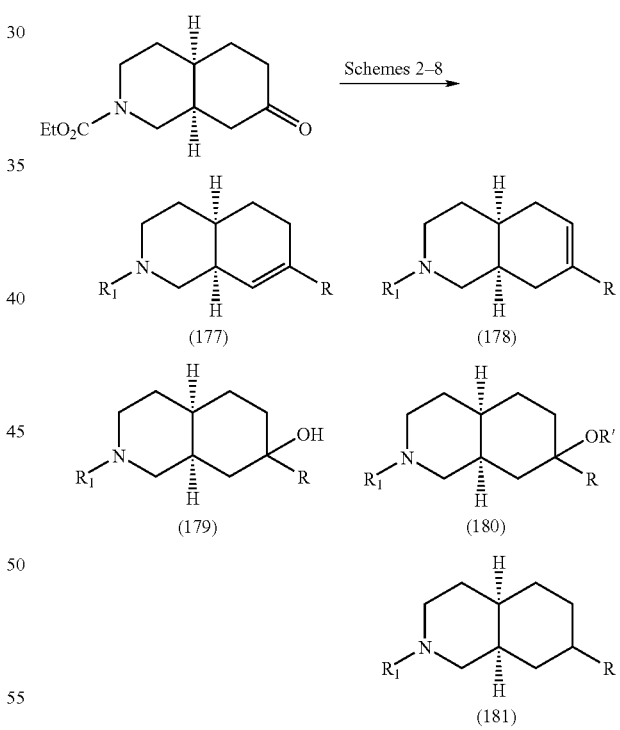

Azabicycles of general formula (177), (178), (179), (180) and (181), wherein R is aryl or heterocycle, R' is alkyl and R₁ is as defined in formula (I), may be prepared as described in Scheme 37. Ethyl (cis)-7-oxooctahydro-2(1H)-isoquinolinecarboxylate, prepared as described in J. Am. Chem. Soc. (1998) 120(41), 10676–10686, may be processed as described in Schemes 2–8 to provide azabicycles of general formula (177), (178), (179), (180) and (181).

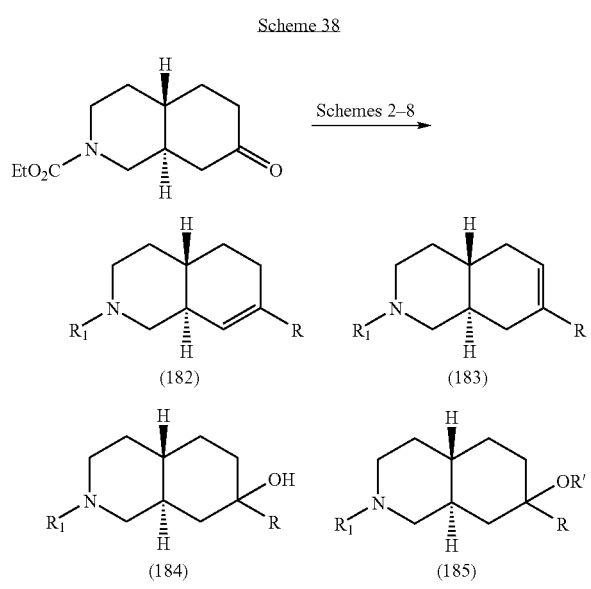

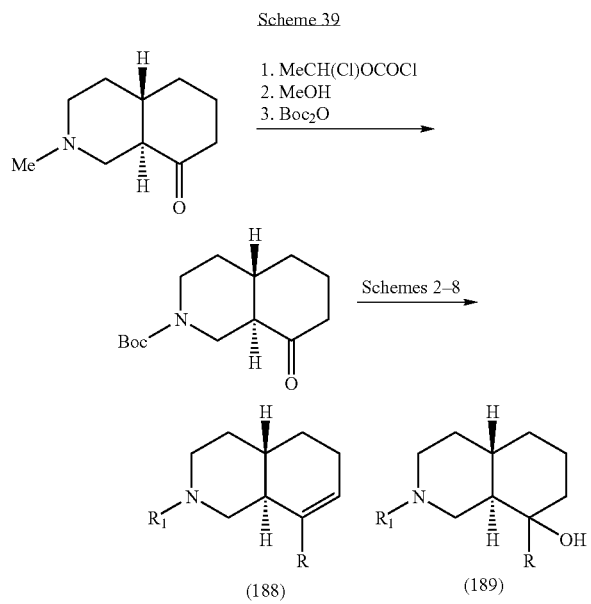

Azabicycles of general formula (182), (183), (184), (185) and (186), wherein R is aryl or heterocycle, R' is alkyl and R₁ is as defined in formula (I), may be prepared as described in Scheme 38. Ethyl (trans)-7-oxooctahydro-2(1H)-isoquinolinecarboxylate, prepared as described in J. Am. Chem. Soc. (1998) 120(41), 10676–10686, may be processed as described in Schemes 2–8 to provide azabicycles of general formula (182), (183), (184), (185) and (186).

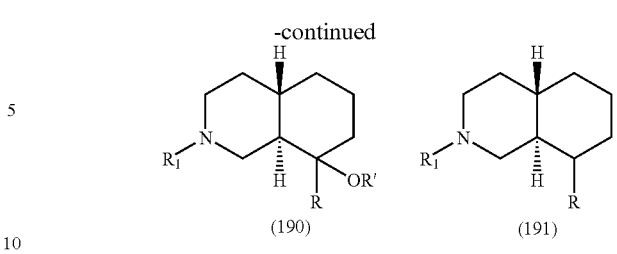

Azabicycles of general formula (188), (189), (190) and (191), wherein R is aryl or heterocycle, R' is alkyl and R₁ is as defined in formula (I), may be prepared as described in Scheme 39. (trans)-2-Methyloctahydro-8(2H)-isoquinolinone, prepared as described in J. Org. Chem. (1974) 39(22), 3210–3215, may be treated with 1-chloroethyl chloroformate followed by methanol and then treatment with di-tert-butyl dicarbonate to provide tert-butyl (trans)-8-oxooctahydro-2(1H)-isoquinolinecarboxylate. tert-Butyl (trans)-8-oxooctahydro-2(1H)-isoquinolinecarboxylate may be processed as described in Schemes 2–8 to provide azabicycles of general formula (188), (189), (190) and (191).

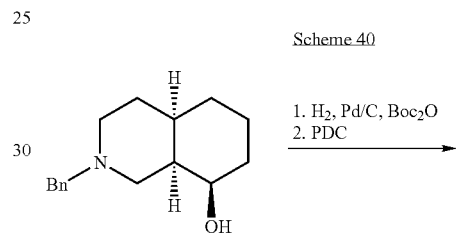

Azabicycles of general formula (192), (193), (194) and (195), wherein R is aryl or heterocycle, R' is alkyl and R₁ is as defined in formula (I), may be prepared as described in Scheme 40. (cis)-2-Benzyldecahydro-8-isoquinolinol, prepared as described in Tetrahedron Lett. (1998) 39(29), 5185–5188, may be treated with a metal catalyst such as, but not limited to, palladium on carbon under a hydrogen atmosphere in the presence of di-tert-butyl dicarbonate and then oxidized with pyridinium dichromate (PDC) to provide tert-butyl (cis)-8-oxooctahydro-2(1H)-isoquinolinecarboxylate. tert-Butyl (cis)-8-oxooctahydro-2(1H)-isoquinolinecarboxylate may be processed as described in Schemes 2–8 to provide azabicycles of general formula (192), (193), (194) and (195).

Scheme 41

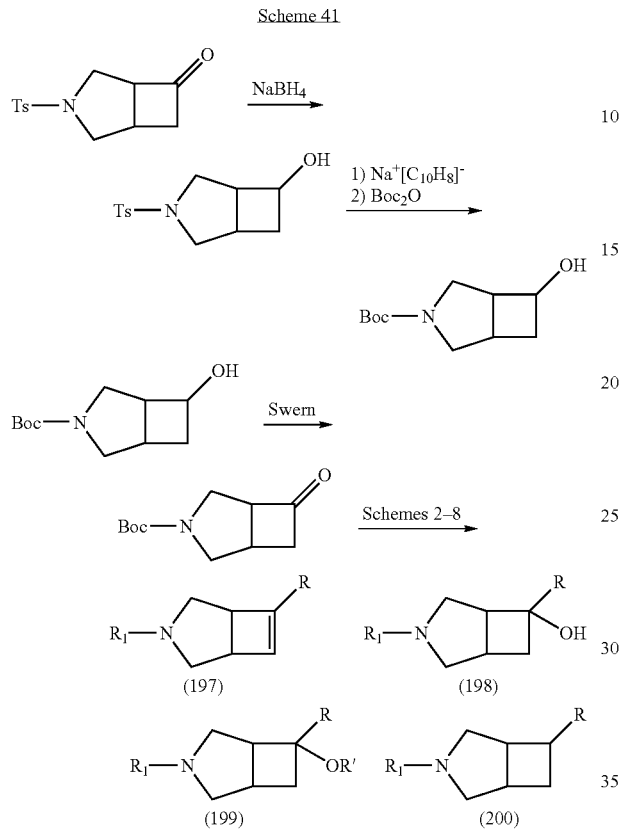

Azabicycles of general formula (197), (198), (199) and (200), wherein R is aryl or heterocycle, R' is alkyl and $R_1$ is as defined in formula (I), may be prepared as described in Scheme 41. (cis)-3-[(4-Methylphenyl)sulfonyl]-3-azabicyclo[3.2.0]heptan-6-one, prepared as described in Heterocycles (1989) 28(1), 29–32, may be treated with a reducing agent such as, but not limited to, sodium borohydride to provide stereoisomeric alcohols. The stereoisomeric alcohols may be treated with sodium naphthalenide and then treated with di-tert-butyl dicarbonate to provide N-boc protected stereoisomeric alcohols. The N-boc protected stereoisomeric alcohols may be oxidized agent under Swern conditions (DMSO/oxalyl chloride/triethylamine) to provide tert-butyl (cis)-6-oxo-3-azabicyclo[3.2.0]heptane-3-carboxylate. tert-Butyl (cis)-6-oxo-3-azabicyclo[3.2.0]heptane-3-carboxylate may be processed as described in Schemes 2–8 to provide azabicycles of general formula (197), (198), (199) and (200).

Scheme 42

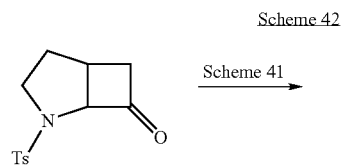

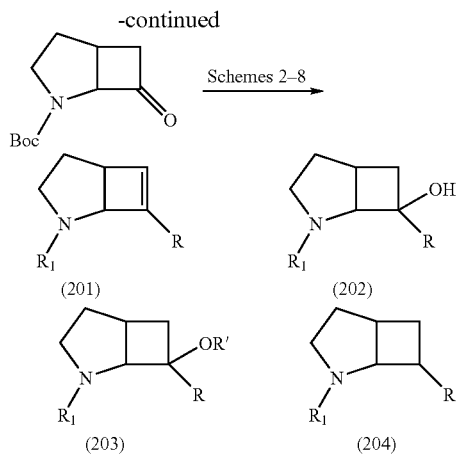

Azabicycles of general formula (201), (202), (203) and (204), wherein R is aryl or heterocycle, R' is alkyl and $R_1$ is as defined in formula (I), may be prepared as described in Scheme 42. (cis)-2-[(4-Methylphenyl)sulfonyl]-2-azabicyclo[3.2.0]heptan-7-one, prepared as described in Heterocycles (1989) 28(1), 29–32, may be processed as described in Scheme 41 to provide tert-butyl (cis)-7-oxo-2-azabicyclo[3.2.0]heptane-2-carboxylate. tert-Butyl (cis)-7-oxo-2-azabicyclo[3.2.0]heptane-2-carboxylate may be processed as described in Schemes 2–8 to provide azabicycles of general formula (201), (202), (203) and (204).

Scheme 43

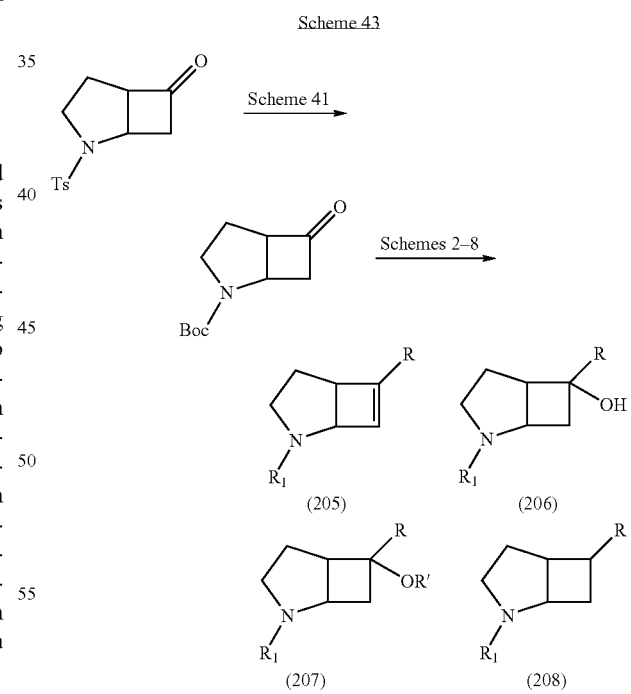

Azabicycles of general formula (205), (206), (207) and (208), wherein R is aryl or heterocycle, R' is alkyl and $R_1$ is as defined in formula (I), may be prepared as described in Scheme 43. (cis)-2-[(4-Methylphenyl)sulfonyl]-2-azabicyclo[3.2.0]heptan-6-one, prepared as described in Tetrahedron Lett. (1993) 34(1), 27–30, may be processed as described in Scheme 41 to provide tert-butyl (cis)-6-oxo-2- azabicyclo[3.2.0]heptane-2-carboxylate. tert-Butyl (cis)-6-oxo-2-azabicyclo[3.2.0]heptane-2-carboxylate may be processed as described in Schemes 2–8 to provide azabicycles of general formula (205), (206), (207) and (208).

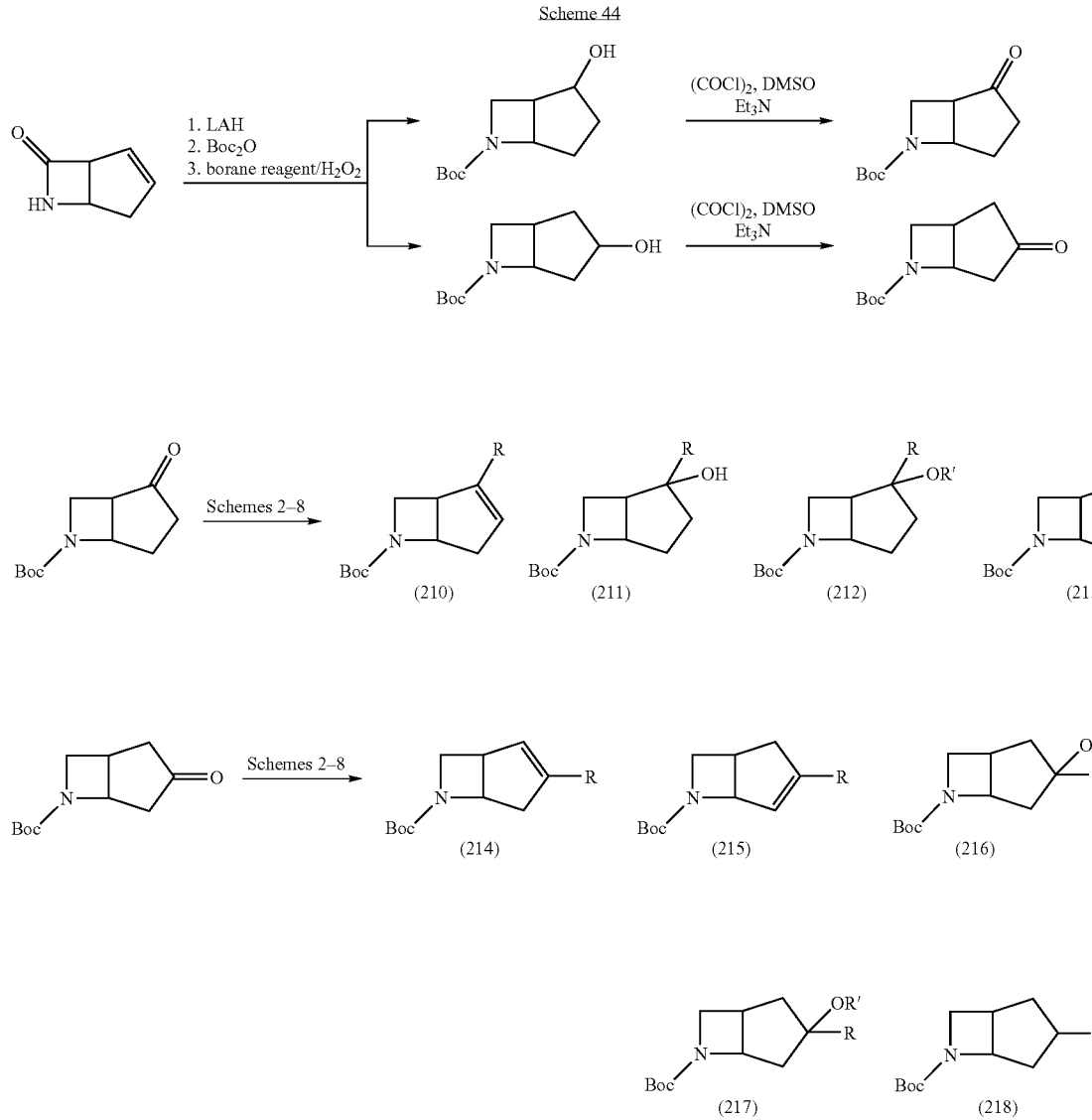

Azabicycles of general formula (210), (211), (212), (213), (214), (215), (216), (217) and (218), wherein R is aryl or heterocycle, R' is alkyl and $R_1$ is as defined in formula (I), may be prepared as described in Scheme 44. (cis)-6-Azabicyclo[3.2.0]hept-2-en-7-one, prepared as described in Tetrahedron Lett. (1999) 40(15), 4857–4860, may be treated with lithium aluminum hydride (LAH) followed by di-tert-butyl dicarbonate and then treatment with a hydroborating agent such as, but not limited to, 9-borabicyclo[3.3.1]nonane to provide a stereoisomeric mixture of alcohols, tert-butyl (cis)-2-hydroxy-6-azabicyclo[3.2.0]heptane-6-carboxylate and tert-butyl (cis)-3-hydroxy-6-azabicyclo[3.2.0]heptane-6-carboxylate. The alcohols may be separated using methods known to those of skill in the art of organic chemistry such as, but not limited to, chromatography and then oxidized under Swern conditions to provide the corresponding ketones. tert-Butyl (cis)-2-oxo-6-azabicyclo[3.2.0]heptane-6-carboxylate may be processed as described in Schemes 2–8 to provide azabicycles of general formula (210), (211), (212) and (213). tert-Butyl (cis)-3-oxo-6-azabicyclo[3.2.0]heptane-6-carboxylate may be processed as described in Schemes 2–8 to provide azabicycles of general formula (214), (215), (216), (217) and (218).

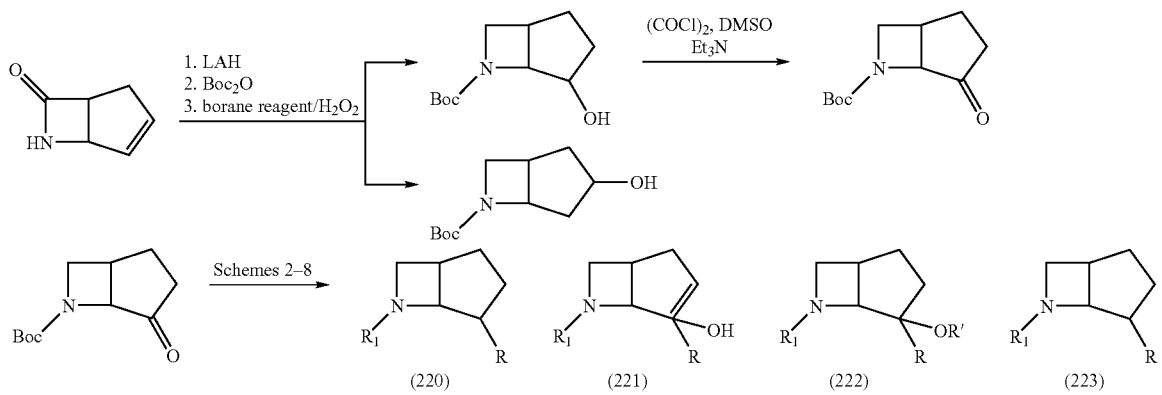

Azabicycles of general formula (220), (221), (222) and (223), wherein R is aryl or heterocycle, R' is alkyl and $R_1$ is as defined in formula (I), may be prepared as described in Scheme 45. (cis)-6-Azabicyclo[3.2.0]hept-3-en-7-one, prepared as described in Tetrahedron Lett. (1985) 26(16), 1907–1910, may be treated with lithium aluminum hydride (LAH) followed by di-tert-butyl dicarbonate and then treatment with a hydroborating agent such as, but not limited to, 9-borabicyclo[3.3.1]nonane to provide a stereoisomeric mixture of alcohols, tert-butyl (cis)-3-hydroxy-6-azabicyclo[3.2.0]heptane-6-carboxylate and tert-butyl (cis)-4-hydroxy-6-azabicyclo[3.2.0]heptane-6-carboxylate. The alcohols may be separated using methods known to those of skill in the art of organic chemistry such as, but not limited to, chromatography and then oxidized under Swern conditions to provide the corresponding ketones. tert-Butyl (cis)-4-oxo-6-azabicyclo[3.2.0]heptane-6-carboxylate may be processed as described in Schemes 2–8 to provide azabicycles of general formula (220), (221), (222) and (223).

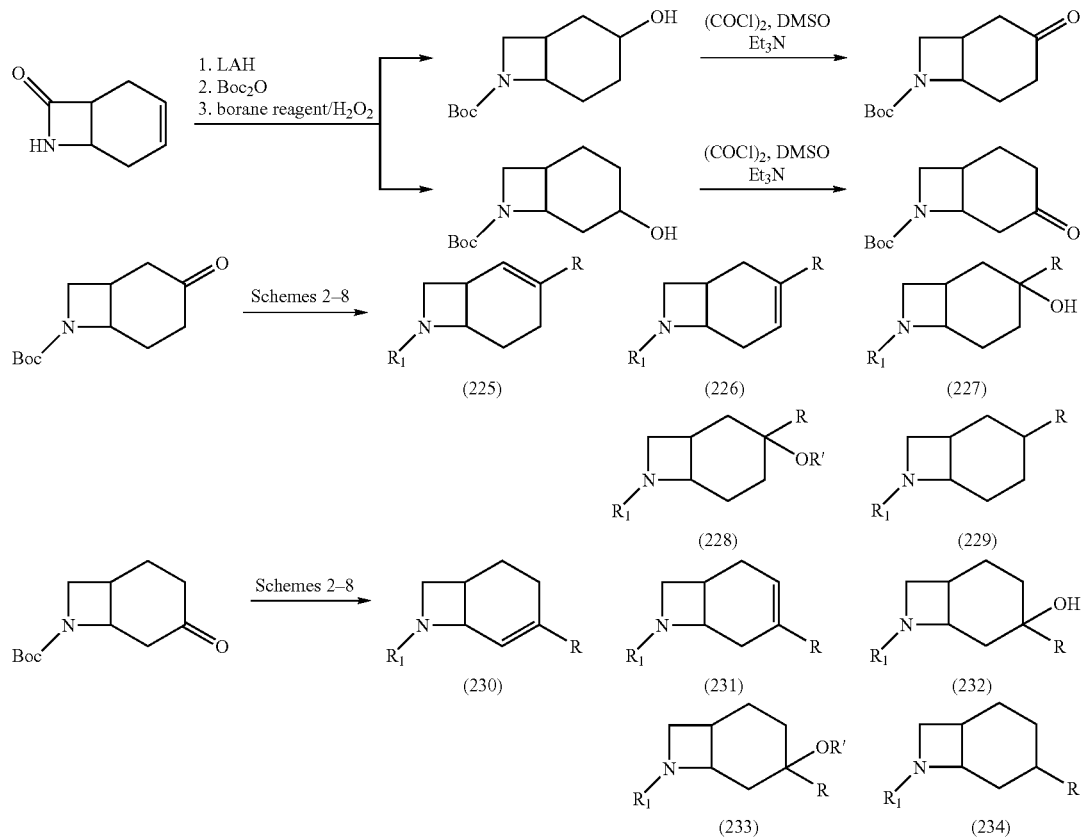

Azabicycles of general formula (225), (226), (227), (228), (229), (230), (231), (232), (233) and (234), wherein R is aryl or heterocycle, R' is alkyl and $R_1$ is as defined in formula (I), may be prepared as described in Scheme 46. (cis)-7-Azabicyclo[4.2.0]oct-3-en-8-one, purchased from Maybridge or prepared as described in J. Am. Chem. Soc. (1968) 90(14), 3897–3898, may be treated with lithium aluminum hydride followed by di-tert-butyl dicarbonate and then treatment with a hydroborating agent such as, but not limited to, 9-borabicyclo[3.3.1]nonane to provide a stereoisomeric mixture of alcohols, tert-butyl (cis)-3-hydroxy-7-azabicyclo [4.2.0]octane-7-carboxylate and tert-butyl (cis)-4-hydroxy-7-azabicyclo[4.2.0]octane-7-carboxylate. The alcohols may be separated using methods known to those of skill in the art of organic chemistry such as, but not limited to, chromatography and then oxidized under Swern conditions to provide the corresponding ketones. tert-Butyl (cis)-3-oxo-7-azabicyclo[4.2.0]octane-7-carboxylate may be processed as described in Schemes 2–8 to provide azabicycles of general formula (225), (226), (227), (228) and (229). tert-Butyl (cis)-4-oxo-7-azabicyclo[4.2.0]octane-7-carboxylate may be processed as described in Schemes 2–8 to provide azabicycles of general formula (230), (231), (232), (233) and (234).

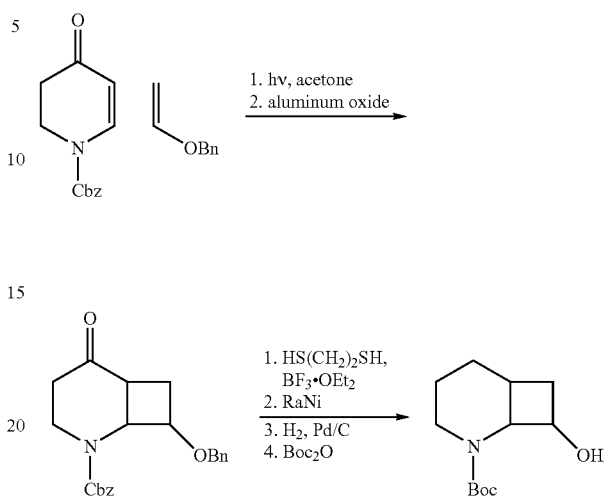

Scheme 48

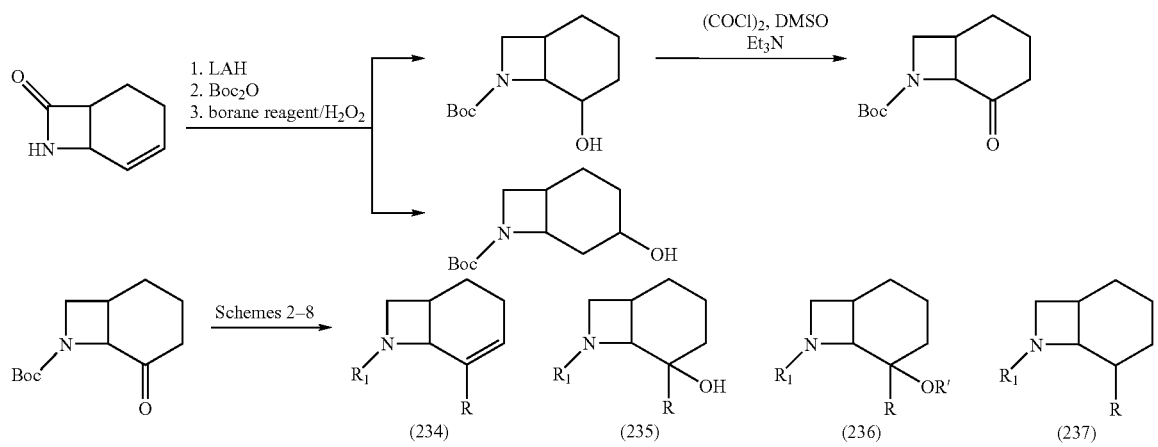

Scheme 47

Azabicycles of general formula (234), (235), (236) and (237), wherein R is aryl or heterocycle, R' is alkyl and $R_1$ is as defined in formula (I), may be prepared as described in Scheme 47. (cis)-7-Azabicyclo[4.2.0]oct-4-en-8-one, prepared as described in J. Chem. Soc., Perkin Trans. I (1977) 874–884, may be treated with lithium aluminum hydride followed by di-tert-butyl dicarbonate and then treatment with a hydroborating agent such as, but not limited to, 9-borabicyclo[3.3.1]nonane to provide a stereoisomeric mixture of alcohols, tert-butyl (cis)4-hydroxy-7-azabicyclo [4.2.0]octane-7-carboxylate and tert-butyl (cis)-5-hydroxy-7-azabicyclo[4.2.0]octane-7-carboxylate. The alcohols may be separated using methods known to those of skill in the art of organic chemistry such as, but not limited to, chromatography and then oxidized under Swern conditions to provide the corresponding ketones. tert-Butyl (cis)-5-oxo-7-azabicyclo[4.2.0]octane-7-carboxylate may be processed as described in Schemes 2–8 to provide azabicycles of general formula (234), (235), (236) and (237).

-continued

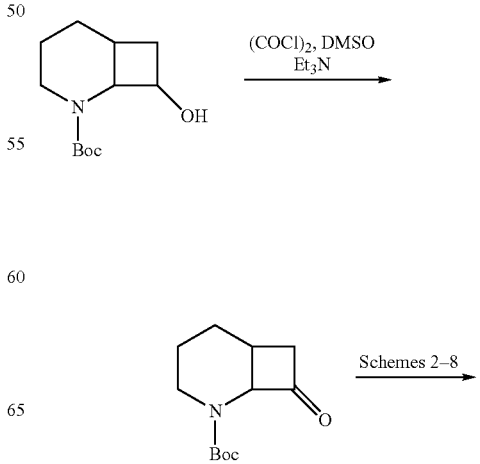

-continued

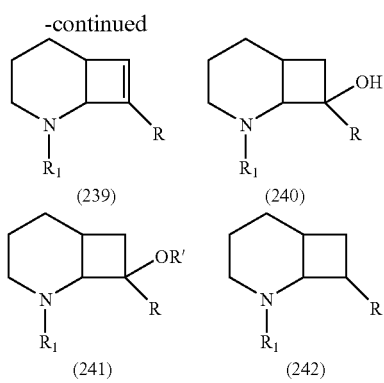

Azabicycles of general formula (239), (240), (241) and (242), wherein R is aryl or heterocycle, R' is alkyl and R$_1$ is as defined in formula (I), may be prepared as described in Scheme 48. Benzyl 4-oxo-3,4-dihydro-1(2H)-pyridinecarboxylate, prepared as described in J. Chem. Soc., Perkin Trans. I (1977) 874–884, may be treated with benzyl vinyl ether in a photochemical [2+2] cycloaddition to provide benzyl (cis)-8-(benzyloxy)-5-oxo-2-azabicyclo[4.2.0]octane-2-carboxylate using methodology described in Helv. Chim. Acta (1991) 74, 163–177. Benzyl (cis)-8-(benzyloxy)-5-oxo-2-azabicyclo[4.2.0]octane-2-carboxylate, may be treated with 1,2-ethanediol and boron trifluoride diethyl etherate and then treated with Raney nickel to provide (cis)-2-azabicyclo[4.2.0]octan-8-ol. (cis)-2-Azabicyclo[4.2.0]octan-8-ol may be treated with a metal catalyst such as, but not limited to, palladium on carbon under a hydrogen atmosphere in the presence of di-tert-butyl dicarbonate and then oxidized under Swern conditions to provide tert-butyl (cis)-8-oxo-2-azabicyclo[4.2.0]octane-2-carboxylate. tert-Butyl (cis)-8-oxo-2-azabicyclo[4.2.0]octane-2-carboxylate may be processed as described in Schemes 2–8 to provide azabicycles of general formula (239), (240), (241) and (242).

Azabicycles of general formula (244), (245), (246) and (247), wherein R is aryl or heterocycle, R' is alkyl and R$_1$ is as defined in formula (I), may be prepared as described in Scheme 49. tert-Butyl (cis)-8-hydroxy-2-azabicyclo[4.2.0]octane-2-carboxylate, prepared as described in Scheme 48, may be treated with methanesulfonyl chloride and a base such as, but not limited to, triethylamine to provide tert-butyl (cis)-2-azabicyclo[4.2.0]oct-7-ene-2-carboxylate. tert-Butyl (cis)-2-azabicyclo[4.2.0]oct-7-ene-2-carboxylate may be treated with a borane reagent such as, but not limited to, 9-borabicyclo[3.3.1]nonane and then basic hydrogen peroxide to provide a mixture of stereoisomeric alcohols. The alcohols may be separated using methods known to those of skill in the art of organic chemistry such as, but not limited to, chromatography and then oxidized under Swern conditions to provide the corresponding ketones. tert-Butyl (cis)-7-oxo-2-azabicyclo[4.2.0]octane-2-carboxylate may be processed as described in Schemes 2–8 to provide azabicycles of general formula (244), (245), (246) and (247).

Scheme 50

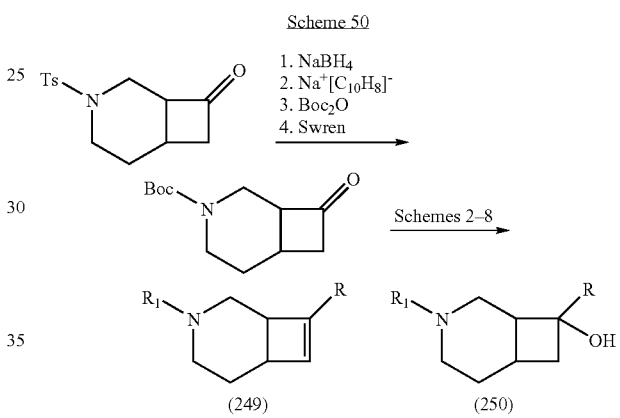

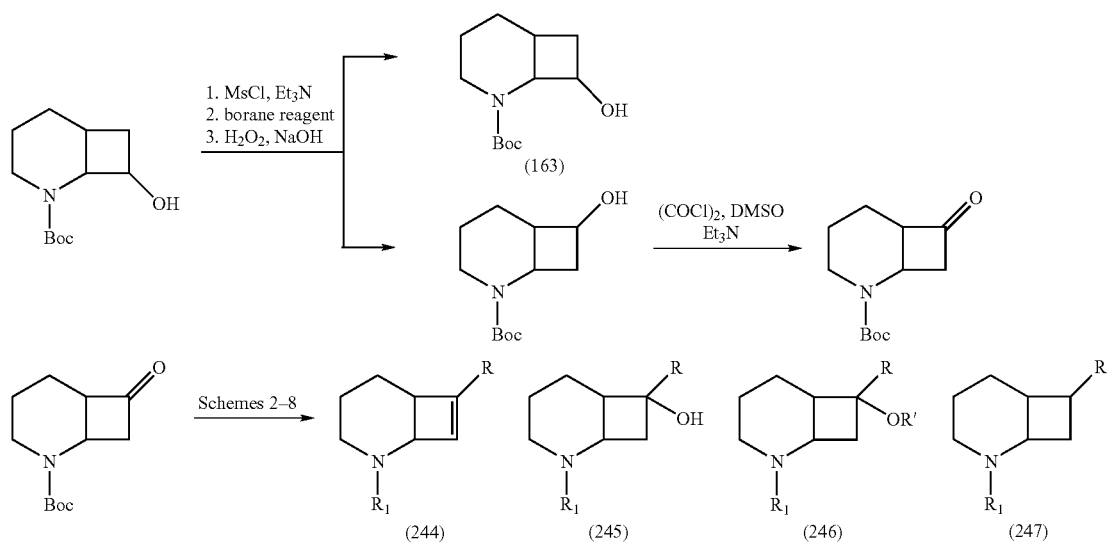

-continued

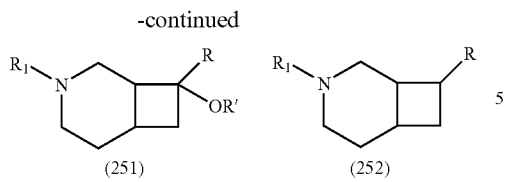

(251)   (252)

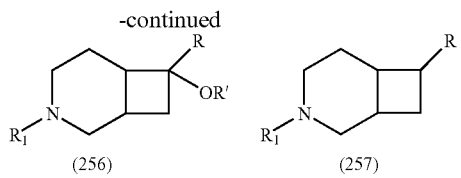

(256)   (257)

Azabicycles of general formula (249), (250), (251) and (252), wherein R is aryl or heterocycle, R' is alkyl and $R_1$ is as defined in formula (I), may be prepared as described in Scheme 50. 3-[(4-Methylphenyl)sulfonyl]-3-azabicyclo[4.2.0]octan-8-one, prepared as described in Heterocycles (1989) 28(1), 29–32, may be treated with a reducing agent such as, but not limited to, sodium borohydride followed by sodium naphthalenide to remove the N-tosyl protecting group. The amine may be treated with di-tert-dicarbonate and then oxidized under Swern conditions (DMSO/oxalyl chloride/triethylamine) to provide to provide tert-butyl (cis)-8-oxo-3-azabicyclo[4.2.0]octane-3-carboxylate. tert-Butyl (cis)-8-oxo-3-azabicyclo[4.2.0]octane-3-carboxylate may be processed as described in Schemes 2–8 to provide azabicycles of general formula (249), (250), (251) and (252).

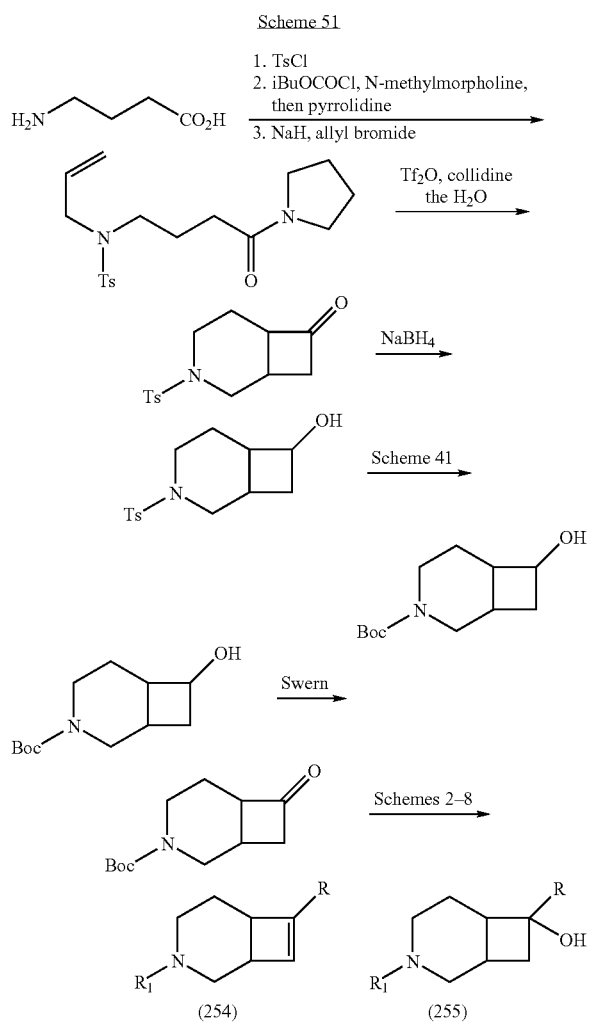

Azabicycles of general formula (254), (255), (256) and (257), wherein R is aryl or heterocycle, R' is alkyl and $R_1$ is as defined in formula (I), may be prepared as described in Scheme 51. 3-[(4-Methylphenyl)sulfonyl]-3-azabicyclo[4.2.0]octan-7-one may be prepared from commercially available 4-aminobutyric acid utilizing synthetic methodology described in Heterocycles (1989) 28(1), 29–32. 4Aminobutyric acid may be treated with 4-methyltoluenesulfonyl chloride to provide the N-protected butyric acid. The N-protected butyric acid may be treated with pyrrolidine and a chloroformate such as, but not limited to, isobutylchloroformate to provide the amide. The amide may be treated with a strong base such as, but not limited to, sodium hydride and allyl bromide to provide N-allyl-4-methyl-N-[4-oxo-4-(1-pyrrolidinyl)butyl]benzenesulfonamide. N-Allyl-4-methyl-N-[4-oxo-4-(1-pyrrolidinyl)butyl]benzenesulfonamide may be treated with trifluoromethanesulfonyl anhydride and a base such as, but not limited to, collidine to provide the iminium 2+2 product which may be treated with water to provide (cis)-3-[(4-methylphenyl)sulfonyl]-3-azabicyclo[4.2.0]octan-7-one. (cis)-3-[(4-Methylphenyl)sulfonyl]-3-azabicyclo[4.2.0]octan-7-one may be treated with a reducing agent such as, but not limited to, sodium borohydride to provide stereoisomeric alcohols. The stereoisomeric alcohols may be processed as described in Scheme 41 to provide the N-boc protected stereoisomeric alcohols. The N-boc protected stereoisomeric alcohols may be oxidized under Swern conditions (DMSO/oxalyl chloride/triethylamine) to provide tert-butyl (cis)-7-oxo-3-azabicyclo[4.2.0]octane-3-carboxylate. tert-Butyl (cis)-7-oxo-3-azabicyclo[4.2.0]octane-3-carboxylate may be processed as described in Scheme 2–8 to provide azabicycles of general formula (254), (255), (256) and (257).

The compounds and processes of the present invention will be better understood by reference to the following Examples, which are intended as an illustration of and not a limitation upon the scope of the invention.

EXAMPLE 1

(cis)-5-(6-chloro-3-pyridinyl)-1,2,3,3a,4,6a-hexahydrocyclopenta[c]pyrrole hydrochloride

EXAMPLE 1A (cis)-2,3,3a,4,7,7a-hexahydro-1H-isoindole

A suspension of lithium aluminum hydride (21.4 g, 0.562 mol) in THF (700 mL) at room temperature was treated with cis-1,2,3,6-tetrahydrophthalimide (Aldrich; 37 g, 0.245 mol) in small portions. The reaction mixture was stirred at 60° C. overnight then cooled to room temperature and quenched carefully by the sequential addition of water (22 mL), THF (22 mL), 15% aqueous KOH (22 mL), and water (80 mL). The mixture was diluted with diethyl ether (100 mL), stirred at room temperature for 1 hour, and then filtered (methylene chloride wash). The filtrate was concentrated under reduced pressure to provide the title compound as an oil (26.1 g). $^1$H NMR (CDCl$_3$, 300 MHz) δ 1.76–2.02 (m, 2H), 2.10–2.33 (m, 3H), 2.34–2.56 (m, 2H), 2.61–2.79 (m, 2H), 2.87–3.17 (m, 2H), 5.53–6.03 (m, 2H); MS (DCI/NH$_3$) m/z 124 (M+H)$^+$.

EXAMPLE 1B tert-butyl (cis)-1,3,3a,4,7,7a-hexahydro-2H-isoindole-2-carboxylate

The product from Example 1A (26 g, 0.21 mol) in methylene chloride (250 mL) at 0° C. was treated with di-tert-butyl dicarbonate (46.1 g, 0.21 mol). The solution was stirred for 30 minutes at 0° C. and then 2 hours at ambient temperature. The reaction mixture was partitioned between methylene chloride and saturated aqueous sodium bicarbonate. The organic extract was washed with saturated aqueous sodium bicarbonate and brine, dried over Na$_2$SO$_4$, filtered and the filtrate was concentrated under reduced pressure. The residue was purified by chromatography (SiO$_2$, 15% ethyl acetate/hexane) to provide the title compound (36 g). $^1$H NMR (CDCl$_3$, 300 MHz) δ 1.45 (s, 9 H), 1.84–1.99 (m, 2H), 2.11–2.40 (m, 4H), 3.07 (m, 1H), 3.18 (m, 1H), 3.33–3.53 (m, 2H), 5.60 (bs, 2H); MS (DCI/NH$_3$) m/z 224 (M+H)$^+$.

EXAMPLE 1C tert-butyl (cis)-3,4-bis(carboxymethyl)-1-pyrrolidinecarboxylate

The product from Example 1B (36 g, 0.16 mol) in carbon tetrachloride (360 mL), acetonitrile (360 mL), and water (540 mL) was treated with sodium periodate (138 g, 0.645 mol) followed by catalytic ruthenium (IV) oxide hydrate (0.885 g, 0.0066 mol). The mixture was stirred vigorously for 24 hours at ambient temperature then diluted with methylene chloride (500 mL) and water (100 mL), and filtered through diatomaceous earth. The filtrate was pass through a small plug of SiO$_2$ (methylene chloride wash), then evaporated under reduced pressure. The solid was crystallized from diethyl ether to provide the title compound (23.3 g). $^1$H NMR (CD$_3$OH, 300 MHz) δ 1.45 (s, 9H), 2.18–2.32 (m, 2H), 2.37–2.52 (m, 2H), 2.52–2.76 (m, 2H), 3.05–3.21(m, 2H), 3.35–3.56 (m, 2H), 3.79–3.89 (m, 1H), 6.11 (m, 1H); MS (DCI/NH$_3$) m/z 288 (M+H)$^+$.

EXAMPLE 1D tert-butyl (cis)-5-oxohexahydrocyclopenta[c]pyrrole-2(1H)-carboxylate The product from Example 1C (23 g) in acetic anhydride (140 mL) was treated with sodium acetate (5.3 g, 0.065 mol). The reaction mixture was stirred at 120° C. for 3 hours then cooled to ambient temperature, filtered (diethyl ether wash) and the filtrate was evaporated under reduced pressure. The residue was purified by chromatography (SiO$_2$, 30% ethyl acetate/hexane) to provide the title compound (11.7 g). $^1$H NMR (CDCl$_3$, 300 MHz) δ 1.45 (s, 9H), 2.12 (m, 1H), 2.19 (m, 1H), 2.44 (m, 1H), 2.51 (m, 1H), 2.93 (m, 2H), 3.22 (m, 2H), 3.65 (m, 2H); MS (DCI/NH$_3$) m/z 226 (M+H)$^+$.

EXAMPLE 1E tert-butyl 5-hydroxy-5-(3-pyridinyl)hexahydrocyclopenta[c]pyrrole-2(1H)-carboxylate 2-Chloro-5-iodopyridine (1.38 g, 5.75 mmol), prepared as described in Tetrahedron Letters, 34, 7493–7496 (1993), in THF (7 mL) was treated with n-butyl lithium (2.5M solution in hexanes, 2.30 mL, 5.75 mmol) dropwise over 20 minutes at –78° C. After stirring at –78° C. for 40 minutes, the mixture was treated dropwise with the product from Example 1D (0.259 g, 1.15 mmol) in diethyl ether (3 mL) dropwise. The reaction mixture was stirred at –78° C. for 30 minutes and then allowed to warm to 0° C. The mixture was quenched with saturated aqueous ammonium chloride and allowed to warm to room temperature. The mixture was partitioned between ethyl acetate and saturated aqueous ammonium chloride. The organic extract was separated, washed with saturated ammonium chloride, water, brine, dried over Na$_2$SO$_4$, filtered and the filtrate was concentrated under reduced pressure. The residue was purified by chromatography (SiO$_2$, 50% ethyl acetate/hexane) to provide the title compound (0.255 g). MS (DCI/NH$_3$) m/z 339 (M+H)$^+$.

EXAMPLE 1F tert-butyl (cis)-5-(6-chloro-3-pyridinyl)-3,3a,4,6a-tetrahydrocyclopenta[c]pyrrole-2(1H)-carboxylate The product from Example 1E (0.098 g, 0.290 mmol) in methylene chloride (4 mL) was treated with methanesulfonyl chloride (0.045 mL, 0.58 mmol), triethylamine (0.080 mL, 0.609 mmol) and catalytic DMAP (0.001 g). After stirring at ambient temperature for 16 hours, the volatiles were evaporated under reduced pressure. The residue was purified by chromatography (SiO$_2$, 50% ethyl acetate/hexane) to provide the title compound (0.036 g, 39%). MS (DCI/NH$_3$) m/z321 (M+H)$^+$.

EXAMPLE 1G (cis)-5-(6-chloro-3-pyridinyl)-1,2,3,3a,4,6a-hexahydrocyclopenta[c]pyrrole hydrochloride The product from Example 1F (0.036 g, 0.112 mmol) in methanol (1 mL) was treated with a 1M solution of HCl in diethyl ether (2 mL). After stirring at ambient temperature for 2 hours, the volatiles were evaporated under reduced pressure. The residue was crystallized from ethanol and diethyl ether to provide the title compound (0.034 g, 100%). $^1$H NMR (CD$_3$OD, 300 MHz) δ 2.75 (m, 1H), 3.15 (m, 2H), 3.32–3.55 (m, 4H), 3.82 (m, 1H), 6.24 (m, 1H), 7.46 (d, J=8.46 Hz, 1H), 7.95 (dd, J=2.57, 8.46 Hz, 1H), 8.47 (d, J=2.21 Hz, 1H); MS (DCI/NH$_3$) m/z 221 (M+H)$^+$; Anal. calculated for C$_{12}$H$_{13}$ClN$_2$.1.8HCl: C, 50.34; H, 5.21; N, 9.78. Found: C, 50.40; H, 5.35; N, 9.61.

EXAMPLE 2

(cis)-5-(5-methoxy-3-pyridinyl)-1,2,3,3a,4,6a-hexahydrocyclopenta[c]pyrrole hydrochloride

EXAMPLE 2A tert-butyl (cis)-5-hydroxy-5-(5-methoxy-3-pyridinyl) hexahydrocyclopenta[c]pyrrole-2(1H)-carboxylate n-Butyl lithium (2.5M solution in hexanes, 1.5 mL, 3.81 mmol) was added dropwise over 20 minutes to 3-bromo-5-methoxypyridine (0.717 g, 3.81 mmol), prepared as described in WO 00/44755 in THF (4 mL) at −78° C. After stirring at −78° C. for 40 minutes, the product from Example 1D (0.286 g, 1.27 mmol) in diethyl ether (4 mL) was added dropwise to the reaction mixture and stirred at −78° C. for an additional 30 minutes. The reaction mixture was then allowed to warm to 0° C. and then quenched with saturated aqueous ammonium chloride and allowed to warm to room temperature. The mixture was partitioned between ethyl acetate and saturated aqueous ammonium chloride. The organic layer was separated, washed with saturated ammonium chloride, water, brine, dried over $Na_2SO_4$, filtered and the filtrate was concentrated under reduced pressure. The residue was purified by chromatography ($SiO_2$, 50% ethyl acetate/hexane) to provide the title compound (0.142 g, 33%). MS ($DCI/NH_3$) m/z 335 (M+H)$^+$.

EXAMPLE 2B tert-butyl (cis)-5-(5-methoxy-3-pyridinyl)-3,3a,4,6a-tetrahydrocyclopenta[c]pyrrole-2(1H)-carboxylate The product from Example 2A (0.207 g, 0.619 mmol) in methylene chloride (6 mL) was treated with methanesulfonyl chloride (0.144 mL, 1.86 mmol), triethylamine (0.27 mL, 1.92 mmol) and catalytic DMAP (0.002 g). After stirring at ambient temperature for 16 hours, the volatiles were evaporated under reduced pressure. The residue was purified by chromatography ($SiO_2$, 50% ethyl acetate/hexane) to provide the title compound (0.038 g, 19%). MS ($DCI/NH_3$) m/z 317 (M+H)$^+$.

EXAMPLE 2C (cis)-5-(5-methoxy-3-pyridinyl)-1,2,3,3a,4,6a-hexahydrocyclopenta[c]pyrrole hydrochloride The product from Example 2B (0.038 g, 0.120 mmol) in methanol (1 mL) was treated with 1M solution of HCl in diethyl ether (2 mL) and stirred at ambient temperature for 2 hours. The volatiles were evaporated under reduced pressure. The residue was crystallized from ethanol and diethyl ether to provide the title compound (0.022 g, 64%). $^1$H NMR ($CD_3OD$, 300 MHz) δ 2.82 (m, 1H), 3.17–3.27 (m, 2H), 3.33–3.61 (m, 4H), 3.88 (m, 1H), 4.07 (s, 3H), 6.54 (m, 1H), 8.17 (bs, 1H), 8.49 (bs, 1H), 8.57 (bs, 1H); MS ($DCI/NH_3$) m/z 217 (M+H)$^+$; Anal. calculated for $C_{13}H_{16}ON_2 \cdot 2.2HCl$: C, 52.66; H, 6.19; N, 9.45. Found: C, 52.45; H, 5.99; N, 9.17.

EXAMPLE 3

(cis)-5-(6-chloro-5-methyl-3-pyridinyl)-1,2,3,3a,4,6a-hexahydrocyclopenta[c]pyrrole hydrochloride

EXAMPLE 3A tert-butyl 5-(6-chloro-5-methyl-3-pyridinyl)-5-hydroxyhexahydrocyclopenta[c]pyrrole-2(1H)-carboxylate n-Butyl lithium (2.5 M solution in hexanes, 1.31 mL, 3.27 mmol) was added dropwise over 20 minutes to a −78° C. solution of 5-bromo-2-chloro-3-methylpyridine (0.675 g, 3.27 mmol) in THF (4 mL). After stirring at −78° C. for 40 minutes, the product from Example 1D (0.368 g, 1.64 mmol) in THF (3 mL) was added dropwise to the reaction mixture. After stirring at −78° C. for 30 minutes, the reaction mixture was allowed to warm to 0° C. and then was quenched with saturated aqueous ammonium chloride and allowed to warm to room temperature. The mixture was partitioned between ethyl acetate and saturated aqueous ammonium chloride. The organic layer was separated, washed with saturated ammonium chloride, water, brine, dried over $Na_2SO_4$, filtered and the filtrate was concentrated under reduced pressure. The residue was purified by chromatography ($SiO_2$, 50% ethyl acetate/hexane) to provide the title compound (0.300 g, 52%). MS ($DCI/NH_3$) m/z 353 (M+H)$^+$.

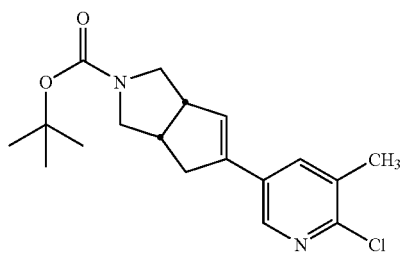

EXAMPLE 3B tert-butyl (cis)-5-(6-chloro-5-methyl-3-pyridinyl)-3,3a,4,6a-tetrahydrocyclopenta[c]pyrrole-2(1H)-carboxylate The product from Example 3A (0.300 g, 0.852 mmol) in methylene chloride (5 mL) was treated with methanesulfonyl chloride (0.198 mL, 2.56 mmol), triethylamine (0.38 mL, 2.73 mmol) and catalytic DMAP (0.003 g). The reaction mixture was stirred at ambient temperature for 16 hours and then the volatiles were evaporated under reduced pressure. The residue was purified by chromatography ($SiO_2$, 50% ethyl acetate/hexane) to provide the title compound (0.167 g, 59%). MS ($DCI/NH_3$) m/z 335 (M+H)$^+$.

EXAMPLE 3C (cis)-5-(6-chloro-5-methyl-3-pyridinyl)-1,2,3,3a,4,6a-hexahydrocyclopenta[c]pyrrole hydrochloride The product from Example 3B (0.167 g, 0.500 mmol) in methanol (1 mL) was treated with 1M solution of HCl in diethyl ether (3 mL). After stirring at ambient temperature for 2 hours, the volatiles were evaporated under reduced pressure. The residue was crystallized from ethanol and diethyl ether to provide the title compound (0.095 g, 70%). $^1$H NMR ($CD_3OD$, 300 MHz) δ 2.40 (s, 3H), 2.74 (m, 1H), 3.11–3.20 (m, 2H), 3.36–3.54 (m, 4H), 3.81 (m, 1H), 6.2 (m, 1H), 7.87 (d, J=2.4 Hz, 1H), 8.30 (d, J=2.6 Hz, 1H); MS ($DCI/NH_3$) m/z 235 (M+H)$^+$; Anal. calculated for $C_{13}H_{15}ClN_2 \cdot 1.1HCl$: C, 56.81; H, 5.90; N, 10.19. Found: C, 56.52; H, 5.90; N, 9.97.

129

EXAMPLE 4

(cis)-5-(3-pyridinyl)-1,2,3,3a,4,6a-hexahydrocyclopenta[c]pyrrole hydrochloride

EXAMPLE 4A tert-butyl (cis)-5-{[(trifluoromethyl)sulfonyl]oxy}-3,3a,4,6a-tetrahydrocyclopenta[c]pyrrole-2(1H)-carboxylate The product from Example 1D (3.0 g, 13.3 mmol) in THF (80 mL) was treated with lithium bis(trimethylsilyl)amide (1.0M solution in THF, 17.3 mL, 17.3 mmol) at −78° C. The reaction mixture was stirred at −78° C. for 30 minutes and then a solution of N-phenyltrifluoromethanesulfonimide (6.65 g, 18.6 mmol) in THF (20 mL) was added slowly. The reaction mixture was stirred at −78° C. for 1 hour and then warmed to −10° C. and stirred for an additional hour. The volatiles were removed under reduced pressure, and the residue was purified by chromatography ($SiO_2$, 10% ethyl acetate/hexane) to provide the title compound as a white solid (4.44 g, 94%). MS ($DCI/NH_3$) m/z 358 $(M+H)^+$.

EXAMPLE 4B tert-butyl (cis)-5-(trimethylstannyl)-3,3a,4,6a-tetrahydrocyclopenta[c]pyrrole-2(1H)-carboxylate The product from Example 4A (1.00 g, 2.80 mmol) in THF (15 mL) was treated with hexamethylditin (0.826 g, 2.52 mmol), lithium chloride (0.712 g, 16.8 mmol) and tetrakis(triphenylphosphine)palladium(0) (0.065 g, 2 mol %) and stirred at 60° C. for 16 hours. The reaction mixture was allowed to cool to ambient temperature, diluted with diethyl ether, washed with 1N aqueous sodium hydroxide, water, brine, dried over $Na_2SO_4$, filtered and the filtrate was concentrated under reduced pressure. The residue was purified by chromatography ($SiO_2$, 10% ethyl acetate/hexane) to provide the title compound as a white solid (0.769 g, 74%). MS ($DCI/NH_3$) m/z 372, 374 $(M+H)^+$.

EXAMPLE 4C tert-butyl (cis)-5-(3-pyridinyl)-3,3a,4,6a-tetrahydrocyclopenta[c]pyrrole-2(1H)-carboxylate 3-Bromopyridine (0.129 g, 0.82 mmol), triphenylarsine (0.020 g, 0.065 mmol) and tris(dibenzylideneacetone)dipalladium(0) (0.015 g, 2 mol %) in anhydrous 1-methyl-2-pyrrolidinone (4 mL) were treated with the product from Example 4B (0.305 g, 0.82 mmol) in 1-methyl-2-pyrrolidinone (2 mL). The reaction mixture was stirred at 60° C. for 16 hours, allowed to cool to ambient temperature and partitioned between ethyl acetate and 1N aqueous sodium hydroxide. The organic portion was separated, washed with 1N aqueous sodium hydroxide, water, brine, dried over $Na_2SO_4$, filtered and the filtrate was evaporated under reduced pressure. The residue was purified by chromatography ($SiO_2$, 50% ethyl acetate/hexane) to provide the title compound (0.163 g, 69%). MS ($DCI/NH_3$) m/z 287 $(M+H)^+$.

130

EXAMPLE 4D (cis)-5-(3-pyridinyl)-1,2,3,3a,4,6a-hexahydrocyclopenta[c]pyrrole hydrochloride hydrochloride The product from Example 4C (0.163 g, 0.570 mmol) in methanol (1 mL) was treated with a 1M solution of HCl in diethyl ether (2 mL). After stirring at ambient temperature for 2 hours, the volatiles were evaporated under reduced pressure. The residue was crystallized from ethanol and diethyl ether to provide the title compound (0.138 g, 93%). $^1$H NMR ($CD_3OD$, 300 MHz) δ 2.85 (m, 1H), 3.19–3.25 (m, 2H), 3.35–3.59 (m, 4H), 3.89 (m, 1H), 6.56 (m, 1H), 8.09 (dd, J=5.8, 8.5 Hz, 1H), 8.75 (m, 1H), 8.97 (d, J=1.4 Hz, 1H); MS ($DCI/NH_3$) m/z 187 $(M+H)^+$; Anal. calculated for $C_{12}H_{14}N_2 \cdot 2HCl \cdot 0.2H_2O$: C, 54.85; H, 6.29; N, 10.66. Found: C, 54.73; H, 6.66; N, 10.58.

EXAMPLE 5

(cis)-5-(3-methyl-5-isoxazolyl)-1,2,3,3a,4,6a-hexahydrocyclopenta[c]pyrrole hydrochloride

EXAMPLE 5A tert-butyl 5-(3-methyl-5-isoxazolyl)-3,3a,4,6a-tetrahydrocyclopenta[c]pyrrole-2(1H)-carboxylate The product from Example 4A (411 mg, 1.15 mmol), triphenylarsine (28 mg, 0.092 mmol) and tris(dibenzylideneacetone)dipalladium(0) (21 mg, 0.023 mmol) in anhydrous 1-methyl-2-pyrrolidinone (6 mL) were treated with 3-methyl-5-(tributylstannyl)isoxazole (448 mg, 1.2 mmol, prepared according to Sakamoto, T.; et. al., Tetrahedon, 1991, 47, 5111) in 1-methyl-2-pyrrolidinone (2 mL). The reaction mixture was stirred at 60° C. overnight, allowed to cool to ambient temperature and 1M aqueous KF (1.5 mL) was added. The mixture was stirred for 0.5 hours, diluted with ethyl acetate and filtered through Celite. The filtrate was washed with water (5×), brine, dried over $Na_2SO_4$, filtered and the filtrate was concentrated under reduced pressure. The residue was purified by chromatography (silica gel, gradient from hexane to 30% EtOAc/hexane) to provide 220 mg (66%) of the title compound. MS ($DCI/NH_3$) m/z 291 $(M+H)^+$.

EXAMPLE 5B (cis)-5-(3-methyl-5-isoxazolyl)-1,2,3,3a,4,6a-hexahydrocyclopenta[c]pyrrole hydrochloride The product from Example 5A (220 mg, 0.759 mmol) in ethyl acetate (5 mL) was treated with a 4M solution of HCl in 1,4-dioxane (1 mL). After stirring at ambient temperature for 1 hour, a few drops of diethyl ether were added resulting in precipitation of a white solid that was collected by filtration and dried at 60° C. to provide 126 mg (73%) of the hydrochloride salt. $^1$H NMR ($CD_3OD$, 300 MHz) δ 2.27 (s, 3H), 2.70 (m, 1H), 3.07–3.20 (m, 2H), 3.35–3.55 (m, 4H), 3.83 (m, 1H), 6.26 (d, J=2.0 Hz, 1 H), 6.31 (s, 1H); MS ($DCI/NH_3$) m/z 191 $(M+H)^+$; Anal. calculated for $C_{11}H_{14}N_2O \cdot HCl$: C, 58.28; H, 6.67; N, 12.36. Found: C, 58.18; H, 6.55; N, 12.27.

131

EXAMPLE 6

(cis)-5-(5,6-dichloro-3-pyridinyl)-1,2,3,3a,4,6a-hexahydrocyclopenta[c]pyrrole hydrochloride

EXAMPLE 6A tert-butyl 5-(5,6-dichloro-3-pyridinyl)-3,3a,4,6a-tetrahydrocyclopenta[c]pyrrole-2(1H)-carboxylate 2,3-Dichloro-5-iodopyridine (0.288 g, 1.05 mmol), triphenylarsine (0.026 g, 0.084 mmol), and tris(dibenzylideneacetone)dipalladium(0)(0.019 g, 2 mol %) in anhydrous 1-methyl-2-pyrrolidinone (5 mL) were treated with the product from Example 4B (0.392 g, 1.05 mmol) in 1-methyl-2-pyrrolidinone (2 mL). After stirring at 60° C. for 5 hours, the reaction mixture was allowed to cool to ambient temperature and partitioned between ethyl acetate and 1N aqueous sodium hydroxide. The organic extract was separated, washed with 1N aqueous sodium hydroxide, water, brine, dried over $Na_2SO_4$, filtered and the filtrate was concentrated under reduced pressure. The residue was purified by chromatography ($SiO_2$, 50% ethyl acetate/hexanes) to provide the title compound (0.228 g, 61%). MS (DCI/$NH_3$) m/z 355 $(M+H)^+$.

EXAMPLE 6B (cis)-5-(5,6-dichloro-3-pyridinyl)-1,2,3,3a,4,6a-hexahydrocyclopenta[c]pyrrole hydrochloride The product from Example 6A (0.228 g, 0.642 mmol) in methanol (1 mL) was treated with a 1M solution of HCl in diethyl ether (2 mL). After stirring at ambient temperature for 2 hours, the volatiles were evaporated under reduced pressure. The residue was crystallized from ethanol and diethyl ether to provide the title compound (0.120 g, 73%). $^1H$ NMR ($CD_3OD$, 300 MHz) δ 2.75 (m, 1H), 3.17 (m, 2H), 3.31–3.55 (m, 4H), 3.83 (m, 1H), 6.30 (m, 1H), 8.10 (d, J=2.0 Hz, 1H), 8.44 (d, J=2.4 Hz, 1H); MS (DCI/$NH_3$) m/z 255 $(M+H)^+$; Anal. calculated for $C_{12}H_{12}Cl_2N_2$.HCl: C, 49.43; H, 4.49; N, 9.61. Found: C, 49.32; H, 4.60; N, 9.38.

EXAMPLE 7

(cis)-2-methyl-5-(3-methyl-5-isoxazolyl)-1,2,3,3a,4,6a-hexahydrocyclopenta[c]pyrrole hydrochloride The product from Example 5B (22 mg, 0.11 mmol), 37% formaldehyde in water and formic acid were stirred at reflux for 2 hours, allowed to cool to room temperature and concentrated under reduced pressure. The residue was purified by chromatography (silica gel, 98:2:0.1 $CH_2Cl_2$/MeOH/$NH_4OH$) to provide 13 mg (54%) of the free base that was processed as described in Example 5B to provide the title compound as the hydrochloride salt. $^1H$ NMR ($CD_3OD$, 300 MHz) δ 2.28 (s, 3H), 2.70 (m, 1H), 2.90 (s, 3H), 3.07–3.22 (m, 2H), 3.30–3.60 (m, 4H), 3.84 (m, 1H), 6.25 (br s, 1 H), 6.32 (s, 1H); MS (DCI/$NH_3$) m/z 205 $(M+H)^+$; Anal. calculated for $C_{11}H_{14}N_2O.HCl.0.25H_2O$: C, 58.77; H, 7.19; N, 11.42. Found: C, 59.09; H, 6.91; N, 11.49.

132

EXAMPLE 8

(cis)-5-(5-chloro-3-pyridinyl)-1,2,3,3a,4,6a-hexahydrocyclopenta[c]pyrrole dihydrochloride

EXAMPLE 8A (cis)-5-(5-chloro-3-pyridinyl)-1,2,3,3a,4,6a-hexahydrocyclopenta[c]pyrrole The product from Example 4B and 5-chloro-3-pyridinyl trifluoromethanesulfonate, prepared as described in (WO 9740012), were processed as described in Example 4C to provide the title compound (42% yield) as a light yellow oil: MS (DCI/$NH_3$) m/z 321, 323 $(M+H)^+$.

EXAMPLE 8B (cis)-5-(5-chloro-3-pyridinyl)-1,2,3,3a,4,6a-hexahydrocyclopenta[c]pyrrole dihydrochloride The product from Example 8A (190 mg, 0.59 mmol) in 10 mL of 1:1 EtOAc/EtOH was treated with a 4M solution of HCl in 1,4-dioxane (1.5 mL, 3.8 mmol). The mixture was refluxed for 1 hour and then allowed to cool to room temperature and stirred overnight. The white solid was collected by filtration to provide 170 mg of the title compound as the dihydrochloride salt. $^1H$ NMR ($CD_3OD$, 400 MHz) δ 2.84 (m, 1H), 3.15–3.24 (m, 2H), 3.30–3.60 (m, 4H), 3.88 (m, 1H), 6.54 (m, 1H), 8.62 (d, J=1.8 Hz, 1H), 8.86–8.88 (m, 2H); MS (DCI/$NH_3$) m/z 221, 223 $(M+H)^+$; Anal. calculated for $C_{12}H_{13}ClN_2$.2HCl: C, 49.09; H, 5.15; N, 9.54. Found: C, 48.83; H, 4.89; N, 9.35.

EXAMPLE 9

(cis)-5-(3-bromo-1,2,4-thiadiazol-5-yl)-1,2,3,3a,4,6a-hexahydrocyclopenta[c]pyrrole hydrochloride 3-Bromo-5-chloro-1,2,4-thiadiazole (Acros; 19.7 mg, 0.099 mmol) in 1-methyl-2-pyrrolidinone (0.2 mL) was treated with 0.1 mL of a solution of tris(dibenzylideneacetone)dipalladium(0) (8.6 mg, 0.02 mmol), triphenylarsine (11.5 mg, 0.08 mmol) and copper(I) iodide (1.8 mg, 0.02 mmol) in 1-methyl-2-pyrrolidinone (0.5 mL). The reaction mixture was then treated with the product from Example 4B (35 mg, 0.094 mmol) in 1-methyl-2-pyrrolidinone (0.1 mL). The reaction mixture was warmed to 60° C., stirred over night and then allowed to cool to room temperature. The mixture was diluted with $CH_2Cl_2$ and washed with 0.5 mL of 1.0N aqueous NaOH. The aqueous phase was extracted twice with 5 mL of $CH_2Cl_2$. All the organic phases were combined and filtered through a 900 mg silica gel cartridge (Alltech). The solvent was removed under reduced pressure and the residue was purified by reverse phase preparative HPLC (Waters Nova-Pak HR C18 6 m 60 25×100 mm, 50–95% MeCN/10 mM $NH_4OAc$ over 10 minutes at 40 mL/min) to provide the free base. The free base was dissolved in MeOH (0.3 mL) and treated with a 1.0M solution of HCl in diethyl ether (0.5 mL, 0.5 mmol). The solution was agitated at 40° C. for 16 hours resulting in the formation of a precipitate. The precipitate was triturated with diethyl ether (2×) and dried under reduced pressure to provide 20.9 mg (82%) of the title compound. $^1H$ NMR ($CD_3OD$) δ 2.82 (ddd, J=2.3, 4.2, 16.9 Hz, 1H), 3.18 (dd, J=5.2, 12.0 Hz, 1H), 3.21–3.26 (m, 1H), 3.34 (m, 1H), 3.40 (dd, J=3.1, 12.2 Hz, 1H), 3.47 (dd, J=8.3, 12.0 Hz, 1H), 3.53 (dd, J=8.7, 12.1, 1H), 3.89 (tt, J=2.7, 8.1 Hz, 1H), 6.69 (dd, J=2.3, 4.2 Hz,

EXAMPLE 10

(cis)-5-(1,3-thiazol-2-yl)-1,2,3,3a,4,6a-hexahydrocyclopenta[c]pyrrole hydrochloride The product from Example 4B and 2-bromothiazole (purchased from Aldrich) were processed as described in Example 9 to provide the title compound. $^1$H NMR (CD$_3$OD) δ 2.86 (ddd, J=2.2, 4.2, 16.7 Hz, 1H), 3.16 (dd, J=5.0, 11.6 Hz, 1H), 3.21–3.26 (m, 1H), 3.37 (dd, J=3.1, 11.6 Hz, 1H), 3.43 (dd, J=8.1, 11.6 Hz, 1H), 3.51 (dd, J=8.7, 11.6 Hz, 1H), 3.84 (tt, J=2.6, 8.0 Hz, 1H), 6.37 (dd, J=2.2, 4.1 Hz, 1H), 7.56 (d, J=3.4 Hz, 1H), 7.80 (d, J=3.4 Hz, 1H); MS (ESI) m/z 193 (M+H)$^+$.

EXAMPLE 11

(cis)-5-(3,5-dimethyl-4-isoxazolyl)-1,2,3,3a,4,6a-hexahydrocyclopenta[c]pyrrole hydrochloride The product from Example 4B and 3,5-dimethyl-4-iodoisoxazole (purchased from Avocado) were processed as described in Example 9 to provide the title compound. $^1$H NMR (CD$_3$OD) δ 2.30 (s, 3H), 2.46 (s, 3H), 2.67 (ddd, J=1.8, 4.2, 16.5 Hz, 1H), 3.08–3.14 (m, 2H), 3.21 (m, 1H), 3.38 (dd, J=7.8, 11.6 Hz, 1H), 3.47 (dd, J=8.7, 11.6 Hz, 1H), 3.73 (m, 1H), 5.73 (dd, J=2.0, 3.9 Hz, 1H); MS (ESI) m/z 205 (M+H)$^+$.

EXAMPLE 12

(cis)-5-(1H-imidazol-4-yl)-1,2,3,3a,4,6a-hexahydrocyclopenta[c]pyrrole hydrochloride The product from Example 4B and 4-iodoimidazole (purchased from Combi-Blocks) were processed as described in Example 9 to provide the title compound. $^1$H NMR (CD$_3$OD) δ 2.71 (dd, J=1.9, 16.5 Hz, 1H), 3.10 (tt, J=2.1, 8.4 Hz, 1H), 3.15 (dd, J=5.5, 12.0 Hz, 1H), 3.35 (dd, J=2.8, 11.5 Hz, 1H), 3.46 (dd, J=8.1, 11.6 Hz, 1H), 3.53 (dd, J=8.7, 11.6 Hz, 1H), 3.84 (m, 1H), 6.19 (dd, J=2.0, 3.9 Hz, 1H), 7.58 (s, 1H), 8.91 (s, 1H); MS (ESI) m/z 176 (M+H)$^+$.

EXAMPLE 13

(cis)-5-(1,3-thiazol-5-yl)-1,2,3,3a,4,6a-hexahydrocyclopenta[c]pyrrole hydrochloride The product from Example 4B and 5-bromothiazole, prepared as described in (Recl. Trav. Chim. Pays-Bas, (1954), 73, 325), were processed as described in Example 9 to provide the title compound. $^1$H NMR (CD$_3$OD) δ 2.79 (d, J=16.5 Hz, 1H), 3.16–3.22 (m, 2H), 3.32–3.38 (m, 2H), 3.43 (dd, J=8.0, 11.7 Hz, 1H), 3.52 (dd, J=8.7, 11.5 Hz, 1H), 3.83 (m, 1H), 6.18 (s, 1H), 8.14 (s, 1H), 9.51 (s, 1H); MS (ESI) m/z 193 (M+H)$^+$.

EXAMPLE 14

(cis)-5-(imidazo[1,2-a]pyridin-3-yl)-1,2,3,3a,4,6a-hexahydrocyclopenta[c]pyrrole hydrochloride The product from Example 4B and 3-bromoimidazo[1,2-a]pyridine, prepared as described in J. Org. Chem. (1965), 30, 4085–4090, were processed as described in Example 9 to provide the title compound. $^1$H NMR (CD$_3$OD) δ 2.80 (dd, J=1.7, 16.5 Hz, 1H), 3.18 (dd, J=5.5, 11.7 Hz, 1H), 3.21 (m, 1H), 3.38 (dd, J=3.0, 11.7 Hz, 1H), 3.47 (dd, J=8.1, 11.6 Hz, 1H), 3.55 (dd, J=8.7, 11.6 Hz, 1H), 3.86 (m, 1H), 6.35 (d, J=1.6 Hz, 1H), 7.81 (d, J=9.4 Hz, 1H), 7.92 (s, 1H), 8.10 (m, 2H), 8.73 (s, 1H); MS (ESI) m/z 226 (M+H)$^+$.

EXAMPLE 15

(cis)-5-(imidazo[1,2-a]pyridin-6-yl)-1,2,3,3a,4,6a-hexahydrocyclopenta[c]pyrrole hydrochloride The product from Example 4B and 6-bromoimidazo[1,2-a]pyridine, prepared as described in J. Org. Chem. (1978), 43, 2900–2906, were processed as described in Example 9 to provide the title compound. $^1$H NMR (CD$_3$OD) δ 2.90 (d, J=14.0 Hz, 1H), 3.25 (dd, J=4.4, 11.6 Hz, 1H), 3.32–3.36 (m, 1H), 3.51 (d, J=5.3 Hz, 1H), 3.57 (dd, J=8.1, 11.5 Hz, 1H), 3.98 (m, 1H), 6.44 (s, 1H), 7.59 (dd, J=5.9, 6.7 Hz, 1H), 7.97–8.04 (m, 2H), 8.14 (s, 1H), 9.05 (d, J=7.2 Hz, 1H); MS (ESI) m/z 226 (M+H)$^+$.

EXAMPLE 16

(cis)-5-(thieno[3,2-b]pyridin-2-yl)-1,2,3,3a,4,6a-hexahydrocyclopenta[c]pyrrole hydrochloride The product from Example 4B and 2-iodothieno[3,2-b]pyridine, prepared as described in J. Heterocycl. Chem. (1984), 21, 785–790, were processed as described in Example 9 to provide the title compound. $^1$H NMR (CD$_3$OD) δ 2.94 (ddd, J=2.2, 3.9, 16.4 Hz, 1H), 3.22 (dd, J=5.2, 12.0 Hz, 1H), 3.26–3.34 (m, 1H), 3.36–3.44 (m, 2H), 3.49 (dd, J=8.1, 11.6 Hz, 1H), 3.57 (dd, J=8.6, 11.7 Hz, 1H), 3.92 (tt, J=2.7, 8.1 Hz, 1H), 6.52 (dd, J=2.2, 4.1 Hz, 1H), 7.65 (s, 1H), 7.85 (dd, J=5.6, 8.1 Hz, 1H), 8.84 (dd, J=1.0, 5.6 Hz, 1H), 9.04 (d, J=8.1 Hz, 1H); MS (ESI) m/z 243 (M+H)$^+$.

EXAMPLE 18

(cis)-5-(1,2,3,3a,4,6a-hexahydrocyclopenta[c]pyrrol-5-yl)-2-thiophenesulfonamide hydrochloride The product from Example 4B and 5-bromothiophene-2-sulfonamide (purchased from Fluorochem USA) were processed as described in Example 9 to provide the title compound. $^1$H NMR (CD$_3$OD) δ 2.74 (m, 1H), 3.10–3.19 (m, 2H), 3.22–3.35 (m, 2H), 3.38 (dd, J=8.5, 11.7 Hz, 1H), 3.50 (dd, J=8.7, 11.8 Hz, 1H), 3.79 (m, 1H), 6.04 (br s, 1H), 7.06 (d, J=3.7 Hz, 1H), 7.48 (d, J=3.8 Hz, 1H); MS (ESI) m/z 271 (M+H)$^+$.

EXAMPLE 19

(cis)-5-(6-methyl-3-pyridinyl)-1,2,3,3a,4,6a-hexahydrocyclopenta[c]pyrrole dihydrochloride

EXAMPLE 19A tert-butyl (cis)-5-(6-methyl-3-pyridinyl)-3,3a,4,6a-tetrahydrocyclopenta[c]pyrrole-2(1H)-carboxylate The product from Example 4B and 5-bromo-2-methylpyridine, prepared as described in WO 0044755, were processed as described in Example 4C to provide the title compound (50% yield). MS (DCI/NH$_3$) m/z 301 (M+H)$^+$.

EXAMPLE 19B (cis)-5-(6-methyl-3-pyridinyl)-1,2,3,3a,4,6a-hexahydrocyclopenta[c]pyrrole dihydrochloride The product from Example 19A was processed as described in Example 8B to provide the title compound (88% yield). $^1$H NMR (CD$_3$OD, 400 MHz) δ 2.78 (s, 3H), 2.82 (m, 1H), 3.15–3.27 (m, 2H), 3.29–3.60 (m, 4H), 3.87 (m, 1H), 6.48 (m, 1H), 7.90 (d, J=8.5 Hz, 1H), 8.60 (dd, J=2.0,8.4 Hz, 1H), 8.75 (d, J=2.1 Hz, 1H); MS (DCI/NH$_3$) m/z 201 (M+H)$^+$; Anal. calculated for C$_{13}$H$_{16}$N$_2$.2HCl: C, 57.15; H, 6.64; N, 10.25. Found: C, 56.88; H, 6.65; N, 10.23.

EXAMPLE 20

(cis)-5-(2-methyl-3-pyridinyl)-1,2,3,3a,4,6a-hexahydrocyclopenta[c]pyrrole hydrochloride

EXAMPLE 20A tert-butyl (cis)-5-(2-methyl-3-pyridinyl)-3,3a,4,6a-tetrahydrocyclopenta[c]pyrrole-2(1H)-carboxylate The product from Example 4B and 3-bromo-2-methylpyridine were processed as described in Example 4C to provide the title compound (19% yield). MS (DCI/NH$_3$) m/z 301 (M+H)$^+$.

EXAMPLE 20B (cis)-5-(2-methyl-3-pyridinyl)-1,2,3,3a,4,6a-hexahydrocyclopenta[c]pyrrole hydrochloride The product from Example 20A was processed as described in Example 8B to provide the title compound (53% yield). $^1$H NMR (CD$_3$OD, 400 MHz) δ 2.78 (m, 1H), 2.85 (s, 3H), 3.20–3.60 (m, 6H), 3.90 (m, 1H), 6.08 (m, 1H), 7.90 (dd, J=5.7, 7.8 Hz, 1H), 8.49 (d, J=8.1 Hz, 1H), 8.62 (dd, J=1.7, 7.5 Hz, 1H); MS (DCI/NH$_3$) m/z 201 (M+H)$^+$; Anal. calculated for C$_{13}$H$_{16}$N$_2$.2HCl.0.25 H$_2$O: C, 56.23; H, 6.71; N, 10.09. Found: C, 56.40; H, 6.57; N, 9.96.

EXAMPLE 21

(cis)-5-(6-chloro-5-fluoro-3-pyridinyl)-1,2,3,3a,4,6a-hexahydrocyclopenta[c]pyrrole hydrochloride

EXAMPLE 21A tert-butyl (cis)-5-(6-chloro-5-fluoro-3-pyridinyl)-3,3a,4,6a-tetrahydrocyclopenta[c]pyrrole-2(1H)-carboxylate 2-Chloro-3-fluoro-5-iodopyridine (0.400 g, 1.08 mmol), prepared as described in J. Org. Chem. (1993), 58, 7832, triphenylarsine (0.026 g, 0.084 mmol) and tris(dibenzylideneacetone)dipalladium(0) (0.019 g, 2 mol %) in anhydrous 1-methyl-2-pyrrolidinone (5 mL) were treated with the product from Example 4B (0.310 g, 1.20 mmol) in 1-methyl-2-pyrrolidinone (2 mL). After stirring at 60° C. for 5 hours, the reaction mixture was allowed to cool to ambient temperature and partitioned between ethyl acetate and 1N aqueous sodium hydroxide. The organic extract was separated, washed with 1N aqueous sodium hydroxide, water, brine, dried over Na$_2$SO$_4$, filtered and the filtrate concentrated under reduced pressure. The residue was purified by chromatography (SiO$_2$, 50% ethyl acetate/hexanes) to provide the title compound (0.226 g, 62%). MS (DCI/NH$_3$) m/z 339 (M+H)$^+$.

EXAMPLE 21B (cis)-5-(6-chloro-5-fluoro-3-pyridinyl)-1,2,3,3a,4,6a-hexahydrocyclopenta[c]pyrrole hydrochloride The product from Example 21A (215 mg, 0.60 mmole) in CH$_2$Cl$_2$ (1 mL) and TFA (1 mL) was stirred at ambient temperature for 1 hour and then concentrated under reduced pressure. The residue was purified by chromatography (silica gel; CHCl$_3$/MeOH/NH$_4$OH 90:10:1) to provide the free base of the title compound. The free base was dissolved in MeOH and treated with a solution of 1M HCl in diethyl ether to provide 137 mg (77%/o) of the title compound. $^1$H NMR (CD$_3$OD, 300 MHz) δ 2.76 (m, 1H), 3.18 (m, 2H), 3.30–3.55 (m, 4H), 3.83 (m, 1H), 6.30 (m, 1H), 7.86 (dd, J=2.0, 9.9 Hz, 1H), 8.35 (d, J=2.0 Hz, 1H); MS (DCI/NH$_3$) m/z 239 (M+H)$^+$; Anal. calculated for C$_{12}$H$_{12}$ClFN$_2$.1.5HCl.0.2CH$_3$OH: C, 48.88; H, 4.81; N, 9.34. Found: C, 49.00; H, 4.53; N, 8.95.

EXAMPLE 23

(cis)-5-(6-fluoro-3-pyridinyl)-1,2,3,3a,4,6a-hexahydrocyclopenta[c]pyrrole hydrochloride

EXAMPLE 23A tert-butyl 5-(6-fluoro-3-pyridinyl)-3,3a,4,6a-tetrahydrocyclopenta[c]pyrrole-2(1H)-carboxylate 5-Bromo-2-flouropyridine (0.200 g, 0.538 mmol), triphenylarsine (0.013 g, 0.043 mmol), and tris(dibenzylideneacetone)dipalladium(0) (0.010 g, 2 mol %) in anhydrous 1-methyl-2-pyrrolidinone (2 mL) were treated with the product from Example 4B (0.392 g, 1.05 mmol) in 1-methyl-2-pyrrolidinone (1 mL). The reaction mixture was stirred at 60° C. for 16 hours, allowed to cool to ambient temperature and partitioned between ethyl acetate and 1N aqueous sodium hydroxide. The organic portion was separated, washed with 1N aqueous sodium hydroxide, water, brine, dried over Na$_2$SO$_4$, filtered and the filtrate concentrated under reduced pressure. The residue was purified by chromatography (SiO$_2$, 50% ethyl acetate/hexanes) to provide the title compound (0.126 g, 77%). MS (DCI/NH$_3$) m/z 305 (M+H)$^+$.

EXAMPLE 23B (cis)-5-(6-fluoro-3-pyridinyl)-1,2,3,3a,4,6a-hexahydrocyclopenta[c]pyrrole hydrochloride The product from Example 23A (0.126 g, 0.414 mmol) in methanol (1 mL) was treated with a 1M solution of HCl in diethyl ether (2 mL). After stirring at ambient temperature for 2 hours, the volatiles were evaporated under reduced pressure. The residue was crystallized from ethanol and diethyl ether to provide the title compound (0.067 g, 67%). $^1$H NMR (CD$_3$OD, 300 MHz) δ 2.76 (m, 1H), 3.13–3.21 (m, 2H), 3.36–3.55 (m, 4H), 3.81 (m, 1H), 6.16 (m, 1H), 7.07 (ddd, J=0.7, 2.7, 8.8 Hz, 1H), 8.09 (ddd, J=2.7, 7.8, 8.6 Hz, 1H); MS (DCI/NH$_3$) m/z 205 (M+H)$^+$.

EXAMPLE 24

(cis)-5-(1,2,3,3a,4,6a-hexahydrocyclopenta[c]pyrrol-5-yl)-2-thiophenecarboximidamide hydrochloride The product from Example 4B and the free base of 5-chloro-2-thiophenecarboximidamide monohydrochloride, prepared as described in EP 819690, were processed as described in Example 9 to provide the title compound. $^1$H NMR (CD$_3$OD) δ 2.74 (br d, J=12.6 Hz, 1H), 3.14–3.24 (m, 2H), 3.27–3.41 (m, 2H), 3.38 (m, 1H), 3.84 (m, 1H), 6.21 (br s, 1H), 7.29 (d, J=4.1 Hz, 1H), 7.88 (d, J=4.0 Hz, 1H); MS (ESI) m/z 234 (M+H)$^+$.

EXAMPLE 25

(cis)-5-(2-methyl-2H-tetraazol-5-yl)-1,2,3,3a,4,6a-hexahydrocyclopenta[c]pyrrole hydrochloride The product from Example 4B and 5-bromo-2-methyl-2H-tetrazole, prepared as described in Can. J. Chem., (1973), 51, 2315–2322, were processed as described in Example 9 to provide the title compound. $^1$H NMR (CD$_3$OD) δ 2.94 (ddd, J=2.2, 4.1, 17.2 Hz, 1H), 3.15 (dd, J=5.3, 11.9Hz, 1H), 3.18–3.24 (m, 1H), 3.37 (dd, J=3.0, 12.0Hz, 1H), 3.45 (dd, J=8.0, 12.0Hz, 1H), 3.52 (dd, J=8.7, 11.9 Hz, 1H), 3.85 (tt, J=2.6, 7.9 Hz, 1H), 4.35 (s, 3H), 6.51 (dd, J=2.2, 4.1 Hz, 1H); MS (ESI) m/z 192 (M+H)$^+$.

EXAMPLE 26

(cis)-5-(thieno[2,3-b]pyridin-5-yl)-1,2,3,3a,4,6a-hexahydrocyclopenta[c]pyrrole hydrochloride The product from Example 4B and 5-bromothieno[2,3-b]pyridine, prepared as described in J. Heterocycl. Chem, (1968), 5, 773–778, were processed as described in Example 9 to provide the title compound. $^1$H NMR (CD$_3$OD) δ 2.87 (dd, J=2.9, 16.4 Hz, 1H), 3.20 (dd, J=5.0, 11.9 Hz, 1H), 3.26 (tt, J=2.2, 8.3 Hz, 1H), 3.32–3.37 (m, 1H), 3.42 (dd, J=2.7, 11.7 Hz, 1H), 3.46 (dd, J=8.0, 11.7 Hz, 1H), 3.55 (dd, J=8.9, 11.7 Hz, 1H), 3.87 (m, 1H), 6.36 (d, J=1.9 Hz, 1H), 7.50 (d, J=5.9 Hz, 1H), 7.87 (d, J=5.9 Hz, 1H), 8.56 (d, J=1.9 Hz, 1H), 8.86 (d, J=1.9 Hz, 1H); MS (ESI) m/z 243 (M+H)$^+$.

EXAMPLE 27

(cis)-5-(imidazo[1,2-a]pyridin-7-yl)-1,2,3,3a,4,6a-hexahydrocyclopenta[c]pyrrole hydrochloride The product from Example 4B and 7-chloroimidazo[1,2-a]pyridine, prepared as described in J. Heterocycl. Chem, (1965), 2, 53–62, were processed as described in Example 9 to provide the title compound. $^1$H NMR (CD$_3$OD) δ 2.85 (dd, J=1.6, 16.5 Hz, 1H), 3.19 (dd, J=5.5, 12.0 Hz, 1H), 3.22–3.28 (m, 1H), 3.35–3.37 (m, 1H), 3.40 (dd, J=3.1, 12.2 Hz, 1H), 3.50 (dd, J=8.3, 11.7 Hz, 1H), 3.57 (dd, J=9.1, 11.6 Hz, 1H), 3.90 (m, 1H), 6.61 (d, J=1.6 Hz, 1H), 7.71–7.74 (m, 2H), 8.00 (d, J=2.2 Hz, 1H), 8.17 (d, J=1.6 Hz, 1H), 8.71 (d, J=7.2 Hz, 1H); MS (ESI) m/z 226 (M+H)$^+$.

EXAMPLE 28

(cis)-5-(2-pyridinyl)-1,2,3,3a,4,6a-hexahydrocyclopenta[c]pyrrole hydrochloride

The product from Example 4B and 2-bromopyridine (purchased from Aldrich) were processed as described in Example 9 to provide the title compound. $^1$H NMR (CD$_3$OD) δ 2.92 (dd, J=1.9, 16.5 Hz, 1H), 3.22 (dd, J=5.5, 12.0 Hz, 1H), 3.26–3.29 (m, 1H), 3.38–3.41 (m, 1H), 3.44 (dd, J=3.3, 12.3 Hz, 1H), 3.53 (dd, J=8.6, 12.0 Hz, 1H), 3.57 (dd, J=8.6, 12.0 Hz, 1H), 3.96 (tt, J=2.7, 8.2 Hz, 1H), 6.87 (d, J=1.6 Hz, 1H), 7.92 (t, J=6.7 Hz, 1H), 8.14 (d, J=8.4 Hz, 1H), 8.53 (dt, J=4.0, 11.1 Hz, 1H), 8.71 (dd, J=0.9, 5.9 Hz, 1H); MS (ESI) m/z 187 (M+H)$^+$.

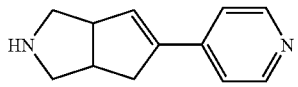

EXAMPLE 29

(cis)-5-(4-pyridinyl)-1,2,3,3a,4,6a-hexahydrocyclopenta[c]pyrrole hydrochloride

The product from Example 4B and the free base of 4-bromopyridine hydrochloride (purchased from Aldrich) were processed as described in Example 9 to provide the title compound. $^1$H NMR(CD$_3$OD)δ 2.86 (dd, J=1.7, 16.7 Hz, 1H), 3.19 (dd, J=5.3, 11.6Hz, 1H), 3.22–3.27 (m, 1H), 3.35–3.40 (m, 1H), 3.42 (dd, J=3.1, 11.6 Hz, 1H), 3.52 (dd, J=8.6, 12.0 Hz, 1H), 3.56 (dd, J=8.7, 11.6 Hz, 1H), 3.93 (m, 1H), 6.87 (dd, J=2.2, 3.7 Hz, 1H), 8.08 (d, J=6.6 Hz, 2H), 8.75 (d, J=6.4 Hz, 2H); MS (ESI) m/z 187 (M+H)$^+$.

EXAMPLE 30

(cis)-5-(5-nitro-1,3-thiazol-2-yl)-1,2,3,3a,4,6a-hexahydrocyclopenta[c]pyrrole hydrochloride The product from Example 4B and 2-bromo-5-nitrothiazole (purchased from Aldrich) were processed as described in Example 9 to provide the title compound. $^1$H NMR (CD$_3$OD) δ 2.85 (dd, J=1.9, 16.9 Hz, 1H), 3.16 (dd, J=5.2, 12.0 Hz, 1H), 3.20–3.27 (m, 1H), 3.33–3.35 (m, 1H), 3.38 (dd, J=3.1, 11.9 Hz, 1H), 3.45 (dd, J=8.3, 12.0 Hz, 1H), 3.51 (dd, J=8.4, 11.6 Hz, 1H), 3.87 (m, 1H), 6.67 (dd, J=2.2, 4.1 Hz, 1H), 8.61 (s, 1H); MS (ESI) m/z 238 (M+H)$^+$.

EXAMPLE 31

(cis)-5-(6-methyl-2-pyridinyl)-1,2,3,3a,4,6a-hexahydrocyclopenta[c]pyrrole hydrochloride The product from Example 4B and 2-bromo-6-methylpyridine (purchased from Aldrich) were processed as described in Example 9 to provide the title compound. $^1$H NMR (CD$_3$OD) δ 2.59 (s, 3H), 2.92 (d, J=16.2 Hz, 1H), 3.30–3.42 (m, 3H), 3.47–3.65 (m, 3H), 3.96 (m, 1H), 6.40 (d, J=1.6 Hz, 1H), 7.92 (t, J=6.9 Hz, 1H), 8.49 (d, J=7.8 Hz, 1H), 8.64 (d, J=5.7 Hz, 1H); MS (ESI) m/z 201 (M+H)$^+$.

EXAMPLE 32

(cis)-5-(1,3,4-thiadiazol-2-yl)-1,2,3,3a,4,6a-hexahydrocyclopenta[c]pyrrole hydrochloride The product from Example 4B and 2-bromo-1,3,4-thiadiazole, prepared as described in Chem. Ber., (1956), 56, 1534–1543, were processed as described in Example 9 to provide the title compound. $^1$H NMR (CD$_3$OD) δ 2.86 (m, 1H), 3.20 (dd, J=4.3, 11.8 Hz, 1H), 3.30–3.60 (m, 5H), 3.84 (m, 1H), 6.52 (br s, 1H), 9.40 (s, 1H); MS (ESI) m/z 194 (M+H)$^+$.

EXAMPLE 34

(endo)-5-(3-pyridinyl)octahydrocyclopenta[c]pyrrole bis(4-methylbenzenesulfonate)

EXAMPLE 34A

(endo)-5-(3-pyridinyl)octahydrocyclopenta[c]pyrrole

The product from Example 1G (0.077 g, 0.263 mmol) in ethanol was treated with hydrogen gas (1 atm) in the presence of Pd/C (0.008 g, 10 wt. %) and stirred at ambient temperature for 4 hours. The reaction vessel was evacuated, purged with nitrogen and the catalyst was removed by filtration through diatomaceous earth. The filtrate was concentrated under reduced pressure and the residue was purified by chromatography (SiO$_2$, CHCl$_3$/MeOH/NH$_4$OH, 90:10:1) to provide the title compound (0.036 g, 39%). MS (DCI/NH$_3$) m/z 189 (M+H)$^+$.

EXAMPLE 34B

(endo)-5-(3-pyridinyl)octahydrocyclopenta[c]pyrrole bis(4-methylbenzenesulfonate)

The product from Example 34A (0.020 g, 0.0795 mmol) in methanol was treated with p-toluenesulfonic acid (0.030 g, 0.159 mmol) and stirred at ambient temperature for 5 minutes. The volatiles were evaporated under reduced pressure and the residue was crystallized from ethanol and diethyl ether to provide the title compound (0.015 g, 30%). $^1$H NMR (CD$_3$OD, 300 MHz) δ 1.67 (m, 2H), 2.37 (s, 6H), 2.52 (m, 2H), 3.11 (m, 2H), 3.29–3.40 (m, 4H), 7.23 (d, J=8.1 Hz, 4H), 7.70 (d, J=8.1 Hz, 4H), 8.03 (dd, J=5.7, 8.1 Hz, 1H), 8.63 (d, J=8.5 Hz, 1H), 8.72 (d, J=5.4 Hz, 1H), 8.82 (s, 1H); MS (DCI/NH$_3$) m/z 189 (M+H)$^+$.

EXAMPLE 35

(cis)-5-(6-chloro-3-pyridinyl)octahydrocyclopenta[c]pyrrol-5-ol

The product from Example 1E (0.044 g, 0.130 mmol) in methanol (1 mL) was treated with a 1M solution of HCl in diethyl ether (1 mL). After stirring at ambient temperature for 2 hours, the volatiles were evaporated under reduced pressure. The residue was crystallized from ethanol and diethyl ether to provide the title compound (0.031 g, 87%). $^1$H NMR (CD$_3$OD, 300 MHz) δ 2.08 (d, J=14.0 Hz, 2H), 2.38 (m, 1H), 2.41 (m, 1H), 3.24 (m, 2H), 3.41 (d, J=5.5 Hz, 4H), 7.44 (d, J=8.5 Hz, 1H), 7.93 (dd, J=2.6, 8.5 Hz, 1H), 8.49 (d, J=2.6 Hz, 1H); MS (DCI/NH$_3$) m/z 239 (M+H)$^+$.

EXAMPLE 36

(endo)-5-(6-chloro-3-pyridinyl)octahydrocyclopenta[c]pyrrole hydrochloride

EXAMPLE 36A

(endo)-5-(6-chloro-3-pyridinyl)octahydrocyclopenta[c]pyrrole

(exo)-5-(6-chloro-3-pyridinyl)octahydrocyclopenta[c]pyrrole

The product from Example 1E (0.336 g, 0.994 mmol) in acetonitrile (5 mL) at 0° C. was treated with 4-(dimethylamino)pyridine (0.672 g, 1.49 mmol) and methyl oxalyl chloride (0.32 mL, 1.19 mmol). The reaction mixture was allowed to warm to room temperature, diluted with ethyl acetate, washed with saturated aqueous sodium bicarbonate (20 mL), water (20 mL), brine (20 mL), dried over Na$_2$SO$_4$, filtered and the filtrate was concentrated under reduced pressure. The residue was dissolved in toluene (5 mL) and treated with tributyltin hydride (0.401 mL, 1.49 mmol) and AIBN (0.024 g, 0.149 mmol). The reaction mixture was stirred at 100° C. for 3 hours, allowed to cool to room temperature and concentrated under reduced pressure. The residue was purified by chromatography (SiO$_2$, 30% ethyl acetate/hexane) to provide 0.019 g (6%) of the exo-isomer and 0.094 g (29%) of the endo-isomer. exo-isomer: $^1$H NMR (CDCl$_3$, 300 MHz) δ 1.47 (s, 9H), 1.86 (m, 2H), 1.99 (m, 2H), 2.90 (m, 2H), 3.14–3.30 (m, 3H), 3.65 (m, 2H), 7.24 (d, J=8.6 Hz, 1H), 7.48 (dd, J=2.4, 8.1 Hz, 1H), 8.26 (d, J=2.5 Hz, 1H); MS (DCI/NH$_3$) m/z 323, 325 (M+H)$^+$. endo-isomer: $^1$H NMR (CDCl$_3$, 300 MHz) δ 1.47 (s, 9H), 1.48 (m, 2H), 2.33 (m, 2H), 2.75 (m, 2H), 3.09 (m, 1H), 3.35 (m, 2H), 3.45 (m, 2H), 7.24 (d, J=8.1 Hz, 1H), 7.51 (dd, J=2.4, 8.1 Hz, 1H). 8.25 (d, J=2.4 Hz); MS (DCI/NH$_3$) m/z 323, 325 (M+H)$^+$.

EXAMPLE 36B

(endo)-5-(6-chloro-3-pyridinyl)octahydrocyclopenta[c]pyrrole hydrochloride

The endo-isomer from Example 36A (0.094 g, 0.292 mmol) in methanol (1 mL) was treated with a 1M solution of HCl in diethyl ether (1 mL). After stirring at ambient temperature for 2 hours, the volatiles were evaporated under reduced pressure. The residue was crystallized from ethanol and diethyl ether to provide the title compound (0.062 g, 32%). $^1$H NMR (CD$_3$OD, 300 MHz) δ 1.51 (m, 2H), 2.47 (m, 2H), 3.07 (m, 2H), 3.13–3.38 (m, 5H), 7.40 (d, J=8.1 Hz, 1H), 7.77 (dd, J=2.7, 8.1 Hz, 1H), 8.28 (d, J=2.7, 1H); MS (DCI/NH$_3$) m/z 223 (M+H)$^+$.

EXAMPLE 37

(exo)-5-(6-chloro-3-pyridinyl)octahydrocyclopenta[c]pyrrole hydrochloride

The exo-isomer from Example 36A (0.019 g, 0.059 mmol) in methanol (1 mL) was treated with a 1M solution of HCl in diethyl ether (1 mL). After stirring at ambient temperature for 2 hours, the volatiles were evaporated under reduced pressure. The residue was crystallized from ethanol and diethyl ether to provide the title compound (0.011 g, 72%). $^1$H NMR (CD$_3$OD, 300 MHz) δ 1.99 (m, 4H), 2.95

(m, 2H), 3.06 (m, 2H), 3.40 (m, 1H), 3.61 (m, 2H), 7.41 (d, J=8.5 Hz, 1H), 7.77 (dd, J=2.6, 8.5 Hz, 1H), 8.29 (d, J=2.6 Hz, 1H); MS (DCI/NH$_3$) m/z 223 (M+H)$^+$.

EXAMPLE 38

(cis)-5-(3-pyridinyl)-1,2,3,3a,4,6a-hexahydrocyclopenta[b]pyrrole fumarate (cis)-5-(3-pyridinyl)-1,2,3,3a,6,6a-hexahydrocyclopenta[b]pyrrole fumarate

EXAMPLE 38A benzyl 5-oxohexahydrocyclopenta[b]pyrrole-1(2H)-carboxylate

Benzyl 6,6-dichloro-5-oxohexahydrocyclopenta[b]pyrrole-1(2H)-carboxylate (3.87 g, 11.8 mmol), prepared as described in Tetrahedron Lett. (1997), 38, 1869–1872, in MeOH (60 mL) at 0° C. was treated with solid ammonium chloride (6.32 g, 118 mmol) followed by zinc duct (Aldrich; 3.09 g, 47.2 mmol). After stirring at room temperature for 1 hour, the reaction mixture was filtered and the filtrate concentrated under reduced pressure. The residue was purified by chromatography (SiO$_2$, 40% EtOAc/hexanes) to provide 2.57 g (84%) of the title compound. MS (DCI/NH$_3$) m/z 260 (M+H)$^+$.

EXAMPLE 38B benzyl 5-{[(trifluoromethyl)sulfonyl]oxy}-3,3a,6,6a-tetrahydrocyclopenta[b]pyrrole-1(2H)-carboxylate benzyl 5-{[(trifluoromethyl)sulfonyl]oxy}-3,3a,4,6a-tetrahydrocyclopenta[b]pyrrole-1(2H)-carboxylate The product from Example 38A (1.56 g, 6.02 mmol) in THF (30 mL) at −78° C. was treated with potassium bis(trimethylsilyl)amide (0.5M solution in toluene, 14.4 mL, 7.22 mmol). The reaction mixture was stirred at −78° C. for 30 minutes and then a solution of N-phenyltrifluoromethanesulfonimide (2.58 g, 7.22 mmol) in THF (5 mL) was added dropwise. The reaction mixture was stirred at −78° C. for 1 hour and then quenched by the addition of water. The mixture was warmed to ambient temperature and extracated with CH$_2$Cl$_2$. The organic extract was washed with saturated aqueous NH$_4$Cl, brine, dried (Na$_2$SO$_4$), filtered and the filtrate concentrated under reduced pressure. The residue was purified by chromatography (SiO$_2$, 20% EtOAc/hexanes) to provide 1.84 g (78%) of a 4:1 mixture of the title compounds. MS (DCI/NH$_3$) m/z 392 (M+H)$^+$.

EXAMPLE 38C benzyl 5-(trimethylstannyl)-3,3a,6,6a-tetrahydrocyclopenta[b]pyrrole-1(2H)-carboxylate benzyl 5-(trimethylstannyl)-3,3a,4,6a-tetrahydrocyclopenta[b]pyrrole-1(2H)-carboxylate The product mixture of Example 38B (260 mg, 0.664 mmol) in THF (3.3 mL) was treated with hexamethylditin (218 mg, 0.664 mmol), lithium chloride (84 mg, 2.0 mmol) and tetrakis(triphenylphosphine)palladium(0) (15 mg, 0.0013 mmol). The resulting mixture was stirred at 60° C. for 14 hours, allowed to cool to room temperature and filtered through Celite (diethyl ether wash). The filtrate was washed with 1N aqueous sodium hydroxide (2×), water, brine, dried (Na$_2$SO$_4$), filtered and the filtrate concentrated under reduced pressure. The residue was purified by chromatography (SiO$_2$, 15% ethyl acetate/hexanes) to provide 160 mg (57%) of a 4:1 mixture of the title compounds. MS (DCI/NH$_3$) m/z 423, 425 (M+H)$^+$.

EXAMPLE 38D benzyl 5-(3-pyridinyl)-3,3a,6,6a-tetrahydrocyclopenta[b]pyrrole-1 (2H)-carboxylate benzyl 5-(3-pyridinyl)-3,3a,4,6a-tetrahydrocyclopenta[b]pyrrole-1 (2H)-carboxylate The mixture of Example 38C (140 mg, 0.332 mmol) and 3-bromopyridine (0.042 mL, 0.43 mmol) were processed as described in Example 4C. Purification by chromatography (SiO$_2$, 30% EtOAc/hexane) provided 90 mg (85%) of a 4:1 mixture of the title compounds. MS (DCI/NH$_3$) m/z 321 (M+H)$^+$.

EXAMPLE 38E (cis)-5-(3-pyridinyl)-1,2,3,3a,4,6a-hexahydrocyclopenta[b]pyrrole fumarate (cis)-5-(3-pyridinyl)-1,2,3,3a,6,6a-hexahydrocyclopenta[b]pyrrole fumarate Iodotrimethylsilane (43 µL, 0.30 mmol) was added to a 0° C. solution of the mixture from Example 38D (80 mg, 0.25 mmol) in 2.5 mL of acetonitrile. The solution was stirred for 3 hours at 0° C. then concentrated under reduced pressure. The residue was passed through a plug of silica gel (10% MeOH/CH$_2$Cl$_2$ wash) to provide 38 mg (82%) of a mixture of the free amines. The free amines were dissolved in MeOH and fumaric acid was added (23 mg, 0.19 mmol). After 30 minutes, a few drops of diethyl ether were added causing formation of a precipitate that was then collected by filtration. The solid was dried under reduced pressure to provide 42 mg of a 4:1 mixture of the title compounds. $^1$H NMR for major isomer (D$_2$O, 300 MHz) δ 1.95 (m, 1H), 2.30 (m, 1H), 2.77 (m, 1H), 3.13–3.49 (m, 5H), 6.36 (m, 1H), 6.60 (s, 2H), 7.77 (dd, J=2.6, 8.5 Hz, 1H), 8.34 (m, 1H), 8.60 (m, 1H), 8.83 (m, 1H); MS (DCI/NH$_3$) m/z 187 (M+H)$^+$. Peaks for the minor isomer in the $^1$H NMR are obscured by the major isomer, except for the olefinic proton (multiplet at 6.45 ppm) that allows for a rough determination of the product ratios.

EXAMPLE 39

(cis)-5-(5-bromo-3-pyridinyl)-1,2,3,3a,4,6a-hexahydrocyclopenta[c]pyrrole fumarate

EXAMPLE 39A tert-butyl (cis)-5-(5-bromo-3-pyridinyl)-3,3a,4,6a-tetrahydrocyclopenta[c]pyrrole-2(1H)-carboxylate 3,5-Dibromopyridine (0.656 g, 2.77 mmol) and the product from Example 4B (1.03 g, 2.77 mmol) were processed as described in Example 4C to provide 477 mg (47%) of the title compound. MS (DCI/NH$_3$) m/z 365, 367 (M+H)$^+$.

EXAMPLE 39B (cis)-5-(5-bromo-3-pyridinyl)-1,2,3,3a,4,6a-hexahydrocyclopenta[c]pyrrole fumarate The product from Example 39A (0.110 g, 0.302 mmol) in $CH_2Cl_2$ (mL) was treated with TFA (1 mL). After stirring for 30 minutes, the solution was concentrated and then diluted with 10% $NH_4OH/MeOH$. This was concentrated under reduced pressure and the residue passed through a pad of silica gel (90:10:1 $CHCl_3$:MeOH:$NH_4OH$ eluent). The filtrate was concentrated to afford the free base of the title compound which was diluted with MeOH and treated with fumaric acid (0.033 g 0.28 mmol) to afford the title compound (77 mg, 67%). $^1H$ NMR ($CD_3OD$, 300 MHz) δ 2.75 (m, 1H), 3.11–3.21 (m, 2H), 3.35–3.59 (m, 4H), 3.89 (m, 1H), 6.29 (m, 1H), 6.65 (s, 2H), 8.12 (dd, J=2.0, 2.1 Hz, 1H), 8.55 (d, J=2.4 Hz, 1H), 8.63 (d, J=2.4 Hz, 1H); MS (DCI/$NH_3$) m/z 265, 267 $(M+H)^+$; Anal. calculated for $C_{12}H_{14}N_2 \cdot C_4H_4O_4$: C, 50.41; H, 4.49; N, 7.35. Found: C, 50.51; H, 4.53; N, 7.33.

EXAMPLE 40

(cis)-5-(5-vinyl-3-pyridinyl)-1,2,3,3a,4,6a-hexahydrocyclopenta[c]pyrrole fumarate

EXAMPLE 40A tert-butyl (cis)-5-(5-vinyl-3-pyridinyl)-3,3a,4,6a-tetrahydrocyclopenta[c]pyrrole-2(1H)-carboxylate Tributyl(vinyl)tin (0.656 g, 2.77 mmol), tetrakis(triphenylphosphine)palladium(0) (0.026 g, 0.23 mmol), in anhydrous toluene were treated with the product from Example 39A (1.03 g, 2.77 mmol). The reaction mixture was stirred for 3 days at 100° C. After cooling to ambient temperature, the volatiles were removed under reduced pressure and the residue was purified by flash chromatography to afford the title compound (279 mg, 93%). MS (DCI/$NH_3$) m/z 312 $(M+H)^+$.

EXAMPLE 40B (cis)-5-(5-vinyl-3-pyridinyl)-1,2,3,3a,4,6a-hexahydrocyclopenta[c]pyrrole fumarate The product from Example 40A (0.279 g, 0.894 mmol) was processed as described in Example 39B to provide the title compound (0.168 g, 57%). $^1H$ NMR ($CD_3OD$, 300 MHz) δ 2.80 (m, 1H), 3.14–3.54 (m, 6H), 3.83 (m, 1H), 5.45 (d, J=11.2 Hz, 1H), 5.98 (d, J=18.0 Hz, 1H), 6.27 (m, 1H), 6.66 (s, 2H), 6.80 (dd, J=11.2,18.0 Hz, 1H), 7.99 (dd, J=20, 2.0 Hz, 1H), 8.49 (d, J=2.0 Hz, 1H), 8.55 (d, J=2.0 Hz, 1H); MS (DCI/$NH_3$) m/z 213 $(M+H)^+$; Anal. calculated for $C_{14}H_{16}N_2 \cdot C_4H_4O_4$: C, 65.84; H, 6.14; N, 8.53. Found: C, 65.64; H, 6.07; N, 8.30.

EXAMPLE 41

(cis)-5-(1,2,3,3a,4,6a-hexahydrocyclopenta[c]pyrrol-5-yl)nicotinonitrile

EXAMPLE 41A tert-butyl (cis)-5-(5-cyano-3-pyridinyl)-3,3a,4,6a-tetrahydrocyclopenta[c]pyrrole-2(1H)-carboxylate 3-Bromo-5-cyanopyridine (0.251 g, 1.37 mmol) and the product from Example 4B (0.510 g, 137 mmol) were processed as described in Example 4C to provide 232 mg (54%) of the title compound. MS (DCI/$NH_3$) m/z 312 $(M+H)^+$.

EXAMPLE 41B (cis)-5-(1,2,3,3a,4,6a-hexahydrocyclopenta[c]pyrrol-5-yl)nicotinonitrile fumarate The product from Example 41A (0.091 g, 0.29 mmol) was processed as described in Example 39B to provide the title compound (0.059 g, 62%). $^1H$ NMR ($CD_3OD$, 300 MHz) δ 2.77 (m, 1H), 3.12–3.33 (m, 2H), 3.28–3.54 (m, 4H), 3.83 (m, 1H), 6.37 (m, 1H), 6.65 (s, 2H), 8.28 (dd, J=2.0, 2.0 Hz, 1H), 8.80 (d, J=1.70 Hz, 1H), 8.83 (d, J=2.0 Hz, 1H); MS (DCI/$NH_3$) m/z 212 $(M+H)^+$; Anal. calculated for $C_{14}H_{16}N_2 \cdot C_4H_4O_4$: C, 62.38; H, 5.23; N, 12.84. Found: C, 62.52; H, 5.27; N, 13.01.

EXAMPLE 42

(cis)-5-(6-chloro-3-pyridinyl)-1,2,3,3a,4,6a-hexahydrocyclopenta[c]pyrrole hydrochloride

EXAMPLE 42A (+)-tert-butyl (cis)-5-(6-chloro-3-pyridinyl)-3,3a,4,6a-tetrahydrocyclopenta[c]pyrrole-2(1H)-carboxylate and (−)-tert-butyl (cis)-5-(6-chloro-3-pyridinyl)-3,3a,4,6a-tetrahydrocyclopenta[c]pyrrole-2(1H)-carboxylate The racemic product from Example 1F was separated into its individual enantiomers on a Chiralpak AS column (4.6 mm×250 mm) using 98:2 hexane:ethanol as eluent. The more mobile enantiomer, retention time=12.54 minutes, $[\alpha]_D$-46.1 (c 2.0, $CH_2Cl_2$). The less mobile enantiomer, retention time =17.66 minutes $[\alpha]_D$ 48.8 (c 2.0, $CH_2Cl_2$).

EXAMPLE 42B (cis)-5-(6-chloro-3-pyridinyl)-1,2,3,3a,4,6a-hexahydrocyclopenta[c]pyrrole hydrochloride The more mobile enantiomer, (−)-tert-Butyl (cis)-5-(6-chloro-3-pyridinyl)-3,3a,4,6a-tetrahydrocyclopenta[c]pyrrole-2(1H)-carboxylate, from Example 42A was processed as described in Example 1G to afford the title compound. $^1H$ NMR ($CD_3OD$, 300 MHz) δ 2.75 (m, 1H), 3.12–3.22 (m, 2H), 3.32–3.55 (m, 4H), 3.82 (m, 1H), 6.24 (m, 1H), 7.45 (d, J=85 Hz, 1H), 7.94 (dd, J=2.4, 8.5 Hz, 1H), 8.47 (d, J=2.1 Hz, 1H); MS (DCI/$NH_3$) m/z 221, 223 $(M+H)^+$.

EXAMPLE 43

(cis)-5-(6-chloro-3-pyridinyl)-1,2,3,3a,4,6a-hexahydrocyclopenta[c]pyrrole hydrochloride The less mobile enantiomer, (+)-tert-Butyl (cis)-5-(6-chloro-3-pyridinyl)-3,3a,4,6a-tetrahydrocyclopenta[c]pyrrole-2(1H)-carboxylate, from Example 42A was processed as described in Example 1G to afford the title compound. $^1H$ NMR (CD$_3$OD, 300 MHz) δ 2.75 (m, 1H), 3.12–3.22 (m, 2H), 3.32–3.55 (m, 4H), 3.82 (m, 1H), 6.24 (m, 1H), 7.45 (d, J=8.5 Hz, 1H), 7.94 (dd, J=2.5, 8.5 Hz, 1H), 8.47 (d, J=2.4 Hz, 1H); MS (DCI/NH$_3$) m/z 221, 223 (M+H)$^+$.

EXAMPLE 44

(cis)-6-(6-chloro-3-pyridinyl)-1,2,3,3a,4,6a-hexahydrocyclopenta[c]pyrrole fumarate

EXAMPLE 44A tert-butyl (cis)-4-oxohexahydrocyclopenta[c]pyrrole-2(1H)-carboxylate (cis)-2-Benzylhexahydrocyclopenta[c]pyrrol-4(1H)-one, prepared as described in Heterocycles (1988), 27(3), 643–644, and di-tert-butyl-dicarbonate in methanol were treated with hydrogen gas in the presence of palladium hydroxide (20 wt. %). After completion of the reaction, the reaction vessel was purged with nitrogen and the catalyst removed by filtration. The filtrate was concentrated under reduced pressure to provide the title compound. $^1$H NMR (CDCl$_3$, 300 MHz) δ 1.45 (s, 9H), 1.87 (m, 1H), 2.16 (m, 1H), 2.34–2.39 (m, 2H), 2.74 (m, 1H), 3.03 (m, 1H), 3.15 (br m, 1H), 3.42–3.74 (m, 3H).

EXAMPLE 44B tert-butyl (cis)-6-{[(trifluoromethyl)sulfonyl]oxy}-3,3a,4,6a-tetrahydrocyclopenta[c]pyrrole-2(1H)-carboxylate The product from Example 44A (1.78 g, 7.88 mmol) was processed as described in Example 4A to afford the title compound (1.57 g, 56%). MS (DCI/NH$_3$) m/z 358 (M+H)$^+$, 375 (M+NH$_4$)$^+$.

EXAMPLE 44C tert-butyl (cis)-6-(trimethylstannyl)-3,3a,4,6a-tetrahydrocyclopenta[c]pyrrole-2(1H)-carboxylate The product from Example 44B (0.303 g, 0.848 mmol) was processed as described in Example 4B to afford the title compound (0.225 g, 71%). MS (DCI/NH$_3$) m/z 372, 374 (M+H)$^+$.

EXAMPLE 44D tert-butyl (cis)-6-(6-chloro-3-pyridinyl)-3,3a,4,6a-tetrahydrocyclopenta[c]pyrrole-2(1H)-carboxylate 2-Chloro-5-iodopyridine and the product from Example 44C were processed as described in Example 4C to afford the title compound. MS (DCI/NH$_3$) m/z 321, 323 (M+H)$^+$.

EXAMPLE 44E (cis)-6-(6-chloro-3-pyridinyl)-1,2,3,3a,4,6a-hexahydrocyclopenta[c]pyrrole fumarate The product from Example 44D was processed as described in Example 39B to afford the title compound: $^1$H NMR (CD$_3$OD, 300 MHz) δ 2.50 (m, 1H), 2.96 (m, 1H), 3.07–3.18 (m, 2H), 3.49–3.62 (m, 2H), 4.10 (m, 1H), 6.39 (m, 1H), 7.46 (dd, J=0.7, 8.1 Hz, 1H), 7.91 (dd, J=2.5, 8.5 Hz, 1H), 8.44 (d, J=2.4 Hz, 1H); MS (DCI/NH$_3$) m/z 221, 223 (M+H)$^+$; Anal. calculated for C$_{12}$H$_{13}$ClN$_2$·C$_4$H$_4$O$_4$: C, 57.06; H, 5.09; N, 8.32. Found: C, 57.15; H, 5.33; N, 8.36.

EXAMPLE 45

(cis)-4-(3-pyridinyl)-octahydrocyclopenta[c]pyrrol-4-ol dihydrochloride

EXAMPLE 45A tert-butyl (cis)-4-hydroxy-4-(3-pyridinyl)-hexahydrocyclopenta[c]pyrrole-2(1H)-carboxylate 3-Bromopyridine (4.36 g, 27.6 mmol) and the product from Example 44A (2.07 g, 9.19 mmol) were processed as described in Example 1E to afford the title compound (0.743 g, 27%). MS (DCI/NH$_3$) m/z 305 (M+H)$^+$

EXAMPLE 45B (cis)-4-(3-pyridinyl)-octahydrocyclopenta[c]pyrrol-4-ol dihydrochloride The product from Example 45A was processed as described in Example 35 to afford the title compound. $^1$H NMR (CD$_3$OD, 300 MHz) δ 1.92 (m, 1H), 2.17 (m, 1H), 2.32–2.51 (m, 2H), 2.98–3.14 (m, 2H), 3.23–3.43 (m, 3H), 3.49 (d, J=11.2 Hz, 1H), 8.11 (dd, J=5.9, 8.4 Hz, 1H), 8.79–8.82 (m, 2H), 9.02 (d, J=1.4 Hz, 1H); MS (DCI/NH$_3$) m/z 205 (M+H)$^+$.

EXAMPLE 45

(cis)-4-(3-pyridinyl)-octahydrocyclopenta[c]pyrrol-4-ol dihydrochloride

EXAMPLE 45A tert-butyl-4-hydroxy-4-(3-pyridinyl)-hexahydrocyclopenta[c]pyrrole-2(1H)-carboxylate 3-Bromopyridine (4.36 g, 27.6 mmol) and the product from Example 44A (2.07 g, 9.19 mmol) were processed as described in Example 1E to afford the title compound (0.743 g, 27%). MS (DCI/NH$_3$) m/z 305 (M+H)$^+$.

EXAMPLE 45B (cis)-4-(3-pyridinyl)-octahydrocyclopenta[c]pyrrol-4-ol dihydrochloride The product from Example 45A was processed as described in Example 35 to afford the title compound. $^1$H NMR (CD$_3$OD, 300 MHz) δ 1.92 (m, 1H), 2.17 (m, 1H), 2.32–2.51 (m, 2H), 2.98–3.14 (m, 2H), 3.23–3.43 (m, 3H), 3.49 (d, J=11.2 Hz, 1H), 8.11 (dd, J=5.9, 8.4 Hz, 1H), 8.79–8.82 (m, 2H), 9.02 (d, J=1.4 Hz, 1H); MS (DCI/NH$_3$) m/z 205 (M+H)$^+$.

EXAMPLE 46

(endo)-4-(6-chloro-3-pyridinyl)octahydrocyclopenta[c]pyrrole 4-methylbenzenesulfonate

EXAMPLE 46A (cis)-tert-butyl-4-hydroxy-4-(6-chloro-3-pyridinyl)-hexahydrocyclopenta[c]pyrrole-2(1H)-carboxylate 5-Bromo-2-chloropyridine (1.82 g, 9.46 mmol) and the product from Example 44A (1.64 g, 7.28 mmol) were processed as described in Example 1E to afford the title compound (1.25 g, 51%). MS (DCI/NH$_3$) m/z 339, 341 (M+H)$^+$.

EXAMPLE 46B (endo)-tert-butyl-4-(6-chloro-3-pyridinyl)octahydro-cyclopenta[c]pyrrole carboxylate (exo)-tert-butyl -4-(6-chloro-3-pyridinyl)octahydro-cyclopenta[c]pyrrole carboxylate The product from Example 46A (0.250 g, 0.738 mmol) was processed as described in Example 36A. The residue was purified by chromatography (SiO$_2$, 10–30% ethyl acetate/hexane gradient) to provide 0.044 g (18%) of the faster eluting exo-isomer and 0.145 g (61%) of the slower eluting endo-isomer. MS (DCI/NH$_3$) m/z 323, 325 (M+H)$^+$.

EXAMPLE 46C (endo)-4-(6-chloro-3-pyridinyl)octahydrocyclopenta[c]pyrrole4-methylbenzenesulfonate The endo-isomer from Example 46B (0.094 g, 0.292 mmol) in EtOAc (5 mL) was treated with p-toluenesulfonic acid monohydrate (0.074 g, 0.39 mmol). The solution was warmed to reflux for 4 hours and then allowed to cool to ambient temperature. The solid was collected by filtration (EtOAc wash) and dried under high vacuum to afford the title compound as a white solid (107 mg, 71%). $^1$H NMR (CD$_3$OD, 300 MHz) δ 1.76 (m, 1H), 1.90–2.10 (m, 3H), 2.37 (s, 3H), 2.50 (dd, J=9.7, 11.5 Hz, 1H), 2.86 (dd, J=7.8, 11.6 Hz, 1H), 2.99–312 (m, 2H), 3.27 (m, 1H), 3.41 (m, 1H), 3.64 (dd, J=8.4, 11.0 Hz, 1H), 7.23 (d, J=7.8 Hz, 2H), 7.42 (d, J=8.3 Hz, 1H), 7.70 (d, J=8.1 Hz, 2H), 7.76 (m, 1H), 8.32 (m, 1H); MS (DCI/NH$_3$) m/z 223, 225 (M+H)$^+$; Anal. calculated for C$_{12}$H$_{15}$ClN$_2$.1.2C$_7$H$_8$O$_3$S: C, 57.07; H, 5.77; N, 6.52. Found: C, 56.92; H, 5.79; N, 6.57.

EXAMPLE 47

(cis)-6-(6-chloro-3-pyridinyl)-3-azabicyclo[3.2.0]hept-6-ene 4-methylbenzenesulfonate

EXAMPLE 47A (cis)-3-[(4-methylphenyl)sulfonyl]-3-azabicyclo[3.2.0]heptan-6-ol (cis)-3-[(4-Methylphenyl)sulfonyl]-3-azabicyclo[3.2.0]heptan-6-one (8.55 g, 32.2 mmol), prepared according to Gobeaux and Ghosez, Heterocycles, (1989) 28(1), 29–32, in 2:1 THF/CH$_2$Cl$_2$ (150 mL) at 0° C. was treated with a 2M solution of LiBH$_4$ (19.3 mL, 38.7 mmol). After 0.5 hours, the reaction mixture was carefully quenched with 2-propanol (10 mL), allowed to warm to ambient temperature and the volatiles removed under reduced pressure. The residue was diluted with water and extracted twice with CH$_2$Cl$_2$. The combined organic extracts were washed with brine, dried over Na$_2$SO$_4$, filtered, and the filtrate concentrated under reduced pressure to afford the title compound as a white solid (8.20 g, 95%).

EXAMPLE 47B (cis)-tert-butyl 6-hydroxy-3-azabicyclo[3.2.0]heptane-3-carboxylate A solution of sodium napthalenide was prepared according to the procedure described by Heathcock et. al., J. Org. Chem. (1989), 54, 1548–1562 by adding naphthalene (15.4 g, 120 mmol) to a suspension of finely cut sodium metal (2.30 g, 100 mmol) in dimethoxyethane (100 mL), and stirring the resulting dark green mixture at room temperature for 2 hours. The product from Example 47A (8.10 g, 30.3 mmol) in 100 mL of DME at –78° C. was treated slowly with the sodium napthalenide solution (~65 mL) until a light green color persisted. The reaction mixture was then quenched at –78° C. by the addition of 200 mL of water. The mixture was allowed to warm to 0° C. and di-tert-butyl dicarbonate (6.94 g, 31.8 mmol) was added. After 0.5 hours the mixture was diluted with EtOAc and the layers were separated. The organic extract was washed with brine, dried over Na$_2$SO$_4$, filtered and the filtrate concentrated under reduced pressure. The residue was purified by chromatography (5 to 30% EtOAc/CH$_2$Cl$_2$ gradient) to afford the title compound as a white solid (5.26 g, 81%). MS (DCI/NH$_3$) m/z 214 (M+H)$^+$.

EXAMPLE 47C (cis)-tert-butyl 6-oxo-3-azabicyclo[3.2.0]heptane-3-carboxylate

DMSO (4.15 mL, 58.5 mmol) was added dropwise to a solution of oxalyl chloride (2.55 mL, 29.3 mmol) in CH$_2$Cl$_2$ (100 mL) at –78° C. (gas evolution). After 15 minutes, a solution of the product from Example 47B (5.20 g, 24.4 mmol) in CH$_2$Cl$_2$ (20 mL) was added dropwise. After 30 minutes, triethylamine was added dropwise and the white mixture was stirred at –78° C. for 6 hours then allowed to warm to –40° C. for an additional hour. The mixture was then diluted with water and allowed to warm to room temperature. The layers were separated and the organic extract was washed with water and brine, dried over Na$_2$SO$_4$ filtered and and the filtrate concentrated under reduced pressure. The residue was purified by chromatography (10 to 20% EtOAc/CH$_2$Cl$_2$ gradient) to afford the title compound as a viscous oil (4.05 g, 79%). MS (DCI/NH$_3$) m/z 212 (M+H)$^+$.

EXAMPLE 47D (cis)-tert-butyl 6-(6-chloro-3-pyridinyl)-6-hydroxy-3-azabicyclo[3.2.0]heptane-3-carboxylate 5-Bromo-2-chloropyridine (0.888 g, 4.62 mmol) and the product from Example 47C (0.750 g, 3.55 mmol) were processed as described in Example 1E to afford the title compound (1.15 g, 66%). MS (DCI/NH$_3$) m/z 325, 327 (M+H)$^+$.

EXAMPLE 47E (cis)-tert-butyl 6-(6-chloro-3-pyridinyl)-3-azabicyclo[3.2.0]hept-6-ene-3-carboxylate The product from Example 47D (0.400 g, 1.23 mmol), triethylamine (0.36 mL, 2.6 mmol), methanesulfonyl chloride (0.19 mL, 2.5 mmol), and 4-dimethylaminopyridine (3 mg) were combined in THF and heated at reflux for 16 hours. The solvent was removed under reduced pressure and the residue was purified by chromatography (10% EtOAc/$CH_2Cl_2$) to afford the title compound as a white foam (0.280 mg, 74%). MS (DCI/$NH_3$) m/z 307, 309 $(M+H)^+$.

EXAMPLE 47F (cis)-6-(6-chloro-3-pyridinyl)-3-azabicyclo[3.2.0]hept-6-ene 4-methylbenzenesulfonate The product from Example 47E (0.160 g, 0.522 mmol) was processed as described in Example 46C to provide the title compound as a white solid (0.122 mg, 62%). $^1$H NMR ($CD_3OD$, 300 MHz) δ 2.36 (s, 3H), 3.00–3.15 (m, 2H), 3.40 (d, J=11.9 Hz, 1H), 3.51 (d, J=12.5 Hz, 1H), 3.67 (dd, J=3.4, 6.4 Hz, 1H), 4.03 (dd, J=3.7, 6.5 Hz, 1H), 6.48 (s, 1H), 7.23 (d, J=7.8 Hz, 2H), 7.42 (dd, J=0.7, 8.5 Hz, 1H), 7.70 (d, J=8.1 Hz, 2H), 7.89 (dd, J=2.4, 8.5 Hz, 1H), 8.47 (d, J=2.4 Hz, 1H); MS (DCI/$NH_3$) m/z 207, 209 $(M+H)^+$; Anal. Calculated for $C_{11}H_{11}ClN_2 \cdot C_7H_8O_3S$: C, 57.06; H, 5.05; N 7.39. Found: C, 56.79; H, 4.93; N, 7.24.

EXAMPLE 48

(endo)-6-(6-chloro-3-pyridinyl)-3-azabicyclo[3.2.0]heptane 4-methylbenzenesulfonate

EXAMPLE 48A (endo)-tert-butyl 6-(6-chloro-3-pyridinyl)-3-azabicyclo[3.2.0]heptane-3-carboxylate (exo)-tert-butyl 6-(6-chloro-3-pyridinyl)-3-azabicyclo[3.2.0]heptane-3-carboxylate The product from Example 47D (0.250 g, 0.770 mmol) was processed as described in Example 36A. The residue was purified by chromatography ($SiO_2$, 5–20% ethyl acetate/$CH_2Cl_2$ gradient) to provide 0.035 g (15%) of the faster eluting exo-isomer and 0.131 g (55%) of the slower eluting endo-isomer. exo-isomer: $^1$H NMR ($CDCl_3$, 300 MHz) δ 1.51 (s, 9H), 2.18–2.36 (m, 2H), 2.84–3.02 (m, 2H), 3.24–3.33 (m, 2H), 3.44 (m, 1H), 3.60–3.74 (m, 2H), 7.29 (d, J=8.1 Hz, 1H), 7.53 (dd, J=2.2, 8.4 Hz, 1H), 8.25 (d, J=2.0 Hz, 1H); MS (DCI/$NH_3$) m/z 309, 311 $(M+H)^+$. endo-isomer: $^1$H NMR ($CDCl_3$, 300 MHz) δ 1.42 (s, 9H), 2.07 (m, 1H), 2.58 (m, 1H), 3.01 (m, 1H), 3.01–3.32 (m, 4H), 3.60 (br m, 1H), 3.70 (m, 1H), 7.28 (d, J=8.5 Hz, 1H), 7.43 (br d, J=7.4 Hz, 1H), 8.25 (br s, 1H); MS (DCI/$NH_3$) m/z 309, 311 $(M+H)^+$.

EXAMPLE 48B (endo)-6-(6-chloro-3-pyridinyl)-3-azabicyclo[3.2.0]heptane 4-methylbenzenesulfonate The endo-isomer from Example 48A (0.130 g, 0.421 mmol) was processed as described in Example 46C to afford the title compound as a white solid (0.135 g, 84%). $^1$H NMR ($CD_3OD$, 300 MHz) δ 2.19 (m, 1H), 2.37 (s, 3H), 2.68, (m, 1H), 3.08 (dd, J=3.9, 13.1 Hz, 1H), 3.25 (m, 1H), 3.30–3.41 (m, 3H), 3.52 (m, 1H), 3.96 (br q, J=9.5 Hz, 1H), 7.23 (d, J=7.8 Hz, 2H), 7.44 (d, J=8.3 Hz, 1H), 7.63 (dd, J=3.7, 8.1 Hz, 1H), 7.69 (d, J=8.2 Hz, 2H), 8.17 (d, J=2.4 Hz, 1H); MS (DCI/$NH_3$) m/z 209, 211 $(M+H)^+$; Anal. Calculated for $C_{11}H_{13}ClN_2 \cdot C_7H_8O_3S$: C, 56.76; H, 5.56; N, 7.35. Found: C, 56.75; H, 5.49; N, 7.26.

EXAMPLE 49

(exo)-6-(6-chloro-3-pyridinyl)-3-azabicyclo[3.2.0]heptane 4-methylbenzenesulfonate The exo-isomer from Example 48A (0.035 g, 0.125 mmol) was processed as described in Example 46C to afford the title compound as a white solid (0.026 g, 60%). $^1$H NMR ($CD_3OD$, 300 MHz) δ 2.25–2.50 (m, 3H), 2.36 (s, 3H), 3.26–3.36 (m, 4H), 3.61 (br d, J=11.2 Hz, 1H), 3.61 (br d, J=11.2 Hz, 1H), 7.23 (d, J=7.8 Hz, 2H), 7.46 (d, J=8.4 Hz, 1H), 7.70 (d, J=8.2 Hz, 2H), 7.84 (m, 1H), 8.27 (d, J=2.4 Hz, 1H); MS (DCI/$NH_3$) m/z 209, 211 $(M+H)^+$; Anal. Calculated for $C_{11}H_{13}ClN_2 \cdot C_7H_8O_3S$: C, 56.76; H, 5.56; N, 7.35. Found: C, 56.45; H, 5.52; N, 7.11.

EXAMPLE 50

(cis)-6-(5,6-dichloro-3-pyridinyl)-3-azabicyclo[3.2.0]hept-6-ene 4-methylbenzenesulfonate

EXAMPLE 50A (cis)-tert-butyl 6-(5,6-dichloro-3-pyridinyl)-6-hydroxy-3-azabicyclo[3.2.0]heptane-3-carboxylate 2,3-Dichloro-5-bromopyridine (0.758 g, 2.77 mmol) and the product from Example 47A (0.450 g, 2.13 mmol) were processed as described in Example 1E to afford the title compound (0.565 g, 74%). MS (DCI/$NH_3$) m/z 359, 361 $(M+H)^+$.

EXAMPLE 50B (cis)-tert-butyl 6-(5,6-dichloro-3-pyridinyl)-3-azabicyclo[3.2.0]hept-6-ene-3-carboxylate The product from Example 50A (0.359 g, 1.00 mmol) was processed as described in Example 47E to afford the title compound as a white solid (0.131 g, 38%). MS (DCI/$NH_3$) m/z 341, 343 $(M+H)^+$.

EXAMPLE 50C (cis)-6-(5,6-dichloro-3-pyridinyl)-3-azabicyclo[3.2.0]hept-6-ene 4-methylbenzenesulfonate The product from Example 50B (0.125 g, 1.00 mmol) was processed as described in Example 46C to afford the title compound as a white solid (0.108 g, 72%). $^1$H NMR ($CD_3OD$, 300 MHz) δ 2.37 (s, 3H), 3.02–3.13 (m, 2H), 3.41 (d, J=12.2 Hz, 1H), 3.52 (d, J=12.6 Hz, 1H), 3.68 (dd, J=3.7, 6.4 Hz, 1H), 4.03 (dd, J=3.8, 6.5 Hz, 1H), 6.54 (s, 1H), 7.23 (d, J=7.8 Hz, 2H), 7.68 (d, J=8.1 Hz, 2H), 8.08 (d, J=2.0 Hz, 1H), 8.42 (d, J=2.0 Hz, 1H); MS (DCI/$NH_3$) m/z 241, 243 $(M+H)^+$; Anal. Calculated for $C_{11}H_{10}Cl_2N_2 \cdot C_7H_8O_3S$: C, 52.31; H, 4.39; N, 6.78. Found: C, 52.25; H, 4.52; N, 6.62.

EXAMPLE 51

(endo)-6-(5,6-dichloro-3-pyridinyl)-3-azabicyclo[3.2.0]heptane 4-methylbenzenesulfonate

EXAMPLE 51A (endo)-tert-butyl 6-(5,6-dichloro-3-pyridinyl)-3-azabicyclo[3.2.0]heptane-3-carboxylate (exo)-tert-butyl 6-(5,6-dichloro-3-pyridinyl)-3-azabicyclo[3.2.0]heptane-3-carboxylate The product from Example 50A (0.185 g, 0.515 mmol) was processed as described in Example 36A. The residue was purified by chromatography (SiO$_2$, 5–20% ethyl acetate/CH$_2$Cl$_2$ gradient) to provide 0.018 g (10%) of the faster eluting exo-isomer and 0.80 g (45%) of the slower eluting endo-isomer. Data for the exo-isomer: $^1$H NMR (CDCl$_3$, 300 MHz) δ 1.51 (s, 9H), 2.18–2.36 (m, 2H), 2.90–3.02 (m, 2H), 3.24–3.33 (m, 2H), 3.44 (m, 1H), 3.60–3.72 (m, 2H), 7.65 (d, J=2.2 Hz, 1H), 8.15 (d, J=2.0 Hz, 1H); MS (DCI/NH$_3$) m/z 343,345 (M+H)$^+$. Data for the endo-isomer: $^1$H NMR (CDCl$_3$, 300 MHz) δ 1.44 (br s, 9H), 2.07 (m, 1H), 2.59 (m, 1H), 3.02 (m, 1H), 3.03–3.32 (m, 4H), 3.58 (br s, 1H), 3.70 (br q, J=9.8 Hz, 1H), 7.57 (br s, 1H), 8.03 (br s, 1H); MS (DCI/NH$_3$) m/z 343, 345 (M+H)$^+$.

EXAMPLE 51B (endo)-6-(5,6-dichloro-3-pyridinyl)-3-azabicyclo[3.2.0]heptane 4-methylbenzenesulfonate The endo-isomer from Example 51A (0.077 g, 0.22 mmol) was processed as described in Example 46C to afford 0.066 g (71%) of the title compound as a white solid. $^1$H NMR (CD$_3$OD, 300 MHz) δ 2.18 (m, 1H), 2.37 (s, 3H), 2.68 (m, 1H), 3.08 (dd, J=3.7, 13.2 Hz, 1H), 3.22 (m, 1H), 3.30–3.42 (m, 3H), 3.53 (m, 1H), 3.97 (br q, J=9.5 Hz, 1H), 7.23 (d, J=7.8 Hz, 2H), 7.70 (d, J=8.5 Hz, 2H), 7.82 (d, J=2.1 Hz, 1H), 8.14 (d, J=2.0 Hz, 1H); MS (DCI/NH$_3$) m/z 243, 245 (M+H)$^+$; Anal. Calculated for C$_{11}$H$_{12}$Cl$_2$N$_2$.C$_7$H$_8$O$_3$S: C, 52.05; H, 4.85; N, 6.74. Found: C, 52.11; H, 4.70; N, 6.63.

EXAMPLE 52

(cis)-5-(6-phenylpyridazin-3-yl)-1,2,3,3a,4,6a-hexahydrocyclopenta[c]pyrrole 4-methylbenzenesulfonate

EXAMPLE 52A tert-butyl 5-(6-phenylpyridazin-3-yl)-3,3a,4,6a-tetrahydrocyclopenta[c]pyrrole-2(1H)-carboxylate The product from Example 4B (0.200 g, 0.538 mmol), 3-chloro-6-phenylpyridazine (0.205 g, 1.08 mmol), bis(tri-t-butylphosphine)palladium(0) (0.00275 g, 0.0538 mmol, commercially available from Strem) and cesium fluoride (0.180 g, 1.18 mmol) were combined in 1,4-dioxane (1 mL), according to the procedure reported by G. C. Fu and coworkers in J. Am. Chem. Soc. (2002) 124, 6343–6348, and stirred at 85° C. for 36 hours. The mixture was cooled to ambient temperature, diluted with ethyl acetate and filtered through of plug of SiO$_2$ (ethyl acetate wash). The filtrate was concentrated and the residue was purified by chromatography (SiO$_2$, 20% ethyl acetate/hexanes) to afford the title compound. MS (DCI/NH$_3$) m/z 364 (M+H)$^+$.

EXAMPLE 52B (cis)-5-(6-phenylpyridazin-3-yl)-1,2,3,3a,4,6a-hexahydrocyclopenta[c]pyrrole 4-methylbenzene sulfonate The product from Example 51A (0.075 g, 0.28 mmol) was processed as described in Example 46C to afford the title compound. $^1$H NMR (CD$_3$OD, 300 MHz) δ 2.36 (s, 3H), 2.98–308 (m, 1H), 3.20 (dd, J=4.4, 11.9 Hz, 1H), 3.30–3.60 (m, 5H), 3.91 (m, 1H), 6.62 (m, 1H), 7.50–7.60 (m, 3H), 7.69 (d, J=8.0 Hz, 2H), 8.02 (d, J=9.2 Hz, 1H), 8.10 (m, 2H), 8.14 (d, J=8.8 Hz, 1H; MS (DCI/NH$_3$) m/z 264 (M+H)$^+$; Anal. calculated for C$_{17}$H$_{17}$N$_3$.C$_7$H$_8$O$_3$S: C, 66.18; H, 5.79; N, 9.65. Found: C, 65.94; H, 5.62; N, 9.54.

EXAMPLE 53

(cis)-2-methyl-5-(6-phenylpyridazin-3-yl)-1,2,3,3a,4,6a-hexahydrocyclopenta[c]pyrrole The product from Example 52B (0.090 g, 0.21 mmol) was processed as described in Example 7 to afford the title compound. $^1$H NMR (CD$_3$OD, 300 MHz) δ 2.33 (s, 3H), 2.58 (m, 2H), 2.74 (m, 2H), 2.85 (m, 1H), 3.14 (m, 1H), 3.23 (m, 1H), 3.62 (m, 1H), 6.63 (m, 1H), 7.47–7.59 (m, 3H), 7.98 (d, J=8.8 Hz, 1H), 8.07–8.10 (m, 3H); MS (DCI/NH$_3$) m/z 278 (M+H)$^+$.

It is understood that the foregoing detailed description and Examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (IV)

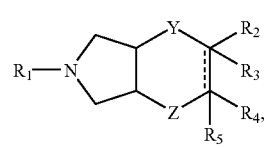

(IV)

wherein

- - - - - represents a double bond;

Y is a covalent bond;

Z is CH$_2$;

R$_1$ is hydrogen:

R$_2$ is hydrogen;

R$_3$ and R$_5$ are absent; and

R$_4$ is heterocycle, wherein the heterocycle is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, furo[2,3-c]pyridine, furo[3,2-c]pyridine, furo[3,2-b]

pyridinyl, furo[2,3-b]pyridinyl, imidazo[1,2-a]pyridinyl, indazolyl, indolyl, indolizinyl, naphthyridinyl, isobenzofuranyl, isobenzothienyl, isoindolyl, isoquinolinyl, phthalazinyl, quinolinyl, quinolizinyl, quinoxalinyl, quinazolinyl, thieno[2,3-c]pyridine, thieno[3,2-c]pyridine, thieno[3,2-b]pyridinyl, and thieno[2,3-b]pyridinyl wherein the heterocycle is substituted with 0, 1, 2, or 3 substituents independently selected from the group consisting of alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, phenyl, triphenylmethyl (trityl), —C(NH)NR$_{10}$R$_{11}$, —NR$_{10}$R$_{11}$, (NR$_{10}$R$_{11}$)alkyl, (NR$_{10}$R$_{11}$)carbonyl, (NR$_{10}$R$_{11}$)carbonylalkyl, (NR$_{10}$R$_{11}$)sulfonyl, —NR$_{12}$S(O)$_2$R$_{13}$, —C(NR$_{12}$)NR$_{13}$R$_{14}$, —CH$_2$C(NR$_{12}$)NR$_{13}$R$_{14}$, —C(NOR$_{12}$)R$_{13}$, —C(NCN)R$_{12}$, —C(NNR$_{12}$R$_{13}$)R$_{14}$, —S(O)$_2$OR$_{12}$, and —S(O)$_2$R$_{12}$, wherein R$_{10}$ and R$_{11}$ are independently selected from hydrogen, alkyl or alkylcarbonyl, and R$_{12}$, R$_{13}$, and R$_{14}$ are independently selected from hydrogen, alkyl, aryl, or arylalkyl.

2. The compound according to claim 1 wherein the heterocycle is selected from the group consisting of imidazolyl, isoxazolyl, pyridazinyl, tetrazolyl, thiadiazolyl, thiazolyl, thienyl, imidazo[1,2-a]pyridinyl, thieno[3,2-b]pyridinyl, and thieno[2,3-b]pyridinyl wherein the heterocycle is substituted with 0, 1, or 2 substituents independently selected from the group consisting of alkenyl, alkenyloxy, alkoxy, alkyl, alkynyl, cyano, halogen, nitro, phenyl, (NR$_{10}$R$_{11}$)sulfonyl, and —C(NH)NR$_{10}$R$_{11}$.

3. The compound according to claim 2 selected from the group consisting of
(cis)-5-(3-methyl-5-isoxazolyl)-1,2,3,3a,4,6a-hexahydrocyclopenta[c]pyrrole;
(cis)-2-methyl-5-(3-methyl-5-isoxazolyl)-1,2,3,3a,4,6a-hexahydrocyclopenta[c]pyrrole;
(cis)-5-(3-bromo-1,2,4-thiadiazol-5-yl)-1,2,3,3a,4,6a-hexahydrocyclopenta[c]pyrrole;
(cis)-5-(1,3-thiazol-2-yl)-1,2,3,3a,4,6a-hexahydrocyclopenta[c]pyrrole;
(cis)-5-(3,5-dimethyl-4-isoxazolyl)-1,2,3,3a,4,6a-hexahydrocyclopenta[c]pyrrole;
(cis)-5-(1H-imidazol-4-yl)-1,2,3,3a,4,6a-hexahydrocyclopenta[c]pyrrole;
(cis)-5-(1,3-thiazol-5-yl)-1,2,3,3a,4,6a-hexahydrocyclopenta[c]pyrrole;
(cis)-5-(imidazo[1,2-a]pyridin-3-yl)-1,2,3,3a,4,6a-hexahydrocyclopenta[c]pyrrole;
(cis)-5-(imidazo[1,2-a]pyridin-6-yl)-1,2,3,3a,4,6a-hexahydrocyclopenta[c]pyrrole;
(cis)-5-(thieno[3,2-b]pyridin-2-yl)-1,2,3,3a,4,6a-hexahydrocyclopenta[c]pyrrole;
(cis)-5-(1-trityl-1H-imidazol-4-yl)-1,2,3,3a,4,6a-hexahydrocyclopenta[c]pyrrole;
(cis)-5-(5-(aminosulfonyl)-2-thienyl)-1,2,3,3a,4,6a-hexahydrocyclopenta[c]pyrrole;
(cis)-5-(5-(amino(imino)methyl)-2-thienyl)-1,2,3,3a,4,6a-hexahydrocyclopenta[c]pyrrole;
(cis)-5-(2-methyl-2H-tetrazol-5-yl)-1,2,3,3a,4,6a-hexahydrocyclopenta[c]pyrrole;
(cis)-5-(thieno[2,3-b]pyridin-5-yl)-1,2,3,3a,4,6a-hexahydrocyclopenta[c]pyrrole;
(cis)-5-(imidazo[1,2-a]pyridin-7-yl)-1,2,3,3a,4,6a-hexahydrocyclopenta[c]pyrrole;
(cis)-5-(5-nitro-1,3-thiazol-2-yl)-1,2,3,3a,4,6a-hexahydrocyclopenta[c]pyrrole;
(cis)-5-(1,3,4-thiadiazol-2-yl)-1,2,3,3a,4,6a-hexahydrocyclopenta[c]pyrrole;
(cis)-5-(6-phenylpyridazin-3-yl)-1,2,3,3a,4,6a-hexahydrocyclopenta[c]pyrrole; and
(cis)-2-methyl-5-(6-phenylpyridazin-3-yl)-1,2,3,3a,4,6a-hexahydrocyclopenta[c]pyrrole.

4. The compound according to claim 1 wherein the heterocycle is pyridinyl substituted with 0, 1, or 2 substituents independently selected from the group consisting of alkenyl, alkenyloxy, alkoxy, alkyl, alkynyl, cyano, halogen, and nitro.

5. The compound according to claim 4 selected from the group consisting of
(cis)-5-(6-chloro-3-pyridinyl)-1,2,3,3a,4,6a-hexahydrocyclopenta[c]pyrrole;
(cis)-5-(5-methoxy-3-pyridinyl)-1,2,3,3a,4,6a-hexahydrocyclopenta[c]pyrrole;
(cis)-5-(6-chloro-5-methyl-3-pyridinyl)-1,2,3,3a,4,6a-hexahydrocyclopenta[c]pyrrole;
(cis)-5-(3-pyridinyl)-1,2,3,3a,4,6a-hexahydrocyclopenta[c]pyrrole;
(cis)-5-(5,6-dichloro-3-pyridinyl)-1,2,3,3a,4,6a-hexahydrocyclopenta[c]pyrrole;
(cis)-5-(5-chloro-3-pyridinyl)-1,2,3,3a,4,6a-hexahydrocyclopenta[c]pyrrole;
(cis)-5-(6-methyl-3-pyridinyl)-1,2,3,3a,4,6a-hexahydrocyclopenta[c]pyrrole;
(cis)-5-(2-methyl-3-pyridinyl)-1,2,3,3a,4,6a-hexahydrocyclopenta[c]pyrrole;
(cis)-5-(6-chloro-5-fluoro-3-pyridinyl)-1,2,3,3a,4,6a-hexahydrocyclopenta[c]pyrrole;
(cis)-5-(6-chloro-3-pyridinyl)-2-cyanomethyl-1,2,3,3a,4,6a-hexahydrocyclopenta[c]pyrrole;
(cis)-5-(6-fluoro-3-pyridinyl)-1,2,3,3a,4,6a-hexahydrocyclopenta[c]pyrrole;
(cis)-5-(2-pyridinyl)-1,2,3,3a,4,6a-hexahydrocyclopenta[c]pyrrole;
(cis)-5-(4-pyridinyl)-1,2,3,3a,4,6a-hexahydrocyclopenta[c]pyrrole;
(cis)-5-(6-methyl-2-pyridinyl)-1,2,3,3a,4,6a-hexahydrocyclopenta[c]pyrrole;
(cis)-5-(5-bromo-3-pyridinyl)-1,2,3,3a,4,6a-hexahydrocyclopenta[c]pyrrole;
(cis)-5-(5-vinyl-3-pyridinyl)-1,2,3,3a,4,6a-hexahydrocyclopenta[c]pyrrole;
(cis)-5-(1,2,3,3a,4,6a-hexahydrocyclopenta[c]pyrrol-5-yl)nicotinonitrile;
(3aS,6aR)-5-(6-chloro-3-pyridinyl)-1,2,3,3a,4,6a-hexahydrocyclopenta[c]pyrrole; and
(3aR,6aS)-5-(6-chloro-3-pyridinyl)-1,2,3,3a,4,6a-hexahydrocyclopenta[c]pyrrole.

* * * * *